US011485975B2

(12) United States Patent
Hagedorn et al.

(10) Patent No.: US 11,485,975 B2
(45) Date of Patent: Nov. 1, 2022

(54) OLIGONUCLEOTIDES FOR MODULATING TMEM106B EXPRESSION

(71) Applicant: Genentech, Inc., South San Francisco, CA (US)

(72) Inventors: Peter Hagedorn, Hørsholm (DK); Marianne L. Jensen, Hørsholm (DK); Lukasz Kielpinski, Hørsholm (DK); Amy Easton, South San Francisco, CA (US); Benny Chih, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/987,030

(22) Filed: Aug. 6, 2020

(65) Prior Publication Data

US 2021/0054383 A1    Feb. 25, 2021

Related U.S. Application Data

(63) Continuation of application No. PCT/EP2019/053116, filed on Feb. 8, 2019.

(60) Provisional application No. 62/669,251, filed on May 9, 2018.

(30) Foreign Application Priority Data

Feb. 9, 2018  (EP) ................... 18156142

(51) Int. Cl.
  *C12N 15/11*   (2006.01)
  *C12N 15/113*  (2010.01)

(52) U.S. Cl.
  CPC ...... *C12N 15/1138* (2013.01); *C12N 2310/11* (2013.01); *C12N 2310/14* (2013.01); *C12N 2310/315* (2013.01); *C12N 2310/321* (2013.01); *C12N 2310/322* (2013.01); *C12N 2310/3231* (2013.01); *C12N 2310/341* (2013.01); *C12N 2310/351* (2013.01)

(58) Field of Classification Search
  None
  See application file for complete search history.

(56) References Cited

U.S. PATENT DOCUMENTS

| 7,229,767 | B2 | 6/2007 | Kmiec et al. | |
| 2005/0246794 | A1* | 11/2005 | Khvorova | A61P 35/02 800/286 |

FOREIGN PATENT DOCUMENTS

| EP | 1752536 A1 | 2/2007 |
| EP | 2213738 A2 | 8/2010 |
| RU | 2603740 C2 | 11/2016 |
| WO | WO-2005/116204 A1 | 12/2005 |
| WO | WO-2006/034348 A2 | 3/2006 |
| WO | WO-2010/129021 A1 | 11/2010 |
| WO | WO-2011/154542 A1 | 12/2011 |
| WO | WO-2011154542 A1 * | 12/2011 | ................ A61P 7/06 |
| WO | WO-2013/173637 A1 | 11/2013 |
| WO | WO-2013/173645 A1 | 11/2013 |
| WO | WO-2013/173647 A1 | 11/2013 |
| WO | WO-2014/076195 A1 | 5/2014 |
| WO | WO-2015/127037 A1 | 8/2015 |
| WO | WO-2016/126995 A1 | 8/2016 |
| WO | WO-2016/127002 A1 | 8/2016 |

OTHER PUBLICATIONS

Berge et al, Pharmaceutical salts, Journal of Pharmaceutical Sciences, 1977, vol. 66, issue 1, pp. 1-19 (Year: 1977).*
Office Action for Russian Patent Application No. 2020125769/10(044944), dated Mar. 3, 2021 (10 pages).
Lai et al., "Directed RNase H Cleavage of Nascent Transcripts Causes Transcription Termination," Mol Cell. 77(5):1032-1043.e4. (2020).
Suzuki et al., "The Lysosomal Trafficking Transmembrane Protein 106B is Linked to Cell Death," J Biol Chem. 291(41):21448-21460 (2016).
Office Action for Iranian Patent Application No. 139950140003004222, dated Jul. 13, 2021 (3 pages).
Stagi et al., "Lysosome size, motility and stress response regulated by fronto-temporal dementia modifier TMEM106B," Mol Cell Neurosci. 61:226-40 (2014).
Schwenk, Michael, thesis: "The FTLD risk factor TMEM106B controls lysosomal trafficking and dendrite outgrowth," Doctorate of Natural Science, Ludwig Maximilians Universitat Milnchen, 2014.
International Search Report for PCT International Patent Application No. PCT/EP2019/053116, dated Jul. 29, 2019 (11 pages).
Nicholson et al., "What we know about TMEM106B in neurodegeneration," Acta Neuropathol. 132(5):639-651 (2016).
Schwenk et al., "The FTLD risk factor TMEM106B and MAP6 control dendritic trafficking of lysosomes," EMBO J. 33(5):450-67 (2013).
Götzl et al., "Common pathobiochemical hallmarks of progranulin-associated frontotemporal lobar degeneration and neuronal ceroid lipofuscinosis," Acta Neuropathol. 127(6):845-60 (2014).
Holler et al., "Intracellular Proteolysis of Progranulin Generates Stable, Lysosomal Granulins that are Haploinsufficient in Patients with Frontotemporal Dementia Caused by GRN Mutations," eNeuro. 4(4):ENEUR0.0100-17.2017 (2017).
Simons et al., "A recurrent de novo mutation in TMEM106B causes hypomyelinating leukodystrophy," Brain. 140(12):3105-3111 (2017).
Gallagher et al., "A Dementia-Associated Risk Variant near TMEM106B Alters Chromatin Architecture and Gene Expression," Am J Hum Genet. 101(5):643-663 (2017).

(Continued)

*Primary Examiner* — Ekaterina Poliakova-Georgantas
(74) *Attorney, Agent, or Firm* — Clark & Elbing LLP; Thomas J. Takara

(57) ABSTRACT

The present invention relates to oligonucleotides that are complementary to and modulate the expression of TMEM106B. The present invention further relates to conjugates of the oligonucleotide and pharmaceutical compositions and methods for treatment of neurological disorders using the oligonucleotide.

30 Claims, 16 Drawing Sheets

Specification includes a Sequence Listing.

(56) References Cited

OTHER PUBLICATIONS

Hu et al., "Association analysis of polymorphisms in VMAT2 and TMEM106B genes for Parkinson's disease, amyotrophic lateral sclerosis and multiple system atrophy," J Neurol Sci. 377:65-71 (2017).

Rostgaard et al., "TMEM106B and ApoE polymorphisms in CHMP2B-mediated frontotemporal dementia (FTD-3)," Neurobiol Aging. 59:221.e1-221.e7 (2017).

Klein et al., "Loss of TMEM106B Ameliorates Lysosomal and Frontotemporal Dementia-Related Phenotypes in Progranulin-Deficient Mice," Neuron. 95(2):281-296 (2017).

Database EMBL [online] EBI Accession No. EM_PAT:HH469680, "Sequence 1346395 from Patent EP2215758," created Aug. 27, 2010.

Database EMBL [Online] EBI accession No. EM PAT:FW775541, "WO 2005116204-A/182067: Double strand polynucleotides generating RNA interference.", created Apr. 18, 2011.

Database Geneseq [Online], "VEGF or VEGFR-specific siRNA sequence—SEQ ID 897.", retrieved from EBI accession No. GSN:AED37096. Database accession No. AED37096 , Dec. 15, 2005.

Database EMBL [Online] EBI accession No. EM PAT:JE140427 , (Jun. 7, 2015), "Sequence 452294 from Patent EP2850184.", created Jun. 7, 2015.

Database EMBL [Online] "Sequence 88168 from Patent EP2849801.", retrieved from EBI accession No. EM PAT:JE659650 Database accession No. JE659650, created Jun. 7, 2015.

Database EMBL [Online], "Sequence 50381 from Patent EP2850185.", retrieved from EBI accession No. EM PAT:LP184046 Database accession No. LP184046, created Mar. 10, 2016.

Database EMBL [Online] (Jun. 7, 2015), "Sequence 848264 from Patent EP2850184.", retrieved from EBI accession No. EM PAT:JE536397 Database accession No. JE536397 & WO 2013/173637 A 1 (Nov. 21, 2013).

Notice of Reasons for Rejection for Japanese Patent Application No. 2020-542377, dated Dec. 14, 2021 (12 pages).

Nicholson et al., "TMEM106B p.T185S regulates TMEM106B protein levels: implications for frontotemporal dementia," available in PMC Sep. 1, 2014, published in final edited form as: J Neurochem. 126(6): 781-791 (2013).

Written Opinion and Search Report for Singapore Patent Application No. 11202007093Y, dated Apr. 6, 2022 (10 pages).

\* cited by examiner

CMP ID NO: 65_1

CMP ID NO: 66_1

CMP ID NO: 71_1

CMP ID NO: 74_1

CMP ID NO: 75_1

OLIGONUCLEOTIDES FOR MODULATING TMEM106B EXPRESSION

SEQUENCE LISTING

The instant application contains a Sequence Listing which has been submitted electronically in ASCII format and is hereby incorporated by reference in its entirety. Said ASCII copy, created on Aug. 6, 2020 is named 51527-002004_Sequence_Listing_8.6.20_ST25 and is 185,670 bytes in size. No new matter has been added.

FIELD OF INVENTION

The present invention relates to oligonucleotides complementary to Transmembrane protein 106B (TMEM106B), which are capable of modulation of the expression of TMEM106B. Modulation of TMEM106B expression is beneficial for a range of medical disorders, such as neurological disorders, in particular neurodegenerative disorders, such as frontotemporal lobar degeneration.

BACKGROUND

Transmembrane protein 106B (TMEM106B) is a single-pass, type 2 integral membrane glycoprotein predominantly located in the membranes of endosomes and lysosomes. It is expressed in in neurons as well as glial and endothelial cells. It is believed to be involved in dendrite morphogenesis, such as dendrite branching as well as in lysosomal functioning. TMEM106B has been associated with several common neurodegenerative disorders including frontotemporal lobar degeneration (FTLD) (Nicholson and Rademakers, Acta Neuropathol. 2016 November; 132(5): 639-651).

Klein et al., 2017, Neuron 95, 281-296 reports that the loss of TMEM106B ameliorates lysosomal and frontotemporal dementia-related phenotypes in progranulin-deficient mice.

Rostgaard et al., Neurobiology of Aging 59 (2017) 221.e1e221.e7 reports on TMEM106B and ApoE polymorphisms in CHMP2B-mediated frontotemporal dementia (FTD-3).

Hu et al., Journal of the Neurological Sciences 377 (2017) 65-71 reports on the association of certain polymorphisms in the TMEM106B genes in Parkinson's disease, amyotrophic lateral sclerosis (ALS) and multiple system atrophy (MSA).

Gallagher et al., The American Journal of Human Genetics 101, 643-663, Nov. 2, 2017 reports on a dementia-associated risk variant near TMEM106B which alters chromatin architecture and gene expression.

Simons et al., Brain 2017: 140; 3105-3111 reports that a recurrent de novo mutation in TMEM106B causes hypomyelinating leukodystrophy.

Holler et al. eNeuro. 2017 July-August; 4(4): ENEURO.0100-17.2017 show that lysosome dysfunction induced by e.g. alkalizing agents or increased expression of TMEM106B inhibits processing of progranulin (PGRN) into granulins (GRNs). They also show that multiple GRNs are haploinsufficient in primary fibroblasts and cortical brain tissue from FTD-GRN patients. This may apply to Neuronal Ceroid Lipofuscinosis (NCL) as homozygous or heterozygous mutations in the GRN gene, encoding progranulin (PGRN), cause neuronal ceroid lipofuscinosis (NCL) or frontotemporal dementia (FTD), respectively.

Gotzl et al. Acta Neuropathol. 127(6):845-60. reports elevations in TMEM106b and GRN proteins in cathepsin D knock out mice, a model of NCL.

Schwenk et al., EMBO J. 2014 Mar. 3; 33(5):450-67 reports on FTLD-TDP risk factor TMEM106B and it functional interaction with MAP6 to control dendritic trafficking of lysosomes. siRNAs against TMEM106B was transfected into HeLa cells showing reduction TMEM106B protein expression resulting in lysosomal clustering near the nucleus. Furthermore TMEM106B knock down using shRNA transfected into hippocampal neurons impaired dendrite branching. The changes caused in dendritic morphology by TMEM106B knock down may cause impaired synaptic strength and plasticity which are common attributes of neurodegenerative diseases. This implies that knock down of TMEM106B may cause neurodegenerative disease.

WO2015/127037 reports on compounds and method for the treatment of neurodegenerative diseases, including small molecule compounds which are reported as being effective in modulating the expression of a range of genes, including TMEM106B. There does not appear to be any data indicating TMEM106B inhibition by the disclosed compounds.

Neurodegenerative disorders represent a major unmet medical need, and there is clear genetic and experimental evidence which indicates TMEM106B expression, and specific TMEM106B allele with neurodegenerative disorders. There is therefore a need for inhibitors of TMEM106B for use in research and therapeutic applications.

OBJECTIVE OF THE INVENTION

The present invention provides nucleic acid inhibitors of TMEM106B which may be used both in vivo and in vitro for down-regulation of TMEM106B expression, and for the therapeutic intervention in neurological disorders.

SUMMARY OF INVENTION

The present invention relates to oligonucleotides that are complementary to and modulate the expression of TMEM106B. The present invention further relates to conjugates of the oligonucleotide and pharmaceutical compositions and methods for treatment of neurological disorders using the oligonucleotide.

The present invention provides oligonucleotide inhibitors of TMEM106B for decreasing the expression of TMEM106B in cells, and which may be used for the treatment of neurological disorders, such as neurodegeneration, frontotemporal lobar degeneration (FTLD), Parkinson's disease (or parkinsonism), hypomyelinating leukodystrophies, amyotrophic lateral sclerosis and multiple system atrophy, Alzheimer's disease, motor neuron disease, corticobasal syndrome, progressive supranuclear palsy, and neuronal ceroid lipofuscinosis (NCL).

The present invention provides oligonucleotide inhibitors of TMEM106B for decreasing the expression of TMEM106B in cells, and which may be used for the treatment of frontotemporal lobar degeneration (FTLD).

The present invention relates to oligonucleotides targeting a nucleic acid capable of inhibiting the expression of TMEM106B and to treat or prevent diseases related to the functioning of the TMEM106B.

The invention provides for an oligonucleotide targeting TMEM106B, which comprises a contiguous nucleotide sequence of 10-30 nucleotides in length with at least 90% complementary, such as fully complementary, to a mammalian TMEM106B target nucleic acid.

The invention provides for an oligonucleotide, 10-40 nucleotides in length, targeting TMEM106B, which comprises a contiguous nucleotide sequence of 10-30 nucleotides in length with at least 90% complementary, such as fully complementary, to a mammalian TMEM106B target nucleic acid.

The oligonucleotide of the invention may for example be an antisense oligonucleotide (ASO), which is capable of inhibiting the expression of TMEM106B in a cell which is expressing TMEM106B.

The oligonucleotide of the invention may for example be a siRNA (or the antisense strand of a siRNA), which is capable of inhibiting the expression of TMEM106B in a cell which is expressing TMEM106B.

The invention provides an oligonucleotide which comprises a contiguous nucleotide sequence of 10 to 30 nucleotides in length with at least 90% complementarity to a mammalian TMEM106B target nucleic acid, wherein the oligonucleotide is capable of inhibiting the expression of TMEM106B in a cell which is expressing the TMEM106B target nucleic acid.

The invention provides an antisense oligonucleotide which comprises a contiguous nucleotide sequence of 10 to 30 nucleotides in length with at least 90% complementarity to a mammalian TMEM106B target nucleic acid, wherein the antisense oligonucleotide is capable of inhibiting the expression of TMEM106B in a cell which is expressing the TMEM106B target nucleic acid. Advantageously, the oligonucleotide may be an antisense oligonucleotide which is capable of recruiting RNaseH, such as human RNaseH1, such as a gapmer oligonucleotide.

The invention provides for a conjugate comprising the oligonucleotide, such as the antisense oligonucleotide or siRNA, according to the invention, and at least one conjugate moiety covalently attached to said oligonucleotide.

The invention provides for a pharmaceutically acceptable salt of the oligonucleotide of the invention, such as the antisense oligonucleotide or siRNA of the invention, or conjugate thereof.

The invention provides for a pharmaceutical composition comprising the oligonucleotide of the invention, such as the antisense oligonucleotide or siRNA of the invention, or conjugate thereof, and a pharmaceutically acceptable diluent, solvent, carrier, salt and/or adjuvant.

The invention provides for a method for modulating TMEM106B expression in a target cell which is expressing TMEM106B, said method comprising administering an oligonucleotide of the invention, such as the antisense oligonucleotide or siRNA of the invention, or conjugate or the pharmaceutical salt or pharmaceutical composition, in an effective amount to said cell. The method may, for example, be an in vitro method or an in vivo method.

The invention provides for a method for treating or preventing a disease comprising administering a therapeutically or prophylactically effective amount of an oligonucleotide of the invention, such as the antisense oligonucleotide or siRNA of the invention, or conjugate thereof, or the pharmaceutical salt or pharmaceutical composition of the invention, to a subject suffering from or susceptible to the disease.

In some embodiments, the method is for treating a neurodegenerative disease in a subject who has been diagnosed with, or is suffering from, a neurodegenerative disease, such as a neurodegenerative disease selected from the group consisting of neurodegeneration, frontotemporal lobar degeneration (FTLD), Parkinson's disease (or parkinsonism), hypomyelinating leukodystrophies, amyotrophic lateral sclerosis and multiple system atrophy, Alzheimer's disease, motor neuron disease, corticobasal syndrome, progressive supranuclear palsy, and neuronal ceroid lipofuscinosis (NCL).

In some embodiments the compounds of the invention are used for the treatment of age associated changes in frontal cortex.

The method for treating or preventing a disease may, for example be for treating or preventing a neurodegenerative disease, such as a disease selected from the list consisting of neurodegeneration, frontotemporal lobar degeneration (FTLD), Parkinson's disease (or parkinsonism), hypomyelinating leukodystrophies, amyotrophic lateral sclerosis and multiple system atrophy, Alzheimer's disease, motor neuron disease, corticobasal syndrome, progressive supranuclear palsy, and neuronal ceroid lipofuscinosis (NCL).

The invention provides for the oligonucleotide, such as the antisense oligonucleotide or siRNA of the invention, or conjugate thereof, or the pharmaceutical salt or pharmaceutical composition of the invention, for use in medicine.

The invention provides for the oligonucleotide, such as the antisense oligonucleotide or siRNA of the invention, or conjugate thereof, or pharmaceutical salt or pharmaceutical composition of the invention, for use in the treatment of a neurodegenerative disease such as a disease selected from the group consisting of prevention of neurodegeneration, frontotemporal lobar degeneration (FTLD), Parkinson's disease (or parkinsonism), hypomyelinating leukodystrophies, amyotrophic lateral sclerosis and multiple system atrophy, Alzheimer's disease, motor neuron disease, corticobasal syndrome, progressive supranuclear palsy, and neuronal Ceroid Lipofuscinosis (NCL).

The invention provides for the use of the oligonucleotide of the invention, such as the antisense oligonucleotide or siRNA of the invention, or the conjugate thereof, or pharmaceutical salt or pharmaceutical composition of the invention, for the preparation of a medicament for treatment or prevention of a neurodegenerative disease such as a disease selected from the group consisting of prevention of neurodegeneration, frontotemporal lobar degeneration (FTLD), Parkinson's disease (or parkinsonism), hypomyelinating leukodystrophies, amyotrophic lateral sclerosis and multiple system atrophy, Alzheimer's disease, motor neuron disease, corticobasal syndrome, progressive supranuclear palsy, and neuronal Ceroid Lipofuscinosis (NCL).

DEFINITIONS

Figure 1:
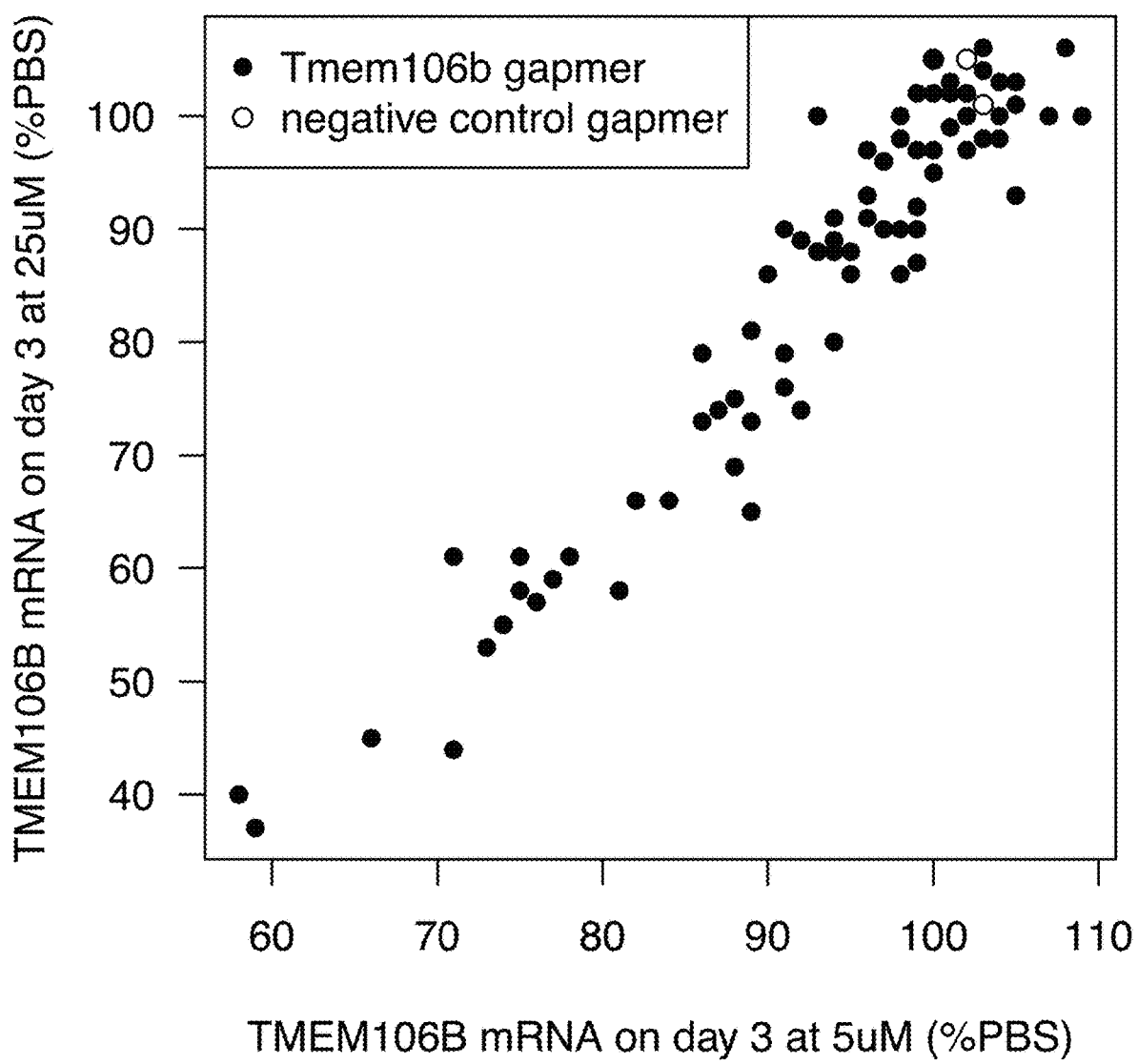
FIG. 1: Target inhibition after 3 days of incubation in mouse Neuro-2a cells at 5 µM vs 25 µM compared to PBS-treated control (mean of two biological replicates).

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and propyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl, cyclohexyl, cycloheptyl and cyclooctyl, more particularly cyclopropyl and cyclobutyl. A particular example of "cycloalkyl" is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy. Particular "alkoxy" are methoxy and ethoxy. Methoxyethoxy is a particular example of "alkoxyalkoxy".

The term "oxy", alone or in combination, signifies the —O— group.

The term "alkenyl", alone or in combination, signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl.

The term "alkynyl", alone or in combination, signifies a straight-chain or branched hydrocarbon residue comprising a triple bond and up to 8, preferably up to 6, particularly preferred up to 4 carbon atoms.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl or trifluoromethyl. Fluoromethyl, difluoromethyl and trifluoromethyl are particular "haloalkyl".

The term "halocycloalkyl", alone or in combination, denotes a cycloalkyl group as defined above substituted with at least one halogen, particularly substituted with one to five halogens, particularly one to three halogens. Particular example of "halocycloalkyl" are halocyclopropyl, in particular fluorocyclopropyl, difluorocyclopropyl and trifluorocyclopropyl.

The terms "hydroxyl" and "hydroxy", alone or in combination, signify the —OH group.

The terms "thiohydroxyl" and "thiohydroxy", alone or in combination, signify the —SH group.

The term "carbonyl", alone or in combination, signifies the —C(O)— group.

The term "carboxy" or "carboxyl", alone or in combination, signifies the —COOH group.

The term "amino", alone or in combination, signifies the primary amino group (—$NH_2$), the secondary amino group (—NH—), or the tertiary amino group (—N—).

The term "alkylamino", alone or in combination, signifies an amino group as defined above substituted with one or two alkyl groups as defined above.

The term "sulfonyl", alone or in combination, means the —$SO_2$ group.

The term "sulfinyl", alone or in combination, signifies the —SO— group.

The term "sulfanyl", alone or in combination, signifies the —S— group.

The term "cyano", alone or in combination, signifies the —CN group.

The term "azido", alone or in combination, signifies the —$N_3$ group.

The term "nitro", alone or in combination, signifies the $NO_2$ group.

The term "formyl", alone or in combination, signifies the —C(O)H group.

The term "carbamoyl", alone or in combination, signifies the —C(O)NH$_2$ group.

The term "cabamido", alone or in combination, signifies the —NH—C(O)—NH$_2$ group.

The term "aryl", alone or in combination, denotes a monovalent aromatic carbocyclic mono- or bicyclic ring system comprising 6 to 10 carbon ring atoms, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of aryl include phenyl and naphthyl, in particular phenyl.

The term "heteroaryl", alone or in combination, denotes a monovalent aromatic heterocyclic mono- or bicyclic ring system of 5 to 12 ring atoms, comprising 1, 2, 3 or 4 heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of heteroaryl include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, carbazolyl or acridinyl.

The term "heterocyclyl", alone or in combination, signifies a monovalent saturated or partly unsaturated mono- or bicyclic ring system of 4 12, in particular 4-9, ring atoms, comprising 1, 2, 3 or 4 ring heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-azabicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl or dihydropyranyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

The term "protecting group", alone or in combination, signifies a group which selectively blocks a reactive site in a multifunctional compound such that a chemical reaction can be carried out selectively at another unprotected reactive site. Protecting groups can be removed. Exemplary protecting groups are amino-protecting groups, carboxy-protecting groups or hydroxy-protecting groups.

If one of the starting materials or compounds of the invention contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

Nucleic Acid Molecule

The term "nucleic acid molecule" or "therapeutic nucleic acid molecule" as used herein is defined as it is generally understood by the skilled person as a molecule comprising two or more covalently linked nucleosides (i.e. a nucleotide sequence). The nucleic acid molecule(s) referred to in the invention are generally oligonucleotides of 10-50 nucleotides in length, and they are generally composed of one or two oligonucleotides. The nucleic acid molecules may be or comprise an antisense oligonucleotide, or may be another oligomeric nucleic acid molecule, such as a CRISPR RNA, a siRNA, shRNA, an aptamer, or a ribozyme. Therapeutic nucleic acid molecules are commonly made in the laboratory by solid-phase chemical synthesis followed by purification and isolation. shRNA's are however often delivered to cells using lentiviral vectors (see for example Soan and Yang 2010 N Am J Med Sci 2(12): 598) which are then transcribed to produce the single stranded RNA that will form a stem loop (hairpin) RNA structure that is capable of interacting with the RNA interference machinery (including the RNA-induced silencing complex (RISC)). When referring to a sequence of the nucleic acid molecule, reference is made to the sequence or order of nucleobase moieties, or modifications thereof, of the covalently linked nucleotides or nucleosides. The nucleic acid molecule(s) of the invention is man-made, and is chemically synthesized, and is typically purified or isolated. The nucleic acid molecule of the invention may comprise one or more modified nucleosides or nucleotides, such as 2'-sugar modified nucleosides, such as a high affinity modified antisense oligonucleotide.

In some embodiments, the nucleic acid molecule of the invention comprises or consists of 8 to 70 nucleotides in length, 10 to 60 nucleotides in length, 12 to 50 nucleotides in length, such as 8 to 40 nucleotides in length, such as from 9 to 35, such as from 10 to 30, such as from 11 to 22, such as from 12 to 20, such as from 13 to 18 or 14 to 16 contiguous nucleotides in length.

In some embodiments, the nucleic acid molecule or contiguous nucleotide sequence thereof comprises or consists of 24 or less nucleotides, such as 22 or less nucleotides, such as 20 or less nucleotides, such as 18 or less nucleotides, such as 14, 15, 16 or 17 nucleotides. It is to be understood that any range given herein includes the range endpoints. Accordingly, if a nucleic acid molecule is said to include from 10 to 30 nucleotides, both 10 and 30 nucleotides are included.

In some embodiments, the contiguous nucleotide sequence comprises or consists of 8, 9, 10, 11, 12, 13, 14, 15, 16, 17, 18, 19, 20, 21, 22, 23, 24, 25, 26, 27, 28, 29 or 30 contiguous nucleotides in length.

The nucleic acid molecule(s) is typically for modulating the expression of a target nucleic acid in a mammal. In some embodiments the nucleic acid molecule(s), such as siRNAs, shRNAs or antisense oligonucleotides, is typically for inhibiting the expression of a target nucleic acid.

In one embodiment of the invention the nucleic acid molecule is selected from a RNAi agent, such as a siRNA, shRNA.

In another embodiment the nucleic acid molecule is an antisense oligonucleotide, such as single stranded antisense oligonucleotide, such as a high affinity modified antisense oligonucleotide interacting with RNaseH.

In some embodiments the nucleic acid molecule comprises phosphorothioate internucleoside linkages. In some embodiments nucleic acid molecule comprise phosphorothioate linkages in the 5' end and the 3' end (e.g. independently 1-3 linkages in each end). In some embodiments the all the internucleoside linkages in nucleic acid molecule consists of phosphorothioate.

In some embodiments the nucleic acid molecule(s) may be conjugated to non-nucleosidic moieties (conjugate moieties).

Oligonucleotide

The term "oligonucleotide" or "therapeutic oligonucleotide" as used herein is defined as it is generally understood by the skilled person as a molecule comprising two or more covalently linked nucleosides. Such covalently bound nucleosides may also be referred to as nucleic acid molecules, oligonucleotides or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides such as 2' sugar modified nucleosides.

The oligonucleotide of the invention comprises a contiguous nucleotide sequence which is complementary to the target nucleic acid or target sequence, and may, in some embodiments further comprise one or more additional nucleotides, such as 1-30, such as 1-20, such as 1-10, such as 1, 2, 3, 4 or 5 further nucleotides in addition to the contiguous nucleotide sequence. In some embodiments the additional nucleotides are complementary to the contiguous nucleotide sequence and are capable of forming a stem loop (hairpin) structure by hybridizing to the contiguous nucleotide sequence. In some embodiments the additional nucleotides are 1 to 5 phosphodiester linked nucleotides. In some embodiments, all the nucleotides of the oligonucleotide form the contiguous nucleotide sequence.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self-complementarity is less than 50% across of the full length of the oligonucleotide.

Advantageously, the single stranded antisense oligonucleotide of the invention does not contain RNA nucleosides, since this will decrease nuclease resistance.

Advantageously, the antisense oligonucleotide of the invention comprises one or more modified nucleosides or nucleotides, such as 2' sugar modified nucleosides. Furthermore, it is advantageous that the nucleosides which are not modified are DNA nucleosides.

RNAi or siRNA

Herein, the term "RNA interference (RNAi) molecule" refers to any molecule inhibiting RNA expression or translation via the RNA reducing silencing complex (RISC) in a cell's cytoplasm, where the RNAi molecule interact with the catalytic RISC component argonaute. A small interfering RNA (siRNA) is typically a double-stranded RNA complex comprising a passenger (sense) and a guide (antisense) oligonucleotide (strand), which when administered to a cell, results in the incorporation of the guide (antisense) strand into the RISC complex (siRISC) resulting in the RISC associated inhibition of translation or degradation of complementary RNA target nucleic acids in the cell. The sense strand is also referred to as the passenger strand, and the antisense strand as the guide strand. A small hairpin RNA (shRNA) is a single nucleic acid molecule which forms a stem loop (hairpin) structure that is able to degrade mRNA via RISC. RNAi nucleic acid molecules may be synthesized chemically (typical for siRNA complexes) or by in vitro transcription, or expressed from a vector.

shRNA molecules are generally between 40 and 70 nucleotides in length, such as between 45 and 65 nucleotides in length, such as 50 and 60 nucleotides in length, and interacts with the endonuclease known as Dicer which is believed to processes dsRNA into 19-23 base pair short interfering RNAs with characteristic two base 3' overhangs which are then incorporated into an RNA-induced silencing complex (RISC).

Typically, the guide (antisense) strand of an siRNA (or antisense region of a shRNA) is 17-25 nucleotide in length, such as 19-23 nucleotides in length and complementary to the target nucleic acid or target sequence. In an siRNA complex, the guide (antisense) strand and passenger (sense) strand form a double stranded duplex, which may comprise 3' terminal overhangs of e.g. 1-3 nucleotides (resembles the product produced by Dicer), or may be blunt ended (no overhang at one or both ends of the duplex).

It will be recognized that RNAi may be mediated by longer dsRNA substrates which are processed into siRNAs within the cell (a process which is thought to involve the dsRNA endonuclease DICER). Effective extended forms of Dicer substrates have been described in U.S. Pat. Nos. 8,349,809 and 8,513,207, hereby incorporated by reference.

RNAi oligonucleotides may be chemically modified using modified internucleotide linkages and high affinity nucleosides such as 2' sugar modified nucleosides, such as 2'-4' bicyclic ribose modified nucleosides, including LNA and cET or 2' substituted modifications like of 2'-O-alkyl-RNA, 2'-O-methyl-RNA, 2'-alkoxy-RNA, 2'-O-methoxyethyl-RNA (MOE), 2'-amino-DNA, 2'-fluoro-DNA, arabino nucleic acid (ANA), 2'-fluoro-ANA. See for example WO 2002/044321 which discloses 2'O-Methyl modified siRNAs, WO2004083430 which discloses the use of LNA nucleosides in siRNA complexes, known as siLNAs, and WO2007107162 which discloses the use of discontinuous passenger strands in siRNA such as siLNA complexes. WO03006477 discloses siRNA and shRNA (also referred to as stRNA) oligonucleotide mediators of RNAi. Harborth et al., Antisense Nucleic Acid Drug Dev. 2003 April; 13(2): 83-105 refers to the sequence, chemical, and structural variation of small interfering RNAs and short hairpin RNAs and the effect on mammalian gene silencing.

In some embodiments RNAi oligonucleotides comprise one or more phosphorothioate internucleoside linkages. In RNAi molecules phosphorothioate internucleoside linkages may reduce or the nuclease cleavage in RICS it is therefore advantageous that not al internucleoside linkages are modified. Phosphorothioate internucleoside linkages can advantageously be place in the 3' and/or 5' end of the RNAi nucleic acid molecule, in particular in the of the part of the molecule that is not complementary to the target nucleic acid (e.g. the sense strand or passenger strand in an siRNA molecule). The region of the RNAi molecule that is complementary to the target nucleic acid (e.g. the antisense or guide strand in a siRNA molecule) may however also be modified in the first 2 to 3 internucleoside linkages in the 3' and/or 5' terminal.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence, such as the flank (also known as wing) and gap region of a gapmer, such as a F-G-F' gapmer region, and may optionally comprise further nucleotide(s), for example a nucleotide linker region which may be used to attach a functional group to the contiguous nucleotide sequence. The nucleotide linker region may or may not be complementary to the target nucleic acid.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprises a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkages

The term "modified internucleoside linkage" is defined as generally understood by the skilled person as linkages other than phosphodiester (PO) linkages, that covalently couples two nucleosides together. The oligonucleotides of the invention may therefore comprise modified internucleoside linkages. In some embodiments, the modified internucleoside linkage increases the nuclease resistance of the oligonucleotide compared to a phosphodiester linkage, this is a particular advantage for therapeutic oligonucleotides. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region of a gapmer oligonucleotide, as well as in regions of modified nucleosides, such as region F and F'.

In an embodiment, the oligonucleotide, e.g. the therapeutic antisense oligonucleotide, shRNA or siRNA, comprises one or more internucleoside linkages modified from the natural phosphodiester, such one or more modified internucleoside linkages that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In some embodiments at least 50% of the internucleoside linkages in the oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are nuclease resistant internucleoside linkages. In some embodiments all of the internucleoside linkages of the oligonucleotide, or contiguous nucleotide sequence thereof, are nuclease resistant internucleoside linkages. It will be recognized that, in some embodiments the nucleosides which link the oligonucleotide of the invention to a non-nucleotide functional group, such as a conjugate, may be phosphodiester.

A preferred modified internucleoside linkage is phosphorothioate.

Phosphorothioate internucleoside linkages are particularly useful due to nuclease resistance, beneficial pharmacokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 80% or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate. The use of fully phosphorothioate modified oligonucleotides or contiguous nucleotide sequences is often used in antisense oligonucleotides, although in siRNAs partial phosphorothioate modifications may be preferred as fully phosphorothioate modifications have been reported to limit RNAi activity, particularly when used in the guide (antisense) strand. Phosphorothioate modifications may be incorporated into the 5' and 3' ends of an antisense strand of a siRNA without unduly limiting RNAi activity.

Nuclease resistant linkages, such as phosphorothioate linkages, are particularly useful in oligonucleotide regions capable of recruiting nuclease when forming a duplex with the target nucleic acid, such as region G for gapmers. Phosphorothioate linkages may, however, also be useful in non-nuclease recruiting regions and/or affinity enhancing regions such as regions F and F' for gapmers. Gapmer oligonucleotides may, in some embodiments comprise one or more phosphodiester linkages in region F or F', or both region F and F', which the internucleoside linkage in region G may be fully phosphorothioate. Advantageously, all the internucleoside linkages in the contiguous nucleotide sequence of the antisense oligonucleotide are phosphorothioate linkages.

It is recognized that, as disclosed in EP2 742 135, antisense oligonucleotide may comprise other internucleoside linkages (other than phosphodiester and phosphorothioate), for example alkyl phosphonate/methyl phosphonate internucleosides, which according to EP2 742 135 may for example be tolerated in an otherwise DNA phosphorothioate the gap region.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the number of nucleotides in percent of a contiguous nucleotide sequence in an oligonucleotide (e.g. oligonucleotide) which, at a given position, are complementary to (i.e. form Watson Crick base pairs with) a contiguous nucleotide sequence, at a given position of a separate oligonucleotide (e.g. the target nucleic acid). The percentage is calculated by counting the number of aligned bases that form pairs between the two sequences (when aligned with the target sequence 5-3' and the oligonucleotide sequence from 3'-5'), dividing by the total number of nucleotides in the oligonucleotide and multiplying by 100. In such a comparison a nucleobase/nucleotide which does not align (form a base pair) is termed a mismatch. Preferably, insertions and deletions are not allowed in the calculation of % complementarity of a contiguous nucleotide sequence.

The term "fully complementary", refers to 100% complementarity.

The following is an example of an oligonucleotide motif (SEQ ID NO: 86) that is fully complementary to the target nucleic acid (SEQ ID NO: 325).

```
                                      (SEQ ID NO: 325)
               5' gaataatatggaaaaacgaaaa 3'

(SEQ ID NO: 86)
                3' tattataccttttttgct 5'
```

Identity

The term "Identity" as used herein, refers to the proportion of nucleotides (expressed in percent) of a contiguous nucleotide sequence in a oligonucleotide (e.g. oligonucleotide) which across the contiguous nucleotide sequence, are identical to a reference sequence (e.g. a sequence motif). The percentage of identity is thus calculated by counting the number of aligned bases that are identical (a match) between two sequences (in the contiguous nucleotide sequence of the compound of the invention and in the reference sequence), dividing that number by the total number of nucleotides in the oligonucleotide and multiplying by 100. Therefore, Percentage of Identity=(Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, Oligonucleotides 13:515-537). The standard state Gibbs free energy $\Delta G°$ is a more accurate representation of binding affinity and is related to the dissociation constant ($K_d$) of the reaction by $\Delta G°=-RT \ln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, Chem. Comm. 36-38 and Holdgate et al., 2005, Drug Discov Today. The skilled person will know that commercial equipment is available for $\Delta G°$ measurements. $\Delta G°$ can also be estimated numerically by using the nearest neighbor model as described by SantaLucia, 1998, Proc Natl Acad Sci USA. 95: 1460-1465 using appropriately derived thermodynamic parameters described by Sugimoto et al., 1995, Biochemistry 34:11211-11216 and McTigue et al., 2004, Biochemistry 43:5388-5405. In order to have the possibility of modulating its intended nucleic acid target by hybridization, oligonucleotides of the present invention hybridize to a target nucleic acid with estimated $\Delta G°$ values below −10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated $\Delta G°$ value of −10 to −60 kcal, such as −12 to −40, such as from −15 to −30 kcal or −16 to −27 kcal such as −18 to −25 kcal.

Target Nucleic Acid

According to the present invention, the target nucleic acid is a nucleic acid which encodes mammalian TMEM106B and may for example be a gene, a RNA, a mRNA, and pre-mRNA, a mature mRNA or a cDNA sequence. The target may therefore be referred to as an TMEM106B target nucleic acid. The oligonucleotide of the invention may for example target exon regions of a mammalian TMEM106B RNA, or may for example target intron region in the TMEM106B pre-mRNA (see Table 1).

TABLE 1 human TMEM106B Exons and Introns regions which may be targeted by the compounds of the invention:

| Exonic regions in the human TMEM106B premRNA (SEQ ID NO 1) | | | Intronic regions in the human TMEM106B premRNA (SEQ ID NO 1) | | |
|---|---|---|---|---|---|
| ID | start | end | ID | start | end |
| e1 | 1 | 204 | i1 | 205 | 2979 |
| e2 | 2980 | 3173 | i2 | 3174 | 3587 |
| e3 | 3588 | 3806 | i3 | 3807 | 7236 |
| e4 | 7237 | 7300 | i4 | 7301 | 13004 |
| e5 | 13005 | 13164 | i5 | 13165 | 18457 |
| e6 | 18458 | 18598 | i6 | 18599 | 19167 |
| e7 | 19168 | 19217 | i7 | 19218 | 19840 |
| e8 | 19841 | 19894 | i8 | 19895 | 20615 |
| e9 | 20616 | 32146 | | | |

Suitably, the target nucleic acid encodes an TMEM106B protein, in particular mammalian TMEM106B, such as human TMEM106B (See for example Tables 2 and 3, which provides the mRNA and pre-mRNA sequences for human, monkey, and mouse TMEM106B).

In some embodiments, the target nucleic acid is selected from the group consisting of SEQ ID NO: 1, 2, 3, 4, 5 and 6 or naturally occurring variants thereof, including SNP variants. A table of known nucleotide polymorphisms (SNPs) of SEQ ID NO: 1 are shown in Table 4. If employing the oligonucleotide of the invention in research or diagnostics the target nucleic acid may be a cDNA or a synthetic nucleic acid derived from DNA or RNA.

The oligonucleotide of the invention is typically capable of inhibiting the expression of the TMEM106B target nucleic acid in a cell which is expressing the TMEM106B target nucleic acid. The contiguous sequence of nucleobases of the oligonucleotide of the invention is typically complementary to the TMEM106B target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides (e.g. region D' or D"). The target nucleic acid may, in some embodiments, be a mature mRNA or a pre-mRNA.

In some embodiments the target nucleic acid is a RNA which encodes mammalian TMEM106B protein, such as human TMEM106B, e.g. the human TMEM106B pre-mRNA sequence, such as that disclosed as SEQ ID NO: 1, or the human mature mRNA, such as that disclosed in SEQ ID NO: 2. Further information on exemplary target nucleic acids is provided in Tables 2 and 3. Table 2: Genome and assembly information for TMEM106B across species.

TABLE 2

Genome and assembly information for TMEM106B across species.

| Species | Chr. | Strand | Genomic coordinates Start | End | Assembly/ Ensemble Gene ID | NCBI reference sequence* accession number for mRNA |
|---|---|---|---|---|---|---|
| Human | 7 | Fwd | 12211222 | 12243367 | GRCh38/ENSG00000106460 | NM_018374 |
| Cynomolgus monkey | 3 | Rv | 108661057 | 108693751 | Macaca_fascicularis_5.0 | XM_005550096 |
| Mouse | 6 | Fwd | 13069744 | 13089269 | GRCm38/ENSMUSG00000029571 | NM_027992 |

Fwd = forward strand.
Rv = reverse strand.
The genome coordinates provide the pre-mRNA sequence (genomic sequence). The NCBI reference provides the mRNA sequence (cDNA sequence).
*The National Center for Biotechnology Information reference sequence database is a comprehensive, integrated, non-redundant, well-annotated set of reference sequences including genomic, transcript, and protein. It is hosted at www.ncbi.nlm.nih.gov/refseq.

TABLE 3

Sequence details for TMEM106B across species.

| Species | RNA type | Length (nt) | SEQ ID NO |
|---|---|---|---|
| Human | premRNA | 32146 | 1 |
| Human | mRNA | 6514 | 2 |
| Monkey | premRNA | 32695 | 3 |
| Monkey | mRNA | 2740 | 4 |
| Mouse | premRNA | 19526 | 5 |
| Mouse | mRNA | 6099 | 6 |

Target Sequence

The term "target sequence" as used herein refers to a sequence of nucleotides present in the target nucleic acid which comprises the nucleobase sequence which is complementary to the oligonucleotide of the invention. In some embodiments, the target sequence consists of a region on the target nucleic acid with a nucleobase sequence that is complementary to the contiguous nucleotide sequence of the oligonucleotide of the invention. This region of the target nucleic acid may interchangeably be referred to as the target nucleotide sequence, target sequence or target region. In some embodiments the target sequence is longer than the complementary sequence of a single oligonucleotide, and may, for example represent a preferred region of the target nucleic acid which may be targeted by several oligonucleotides of the invention.

In some embodiments, the target sequence is present in an intronic region of the TMEM106B nucleic acid, such as SEQ ID NO: 1.

In some embodiments, the target sequence is present in exon 9, such as in the 3'UTR of the TMEM106B nucleic acid.

The inventors have identified that the 3'UTR of the human and mouse TMEM106B is an advantageous target sequence. In some embodiments, the oligonucleotide of the invention, or contiguous nucleotide sequence thereof, is at least 90% complementary, such as is fully complementary, to the 3'UTR of a mammalian TMEM106B mRNA, such as the target nucleic acid referred to herein (e.g. SEQ ID NO: 1, 3 or 5). In one embodiment the 3' UTR is located from position 20755-32146 of SEQ ID NO: 1. As illustrated in the examples, the inventors have further identified advantageous target sequences within the 3'UTR of the human TMEM106B transcript. In some embodiments, the target sequence is from position 20755 to position 26403 of SEQ ID NO: 1. In some embodiments, the target sequence is from position 21084 to position 21213 of SEQ ID NO: 1. In some embodiments, the target sequence is from position 23086 to position 24077 of SEQ ID NO: 1.

In some embodiments the target sequence is a sequence selected from the group consisting of a human TMEM106B mRNA exon, such as a TMEM106B human mRNA exon selected from the group consisting of e1, e2, e3, e4, e5, e6, e7, e8, and e9 (see Table 1 above). In some embodiments the target sequence is exon e2.

In some embodiments, the target sequence is a sequence selected from the group consisting of a human TMEM106B mRNA intron, such as a TMEM106B human mRNA intron selected from the group consisting of i1, i2, i3, i4, i5, i6, i7, and i8 (see Table 1 above). In some embodiments, the target sequence is intron i8, or the 3'UTR region.

In some embodiments, the target sequence is selected from a TMEM106B human mRNA intron selected from the group consisting of i1, i2, i3, i4, i5, i6, i7, and i8 and the TMEM106B human mRNA 3'UTR.

In some embodiments the target sequence is a sequence the TMEM106B human mRNA intron i8 or 3'UTR (see Table 1 above).

In some embodiments, the target sequence is or comprises the nucleotide sequence from position 20227 to position 20243 of SEQ ID NO 1.

In some embodiments, the target sequence is or comprises the nucleotide sequence from position 20227 to position 26403 of SEQ ID NO 1.

In some embodiments, the target sequence is or comprises the nucleotide sequence from position 20227 to position 21213 of SEQ ID NO 1.

In some embodiments, the target sequence is or comprises the nucleotide sequence from position 20227 to position 24077 of SEQ ID NO 1.

The oligonucleotide of the invention comprises a contiguous nucleotide sequence which is complementary to or hybridizes to the target nucleic acid, such as a target sequence described herein.

The target sequence to which the oligonucleotide is complementary or hybridizes to generally comprises a contiguous nucleobases sequence of at least 10 nucleotides. In some embodiments, such as antisense oligonucleotides of the invention, the contiguous nucleotide sequence is between 10 to 50 nucleotides, such as 10 to 30 nucleotides, such as 14 to 20, such as 15 to 18 contiguous nucleotides.

For siRNA oligonucleotides, the target sequence to which the antisense strand oligonucleotide is complementary or hybridizes to, may comprise a contiguous nucleobases sequence of at least 16 or 17 nucleotides. In some embodiments, the contiguous nucleotide sequence is between 17 to 25 nucleotides, such as 19 to 23 contiguous nucleotides.

Target Cell

The term a "target cell" as used herein refers to a cell which is expressing the target nucleic acid. In some embodiments the target cell may be in vivo or in vitro. In some embodiments the target cell is a mammalian cell such as a rodent cell, such as a mouse cell or a rat cell, or a primate cell such as a monkey cell or a human cell.

In some embodiments the target cell is a neuronal cell. In some embodiments the cell which is expressing TMEM106B may be a neuronal cell.

In some embodiments the target cell expresses TMEM106B mRNA, such as the TMEM106B pre-mRNA or TMEM106B mature mRNA. The poly A tail of TMEM106B mRNA is typically disregarded for antisense oligonucleotide targeting.

In some embodiments, human SK-N-BE(2) neuroblastoma cells acquired from ATCC (CRL-2271) or mouse Neuro-2a neuroblastoma cell acquired from ATCC (CCL-131) may be used to determine whether an oligonucleotide is capable of down regulating the target nucleic acid (see examples).

Naturally Occurring Variant

The term "naturally occurring variant" refers to variants of TMEM106B gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms (SNPs), and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian TMEM106B target nucleic acid, such as a target nucleic acid selected form the group consisting of SEQ ID NO 1-6. In some embodiments the naturally occurring variants have at least 99% homology to the human TMEM106B target nucleic acid of SEQ ID NO: 1 or SEQ ID NO 2. In some embodiments the naturally occurring variants are the polymorphisms listed in Table 4.

TABLE 4

Examples of single nucleotide polymorphisms which are known in the human TMEM106B gene (human premRNA start/reference sequence is SEQ ID NO 1).

| Variant name | Position in SEQ ID NO 1 | Ancestral allele (in reference genome) | Variant alleles | Which allele is minor allele | Minor allele frequency |
|---|---|---|---|---|---|
| rs111783004 | 92 | G | A, G | A | 0.02 |
| rs73299040 | 338 | G | A, G | A | 0.17 |
| rs4721056 | 415 | T | G, T | T | 0.37 |
| rs13223216 | 641 | T | C, T | C | 0.03 |
| rs7781670 | 713 | C | C, G | C | 0.45 |
| rs73299043 | 748 | C | C, G | G | 0.08 |
| rs73678689 | 822 | T | G, T | G | 0.17 |
| rs1019309 | 824 | T | T, A | T | 0.45 |
| rs77287807 | 862 | A | A, G | G | 0.01 |
| rs1019308 | 879 | G | G, C | G | 0.32 |
| rs1019307 | 943 | G | G, C | G | 0.45 |
| rs1019306 | 979 | C | T, C | C | 0.33 |
| rs57209188 | 1094 | A | A, G | G | 0.02 |
| rs73301009 | 1131 | A | A, G | G | 0.01 |
| rs56761518 | 1273 | — | —, T, TTTT | — | 0.47 |
| rs1468800 | 1296 | A | T, A | T | 0.09 |
| rs6460895 | 1693 | C | C, G | C | 0.41 |
| rs6460896 | 1812 | G | A, G | G | 0.41 |
| rs6460897 | 1894 | T | G, T | T | 0.41 |
| rs73678692 | 1897 | G | A, G | A | 0.13 |
| rs6460898 | 2046 | A | A, G | A | 0.41 |
| rs10644564 | 2056 | — | —, CT | — | 0.41 |
| rs201303186 | 2073 | — | —, A | A | 0.08 |
| rs6460899 | 2203 | A | A, C | A | 0.41 |
| rs6460900 | 2241 | A | A, G | A | 0.41 |
| rs6974465 | 2331 | T | C, T | T | 0.33 |
| rs74964643 | 2372 | G | A, G | A | 0.03 |
| rs12699323 | 2515 | T | C, T | T | 0.41 |
| rs12699324 | 2525 | T | C, T | T | 0.41 |
| rs76235203 | 2612 | C | C, G | G | 0.08 |
| rs10234805 | 2696 | T | C, T | T | 0.41 |
| rs10278257 | 2716 | C | C, T | C | 0.41 |
| rs138861467 | 2851 | C | C, G | G | 0.01 |
| rs2043540 | 3020 | A | C, A | C | 0.28 |
| rs2043539 | 3033 | G | G, A | G | 0.41 |
| rs2043538 | 3046 | T | T, C | C | 0.38 |
| rs73301022 | 3099 | C | A, C | A | 0.02 |
| rs62435714 | 3165 | A | A, G | G | 0.14 |
| rs6959892 | 3421 | C | C, T | T | 0.04 |
| rs17149894 | 4092 | C | C, T | T | 0.30 |
| rs78492048 | 4107 | A | A, G | G | 0.03 |
| rs6460901 | 4587 | C | C, T | C | 0.41 |
| rs6460902 | 4664 | G | A, G | G | 0.39 |
| rs1020006 | 4817 | G | G, A | G | 0.41 |
| rs1020005 | 4821 | C | C, A | C | 0.33 |

TABLE 4-continued

Examples of single nucleotide polymorphisms which are known in the human TMEM106B gene (human premRNA start/reference sequence is SEQ ID NO 1).

| Variant name | Position in SEQ ID NO 1 | Ancestral allele (in reference genome) | Variant alleles | Which allele is minor allele | Minor allele frequency |
|---|---|---|---|---|---|
| rs1020004 | 4931 | T | T, C | C | 0.30 |
| rs5882345 | 5160 | A | —, A | A | 0.32 |
| rs76689854 | 5275 | T | G, T | G | 0.02 |
| rs11974384 | 5693 | A | A, G | G | 0.38 |
| rs11971133 | 5701 | T | C, T | T | 0.41 |
| rs111886724 | 5802 | G | C, G | C | 0.02 |
| rs577850861 | 5806 | TT | —, TT | — | 0.35 |
| rs574034412 | 5807 | T | —, T | — | 0.49 |
| rs12699325 | 5827 | T | C, T | C | 0.03 |
| rs73677511 | 5863 | T | C, T | C | 0.13 |
| rs73301032 | 5952 | C | C, G | G | 0.08 |
| rs6947327 | 6322 | C | C, G | C | 0.32 |
| rs10464275 | 6381 | A | A, C | C | 0.08 |
| rs73301035 | 6512 | G | A, G | A | 0.14 |
| rs7785189 | 6680 | C | C, T | C | 0.41 |
| rs7785087 | 6702 | A | A, G | A | 0.41 |
| rs6460903 | 6881 | T | C, T | T | 0.33 |
| rs11342660 | 7019 | T | —, T | T | 0.45 |
| rs73301040 | 7079 | A | A, G | G | 0.02 |
| rs6415232 | 7091 | A | A, G | A | 0.33 |
| rs3887296 | 7119 | A | A, G | G | 0.08 |
| rs139417104 | 7220 | — | —, A | A | 0.02 |
| rs116705963 | 7413 | G | A, G | A | 0.01 |
| rs17165735 | 7587 | A | A, G | G | 0.08 |
| rs17165736 | 7675 | G | A, G | A | 0.14 |
| rs35982495 | 7819 | — | —, A | — | 0.40 |
| rs3823612 | 7908 | G | G, C | G | 0.40 |
| rs202184519 | 8740 | — | —, A | A | 0.01 |
| rs17165737 | 8788 | C | A, C | A | 0.13 |
| rs78663549 | 9001 | G | G, T | T | 0.09 |
| rs28459566 | 9243 | T | C, T | C | 0.11 |
| rs12666249 | 9699 | C | C, T | T | 0.38 |
| rs12666279 | 9705 | G | A, G | A | 0.14 |
| rs12699326 | 9719 | A | A, G | G | 0.03 |
| rs139345875 | 9974 | A | A, T | T | 0.01 |
| rs147697289 | 10156 | G | G, T | T | 0.01 |
| rs73301046 | 10400 | G | A, G | A | 0.05 |
| rs80041000 | 10520 | A | A, G | G | 0.08 |
| rs10950391 | 10982 | A | A, G | A | 0.40 |
| rs11509880 | 11064 | G | A, G | G | 0.42 |
| rs141482004 | 11096 | A | A, T | T | 0.01 |
| rs76188878 | 11318 | G | A, G | A | 0.02 |
| rs3800847 | 11395 | G | G, A | G | 0.40 |
| rs1435527 | 11724 | C | T, C | C | 0.41 |
| rs6978684 | 11740 | C | C, G | G | 0.14 |
| rs13311466 | 11755 | T | C, T | C | 0.03 |
| rs1435526 | 11807 | A | G, A | A | 0.33 |
| rs1435525 | 11870 | T | T, C | T | 0.41 |
| rs1435524 | 11954 | G | G, A | G | 0.41 |
| rs11368032 | 12122 | T | —, T | T | 0.41 |
| rs55635711 | 12156 | A | —, A | — | 0.12 |
| rs73677523 | 12199 | A | A, G | G | 0.09 |
| rs73301054 | 12213 | C | A, C | A | 0.04 |
| rs115923636 | 12244 | A | A, G | G | 0.01 |
| rs5882346 | 12337 | A | —, A | A | 0.41 |
| rs1435543 | 12387 | C | T, C | C | 0.32 |
| rs17165744 | 12442 | A | A, G | G | 0.13 |
| rs76130803 | 12457 | T | C, T | C | 0.02 |
| rs11981005 | 12523 | A | A, G | A | 0.32 |
| rs11974335 | 12531 | G | G, T | G | 0.40 |
| rs11974304 | 12590 | C | C, T | C | 0.40 |
| rs10950392 | 12691 | T | C, T | T | 0.40 |
| rs10950393 | 12699 | T | C, T | T | 0.40 |
| rs10950394 | 12740 | C | C, T | C | 0.40 |
| rs144830416 | 12745 | G | C, G | C | 0.08 |
| rs113404588 | 12766 | G | A, G | A | 0.05 |
| rs141956872 | 12776 | G | C, G | C | 0.01 |
| rs116565082 | 12794 | C | C, T | T | 0.03 |
| rs113047067 | 12829 | C | C, G | G | 0.03 |
| rs17165746 | 12878 | T | A, T | A | 0.14 |
| rs11509137 | 12952 | T | C, T | T | 0.40 |

TABLE 4-continued

Examples of single nucleotide polymorphisms which are known in the human TMEM106B gene (human premRNA start/reference sequence is SEQ ID NO 1).

| Variant name | Position in SEQ ID NO 1 | Ancestral allele (in reference genome) | Variant alleles | Which allele is minor allele | Minor allele frequency |
|---|---|---|---|---|---|
| rs11509153 | 12953 | G | A, G | G | 0.41 |
| rs147889591 | 13124 | G | A, G | A | 0.01 |
| rs3800845 | 13304 | G | G, C | G | 0.33 |
| rs3800844 | 13373 | G | G, C | G | 0.33 |
| rs3839693 | 13415 | — | —, A | — | 0.40 |
| rs3800843 | 13450 | G | G, A | G | 0.40 |
| rs75163637 | 13487 | A | A, G | G | 0.01 |
| rs77799203 | 13585 | C | C, G | G | 0.06 |
| rs10950395 | 13620 | T | C, T | T | 0.40 |
| rs149105187 | 13795 | C | C, T | T | 0.02 |
| rs10950396 | 13819 | T | C, T | T | 0.40 |
| rs11983898 | 13862 | G | A, G | A | 0.27 |
| rs10950397 | 13890 | C | C, T | C | 0.41 |
| rs137900300 | 13937 | G | A, G | A | 0.03 |
| rs10950398 | 14024 | G | A, G | G | 0.39 |
| rs76854159 | 14212 | A | A, G | A | 0.39 |
| rs138328979 | 14275 | G | C, G | C | 0.01 |
| rs79222644 | 14302 | A | A, T | T | 0.06 |
| rs150465020 | 14345 | T | C, T | T | 0.40 |
| rs147309966 | 14427 | G | G, T | T | 0.27 |
| rs140918518 | 14440 | A | A, G | G | 0.01 |
| rs143141037 | 14462 | C | C, T | T | 0.04 |
| rs13246340 | 14476 | G | A, G | A | 0.03 |
| rs142820543 | 14492 | G | A, G | A | 0.04 |
| rs75738247 | 14583 | G | G, T | T | 0.27 |
| rs139628525 | 14595 | C | C, G | G | 0.01 |
| rs143477885 | 14618 | A | A, G | G | 0.14 |
| rs201845319 | 14754 | T | —, T | — | 0.02 |
| rs112430481 | 14891 | C | C, G | G | 0.08 |
| rs6966602 | 14892 | C | C, G | G | 0.30 |
| rs145413472 | 14911 | C | C, T | T | 0.11 |
| rs11438918 | 14921 | — | —, T | — | 0.33 |
| rs6948844 | 15001 | T | C, T | T | 0.40 |
| rs6967026 | 15058 | G | G, T | T | 0.27 |
| rs73284389 | 15080 | C | C, G | G | 0.14 |
| rs6966757 | 15105 | A | A, T | A | 0.40 |
| rs6966915 | 15141 | C | C, T | C | 0.41 |
| rs77145882 | 15152 | G | A, G | A | 0.09 |
| rs115474060 | 15154 | C | C, G | G | 0.02 |
| rs143032237 | 15190 | G | C, G | C | 0.01 |
| rs17165750 | 15272 | T | C, T | C | 0.14 |
| rs117574031 | 15285 | C | C, G | G | 0.01 |
| rs571665718 | 15455 | T | A, T | A | 0.01 |
| rs539782765 | 15456 | C | C, T | T | 0.01 |
| rs3839692 | 15474 | — | —, A | A | 0.30 |
| rs35642626 | 15705 | A | —, A | A | 0.40 |
| rs75275529 | 15780 | A | A, G | G | 0.08 |
| rs7804433 | 15859 | G | A, G | G | 0.39 |
| rs61225336 | 15864 | T | C, T | C | 0.19 |
| rs7804234 | 15967 | A | A, G | A | 0.40 |
| rs7804736 | 16020 | G | G, T | G | 0.41 |
| rs78536513 | 16336 | A | A, C | C | 0.02 |
| rs4721057 | 16374 | A | A, G | A | 0.40 |
| rs4721058 | 16409 | C | C, T | C | 0.40 |
| rs73286304 | 16568 | C | A, C | A | 0.03 |
| rs4721059 | 16648 | G | C, G | G | 0.40 |
| rs4721060 | 16705 | G | A, G | G | 0.40 |
| rs4721061 | 16712 | G | C, G | G | 0.40 |
| rs7792410 | 16767 | T | C, T | T | 0.40 |
| rs536653563 | 16768 | C | C, T | T | 0.04 |
| rs35390376 | 16806 | T | C, T | C | 0.03 |
| rs7809700 | 16887 | G | A, G | G | 0.40 |
| rs115298566 | 16902 | G | G, T | T | 0.01 |
| rs13229988 | 16990 | A | A, G | A | 0.40 |
| rs149578700 | 17020 | C | C, T | T | 0.02 |
| rs201723928 | 17022 | T | —, T | — | 0.01 |
| rs34046032 | 17236 | TTAA | —, TTAA | TTAA | 0.40 |
| rs28549831 | 17270 | C | C, T | C | 0.40 |
| rs13230513 | 17396 | C | A, C | C | 0.40 |
| rs12667950 | 17621 | G | G, T | G | 0.41 |
| rs5011431 | 17704 | G | A, G | G | 0.40 |

TABLE 4-continued

Examples of single nucleotide polymorphisms which
are known in the human TMEM106B gene
(human premRNA start/reference sequence is SEQ ID NO 1).

| Variant name | Position in SEQ ID NO 1 | Ancestral allele (in reference genome) | Variant alleles | Which allele is minor allele | Minor allele frequency |
|---|---|---|---|---|---|
| rs5011432 | 17821 | A | A, C | A | 0.48 |
| rs5011433 | 17848 | T | A, T | T | 0.32 |
| rs5011434 | 17870 | C | C, T | C | 0.40 |
| rs5011435 | 17879 | T | C, T | C | 0.13 |
| rs5011436 | 17911 | A | A, C | A | 0.40 |
| rs5011437 | 17945 | A | A, T | A | 0.40 |
| rs5011438 | 17951 | C | C, T | C | 0.40 |
| rs5011439 | 17964 | G | C, G | G | 0.40 |
| rs13233991 | 18067 | C | C, T | T | 0.03 |
| rs60699002 | 18199 | C | A, C | A | 0.09 |
| rs13234238 | 18366 | A | A, C | C | 0.03 |
| rs3839691 | 18414 | — | —, TTGT | TTGT | 0.49 |
| rs3173615 | 18570 | C | C, G | G | 0.50 |
| rs13237715 | 18728 | G | C, G | G | 0.41 |
| rs13237518 | 18746 | C | A, C | C | 0.39 |
| rs59265139 | 18794 | G | A, G | A | 0.04 |
| rs143516511 | 18796 | G | A, G | A | 0.01 |
| rs35562417 | 18833 | — | —, A, AA | — | 0.41 |
| rs114069088 | 18885 | T | A, T | A | 0.01 |
| rs12699332 | 18915 | G | G, T | G | 0.41 |
| rs12699333 | 18957 | C | C, T | C | 0.40 |
| rs12668625 | 18970 | G | A, G | G | 0.40 |
| rs3815535 | 19672 | G | G, A | G | 0.40 |
| rs3214372 | 19719 | — | —, T | — | 0.41 |
| rs3217132 | 19737 | TTA | —, ATT | — | 0.14 |
| rs2302635 | 19778 | G | G, A | G | 0.41 |
| rs2302634 | 19923 | T | T, A | A | 0.50 |
| rs73677558 | 19944 | T | C, T | C | 0.10 |
| rs2302633 | 19968 | C | T, C | C | 0.41 |
| rs73677559 | 19972 | A | A, C | C | 0.08 |
| rs16877361 | 20053 | C | C, T | T | 0.17 |
| rs2302632 | 20120 | A | G, A | G | 0.36 |
| rs7808568 | 20405 | T | C, T | T | 0.39 |
| rs12699334 | 20406 | G | A, G | A | 0.03 |
| rs3800842 | 20605 | A | G, C, A | A | 0.40 |
| rs1042946 | 20819 | G | G, T | T | 0.03 |
| rs12669919 | 21150 | G | A, G | G | 0.41 |
| rs16877363 | 21179 | A | A, G | G | 0.14 |
| rs1042949 | 21269 | C | C, G | C | 0.41 |
| rs3800841 | 21721 | A | T, A | A | 0.40 |
| rs17165789 | 21903 | A | A, C | C | 0.03 |
| rs34252347 | 22017 | — | —, TG | TG | 0.44 |
| rs14978 | 22305 | A | G, A | G | 0.43 |
| rs1054168 | 22566 | C | C, T | C | 0.40 |
| rs1054169 | 22649 | G | A, G | G | 0.40 |
| rs79340241 | 22780 | — | —, A | A | 0.08 |
| rs12539421 | 22924 | T | G, T | G | 0.08 |
| rs13309255 | 23361 | G | G, T | T | 0.03 |
| rs10488193 | 23373 | A | G, A | G | 0.09 |
| rs35337387 | 23567 | — | —, T | — | 0.40 |
| rs17165790 | 24003 | A | A, G | G | 0.01 |
| rs71529336 | 24086 | A | A, G | G | 0.03 |
| rs1468804 | 24661 | T | T, C | T | 0.39 |
| rs5882347 | 24778 | — | —, TTTTC | — | 0.40 |
| rs1468803 | 24828 | A | C, A | A | 0.39 |
| rs1060700 | 24971 | A | G, A | A | 0.39 |
| rs73288318 | 25015 | G | A, G | A | 0.03 |
| rs1468802 | 25164 | G | G, A | G | 0.39 |
| rs2160268 | 25178 | A | T, A | T | 0.13 |
| rs2160267 | 25187 | T | T, A | A | 0.33 |
| rs1468801 | 25198 | G | G, C | G | 0.39 |
| rs1047601 | 25674 | C | C, T | T | 0.08 |
| rs929637 | 25675 | G | T, G | T | 0.33 |
| rs57824581 | 25834 | — | —, A | A | 0.05 |
| rs112281135 | 25903 | — | —, ATG | — | 0.01 |
| rs117623176 | 25985 | C | C, T | T | 0.01 |
| rs2356065 | 26038 | T | C, T | T | 0.39 |
| rs140537895 | 26149 | TACTT | —, TACTT | — | 0.09 |
| rs12699335 | 26173 | T | C, T | C | 0.36 |
| rs10488192 | 26234 | G | G, A | A | 0.14 |
| rs199711002 | 26589 | T | C, T | C | 0.13 |

TABLE 4-continued

Examples of single nucleotide polymorphisms which
are known in the human TMEM106B gene
(human premRNA start/reference sequence is SEQ ID NO 1).

| Variant name | Position in SEQ ID NO 1 | Ancestral allele (in reference genome) | Variant alleles | Which allele is minor allele | Minor allele frequency |
|---|---|---|---|---|---|
| rs13234969 | 26591 | T | C, T | T | 0.43 |
| rs13234970 | 26595 | T | C, T | T | 0.43 |
| rs7797705 | 26926 | G | A, G | G | 0.40 |
| rs6460904 | 27302 | G | A, G | A | 0.17 |
| rs34391411 | 27560 | CAA | —, CAA | — | 0.03 |
| rs6969722 | 27590 | G | A, G | A | 0.35 |
| rs4330594 | 27768 | G | A, G | A | 0.07 |
| rs62448695 | 27946 | T | C, T | C | 0.05 |
| rs73288387 | 27958 | T | C, T | C | 0.05 |
| rs10257722 | 28065 | G | A, G | A | 0.01 |
| rs548644997 | 28119 | T | G, T | G | 0.21 |
| rs7802952 | 28280 | A | A, G | G | 0.13 |
| rs2098363 | 28351 | G | G, A | G | 0.33 |
| rs57685335 | 28672 | G | A, G | A | 0.04 |
| rs1548885 | 28712 | G | G, C | C | 0.35 |
| rs75956572 | 28891 | A | A, G | G | 0.03 |
| rs1548884 | 28914 | A | C, A | A | 0.39 |
| rs1548883 | 28946 | G | G, A | A | 0.13 |
| rs2356066 | 28986 | G | A, G | A | 0.35 |
| rs73288393 | 29090 | T | G, T | G | 0.04 |
| rs77273680 | 29280 | A | A, G | G | 0.08 |
| rs73677570 | 29482 | T | C, T | C | 0.07 |
| rs149200435 | 29591 | AGA | —, AGA | — | 0.08 |
| rs79100376 | 29598 | C | C, G | G | 0.09 |
| rs75911624 | 29661 | A | A, G | G | 0.02 |
| rs10281425 | 29883 | T | A, T | T | 0.39 |
| rs150586332 | 29900 | C | C, G | G | 0.01 |
| rs10236369 | 29991 | A | A, G | G | 0.37 |
| rs116132326 | 30039 | T | A, T | A | 0.02 |
| rs570235340 | 30253 | — | —, TCCCACTTATGAGTGGCAACT | TCCCACTTATGAGTGGCAACT | 0.04 |
| rs139600599 | 30445 | G | G, T | T | 0.07 |
| rs115077070 | 30833 | T | G, T | G | 0.02 |
| rs139393760 | 30857 | A | —, A | A | 0.39 |
| rs6948681 | 31146 | G | A, G | A | 0.10 |
| rs146083730 | 31293 | — | —, T | T | 0.01 |
| rs7805419 | 31604 | T | C, T | T | 0.46 |
| rs149298119 | 31821 | A | A, T | T | 0.01 |
| rs59410610 | 32000 | A | A, G | G | 0.07 |

Modulation of Expression

The term "modulation of expression" as used herein is to be understood as an overall term for an oligonucleotide's ability to alter the amount of TMEM106B when compared to the amount of TMEM106B before administration of the oligonucleotide. Alternatively modulation of expression may be determined by reference to a control experiment. It is generally understood that the control is an individual or target cell treated with a saline composition or an individual or target cell treated with a non-targeting oligonucleotide (mock).

One type of modulation is an oligonucleotide's ability to inhibit, down-regulate, reduce, suppress, remove, stop, block, prevent, lessen, lower, avoid or terminate expression of TMEM106B, e.g. by degradation of mRNA or blockage of transcription. Another type of modulation is an oligonucleotide's ability to restore, increase or enhance expression of TMEM106B, e.g. by repair of splice sites or prevention of splicing or removal or blockage of inhibitory mechanisms such as microRNA repression.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T_m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

2' Sugar Modified Nucleosides

A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been spent on developing 2' substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

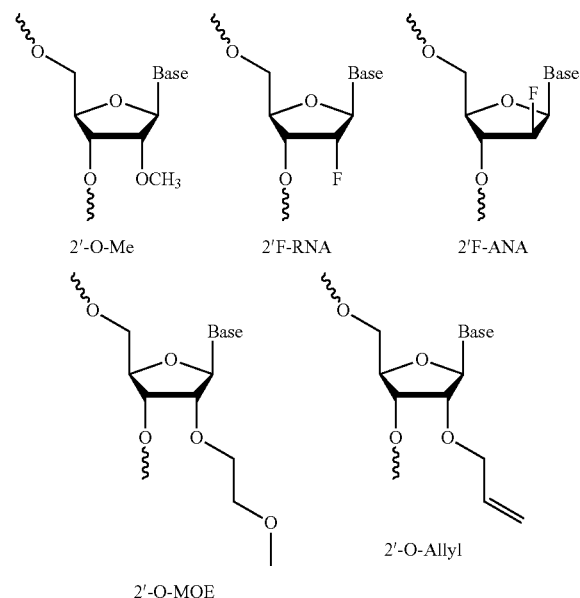

2'-O-Me

2'F-RNA

2'F-ANA

2'-O-MOE

2'-O-Allyl

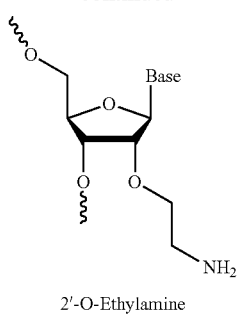

2'-O-Ethylamine

In relation to the present invention 2' substituted does not include 2' bridged molecules like LNA.

Locked Nucleic Acids (LNA)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238, and Wan and Seth, J. Medical Chemistry 2016, 59, 9645-9667. Further non limiting, exemplary LNA nucleosides are disclosed in Scheme 1.

Scheme 1:

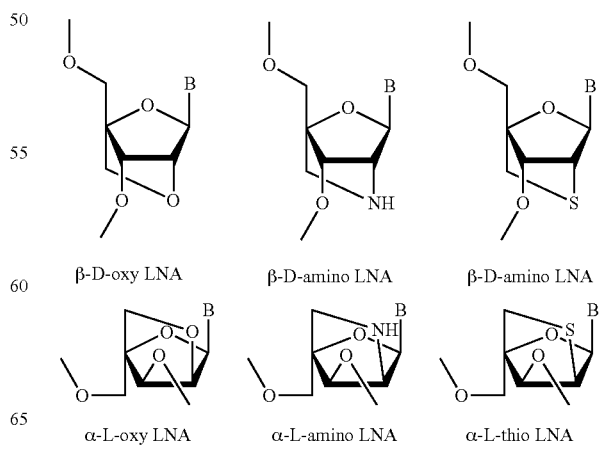

β-D-oxy LNA    β-D-amino LNA    β-D-amino LNA

α-L-oxy LNA    α-L-amino LNA    α-L-thio LNA

-continued

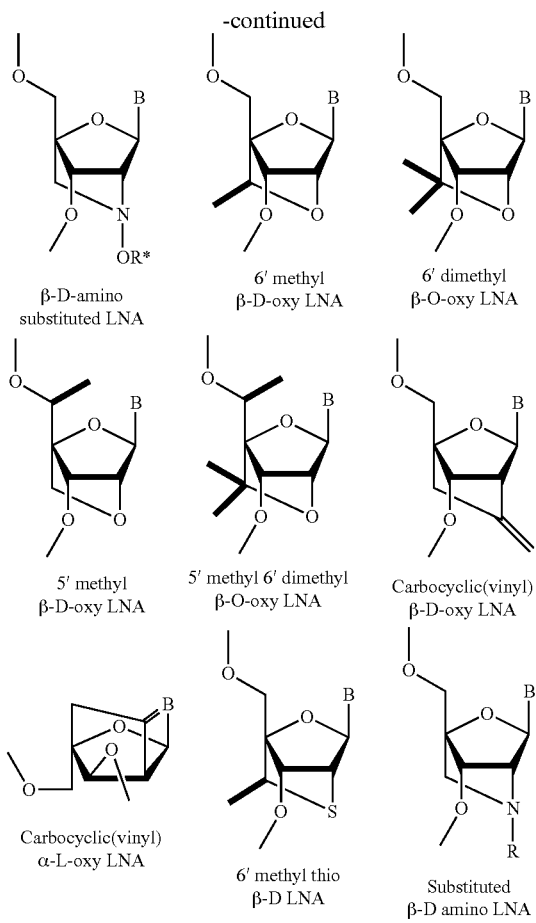

Particular LNA nucleosides are beta-D-oxy-LNA, 6'-methyl-beta-D-oxy LNA such as (S)-6'-methyl-beta-D-oxy-LNA (ScET) and ENA.

A particularly advantageous LNA is beta-D-oxy-LNA. In some embodiments the oligonucleotide of the invention comprises at least one beta-D-oxy-LNA or 6'-methyl-beta-D-oxy-LNA nucleoside.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Lubio Science GmbH, Lucerne, Switzerland.

Gapmer

The antisense oligonucleotide of the invention, or contiguous nucleotide sequence thereof may be a gapmer. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5→3' orientation. The "gap" region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further be defined by having at least one sugar modified nucleoside at the end most distant from the gap region, i.e. at the 5' end of the 5' flank and at the 3' end of the 3' flank.

Regions F-G-F' form a contiguous nucleotide sequence. Antisense oligonucleotides of the invention, or the contiguous nucleotide sequence thereof, may comprise a gapmer region of formula F-G-F'.

The overall length of the gapmer design F-G-F' may be, for example 12 to 32 nucleosides, such as 13 to 24, such as 14 to 22 nucleosides, Such as from 14 to 17, such as 16 to 18 nucleosides. By way of example, the gapmer oligonucleotide of the present invention can be represented by the following formulae:

$F_{1-8}-G_{5-16}-F'_{1-8}$, such as $F_{1-8}-G_{7-16}-F'_{2-8}$ with the proviso that the overall length of the gapmer regions F-G-F' is at least 12, such as at least 14 nucleotides in length.

Regions F, G and F' are further defined below and can be incorporated into the F-G-F' formula.

Gapmer—Region G

Region G (gap region) of the gapmer is a region of nucleosides which enables the oligonucleotide to recruit RNaseH, such as human RNase H1, typically DNA nucleosides. RNaseH is a cellular enzyme which recognizes the duplex between DNA and RNA, and enzymatically cleaves the RNA molecule. Suitably gapmers may have a gap region (G) of at least 5 or 6 contiguous DNA nucleosides, such as 5-16 contiguous DNA nucleosides, such as 6-15 contiguous DNA nucleosides, such as 7-14 contiguous DNA nucleosides, such as 8-12 contiguous DNA nucleotides, such as 8-12 contiguous DNA nucleotides in length. The gap region G may, in some embodiments consist of 6, 7, 8, 9, 10, 11, 12, 13, 14, 15 or 16 contiguous DNA nucleosides. One or more cytosine (C) DNA in the gap region may in some instances be methylated (e.g. when a DNA c is followed by a DNA g) such residues are either annotated as 5-methyl-cytosine ($^{me}C$). In some embodiments the gap region G may consist of 6, 7, 8, 9, 10, 11, 12, 13, 14, 15 or 16 contiguous phosphorothioate linked DNA nucleosides. In some embodiments, all internucleoside linkages in the gap are phosphorothioate linkages. Whilst traditional gapmers have a DNA gap region, there are numerous examples of modified nucleosides which allow for RNaseH recruitment when they are used within the gap region. Modified nucleosides which have been reported as being capable of recruiting RNaseH when included within a gap region include, for example, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked "sugar" residue. The modified nucleosides used in such gapmers may be nucleosides which adopt a 2' endo (DNA like) structure when introduced into the gap region, i.e. modifications which allow for RNaseH recruitment). In some embodiments the DNA Gap region (G) described herein may optionally contain 1 to 3 sugar modified nucleosides which adopt a 2' endo (DNA like) structure when introduced into the gap region.

Region G—"Gap-Breaker"

Alternatively, there are numerous reports of the insertion of a modified nucleoside which confers a 3' endo conformation into the gap region of gapmers, whilst retaining some RNaseH activity. Such gapmers with a gap region comprising one or more 3'endo modified nucleosides are referred to as "gap-breaker" or "gap-disrupted" gapmers, see for example WO2013/022984. Gap-breaker oligonucleotides retain sufficient region of DNA nucleosides within the gap region to allow for RNaseH recruitment. The ability of gapbreaker oligonucleotide design to recruit RNaseH is typically sequence or even compound specific—see Rukov et al. 2015 Nucl. Acids Res. Vol. 43 pp. 8476-8487, which discloses "gapbreaker" oligonucleotides which recruit RNaseH which in some instances provide a more specific cleavage of the target RNA. Modified nucleosides used within the gap region of gap-breaker oligonucleotides may for example be modified nucleosides which confer a 3'endo confirmation, such 2'-O-methyl (OMe) or 2'-O-MOE (MOE) nucleosides, or beta-D LNA nucleosides (the bridge between C2' and C4' of the ribose sugar ring of a nucleoside is in the beta conformation), such as beta-D-oxy LNA or ScET nucleosides.

As with gapmers containing region G described above, the gap region of gap-breaker or gap-disrupted gapmers, have a DNA nucleoside at the 5' end of the gap (adjacent to the 3' nucleoside of region F), and a DNA nucleoside at the 3' end of the gap (adjacent to the 5' nucleoside of region F'). Gapmers which comprise a disrupted gap typically retain a region of at least 3 or 4 contiguous DNA nucleosides at either the 5' end or 3' end of the gap region. Exemplary designs for gap-breaker oligonucleotides include

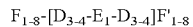

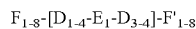

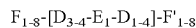

wherein region G is within the brackets $[D_n\text{-}E_l\text{-}D_m]$, D is a contiguous sequence of DNA nucleosides, E is a modified nucleoside (the gap-breaker or gap-disrupting nucleoside), and F and F' are the flanking regions as defined herein, and with the proviso that the overall length of the gapmer regions F-G-F' is at least 12, such as at least 14 nucleotides in length. In some embodiments, region G of a gap disrupted gapmer comprises at least 6 DNA nucleosides, such as 6, 7, 8, 9, 10, 11, 12, 13, 14, 15 or 16 DNA nucleosides. As described above, the DNA nucleosides may be contiguous or may optionally be interspersed with one or more modified nucleosides, with the proviso that the gap region G is capable of mediating RNaseH recruitment.

Gapmer—Flanking Regions, F and F'

Region F is positioned immediately adjacent to the 5' DNA nucleoside of region G. The 3' most nucleoside of region F is a sugar modified nucleoside, such as a high affinity sugar modified nucleoside, for example a 2' substituted nucleoside, such as a MOE nucleoside, or an LNA nucleoside.

Region F' is positioned immediately adjacent to the 3' DNA nucleoside of region G. The 5' most nucleoside of region F' is a sugar modified nucleoside, such as a high affinity sugar modified nucleoside, for example a 2' substituted nucleoside, such as a MOE nucleoside, or an LNA nucleoside.

Region F is 1-8 contiguous nucleotides in length, such as 2-6, such as 3-4 contiguous nucleotides in length. Advantageously the 5' most nucleoside of region F is a sugar modified nucleoside. In some embodiments the two 5' most nucleoside of region F are sugar modified nucleoside. In some embodiments the 5' most nucleoside of region F is an LNA nucleoside. In some embodiments the two 5' most nucleoside of region F are LNA nucleosides. In some embodiments the two 5' most nucleoside of region F are 2' substituted nucleoside nucleosides, such as two 3' MOE nucleosides. In some embodiments the 5' most nucleoside of region F is a 2' substituted nucleoside, such as a MOE nucleoside.

Region F' is 2-8 contiguous nucleotides in length, such as 3-6, such as 4-5 contiguous nucleotides in length. Advantageously, embodiments the 3' most nucleoside of region F' is a sugar modified nucleoside. In some embodiments the two 3' most nucleoside of region F' are sugar modified nucleoside. In some embodiments the two 3' most nucleoside of region F' are LNA nucleosides. In some embodiments the 3' most nucleoside of region F' is an LNA nucleoside. In some embodiments the two 3' most nucleoside of region F' are 2' substituted nucleoside nucleosides, such as two 3' MOE nucleosides. In some embodiments the 3' most nucleoside of region F' is a 2' substituted nucleoside, such as a MOE nucleoside. It should be noted that when the length of region F or F' is one, it is advantageously an LNA nucleoside.

In some embodiments, region F and F' independently consists of or comprises a contiguous sequence of sugar modified nucleosides. In some embodiments, the sugar modified nucleosides of region F may be independently selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments, region F and F' independently comprises both LNA and a 2' substituted modified nucleosides (mixed wing design).

In some embodiments, region F and F' consists of only one type of sugar modified nucleosides, such as only MOE or only beta-D-oxy LNA or only ScET. Such designs are also termed uniform flanks or uniform gapmer design.

In some embodiments, all the nucleosides of region F or F', or F and F' are LNA nucleosides, such as independently selected from beta-D-oxy LNA, ENA or ScET nucleosides. In some embodiments region F consists of 1-5, such as 2-4, such as 3-4 such as 1, 2, 3, 4 or 5 contiguous LNA nucleosides. In some embodiments, all the nucleosides of region F and F' are beta-D-oxy LNA nucleosides.

In some embodiments, all the nucleosides of region F or F', or F and F' are 2' substituted nucleosides, such as OMe or MOE nucleosides. In some embodiments region F consists of 1, 2, 3, 4, 5, 6, 7, or 8 contiguous OMe or MOE nucleosides. In some embodiments only one of the flanking regions can consist of 2' substituted nucleosides, such as OMe or MOE nucleosides. In some embodiments it is the 5' (F) flanking region that consists 2' substituted nucleosides, such as OMe or MOE nucleosides whereas the 3' (F') flanking region comprises at least one LNA nucleoside, such as beta-D-oxy LNA nucleosides or cET nucleosides. In some embodiments it is the 3' (F') flanking region that consists 2' substituted nucleosides, such as OMe or MOE nucleosides whereas the 5' (F) flanking region comprises at least one LNA nucleoside, such as beta-D-oxy LNA nucleosides or cET nucleosides.

In some embodiments, all the modified nucleosides of region F and F' are LNA nucleosides, such as independently selected from beta-D-oxy LNA, ENA or ScET nucleosides, wherein region F or F', or F and F' may optionally comprise DNA nucleosides (an alternating flank, see definition of these for more details). In some embodiments, all the modified nucleosides of region F and F' are beta-D-oxy LNA nucleosides, wherein region F or F', or F and F' may optionally comprise DNA nucleosides (an alternating flank, see definition of these for more details).

In some embodiments the 5' most and the 3' most nucleosides of region F and F' are LNA nucleosides, such as beta-D-oxy LNA nucleosides or ScET nucleosides.

In some embodiments, the internucleoside linkage between region F and region G is a phosphorothioate internucleoside linkage. In some embodiments, the internucleoside linkage between region F' and region G is a phosphorothioate internucleoside linkage. In some embodiments, the internucleoside linkages between the nucleosides of region F or F', F and F' are phosphorothioate internucleoside linkages.

LNA Gapmer

An LNA gapmer is a gapmer wherein either one or both of region F and F' comprises or consists of LNA nucleosides. A beta-D-oxy gapmer is a gapmer wherein either one or both of region F and F' comprises or consists of beta-D-oxy LNA nucleosides.

In some embodiments the LNA gapmer is of formula: [LNA]$_{1-5}$-[region G]-[LNA]$_{1-5}$, wherein region G is as defined in the Gapmer region G definition.

MOE Gapmers

A MOE gapmers is a gapmer wherein regions F and F' consist of MOE nucleosides. In some embodiments the MOE gapmer is of design [MOE]$_{1-8}$-[Region G]-[MOE]$_{1-8}$, such as [MOE]$_{2-7}$-[Region G]$_{5-16}$-[MOE]$_{2-7}$, such as [MOE]$_{3-8}$-[Region G]-[MOE]$_{3-6}$, wherein region G is as defined in the Gapmer definition. MOE gapmers with a 5-10-5 design (MOE-DNA-MOE) have been widely used in the art.

Mixed Wing Gapmer

A mixed wing gapmer is an LNA gapmer wherein one or both of region F and F' comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units and 2'-fluoro-ANA units, such as a MOE nucleoside. In some embodiments wherein at least one of region F and F', or both region F and F' comprise at least one LNA nucleoside, the remaining nucleosides of region F and F' are independently selected from the group consisting of MOE and LNA. In some embodiments wherein at least one of region F and F', or both region F and F' comprise at least two LNA nucleosides, the remaining nucleosides of region F and F' are independently selected from the group consisting of MOE and LNA. In some mixed wing embodiments, one or both of region F and F' may further comprise one or more DNA nucleosides.

Mixed wing gapmer designs are disclosed in WO2008/049085 and WO2012/109395, both of which are hereby incorporated by reference.

Alternating Flank Gapmers

Oligonucleotides with alternating flanks are LNA gapmer oligonucleotides where at least one of the flanks (F or F') comprises DNA in addition to the LNA nucleoside(s). In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F and/or F' region are LNA nucleosides.

In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F or F' region are LNA nucleosides, and there is at least one DNA nucleoside positioned between the 5' and 3' most LNA nucleosides of region F or F' (or both region F and F').

Region D' or D" in an Oligonucleotide

The oligonucleotide of the invention may in some embodiments comprise or consist of the contiguous nucleotide sequence of the oligonucleotide which is complementary to the target nucleic acid, such as the gapmer F-G-F', and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the gapmer, to a conjugate moiety or another functional group. When used for joining the contiguous nucleotide sequence with a conjugate moiety is can serve as a biocleavable linker. Alternatively, it may be used to provide exonuclease protection or for ease of synthesis or manufacture.

Region D' and D" can be attached to the 5' end of region F or the 3' end of region F', respectively to generate designs of the following formulas D'-F-G-F', F-G-F'-D" or D'-F-G-F'-D". In this instance the F-G-F' is the gapmer portion of the oligonucleotide and region D' or D" constitute a separate part of the oligonucleotide.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments the additional 5' and/or 3' end nucleotides are linked with phosphodiester linkages, and are DNA or RNA. Nucleotide based biocleavable linkers suitable for use as region D' or D" are disclosed in WO2014/076195, which include by way of example a phosphodiester linked DNA dinucleotide. The use of biocleavable linkers in poly-oligonucleotide constructs is disclosed in WO2015/113922, where they are used to link multiple antisense constructs (e.g. gapmer regions) within a single oligonucleotide.

In one embodiment the oligonucleotide of the invention comprises a region D' and/or D" in addition to the contiguous nucleotide sequence which constitutes the gapmer.

In some embodiments, the oligonucleotide of the present invention can be represented by the following formulae:

F-G-F'; in particular $F_{1-8}$-$G_{5-16}$-$F'_{2-8}$

D'-F-G-F', in particular $D'_{1-3}$-$F_{1-8}$-$G_{5-16}$-$F'_{2-8}$

F-G-F'-D", in particular $F_{1-8}$-$G_{5-16}$-$F'_{2-8}$-$D''_{1-3}$

D'-F-G-F'-D", in particular $D'_{1-3}$-$F_{1-8}$-$G_{5-16}$-$F'_{2-8}$-$D''_{1-3}$ In some embodiments the internucleoside linkage positioned between region D' and region F is a phosphodiester linkage. In some embodiments the internucleoside linkage positioned between region F' and region D" is a phosphodiester linkage.

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety modifies or enhances the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. At the same time the conjugate may serve to reduce activity of the oligonucleotide in non-target cell types, tissues or organs, e.g. off target activity or activity in non-target cell types, tissues or organs.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

In some embodiments, the conjugate is an antibody or an antibody fragment which has a specific affinity for a transferrin receptor, for example as disclosed in WO 2012/143379 herby incorporated by reference. In some embodiments the non-nucleotide moiety is an antibody or antibody fragment, such as an antibody or antibody fragment that facilitates delivery across the blood-brain-barrier, in particular an antibody or antibody fragment targeting the transferrin receptor.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence or gapmer region F-G-F' (region A).

In some embodiments of the invention the conjugate or oligonucleotide conjugate of the invention may optionally, comprise a linker region (second region or region B and/or region Y) which is positioned between the oligonucleotide or contiguous nucleotide sequence complementary to the target nucleic acid (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. DNA phosphodiester containing biocleavable linkers are described in more detail in WO 2014/076195 (hereby incorporated by reference)—see also region D' or D" herein.

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups. The oligonucleotide conjugates of the present invention can be constructed of the following regional elements A-C, A-B-C, A-B-Y-C, A-Y-B-C or A-Y-C. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic. In some embodiments treatment is performed on a patient who has been diagnosed with a neurological disorder, such as a neurological disorder selected from the group consisting of neurodegeneration, frontotemporal lobar degeneration (FTLD), Parkinson's disease (or parkinsonism), hypomyelinating leukodystrophies, amyotrophic lateral sclerosis and multiple system atrophy, Alzheimer's disease, motor neuron disease, corticobasal syndrome, progressive supranuclear palsy, and neuronal ceroid lipofuscinosis (NCL).

In some embodiments the compounds of the invention are for use in the treatment of frontotemporal lobar degeneration (FTLD).

A desired effect of the treatment is to reduce the TMEM106B mRNA in the frontal cortex of the subject to be treated to normal levels which corresponds to the average TMEM106B mRNA levels in non-demented individuals. It is advantageous the reduction of TMEM106B mRNA is not reduced below 40% of normal levels, such as less than 30% below normal levels, such as less than 20% below of normal levels, such as within the range of 40% below normal levels and 20% above normal levels, such as 30% below normal levels and 15% above normal levels, such as 20% below normal levels and 10% above normal levels.

Pharmaceutically Acceptable Salts

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

Protecting Group

The term "protecting group", alone or in combination, signifies a group which selectively blocks a reactive site in a multifunctional compound such that a chemical reaction can be carried out selectively at another unprotected reactive site. Protecting groups can be removed. Exemplary protecting groups are amino-protecting groups, carboxy-protecting groups or hydroxy-protecting groups.

DETAILED DESCRIPTION OF THE INVENTION

The Oligonucleotides of the Invention

The invention relates to an oligonucleotide capable of modulating expression of TMEM106B, such as inhibiting (down-regulating) TMEM106B. The modulation is achieved by hybridizing to a target nucleic acid encoding TMEM106B or which is involved in the regulation of TMEM106B. The target nucleic acid may be a mammalian TMEM106B sequence, such as a sequence selected from the group consisting of SEQ ID NO: 1-6.

Advantageously, the oligonucleotide of the invention may be selected from an antisense oligonucleotide, an siRNA or shRNA which targets TMEM106B.

In some embodiments the oligonucleotide of the invention is capable of modulating the expression of the target by inhibiting or down-regulating it. Preferably, such modulation produces an inhibition of expression of at least 20% compared to the normal expression level of the target, more preferably at least 30%, at least 40%, at least 50%, at least 60%, at least 70%, at least 80%, or at least 90% inhibition compared to the normal expression level of the target. In some embodiments oligonucleotides of the invention may be capable of inhibiting expression levels of TMEM106B mRNA by at least 60% or 70% in vitro using human SK-N-BE(2) neuroblastoma cells, which may be acquired from ATCC (CRL-2271). In some embodiments compounds of the invention may be capable of inhibiting expression levels of TMEM106B protein by at least 50% in vitro using human SK-N-BE(2) neuroblastoma cells. Suitably, the examples provide assays which may be used to measure TMEM106B RNA or protein inhibition. The target modulation is triggered by the hybridization between a contiguous nucleotide sequence of the oligonucleotide and the target nucleic acid. In some embodiments the oligonucleotide of the invention comprises mismatches between the oligonucleotide and the target nucleic acid. Despite mismatches hybridization to the target nucleic acid may still be sufficient to show a desired modulation of TMEM106B expression. Reduced binding affinity resulting from mismatches may advantageously be compensated by increased number of nucleotides in the oligonucleotide and/or an increased number of modified nucleosides capable of increasing the binding affinity to the target, such as 2' sugar modified nucleosides, including LNA, present within the oligonucleotide sequence.

An aspect of the present invention relates to an antisense oligonucleotide which comprises a contiguous nucleotide sequence of 10 to 30 nucleotides in length with at least 90% complementarity to a mammalian TMEM106B nucleic acid, for example SEQ ID NO: 1-6, such as SEQ ID NO: 1, 2, 3, 4, 5 or 6.

In some embodiments, the oligonucleotide comprises a contiguous sequence of 10 to 30 nucleotides in length, which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid or a target sequence.

In a preferred embodiment the oligonucleotide of the invention, or contiguous nucleotide sequence thereof is fully complementary (100% complementary) to a region of the target nucleic acid, or in some embodiments may comprise one or two mismatches between the oligonucleotide and the target nucleic acid.

In some embodiments the oligonucleotide comprises a contiguous nucleotide sequence of 10 to 30 nucleotides in length with at least 90% complementary, such as fully (or 100%) complementary, to a region target nucleic acid region present in SEQ ID NO: 1 and/or 2. In some embodiments the oligonucleotide sequence is 100% complementary to a corresponding target nucleic acid region present in SEQ ID NO: 1 and either SEQ ID NO: 3 or SEQ ID NO 5 (or both SEQ ID NO: 3 & 5). In some embodiments the oligonucleotide sequence is 100% complementary to a corresponding target nucleic acid region present SEQ ID NO: 1, 3 and 5.

In some embodiments the oligonucleotide sequence is 100% complementary to a corresponding target nucleic acid region present in SEQ ID NO: 2 and either SEQ ID NO: 4 or SEQ ID NO: 6 (or both SEQ ID NO: 4 & 6). In some embodiments the oligonucleotide sequence is 100% complementary to a corresponding target nucleic acid region present SEQ ID NO: 2, 4 and 6.

In some embodiments, the oligonucleotide of the invention is at least 90% complementary, such as 100% complementary to exon 9 of SEQ ID NO 1.

In some embodiments, the oligonucleotide comprises a contiguous nucleotide sequence of 10 to 30 nucleotides in length with at least 90% complementary, such as 100% complementarity, to a corresponding target nucleic acid region present in SEQ ID NO: 1, wherein the target nucleic acid region is selected from the group consisting of Reg. A1 to A80 in Table 5.

TABLE 5

Selected regions of SEQ ID NO: 1 which may be targeted using oligonucleotide of the invention

| Reg. A | Position in SEQ ID NO 1 | |
|---|---|---|
| | from | to |
| 1 | 546 | 563 |
| 2 | 2122 | 2140 |
| 3 | 2143 | 2160 |
| 4 | 2165 | 2183 |
| 5 | 2300 | 2317 |
| 6 | 2392 | 2410 |
| 7 | 2548 | 2565 |
| 8 | 3507 | 3524 |
| 9 | 3678 | 3694 |
| 10 | 3736 | 3753 |
| 11 | 3752 | 3767 |
| 12 | 3802 | 3819 |
| 13 | 3908 | 3925 |
| 14 | 4321 | 4337 |
| 15 | 4701 | 4720 |
| 16 | 4948 | 4965 |
| 17 | 5063 | 5080 |
| 18 | 5069 | 5086 |
| 19 | 5172 | 5190 |
| 20 | 5512 | 5530 |
| 21 | 5583 | 5599 |
| 22 | 6015 | 6032 |
| 23 | 6032 | 6047 |
| 24 | 6125 | 6140 |
| 25 | 6136 | 6154 |
| 26 | 6172 | 6189 |
| 27 | 6200 | 6216 |
| 28 | 6214 | 6231 |
| 29 | 6401 | 6417 |
| 30 | 6458 | 6476 |
| 31 | 6837 | 6853 |
| 32 | 8453 | 8472 |
| 33 | 8983 | 9001 |
| 34 | 9533 | 9549 |
| 35 | 9628 | 9644 |
| 36 | 11065 | 11083 |
| 37 | 11117 | 11134 |
| 38 | 11264 | 11281 |
| 39 | 12310 | 12325 |
| 40 | 12870 | 12887 |
| 41 | 13050 | 13065 |
| 42 | 13397 | 13414 |
| 43 | 15061 | 15079 |
| 44 | 15249 | 15266 |
| 45 | 15318 | 15336 |
| 46 | 15368 | 15385 |
| 47 | 15440 | 15457 |
| 48 | 15632 | 15649 |
| 49 | 15823 | 15842 |
| 50 | 16496 | 16513 |
| 51 | 19090 | 19109 |
| 52 | 19198 | 19217 |
| 53 | 19211 | 19228 |
| 54 | 19699 | 19718 |
| 55 | 20217 | 20236 |

TABLE 5-continued

Selected regions of SEQ ID NO: 1 which may be targeted using oligonucleotide of the invention

| Reg. A | Position in SEQ ID NO 1 | |
|---|---|---|
| | from | to |
| 56 | 20227 | 20243 |
| 57 | 20767 | 20786 |
| 58 | 20880 | 20896 |
| 59 | 21084 | 21101 |
| 60 | 21214 | 21231 |
| 61 | 21425 | 21442 |
| 62 | 22110 | 22128 |
| 63 | 23374 | 23393 |
| 64 | 23435 | 23452 |
| 65 | 23806 | 23822 |
| 66 | 23874 | 23890 |
| 67 | 24045 | 24063 |
| 68 | 24060 | 24077 |
| 69 | 24060 | 24076 |
| 70 | 24064 | 24083 |
| 71 | 24081 | 24098 |
| 72 | 24801 | 24819 |
| 73 | 24812 | 24828 |
| 74 | 25050 | 25067 |
| 75 | 25372 | 25387 |
| 76 | 25392 | 25406 |
| 77 | 25773 | 25790 |
| 78 | 25796 | 25814 |
| 79 | 25969 | 25985 |
| 80 | 29351 | 29367 |
| 81 | | |
| 82 | | |
| 83 | | |
| 84 | | |
| 85 | | |
| 86 | | |
| 87 | | |
| 88 | | |
| 89 | | |
| 90 | | |

In some embodiments, the oligonucleotide comprises a contiguous nucleotide sequence of 10 to 30 nucleotides in length with at least 90% complementary, such as 100% complementarity, to a corresponding target nucleic acid region present in SEQ ID NO: 1, wherein the target nucleic acid region is selected from the group consisting of Reg B1 to B29 in Table 6.

TABLE 6

Selected regions of SEQ ID NO: 2 which may be targeted using oligonucleotide of the invention

| Reg. B | Position in SEQ ID NO 2 | |
|---|---|---|
| | To | From |
| 1 | 489 | 505 |
| 2 | 547 | 564 |
| 3 | 563 | 578 |
| 4 | 727 | 742 |
| 5 | 1013 | 1032 |
| 6 | 1238 | 1257 |
| 7 | 1351 | 1367 |
| 8 | 1555 | 1572 |
| 9 | 1685 | 1702 |
| 10 | 1896 | 1913 |
| 11 | 2581 | 2599 |
| 12 | 3845 | 3864 |
| 13 | 3906 | 3923 |
| 14 | 4277 | 4293 |
| 15 | 4345 | 4361 |
| 16 | 4516 | 4534 |
| 17 | 4531 | 4548 |

TABLE 6-continued

Selected regions of SEQ ID NO: 2 which may be targeted using oligonucleotide of the invention

| Reg. B | Position in SEQ ID NO 2 | |
|---|---|---|
| | To | From |
| 18 | 4531 | 4547 |
| 19 | 4535 | 4554 |
| 20 | 4552 | 4569 |
| 21 | 5272 | 5290 |
| 22 | 5283 | 5299 |
| 23 | 5521 | 5538 |
| 24 | 5843 | 5858 |
| 25 | 5863 | 5877 |
| 26 | 6244 | 6261 |
| 27 | 6267 | 6285 |
| 28 | 6440 | 6456 |
| 29 | 574 | 578 |

In some embodiments, the oligonucleotide of the invention comprises or consists of 8 to 70 nucleotides in length, such as 10 to 60 nucleotides in length, such as 10 to 50 nucleotides in length, such as 12 to 50 nucleotides in length, such as 8 to 40 nucleotides in length, such as from 9 to 35, such as from 10 to 30, such as from 11 to 22, such as from 12 to 20, such as from 13 to 18 or 14 to 16 nucleotides in length.

In some embodiments, the antisense oligonucleotide of the invention, or contiguous nucleotide sequence thereof, comprises or consists of 10 to 35 nucleotides in length, such as from 10 to 30, such as 11 to 22, such as from 12 to 20, such as from 14 to 18 or 14 to 16 contiguous nucleotides in length. Advantageously, the antisense oligonucleotide, or contiguous nucleotide sequence thereof, comprises or consists of 14, 15, 16, 17 or 18 nucleotides in length.

In some embodiments, the antisense oligonucleotide or contiguous nucleotide sequence thereof comprises or consists of 22 or less nucleotides, such as 20 or less nucleotides, such as 18 or less nucleotides, such as 14, 15, 16 or 17 nucleotides. It is to be understood that any range given herein includes the range endpoints. Accordingly, if an oligonucleotide is said to include from 10 to 30 nucleotides, both 10 and 30 nucleotides are included.

In some embodiments, the contiguous nucleotide sequence thereof, comprises or consists of 10 to 35 nucleotides in length, such as from 10 to 30, such as 11 to 22, such as from 12 to 20, such as from 14 to 18 or 14 to 16 contiguous nucleotides in length.

In some embodiments, the contiguous nucleotide sequence comprises or consists of 10, 11, 12, 13, 14, 15, 16, 17, 18, 19, 20, 21, 22, 23, 24, 25, 26, 27, 28, 29 or 30 contiguous nucleotides in length. It is generally understood that the oligonucleotide cannot be shorter than the contiguous nucleotide sequence.

In some embodiments, the oligonucleotide or contiguous nucleotide sequence comprises or consists of a sequence which is fully complementary to a target sequence RegA1-A80 or RegB1 to B29 as provided in tables 5 and 6 respectively.

In some embodiments, the oligonucleotide of the invention or the contiguous nucleotide sequence there comprises at least 10 contiguous nucleotides which are at least 90% identical, such as 100% identical, to a sequence selected from the group consisting of SEQ ID NO: 7 to 164, such as SEQ ID NOs 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86 (see motif sequences listed in Table 7 & 8). It is advantageous if the sequence is complementary to both human and cyno, such as a sequence selected from the group consisting of SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 46, 48, 49, 50, 51, 53, 54, 55, 56, 57, 58, 59, 60, 61, 62, 63, 64, 65, 66, 67, 69, 70, 71, 72, 76, 77, 78, 79, 80, 81, 83, 84 and 85.

In some embodiments, the oligonucleotide of the invention or the contiguous nucleotide sequence there comprises at least 12 contiguous nucleotides which are at least 90% identical, such as 100% identical, to a sequence selected from the group consisting of SEQ ID NO: 7 to 164, such as SEQ ID NOs 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86 (see motif sequences listed in Table 7 & 8). It is advantageous if the sequence is complementary to both human and cyno, such as a sequence selected from the group consisting of SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 46, 48, 49, 50, 51, 53, 54, 55, 56, 57, 58, 59, 60, 61, 62, 63, 64, 65, 66, 67, 69, 70, 71, 72, 76, 77, 78, 79, 80, 81, 83, 84 and 85.

In some embodiments, the oligonucleotide of the invention or the contiguous nucleotide sequence there comprises at least 13 contiguous nucleotides which are at least 90% identical, such as 100% identical, to a sequence selected from the group consisting of SEQ ID NO: 7 to 164, such as SEQ ID NOs 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86 (see motif sequences listed in Table 7 & 8). It is advantageous if the sequence is complementary to both human and cyno, such as a sequence selected from the group consisting of SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 46, 48, 49, 50, 51, 53, 54, 55, 56, 57, 58, 59, 60, 61, 62, 63, 64, 65, 66, 67, 69, 70, 71, 72, 76, 77, 78, 79, 80, 81, 83, 84 and 85.

In some embodiments, the oligonucleotide of the invention or the contiguous nucleotide sequence there comprises at least 14 contiguous nucleotides which are at least 90% identical, such as 100% identical, to a sequence selected from the group consisting of SEQ ID NO: 7 to 164, such as SEQ ID NOs 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86 (see motif sequences listed in Table 7 & 8). It is advantageous if the sequence is complementary to both human and cyno, such as a sequence selected from the group consisting of SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 46, 48, 49, 50, 51, 53, 54, 55, 56, 57, 58, 59, 60, 61, 62, 63, 64, 65, 66, 67, 69, 70, 71, 72, 76, 77, 78, 79, 80, 81, 83, 84 and 85.

In some embodiments, the oligonucleotide of the invention or the contiguous nucleotide sequence there comprises at least 15 contiguous nucleotides which are at least 90% identical, such as 100% identical, to a sequence selected from the group consisting of SEQ ID NO: 7 to 164, such as SEQ ID NOs 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86. It is advantageous if the sequence is complementary to both human and cyno, such as a sequence selected from the group consisting of SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 46, 48, 49, 50, 51, 53, 54, 55, 56, 57, 58, 59, 60, 61, 62, 63, 64, 65, 66, 67, 69, 70, 71, 72, 76, 77, 78, 79, 80, 81, 83, 84 and 85.

In some embodiments, the oligonucleotide of the invention or the contiguous nucleotide sequence there comprises at least 16 contiguous nucleotides which are at least 90% identical, such as 100% identical, to a sequence selected from the group consisting of SEQ ID NO: 7 to 164, such as SEQ ID NOs 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86 (see motif sequences listed in Table 7 & 8). It is advantageous if the sequence is complementary to both human and cyno, such as a sequence selected from the group consisting of SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 46, 48, 49, 50, 51, 53, 54, 55, 56, 57, 58, 59, 60, 61, 62, 63, 64, 65, 66, 67, 69, 70, 71, 72, 76, 77, 78, 79, 80, 81, 83, 84 and 85.

In some embodiments, the oligonucleotide of the invention or the contiguous nucleotide sequence there comprises at least 17 contiguous nucleotides which are at least 90% identical, such as 100% identical, to a sequence selected from the group consisting of SEQ ID NO: 65, 66, 71, 74 and 75 (see motif sequences listed in Table 7 & 8). It is advantageous if the sequence is complementary to both human and cyno, such as a sequence selected from the group consisting of SEQ ID NO: 65, 66, and 71.

In some embodiments of the invention the oligonucleotide of the invention, or contiguous nucleotide sequence thereof, comprises at least 10 contiguous nucleotides which are is at least 90% complementary to, such as fully complementary to a sequence selected from the group consisting of SEQ ID Nos 167-246, such as SEQ ID NO: 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246. It is advantageous to target sequences which are present in both human and cyno, such as a sequence selected from the group consisting of SEQ ID NO: 167, 168, 169, 170, 171, 172, 173, 174, 175, 176, 177, 178, 179, 180, 181, 182, 183,184, 185, 186, 187, 188,189, 190, 191, 192, 193,194, 195, 196, 197,198, 199,200, 201, 202, 203, 204, 206, 208, 209, 210, 211, 213, 214, 215, 216, 217, 218, 219, 220, 221, 222, 223, 224, 225, 226, 227, 229, 230, 231, 232, 236, 237, 238, 239, 240, 241, 243, 244 and 245.

In some embodiments of the invention the oligonucleotide of the invention, or contiguous nucleotide sequence thereof, comprises at least 10 contiguous nucleotides which are is at least 90% complementary to, such as fully complementary to a sequence selected from the group consisting of SEQ ID Nos 247-326, such as SEQ ID NO: 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320 and 321.

In some embodiments of the invention the oligonucleotide of the invention, or contiguous nucleotide sequence thereof, comprises at least 12 contiguous nucleotides which are is at least 90% complementary to, such as fully complementary to a sequence selected from the group consisting of SEQ ID Nos 167-246, such as SEQ ID NO: 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246. It is advantageous to target sequences which are present in both human and cyno, such as a sequence selected from the group consisting of SEQ ID NO: 167, 168, 169, 170, 171, 172, 173, 174, 175, 176, 177, 178,179, 180, 181, 182, 183, 184, 185, 186, 187, 188, 189, 190, 191, 192, 193, 194, 195, 196, 197,198, 199,200, 201, 202, 203, 204, 206, 208, 209, 210, 211, 213, 214, 215, 216, 217, 218, 219, 220, 221, 222, 223, 224, 225, 226, 227, 229, 230, 231, 232, 236, 237, 238, 239, 240, 241, 243, 244 and 245.

In some embodiments of the invention the oligonucleotide of the invention, or contiguous nucleotide sequence thereof, comprises at least 12 contiguous nucleotides which are is at least 90% complementary to, such as fully complementary to a sequence selected from the group consisting of SEQ ID Nos 247-326, such as SEQ ID NO: 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320 and 321.

In some embodiments of the invention the oligonucleotide of the invention, or contiguous nucleotide sequence thereof, comprises at least 13 contiguous nucleotides which are is at least 90% complementary to, such as fully complementary to a sequence selected from the group consisting of SEQ ID Nos 167-246, such as SEQ ID NO: 167, 168, 169, 170, 171, 172, 173, 174, 175, 176, 177, 178,179, 180, 181, 182, 183,184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246. It is advantageous to target sequences which are present in both human and cyno, such as a sequence selected from the group consisting of SEQ ID NO: 167, 168, 169, 170, 171, 172, 173, 174, 175, 176, 177, 178,179, 180,181, 182, 183,184, 185, 186, 187, 188,189, 190, 191, 192, 193, 194, 195, 196, 197,198, 199,200, 201, 202, 203, 204, 206, 208, 209, 210, 211, 213, 214, 215, 216, 217, 218, 219, 220, 221, 222, 223, 224, 225, 226, 227, 229, 230, 231, 232, 236, 237, 238, 239, 240, 241, 243, 244 and 245

In some embodiments of the invention the oligonucleotide of the invention, or contiguous nucleotide sequence thereof, comprises at least 13 contiguous nucleotides which are is at least 90% complementary to, such as fully complementary to a sequence selected from the group consisting of SEQ ID Nos 247-326, such as SEQ ID NO: 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320 and 321.

In some embodiments of the invention the oligonucleotide of the invention, or contiguous nucleotide sequence thereof, comprises at least 14 contiguous nucleotides which are is at least 90% complementary to, such as fully complementary to a sequence selected from the group consisting of SEQ ID Nos 167-246, such as SEQ ID NO: 167, 168, 169, 170, 171, 172, 173, 174, 175, 176, 177, 178,179, 180, 181, 182, 183,184, 185, 186, 187, 188, 189, 190, 191, 192, 193, 194, 195, 196, 197,198, 199,200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246. It is advantageous to target sequences which are present in both human and cyno, such as a sequence selected from the group consisting of SEQ ID NO: 167, 168, 169, 170, 171, 172, 173, 174, 175, 176,177, 178,179, 180, 181, 182, 183,184, 185, 186, 187, 188,189, 190, 191, 192, 193, 194, 195, 196, 197,198, 199,200, 201, 202, 203, 204, 206, 208, 209, 210, 211, 213, 214, 215, 216, 217, 218, 219, 220, 221, 222, 223, 224, 225, 226, 227, 229, 230, 231, 232, 236, 237, 238, 239, 240, 241, 243, 244 and 245.

In some embodiments of the invention the oligonucleotide of the invention, or contiguous nucleotide sequence thereof, comprises at least 14 contiguous nucleotides which are is at least 90% complementary to, such as fully complementary to a sequence selected from the group consisting of SEQ ID Nos 247-326, such as SEQ ID NO: 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320 and 321.

In some embodiments of the invention the oligonucleotide of the invention, or contiguous nucleotide sequence thereof, comprises at least 15 contiguous nucleotides which are is at least 90% complementary to, such as fully complementary to a sequence selected from the group consisting of SEQ ID Nos 167-246, such as SEQ ID NO: 167, 168, 169, 170, 171, 172, 173, 174, 175, 176, 177, 178,179, 180, 181, 182, 183,184, 185, 186, 187, 188, 189, 190, 191, 192, 193, 194, 195, 196, 197,198, 199,200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246. It is advantageous to target sequences which are present in both human and cyno, such as a sequence selected from the group consisting of SEQ ID NO: 167, 168, 169, 170, 171, 172, 173, 174, 175,176, 177, 178, 179, 180, 181, 182, 183, 184, 185, 186, 187, 188, 189, 190, 191, 192, 193, 194, 195, 196, 197, 198, 199, 200, 201, 202, 203, 204, 206, 208, 209, 210, 211, 213, 214, 215, 216, 217, 218, 219, 220, 221, 222, 223, 224, 225, 226, 227, 229, 230, 231, 232, 236, 237, 238, 239, 240, 241, 243, 244 and 245.

In some embodiments of the invention the oligonucleotide of the invention, or contiguous nucleotide sequence thereof, comprises at least 15 contiguous nucleotides which are is at least 90% complementary to, such as fully complementary to a sequence selected from the group consisting of SEQ ID Nos 247-326, such as SEQ ID NO: 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320 and 321.

In some embodiments of the invention the oligonucleotide of the invention, or contiguous nucleotide sequence thereof, comprises at least 16 contiguous nucleotides which are is at least 90% complementary to, such as fully complementary to a sequence selected from the group consisting of SEQ ID Nos 167-246, such as SEQ ID NO: 167, 168, 169, 170, 171, 172, 173, 174, 175, 176, 177, 178, 179, 180, 181, 182, 183, 184, 185, 186, 187, 188, 189, 190, 191, 192, 193, 194, 195,196, 197,198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246. It is advantageous to target sequences which are present in both human and cyno, such as a sequence selected from the group consisting of SEQ ID NO: 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 206, 208, 209, 210, 211, 213, 214, 215, 216, 217, 218, 219, 220, 221, 222, 223, 224, 225, 226, 227, 229, 230, 231, 232, 236, 237, 238, 239, 240, 241, 243, 244 and 245.

In some embodiments of the invention the oligonucleotide of the invention, or contiguous nucleotide sequence thereof, comprises at least 16 contiguous nucleotides which are is at least 90% complementary to, such as fully complementary to a sequence selected from the group consisting of SEQ ID Nos 247-326, such as SEQ ID NO: 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320 and 321.

In some embodiments of the invention the oligonucleotide of the invention, or contiguous nucleotide sequence thereof, is at least 90% complementary to, such as fully complementary to a sequence selected from the group consisting of SEQ ID Nos 167-246, such as SEQ ID NO: 167, 168, 169, 170, 171,172, 173, 174, 175, 176,177, 178, 179, 180, 181, 182, 183, 184, 185, 186, 187, 188, 189, 190,191, 192, 193, 194, 195,196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246. It is advantageous to target sequences which are present in both human and cyno, such as a sequence selected from the group consisting of SEQ ID NO: 167, 168, 169, 170, 171, 172,173, 174, 175, 176, 177,178, 179, 180, 181, 182,183, 184, 185, 186, 187, 188, 189, 190, 191,192, 193, 194, 195, 196,197, 198, 199, 200, 201, 202, 203, 204, 206, 208, 209, 210, 211, 213, 214, 215, 216, 217, 218, 219, 220, 221, 222, 223, 224, 225, 226, 227, 229, 230, 231, 232, 236, 237, 238, 239, 240, 241, 243, 244 and 245.

In some embodiments of the invention the oligonucleotide of the invention, or contiguous nucleotide sequence thereof, is at least 90% complementary to, such as fully complementary to a sequence selected from the group consisting of SEQ ID Nos 247-326, such as SEQ ID NO: 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320 and 321.

In some embodiments of the invention the target sequence is selected from the group consisting of SEQ ID Nos 167-246, such as SEQ ID NO: 167, 168, 169, 170, 171, 172, 173, 174, 175, 176,177, 178,179, 180, 181, 182, 183,184, 185, 186, 187, 188,189, 190, 191, 192, 193, 194, 195,196, 197,198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246. It is advantageous to target sequences which are present in both human and cyno, such as a sequence selected from the group consisting of SEQ ID NO: 167, 168, 169, 170, 171, 172, 173, 174, 175, 176, 177, 178, 179, 180, 181, 182, 183,184, 185, 186, 187, 188, 189, 190, 191, 192, 193, 194, 195, 196, 197,198, 199,200, 201, 202, 203, 204, 206, 208, 209, 210, 211, 213, 214, 215, 216, 217, 218, 219, 220, 221, 222, 223, 224, 225, 226, 227, 229, 230, 231, 232, 236, 237, 238, 239, 240, 241, 243, 244 and 245.

In some embodiments of the invention the target sequence is selected from the group consisting of SEQ ID Nos 247-326, such as SEQ ID NO: 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320 and 321.

In some embodiment the oligonucleotide or contiguous nucleotide sequence comprises at least 10 contiguous nucleotides which are fully complementary to a region of the target nucleic acid, such as a target sequence selected from the group consisting of SEQ ID NO 222, 225, 226, 231, 234 and 235.

In some embodiment the oligonucleotide or contiguous nucleotide sequence comprises at least 12 contiguous nucleotides which are fully complementary to a region of the target nucleic acid, such as a target sequence selected from the group consisting of SEQ ID NO 222, 225, 226, 231, 234 and 235.

In some embodiment the oligonucleotide or contiguous nucleotide sequence comprises at least 13 contiguous nucleotides which are fully complementary to a region of the target nucleic acid, such as a target sequence selected from the group consisting of SEQ ID NO 222, 225, 226, 231, 234 and 235.

In some embodiment the oligonucleotide or contiguous nucleotide sequence comprises at least 14 contiguous nucleotides which are fully complementary to a region of the target nucleic acid, such as a target sequence selected from the group consisting of SEQ ID NO 222, 225, 226, 231, 234 and 235.

In some embodiment the oligonucleotide or contiguous nucleotide sequence comprises at least 15 contiguous nucleotides which are fully complementary to a region of the target nucleic acid, such as a target sequence selected from the group consisting of SEQ ID NO 222, 225, 226, 231, 234 and 235.

In some embodiment the oligonucleotide or contiguous nucleotide sequence comprises at least 16, such as at least 17, contiguous nucleotides which are fully complementary to a region of the target nucleic acid, such as a target sequence selected from the group consisting of SEQ ID NO 222, 225, 226, 231, 234 and 235.

In some embodiments the oligonucleotide or contiguous nucleotide sequence comprises at least 16, such as at least 17, contiguous nucleotides which are fully complementary to a region of the target nucleic acid from position 21084 to 21101 (Region A59, Table 5), position 21214-21231 (Region A60 Table 5), position 23806 to 23822 (Region A70 Table 5), position 24060 to 24077 (Region A68 Table 5) or position 24045 to 24098 (Region A67-A70 Table 5) of SEQ ID NO: 1. In some embodiments, the oligonucleotide comprises or consists of a contiguous nucleotide sequence which is 100% identical to a sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 12 contiguous nucleotides thereof.

In some embodiments, the oligonucleotide comprises or consists of a contiguous nucleotide sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 12 contiguous nucleotides thereof.

In some embodiments, the antisense oligonucleotide comprises or consists of a contiguous nucleotide sequence which is 100% identical to a sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 12 contiguous nucleotides thereof.

In some embodiments, the antisense oligonucleotide comprises or consists of a contiguous nucleotide sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 12 contiguous nucleotides thereof.

In some embodiments, the antisense oligonucleotide comprises or consists of a contiguous nucleotide sequence which is 100% identical to a sequence selected from the group consisting of SEQ ID NO 65, 66, 71, 74 and 75, or at least 16 contiguous nucleotides thereof.

It is understood that the contiguous nucleobase sequences (motif sequence) can be modified to for example increase nuclease resistance and/or binding affinity to the target nucleic acid.

The pattern in which the modified nucleosides (such as high affinity modified nucleosides) are incorporated into the oligonucleotide sequence is generally termed oligonucleotide design.

The oligonucleotides of the invention are designed with modified nucleosides and DNA nucleosides. Advantageously, high affinity modified nucleosides are used.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. Suitable modifications are described in the "Definitions" section under "modified nucleoside", "high affinity modified nucleosides", "sugar modifications", "2' sugar modifications" and Locked nucleic acids (LNA)".

In an embodiment, the oligonucleotide comprises one or more sugar modified nucleosides, such as 2' sugar modified nucleosides. Preferably the oligonucleotide of the invention comprises one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA).

In a further embodiment the oligonucleotide comprises at least one modified internucleoside linkage. Suitable internucleoside modifications are described in the "Definitions" section under "Modified internucleoside linkage". It is advantageous if at least 75%, such as all, the internucleoside linkages within the contiguous nucleotide sequence are phosphorothioate or boranophosphate internucleoside linkages. In some embodiments all the internucleotide linkages in the contiguous sequence of the oligonucleotide are phosphorothioate linkages.

In some embodiments, the oligonucleotide of the invention comprises at least one LNA nucleoside, such as 1, 2, 3, 4, 5, 6, 7, or 8 LNA nucleosides, such as from 2 to 6 LNA nucleosides, such as from 3 to 7 LNA nucleosides, 4 to 8 LNA nucleosides or 3, 4, 5, 6, 7 or 8 LNA nucleosides. In some embodiments, at least 75% of the modified nucleosides in the oligonucleotide are LNA nucleosides, such as 80%, such as 85%, such as 90% of the modified nucleosides are LNA nucleosides. In a still further embodiment all the modified nucleosides in the oligonucleotide are LNA nucleosides. In a further embodiment, the oligonucleotide may comprise both beta-D-oxy-LNA, and one or more of the following LNA nucleosides: thio-LNA, amino-LNA, oxy-LNA, ScET and/or ENA in either the beta-D or alpha-L configurations or combinations thereof. In a further embodiment, all LNA cytosine units are 5-methyl-cytosine. It is advantageous for the nuclease stability of the oligonucleotide or contiguous nucleotide sequence to have at least 1 LNA nucleoside at the 5' end and at least 2 LNA nucleosides at the 3' end of the nucleotide sequence.

In an embodiment of the invention the oligonucleotide of the invention is capable of recruiting RNase H.

In the current invention an advantageous structural design is a gapmer design as described in the "Definitions" section under for example "Gapmer", "LNA Gapmer", "MOE gapmer" and "Mixed Wing Gapmer" "Alternating Flank Gapmer". The gapmer design includes gapmers with uniform flanks, mixed wing flanks, alternating flanks, and gapbreaker designs. In the present invention it is advantageous if the oligonucleotide of the invention is a gapmer with an F-G-F' design. In some embodiments the gapmer is an LNA gapmer wherein at least one or both of regions F and F' comprise at least one LNA unit.

In some embodiments the oligonucleotide of the invention does not comprise 6'-methyl-beta-D-oxy-LNA nucleosides. In some embodiments the oligonucleotide of the invention does not comprise 2'-O-methoxyethyl nucleosides.

In some embodiments, the LNA gapmer comprises or consists of a contiguous nucleotide sequence which is 100% identical to a sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 12 contiguous nucleotides thereof.

In some embodiments, the LNA gapmer comprises or consists of a contiguous nucleotide sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 12 contiguous nucleotides thereof.

In some embodiments, the LNA gapmer comprises or consists of a contiguous nucleotide sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 13 contiguous nucleotides thereof.

In some embodiments, the LNA gapmer comprises or consists of a contiguous nucleotide sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 14 contiguous nucleotides thereof.

In some embodiments, the LNA gapmer comprises or consists of a contiguous nucleotide sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 15 contiguous nucleotides thereof.

In some embodiments, the LNA gapmer comprises or consists of a contiguous nucleotide sequence selected from the group consisting of SEQ ID NO 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, or at least 16 contiguous nucleotides thereof.

In some embodiments, the LNA gapmer comprises or consists of a contiguous nucleotide sequence selected from the group consisting of SEQ ID NO 65, 66, 71, 74, and 75, or at least 16 contiguous nucleotides thereof.

In some embodiments, the compound of the invention comprises or consists of a contiguous nucleotide sequence selected from the group consisting of SEQ ID NO: 7-86, such as SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85 and 86, wherein the designs of the sequence correspond to that listed in Table 7. In particular the flanks (F and F') are selected from 2'-sugar modified nucleosides (M), such as LNA, cET, or MOE, and the gap constitutes a stretch of DNA (D). In gapmers with alternating flank designs the flanks of oligonucleotide is annotated as a series of integers, representing a number of 2' sugar modified nucleosides (M) followed by a number of DNA nucleosides (D). For example a flank with a 2-2-1 motif represents 5' [M]$_2$-[D]$_2$-[M] 3' and a 1-1-1-1-1 motif represents 5' [M]-[D]-[M]-[D]-[M] 3'. Both flanks have a 2' sugar modified nucleoside at the 5' and 3' terminal. The gap region (G), is constituted of a number of DNA nucleosides (typically between 5 and 16), located between the flanks.

In some embodiments, the compound of the invention comprises or consists of a contiguous nucleotide sequence selected from the group consisting of CMP ID NO: 7_1-86_1, such as 7_1, 8_1, 9_1, 10_1, 11_1, 12_1, 13_1, 14_1, 15_1, 16_1, 17_1, 18_1, 19_1, 20_1, 21_1, 22_1, 23_1, 24_1, 25_1, 26_1, 27_1, 28_1, 29_1, 30_1, 31_1, 32_1, 33_1, 34_1, 35_1, 36_1, 371, 38_1, 39_1, 40_1, 41_1, 42_1_43_1, 44_1, 45_1, 46_1, 47_1, 48_1, 49_1, 50_1, 51_1, 52_1, 53_1, 54_1, 55_1, 56_1, 57_1, 58_1, 59_1, 60_1, 61_1, 62_1, 63_1, 64_1, 65_1, 66_1, 67_1, 68_1, 69_1, 70_1, 71_1, 72_1, 73_1, 74_1, 75_1, 76_1, 77_1, 78_1, 79_1, 80_1, 81_1, 82_1, 83_1, 84_1, 85_1, and 86_1, wherein a capital letter is a LNA nucleoside, a lower case letter is a DNA nucleoside, LNA cytosine nucleosides are optionally 5 methyl cytosine LNA, DNA cytosine are optionally 5-methyl cytosine DNA.

In some embodiments, the compound of the invention comprises or consists of a contiguous nucleotide sequence selected from the group consisting of CMP-ID-NO: 7_1-86_1, such as 7_1, 8_1, 9_1, 10_1, 11_1, 12_1, 13_1, 14_1, 15_1, 16_1, 17_1, 18_1, 19_1, 20_1, 21_1, 22_1, 23_1, 24_1, 25_1, 26_1, 27_1, 28_1, 29_1, 30_1, 31_1, 32_1, 33_1, 34_1, 35_1, 36_1, 37_1, 38_1, 39_1, 40_1, 41_1, 42_1, 43_1, 44_1, 45_1, 46_1, 47_1, 48_1, 49_1, 50_1, 51_1, 52_1, 53_1, 54_1, 55_1, 56_1, 57_1, 58_1, 59_1, 60_1, 61_1, 62_1, 63_1, 64_1_65_1, 66_1, 67_1, 68_1, 69_1, 70_1, 71_1, 72_1, 73_1, 74_1, 75_1, 76_1, 77_1, 78_1, 79_1, 80_1, 81_1, 82_1, 83_1, 84_1, 85_1, and 86_1, wherein a capital letter is a LNA nucleoside, a lower case letter is a DNA nucleoside, LNA cytosine nucleosides optionally 5 methyl cytosine LNA, DNA cytosine are optionally 5-methyl cytosine DNA, and the internucleoside linkages between all nucleosides within the contiguous nucleotide sequence are phosphorothioate internucleoside linkages.

In some embodiments, the compound of the invention comprises or consists of a contiguous nucleotide sequence selected from the group consisting of CMP-ID-NO: 7_1-86_1, such as 7_1, 8_1, 9_1, 10_1, 11_1, 12_1, 13_1, 14_1, 15_1, 16_1, 17_1, 18_1, 19_1, 20_1, 21_1, 22_1, 23_1, 24_1, 25_1, 26_1, 27_1, 28_1, 29_1, 30_1, 31_1, 32_1, 33_1, 34_1, 35_1, 36_1, 37_1, 38_1, 39_1, 40_1, 41_1, 42_1, 43_1, 44_1, 45_1, 46_1, 47_1, 48_1, 49_1, 50_1, 51_1, 52_1, 53_1, 54_1, 55_1, 56_1, 571, 58_1, 59_1, 601, 61_1, 62_1, 63_1, 64_1, 65_1, 66_1, 67_1, 68_1, 69_1, 70_1, 711, 72_1, 73_1, 74_1, 75_1, 76_1, 77_1, 78_1, 79_1, 80_1, 81_1, 82_1, 83_1, 84_1, 85_1, and 86_1, wherein a capital letter is a beta-D-oxy LNA nucleoside, a lower case letter is a DNA nucleoside, LNA cytosine nucleosides are 5 methyl cytosine LNA, and the internucleoside linkages between all nucleosides within the contiguous nucleotide sequence are phosphorothioate internucleoside linkages, as indicated in Table 7.

In some embodiments, the compound of the invention is selected from the group of compounds of CMP-ID-NO: 71-86_1, 7_1, 8_1, 9_1, 10_1, 11_1, 12_1, 13_1, 14_1, 15_1, 16_1, 17_1, 18_1, 19_1, 20_1, 21_1, 22_1, 23_1, 24_1, 25_1, 26_1, 27_1, 28_1, 29_1, 30_1, 31_1, 32_1, 33_1, 34_1, 35_1, 36_1, 37_1, 38_1, 39_1, 40_1, 41_1, 42_1, 43_1, 44_1, 45_1, 46_1, 47_1, 48_1, 49_1, 50_1, 51_1, 52_1, 53_1, 54_1, 55_1, 56_1, 57_1, 58_1, 59_1, 60_1, 61_1, 62_1, 63_1, 64_1, 65_1, 66_1, 67_1, 68_1, 69_1, 70_1, 71_1, 72_1, 73_1, 74_1, 75_1, 76_1, 77_1, 78_1, 79_1, 80_1, 81_1, 82_1, 83_1, 84_1, 85_1, and 86_1, wherein a capital letter is a LNA nucleoside, a lower case letter is a DNA nucleoside, LNA cytosine nucleosides are optionally 5 methyl cytosine LNA, DNA cytosine are optionally 5-methyl cytosine DNA, and the internucleoside linkages between DNA nucleosides are phosphorothioate internucleoside linkages.

In some embodiments, the compound of the invention is selected from the group of compounds,
ATGTttatcaccaaAATT (SEQ ID NO: 65, CMP ID NO: 65_1)
CTGAaatactaccaTATA (SEQ ID NO: 66, CMP ID NO: 66_1)
TTTAatcataccaATCT (SEQ ID NO: 71, CMP ID NO: 71_1)
TTCTtatttcaaatCTCA (SEQ ID NO: 74, CMP ID NO: 74_1)
TCTTtatttcaaatCTCA (SEQ ID NO: 75, CMP ID NO: _1)
wherein a capital letter is a LNA nucleoside, such as a beta-D-oxy-LNA, a lower case letter is a DNA nucleoside, LNA cytosine nucleosides are optionally 5 methyl cytosine LNA, DNA cytosine nucleosides are optionally 5-methyl cytosine DNA, the internucleoside linkages between DNA nucleosides are phosphorothioate internucleoside linkages.

In some embodiments, the compound of the invention is selected from the group of compounds of CMP-ID-NO: 7_1-86_1, wherein a capital letter is a LNA nucleoside, a lower case letter is a DNA nucleoside, LNA cytosine nucleosides are optionally 5 methyl cytosine LNA, DNA cytosine are optionally 5-methyl cytosine DNA, and all the internucleoside linkages the nucleosides are phosphorothioate internucleoside linkages.

Advantageously, the compound of the invention is in the form of a pharmaceutically acceptable salt.

In a further embodiment of the invention the oligonucleotide may comprise at least one stereodefined internucleoside linkages, such as a stereodefined phosphorothioate internucleoside linkage. An advantage of generating stereodefined oligonucleotide variants is the ability to increase the diversity across a sequence motif, and select stereodefined oligonucleotides including sub-libraries of stereodefined oligonucleotides, which have improved medicinal chemical properties as compared to a non stereodefined oligonucleotide.

The invention provides a conjugate comprising the oligonucleotide or antisense oligonucleotide according to the invention, and at least one conjugate moiety covalently attached to said oligonucleotide. In some embodiments the conjugate moiety is a conjugate that facilitates delivery across the blood brain barrier, such as an antibody or antibody fragment targeting the transferrin receptor.

The invention provides a pharmaceutically acceptable salt of the oligonucleotide or antisense oligonucleotide, or the conjugate, of the invention.

In some embodiments the contiguous nucleotide sequence of the invention does not comprise 10 or more contiguous nucleotides present in the sequence GATCAGAGATTAAGGCCAA (SEQ ID NO 322). In some embodiments the contiguous nucleotide sequence of the invention does not comprise 10 or more contiguous nucleotides present in the sequence GCAGATTGATTATACGGTA (SEQ ID NO 323) or GTGGAAGGAACACGACTTA (SEQ ID NO 324).

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phosphoramidite chemistry (see for example Caruthers et al, 1987, Methods in Enzymology vol. 154, pages 287-313). In a further embodiment the method further comprises reacting the contiguous nucleotide sequence with a conjugating moiety (ligand) to covalently attach the conjugate moiety to the oligonucleotide. In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Salt

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt.

In a further aspect the invention provides a pharmaceutically acceptable salt of the antisense oligonucleotide or a conjugate thereof. In a preferred embodiment, the pharmaceutically acceptable salt is a sodium or a potassium salt.

Pharmaceutical Composition

In a further aspect, the invention provides pharmaceutical compositions comprising any of the aforementioned oligonucleotides and/or oligonucleotide conjugates or salts thereof and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments the pharmaceutically acceptable diluent is sterile phosphate buffered saline. In some embodiments the oligonucleotide is used in the pharmaceutically acceptable diluent at a concentration of 50-300 µM solution.

Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

Oligonucleotides or oligonucleotide conjugates of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some embodiments, the oligonucleotide or oligonucleotide conjugate of the invention is a prodrug. In particular with respect to oligonucleotide conjugates the conjugate moiety is cleaved of the oligonucleotide once the prodrug is delivered to the site of action, e.g. the target cell.

Applications

The oligonucleotides of the invention may be utilized as research reagents for, for example, diagnostics, therapeutics and prophylaxis.

In research, such oligonucleotides may be used to specifically modulate the synthesis of TMEM106B protein in cells (e.g. in vitro cell cultures) and experimental animals thereby facilitating functional analysis of the target or an appraisal of its usefulness as a target for therapeutic intervention. Typically the target modulation is achieved by degrading or inhibiting the mRNA producing the protein, thereby prevent protein formation or by degrading or inhibiting a modulator of the gene or mRNA producing the protein.

If employing the oligonucleotide of the invention in research or diagnostics the target nucleic acid may be a cDNA or a synthetic nucleic acid derived from DNA or RNA.

The present invention provides an in vivo or in vitro method for modulating TMEM106B expression in a target cell which is expressing TMEM106B, said method comprising administering an oligonucleotide of the invention in an effective amount to said cell.

In some embodiments the target cell is a neuronal cell. In some embodiments the target cell is a microglial cell.

In some embodiments, the target cell, is a mammalian cell in particular a human cell. The target cell may be an in vitro cell culture or an in vivo cell forming part of a tissue in a mammal. In preferred embodiments the target cell is present in the CNS, such as the brain, such as in the frontal temporal lobes.

In some embodiments the target cell is a CNS cell, a brain cell, a frontal cortex cell or a frontal temporal lobe cell.

In some embodiments the target cell is a cell which is present in the thalamus, hippocampus, striatum, retina, or spinal cord.

In some embodiments the target cell is a thalamus cell, a hippocampus cell, a striatum cell, a retina cell, or a spinal cord cell.

It will be understood that for in vitro use, such as for evaluation of TMEM106B expression or inhibition thereof, or targeting, in a cell, such as a target cell, the cell may be isolated from the tissue or may be derived from the tissue (e.g. an established or immortalized cell line), such as CNS tissue, brain tissue, frontal cortex, frontal temporal lobe tissue, thalamus tissue, hippocampus tissue, striatum tissue, retinal tissue, or spinal cord tissue. Cells which are isolated from the target tissue are referred to as primary cells.

In diagnostics the oligonucleotides may be used to detect and quantitate TMEM106B expression in cell and tissues by northern blotting, in-situ hybridisation or similar techniques.

For therapeutics, the oligonucleotides may be administered to an animal or a human, suspected of having a disease or disorder, which can be treated by modulating the expression of TMEM106B.

The invention provides methods for treating or preventing a disease, comprising administering a therapeutically or prophylactically effective amount of an oligonucleotide, an oligonucleotide conjugate or a pharmaceutical composition of the invention to a subject suffering from or susceptible to the disease.

The invention also relates to an oligonucleotide, a composition or a conjugate as defined herein for use as a medicament.

The oligonucleotide, oligonucleotide conjugate or a pharmaceutical composition according to the invention is typically administered in an effective amount.

The invention also provides for the use of the oligonucleotide or oligonucleotide conjugate of the invention as described for the manufacture of a medicament for the treatment of a disorder as referred to herein, or for a method of the treatment of as a disorder as referred to herein.

The disease or disorder, as referred to herein, is associated with expression of TMEM106B. In some embodiments disease or disorder may be associated with a mutation in the TMEM106B gene or a gene whose protein product is associated with or interacts with TMEM106B. Therefore, in some embodiments, the target nucleic acid is a mutated form of the TMEM106B sequence and in other embodiments, the target nucleic acid is a regulator of the TMEM106B sequence.

The methods of the invention are preferably employed for treatment or prophylaxis against diseases caused by abnormal levels and/or activity of TMEM106B.

The invention further relates to use of an oligonucleotide, oligonucleotide conjugate or a pharmaceutical composition as defined herein for the manufacture of a medicament for the treatment of abnormal levels and/or activity of TMEM106B.

In some aspects, the invention relates to oligonucleotides, oligonucleotide conjugates or pharmaceutical compositions of the invention, for use in the treatment of diseases or disorders selected from neurodegeneration, frontotemporal lobar degeneration (FTLD), Parkinson's disease (or parkinsonism), hypomyelinating leukodystrophies, amyotrophic lateral sclerosis and multiple system atrophy, Alzheimer's disease, motor neuron disease, corticobasal syndrome, progressive supranuclear palsy, and neuronal ceroid lipofuscinosis (NCL).

In some embodiments the compounds of the invention are used for the treatment of age associated changes in frontal cortex.

In one aspect, the invention relates to oligonucleotides, oligonucleotide conjugates or pharmaceutical compositions, of the invention, for use in the treatment of frontotemporal lobar degeneration (FTLD). The oligonucleotides, oligonucleotide conjugates or pharmaceutical compositions may be advantageous in the treatment of FTLD characterized by intranuclear and/or cytoplasmic accumulations of ubiquitinated proteins (FTLD-U), in particular FTDL-TDP which is characterized by the presence of ubiquitinated TAR DNA binding protein 43 (TDP-43) accumulations in frontal and temporal brain regions and in other TDP-43 proteinopathies.

Administration The oligonucleotides or pharmaceutical compositions of the present invention may be administered via parenteral (such as, intravenous, subcutaneous, intramuscular, intracerebral, intracerebroventricular intraocular, or intrathecal administration).

In some embodiments, the administration is via intrathecal administration.

Advantageously, e.g. for treatment of neurological disorders, the oligonucleotide or pharmaceutical compositions of the present invention are administered intrathecally or intracranially, e.g. via intracerebral or intraventricular administration.

The invention also provides for the use of the oligonucleotide or conjugate thereof, such as pharmaceutical salts or compositions of the invention, for the manufacture of a medicament wherein the medicament is in a dosage form for subcutaneous administration.

The invention also provides for the use of the oligonucleotide of the invention, or conjugate thereof, such as pharmaceutical salts or compositions of the invention, for the manufacture of a medicament wherein the medicament is in a dosage form for intrathecal administration.

Combination Therapies

In some embodiments the oligonucleotide, oligonucleotide conjugate or pharmaceutical composition of the invention is for use in a combination treatment with another therapeutic agent. The therapeutic agent can for example be the standard of care for the diseases or disorders described above.

Embodiments

1. An oligonucleotide targeting TMEM106B, which comprises a contiguous nucleotide sequence of 10-30 nucleotides in length with at least 90% complementary, such as fully complementary, to a mammalian TMEM106B target nucleic acid.
2. The oligonucleotide according to embodiment 1, wherein the oligonucleotide is capable of reducing the expression of the mammalian TMEM106B target nucleic acid in a cell.
3. The oligonucleotide according to any one of embodiments 1 to 2, wherein the oligonucleotide is a therapeutic oligonucleotide.
4. The oligonucleotide according to any one of embodiment 1 to 3, wherein the mammalian TMEM106B target nucleic acid is selected from the group consisting of SEQ ID NO: 1, 2, 3, 4, 5 and 6, or a naturally occurring variant thereof.
5. The oligonucleotide according to embodiment 4, wherein the naturally occurring variant is selected from the polymorphisms listed in Table 4.
6. The oligonucleotide of embodiment 1 to 5, wherein the target nucleic acid is RNA.
7. The oligonucleotide of embodiment 6, wherein the RNA is mRNA.
8. The oligonucleotide of embodiment 7, wherein the mRNA is pre-RNA or mature RNA
9. The oligonucleotide according to any one of embodiments 1 to 8, wherein the contiguous nucleotide sequence, comprises at least 10 contiguous nucleotides, which are at least 90% complementary to, such as fully complementary, to a sequence selected from the group consisting of SEQ ID NO: 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246, or a group consisting of SEQ ID NO: 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320 and 321.
10. The oligonucleotide according to any one of embodiment 1 to 9, wherein the oligonucleotide or contiguous nucleotide sequence is fully complementary to SEQ ID NO: 1 and/or 2, or a naturally occurring variant thereof.
11. The oligonucleotide according to any one of embodiments 1 to 10, wherein the contiguous nucleotide sequence comprises at least 10 contiguous nucleotides which are at least 90% complementary, such as is fully complementary, to a region of SEQ ID NO 1, wherein the regions is selected from the group consisting of position 546-563; 2122-2140; 2143-2160; 2165-2183; 2300-2317; 2392-2410; 2548-2565; 3507-3524; 3678-3694; 3736-3753; 3752-3767; 3802-3819; 3908-3925; 3908-6417; 4321-4337; 4701-4720; 4948-4965; 5063-5080; 5069-5086; 5172-5190; 5512-5530; 5583-5599; 6015-6047; 6015-6032; 6032-6047; 6125-6154; 6125-6140; 6136-6154; 6172-6189; 6200-6231; 6200-6216; 6214-6231; 6401-6417; 6458-6476; 6837-6853; 8453-8472; 8983-9001; 9533-9549; 9628-9644; 11065-11083; 11117-11134; 11264-11281; 12310-12325; 12870-12887; 13050-13065; 13397-13414; 15061-15079; 15249-15266; 15318-15336; 15368-15385; 15440-15457; 15632-15649; 15823-15842; 16496-16513; 19090-19109; 19198-19217; 19211-19228; 19699-19718; 20217-20243; 20217-20236; 20227-20243; 20755-26403; 20767-20786; 20880-20896; 21084-21101; 21214-21231; 21425-21442; 22110-25406; 22110-22128; 23374-23393; 23435-23452; 23806-23822; 23874-23890; 24045-24098; 24045-24063; 24060-24077; 24060-24076; 24064-24083; 24081-24098; 24045-24098; 24801-24828; 24801-24819; 24812-24828; 25050-25067; 25372-25387; 25392-25406; 25773-25790; 25796-25814; 25969-25985; and 29351-29367 of SEQ ID NO: 1.
12. The oligonucleotide according to any one of embodiments 1 to 11, wherein the contiguous nucleotide sequence, comprises at least 10 contiguous nucleotides, which are at least 90% complementary to, such as fully complementary, to a sequence selected from the group consisting of SEQ ID NO: 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246.
13. The oligonucleotide according to any one of embodiment 1 to 12, wherein the contiguous nucleotide sequence is complementary, such as fully complementary, to SEQ ID NO: 1 and SEQ ID NO: 3, or a naturally occurring variants thereof.
14. The oligonucleotide according to embodiment 13, wherein the contiguous nucleotide sequence, comprises at least 10 contiguous nucleotides, which are at least 90% complementary to, such as fully complementary to a sequence selected from the group consisting of SEQ ID NO: 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 206, 208, 209, 210, 211, 213, 214, 215, 216, 217, 218, 219, 220, 221, 222, 223, 224, 225, 226, 227, 229, 230, 231, 232, 236, 237, 238, 239, 240, 241, 243, 244 and 245.
15. The oligonucleotide according to any one of embodiments 1 to 14, which comprises a contiguous nucleotide sequence of 10 to 30 nucleotides in length with at least 90% complementary, such as fully complementary, to the 3'UTR of a mammalian TMEM106B target nucleic acid.
16. The oligonucleotide according to any one of embodiments 1 to 15, wherein the contiguous nucleotide sequence of at least 10 nucleotides in length has at least 90% complementary, such as fully complementary to the sequence from position 20227 to 26403 or from position 20227 to 24077 of SEQ ID NO 1.
17. The oligonucleotide according to any one of embodiments 1 to 16, wherein the contiguous nucleotide sequence is at least 90% complementary, such as fully complementary, to position 20755 to 26403 of SEQ ID NO: 1.

18. The oligonucleotide according to any one of embodiments 1 to 17, wherein the contiguous nucleotide sequence of at least 10 nucleotides in length, has at least 90% complementary, such as fully complementary, to the sequence from position 21084 to 21231, such as from position 21084 to 21213 of SEQ ID NO 1.
19. The oligonucleotide according to any one of embodiments 1 to 17, wherein, the contiguous nucleotide sequence of at least 10 nucleotides in length, has at least 90% complementary, such as fully complementary, to position 22110 to 25406 of SEQ ID NO: 1.
20. The oligonucleotide according to any one of embodiments 1 to 17, wherein the contiguous nucleotide sequence of at least 10 nucleotides in length has at least 90% complementary, such as fully complementary, to the sequence from position 23086 to 24077 of SEQ ID NO 1.
21. The oligonucleotide according to any one of embodiments 1 to 17, wherein the contiguous nucleotide sequence of at least 10 nucleotides in length has at least 90% complementary, such as fully complementary to the sequence from position 20227 to 20243 of SEQ ID NO 1.
22. The oligonucleotide according to any one of embodiments 1 to 17, wherein the contiguous nucleotide sequence of at least 10 nucleotides in length has at least 90% complementary, such as fully complementary to the sequence from position 20227 to 26403 of SEQ ID NO 1.
23. The invention provides an oligonucleotide targeting TMEM106B, which comprises a contiguous nucleotide sequence of at least 10 nucleotides in length has at least 90% complementary, such as fully complementary to the sequence from position 24045 to 24098, of SEQ ID NO 1.
24. The oligonucleotide according to any one of embodiments 1 to 17, wherein the contiguous nucleotide sequence of at least 10 nucleotides in length has at least 90% complementary, such as fully complementary to a region selected from the group consisting of position 22110-22128, 24045-24063, 24060-24077, 24812-24828, and 25392-25406 of SEQ ID NO 1.
25. The oligonucleotide according to any one of embodiments 1 to 14, wherein the contiguous nucleotide sequence of at least 10 nucleotides in length has at least 90% complementary, such as fully complementary to position from 3908-6417 of SEQ ID NO: 1.
26. The oligonucleotide according to embodiment 25, wherein the contiguous nucleotide sequence of at least 10 nucleotides in length, has at least 90% complementary, such as fully complementary to a region selected from the group consisting of position 3908-3925, 6136-6154, 5172-5190, 6200-6216, and 6401-6417 of SEQ ID NO: 1.
27. The oligonucleotide according to any one of embodiments 1-26, wherein the contiguous nucleotide sequence is fully complementary to SEQ ID NO: 1 or to one of the SEQ ID NO's listed in embodiment 12 or 14.
28. The oligonucleotide according to any one of embodiments 1 to 27, wherein the oligonucleotide is capable of hybridizing with a ΔG° below −10 kcal to a target nucleic acid of SEQ ID NO: 1 or to a target sequence selected from the group consisting of SEQ ID NO: 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245 and 246.
29. The oligonucleotide according to any one of embodiments 1 to 28, wherein the contiguous nucleotide sequence comprises at least 10 contiguous, such as at least 12 or at least 14 contiguous nucleotides present in a sequence selected from the group consisting of SEQ ID NO 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86.
30. The oligonucleotide according to any one of embodiments 1 to 29, wherein the contiguous nucleotide sequence comprises at least 10 contiguous nucleotides selected from the group consisting of SEQ ID NO: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 46, 48, 49, 50, 51, 53, 54, 55, 56, 57, 58, 59, 60, 61, 62, 63, 64, 65, 66, 67, 69, 70, 71, 72, 76, 77, 78, 79, 80, 81, 83, 84 and 85.
31. The oligonucleotide according to any one of embodiments 1 to 9, wherein the contiguous nucleotide sequence comprises at least 10 contiguous nucleotides selected from the group consisting of SEQ ID NO: 87, 88, 89, 90, 91, 92, 93, 94, 95, 96, 97, 98, 99, 100, 101, 102, 103, 104, 105, 106, 107, 108, 109, 110,111, 112, 113, 114, 115,116, 117, 118, 119, 120, 121, 122, 123,124, 125,126, 127, 128,129, 130, 131, 132, 133,134, 135, 136, 137, 138, 139, 140, 141,142, 143, 144, 145, 146,147, 148, 149, 150, 151,152, 153, 154, 155, 156, 157, 158, 159, 160 and 161.
32. The oligonucleotide according to any one of embodiments 1 to 31, wherein the oligonucleotide is shorter than 60 nucleotides in length, such as shorter than 50 nucleotides in length, such as between 10 and 60 or 10 and 50 nucleotides in length.
33. The oligonucleotide of embodiment 1-32, wherein the contiguous nucleotide sequence comprises or consists of at least 10 contiguous nucleotides, particularly 11, 12, 13, 14, 15, 16, 17, 18, 19, 20, 21, 22, 23, 24, 25, 26, 27, 28, or 29 contiguous nucleotides.
34. The oligonucleotide according embodiment 33, wherein the contiguous nucleotide sequence is at least 12 nucleotides in length, such as at least 14 nucleotides in length which are fully complementary to SEQ ID NO 1 or to one of the SEQ ID NO's listed in embodiment 12 or 14.
35. The oligonucleotide according to any one of embodiments 1 to 32, wherein the contiguous nucleotide sequence comprises or consists of from 12 to 22 nucleotides.
36. The oligonucleotide of embodiment 35, wherein the contiguous nucleotide sequence comprises or consists of from 14-20 nucleotides.
37. The oligonucleotide according to any one of embodiments 1 to 36, wherein the contiguous nucleotide sequence has zero to three mismatches compared to the target nucleic acid it is complementary to.
38. The oligonucleotide of embodiment 37, wherein the contiguous nucleotide sequence has one mismatch compared to the target nucleic acid.
39. The oligonucleotide of embodiment 37, wherein the contiguous nucleotide sequence has two mismatches compared to the target nucleic acid.
40. The oligonucleotide of embodiment 37, wherein the contiguous nucleotide sequence is fully complementary to the target nucleic acid sequence.

41. The oligonucleotide according to any one of embodiments 1 to 40, wherein the oligonucleotide comprises one or more 2' sugar modified nucleosides.
42. The oligonucleotide according to embodiment 41, wherein the one or more 2'-sugar modified nucleosides are independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.
43. The oligonucleotide according to embodiment 42, wherein at least one of the one or more 2'-sugar modified nucleosides is a LNA nucleoside.
44. The oligonucleotide according to embodiment 43, wherein the modified LNA nucleoside is selected from oxy-LNA, amino-LNA, thio-LNA, cET, and ENA.
45. The oligonucleotide according to embodiment 43 or 44, wherein the modified LNA nucleoside is oxy-LNA with the following 2'-4' bridge —O-CH2-.
46. The oligonucleotide according to embodiment 45, wherein the oxy-LNA is beta-D-oxy-LNA.
47. The oligonucleotide according to embodiment 43 or 44, wherein the modified LNA nucleoside is cET with the following 2'-4' bridge —O—CH(CH3)-.
48. The oligonucleotide according to embodiment 47, wherein the cET is (S)cET, i.e. 6'(S)methyl-beta-D-oxy-LNA.
49. The oligonucleotide according to embodiment 43 or 44, wherein the LNA is ENA, with the following 2'-4' bridge —O-CH2-CH2-.
50. The oligonucleotide according to any one of embodiments 1-49, wherein the contiguous nucleotide sequence comprises at least one modified internucleoside linkage.
51. The oligonucleotide according to any one of embodiments 1-50, wherein the continuous nucleotide sequence comprises at least one phosphorothioate modified internucleoside linkage.
52. The oligonucleotide according to any one of embodiments 1 to 51, wherein the oligonucleotide is a siRNA or shRNA or forms the guide strand of a siRNA or shRNA complex.
53. The oligonucleotide according to embodiments 52, wherein the oligonucleotide is a double stranded siRNA oligonucleotide or shRNA oligonucleotide capable of interacting with the RISC complex.
54. The oligonucleotide according to any one of embodiments 1 to 51, where the oligonucleotide is an antisense oligonucleotide.
55. The antisense oligonucleotide according to embodiment 54, wherein the oligonucleotide is single stranded.
56. The oligonucleotide according to embodiments 54 or 55, wherein at least 75% or all of the internucleoside linkages between the nucleosides of the contiguous nucleotide sequence are phosphorothioate internucleoside linkages.
57. The oligonucleotide according to any one of embodiments 54 to 56, wherein the oligonucleotide is capable of recruiting RNase H1.
58. The antisense oligonucleotide according to embodiment 57, wherein oligonucleotide is an antisense oligonucleotide gapmer.
59. The antisense oligonucleotide according to embodiment 57 or 58, wherein the antisense oligonucleotide, or contiguous nucleotide sequence thereof, consists or comprises a gapmer of formula 5'-F-G-F'-3', where region F and F' independently comprise 1-8 nucleosides, of which 1-5 independently are 2' sugar modified and defines the 5' and 3' end of the F and F' region, and G is a region between 5 and 18 nucleosides which are capable of recruiting RNaseH, such as a region comprising 5-18 DNA nucleosides.
60. The antisense oligonucleotide of embodiment 59, wherein the 2' sugar modified nucleoside independently is selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.
61. The antisense oligonucleotide of embodiment 59 or 60, wherein one or more of the 2' sugar modified nucleosides in region F and F' is a LNA nucleoside
62. The antisense oligonucleotide according to any one of embodiments 60 or 61, wherein the LNA nucleoside is selected from beta-D-oxy-LNA, alpha-L-oxy-LNA, beta-D-amino-LNA, alpha-L-amino-LNA, beta-D-thio-LNA, alpha-L-thio-LNA, (S)cET, (R)cET beta-D-ENA and alpha-L-ENA.
63. The antisense oligonucleotide according to any one of embodiments 54 to 62, wherein the antisense oligonucleotide is selected from the group consisting of a LNA gapmer, a mixed wing gapmer and an alternating flank gapmer.
64. The oligonucleotide of embodiment 59-63, wherein
   a. the F region is between 1 and 5 nucleotides in length and consists of 1-4 identical LNA nucleosides and 0-2 DNA nucleosides; and
   b. the F' region is between 2 and 5 nucleotides in length and consists of 2-4 identical LNA nucleosides and 0-2 DNA nucleosides; and
   c. region G is between 8 and 16 DNA nucleotides.
65. The antisense oligonucleotide of embodiment 59 to 62, wherein region F and F' consist of identical LNA nucleosides.
66. The antisense oligonucleotide of embodiment 59 to 62, wherein all the 2' sugar modified nucleosides in region F and F' are oxy-LNA nucleosides.
67. The antisense oligonucleotide according to any one of embodiments 54 to 60, wherein the antisense oligonucleotide is 2'-MOE gapmer.
68. The antisense oligonucleotide of any one of embodiments 54 to 67, wherein the nucleosides in region G is DNA and/or alpha-L-LNA nucleosides.
69. The antisense oligonucleotide of embodiment 68, wherein region G consists of at least 75% DNA nucleosides.
70. The antisense oligonucleotide of embodiment 69, where all the nucleosides in region G are DNA nucleosides.
71. The oligonucleotide according to any one of embodiments 1-51 or 54 to 70, wherein the oligonucleotide or contiguous nucleotide sequence thereof, is selected from the motif sequences in combination with the indicated designs as listed in Table 7.
72. The oligonucleotide according to any one of embodiments 1-51 or 54 to 71, wherein the oligonucleotide or contiguous nucleotide sequence thereof, is selected from the group consisting of CMP ID NO: 7_1, 8_1, 9_1, 10_1, 11_1, 12_1, 13_1, 14_1, 15_1, 16_1, 17_1, 18_1, 19_1, 20_1, 21_1, 22_1, 23_1, 24_1, 25_1, 26_1, 27_1, 28_1, 29_1, 301, 31_1, 32_1, 33_1, 34_1, 35_1, 36_1, 371, 38_1, 39_1, 40_1, 41_1, 42_1, 43_1, 44_1, 45_1, 46_1, 47_1, 48_1, 49_1, 50_1, 51_1, 52_1, 53_1, 54_1, 55_1, 56_1, 57_1, 58_1, 59_1, 60_1, 61_1, 62_1, 63_1, 64_1, 65_1, 66_1, 67_1, 68_1, 69_1, 70_1, 71_1, 72_1, 73_1, 74_1, 75_1, 76_1, 77_1, 78_1, 79_1, 80_1, 81_1, 82_1, 83_1, 84_1, 85_1, 86_1, 87_1, 88_1, 89_1, 90_1, 91_1, 92_1, 931, 94_1, 95_1, 96_1, 97_1, 98_1, 99_1, 100_1, 101_1, 102_1, 103_1, 104_1, 105_1, 106_1, 107_1, 108_1, 109_1, 110_1, 111_1, 112_1, 113_1, 114_1, 115_1, 116_1, 117_1, 118_1, 119_1, 120_1, 121_1, 122_1, 123_1, 124_1, 125_1, 126_1, 127_1, 128_1, 129_1, 130_1, 131_1, 132_1, 133_1, 134_1, 135_1, 136_1, 137_1, 138_1, 139_1, 140_1, 141_1, 142_1, 143_1, 144_1, 145_1, 146_1, 147_1, 148_1, 149_1, 150_1, 151_1, 152_1, 153_1, 154_1, 155_1, 156_1, 157_1, 158_1, 159_1, 160_1 and 161_1 as listed in Table 7.

73. The oligonucleotide according to any one of embodiments 1-51 or 54 to 72, wherein the oligonucleotide or contiguous nucleotide sequence thereof, is selected from the group consisting of:
ATGTttatcaccaaAATT (SEQ ID NO: 65, CMP ID NO: 65_1)
CTGAaatactaccaTATA (SEQ ID NO: 66, CMP ID NO: 66_1)
TTTAatcataccaATCT (SEQ ID NO: 71, CMP ID NO: 71_1)
TTCTtatttcaaatCTCA (SEQ ID NO: 74, CMP ID NO: 74_1)
TCTTatttcaaatCTCA (SEQ ID NO: 75, CMP ID NO: _1)
wherein a capital letter is a LNA nucleoside, such as a beta-D-oxy-LNA, a lower case letter is a DNA nucleoside, LNA cytosine nucleosides are optionally 5 methyl cytosine LNA, DNA cytosine nucleosides are optionally 5-methyl cytosine DNA, the internucleoside linkages between DNA nucleosides are phosphorothioate internucleoside linkages 74. A conjugate comprising the oligonucleotide or antisense oligonucleotide according to any one of embodiments 1-73, and at least one conjugate moiety covalently attached to said oligonucleotide.

75. The oligonucleotide conjugate according to embodiment 74, wherein the conjugate moiety is selected from carbohydrates, cell surface receptor ligands, drug substances, hormones, lipophilic substances, polymers, proteins, peptides, toxins, vitamins, viral proteins or combinations thereof.

76. The oligonucleotide conjugate according to embodiment 74 or 75, wherein the conjugate facilitates delivery across the blood brain barrier.

77. The oligonucleotide conjugate according to embodiment 76, wherein the conjugate is an antibody or antibody fragment targeting the transferrin receptor.

78. A pharmaceutically acceptable salt of the oligonucleotide or antisense oligonucleotide according to any one of embodiments 1-72, or the conjugate according to embodiment 74-77.

79. A pharmaceutical composition comprising the oligonucleotide or antisense oligonucleotide according to any one of embodiments 1-72 or the conjugate according to embodiment 74-77 and a pharmaceutically acceptable diluent, solvent, carrier, salt and/or adjuvant.

80. An in vitro or in vivo method for modulating TMEM106B expression in a target cell which is expressing TMEM106B, said method comprising administering an oligonucleotide or antisense oligonucleotide according to any one of embodiments 1-72, conjugate according to embodiment 74-77, or the pharmaceutical salt according to embodiment 78, or pharmaceutical composition according to embodiment 79 in an effective amount to said cell.

81. A method for treating or preventing a disease comprising administering a therapeutically or prophylactically effective amount of an oligonucleotide or antisense oligonucleotide according to any one of embodiments 1-72, conjugate according to embodiment 74-77, or the pharmaceutical salt according to embodiment 78, or pharmaceutical composition according to embodiment 79, to a subject suffering from or susceptible to the disease.

82. The oligonucleotide or antisense oligonucleotide according to any one of embodiments 1-72, conjugate according to embodiment 74-77, or the pharmaceutical salt according to embodiment 78, or pharmaceutical composition according to embodiment 79 for use in medicine for treatment or prevention of a disease in a subject.

83. The oligonucleotide or antisense oligonucleotide according to any one of embodiments 1-72, conjugate according to embodiment 74-77, or the pharmaceutical salt according to embodiment 78, or pharmaceutical composition according to embodiment 79 for use in the treatment or prevention of a disease selected from the group consisting of neurodegeneration, frontotemporal lobar degeneration (FTLD), Parkinson's disease (or parkinsonism), hypomyelinating leukodystrophies, amyotrophic lateral sclerosis and multiple system atrophy, Alzheimer's disease, motor neuron disease, corticobasal syndrome, progressive supranuclear palsy, and neuronal ceroid lipofuscinosis (NCL).

84. Use of the oligonucleotide or antisense oligonucleotide according to any one of embodiments 1-72, conjugate according to embodiment 74-77, or the pharmaceutical salt according to embodiment 78, or pharmaceutical composition according to embodiment 79, for the preparation of a medicament for treatment or prevention of a disease.

85. The oligonucleotide for use, or the use or the method according to any one of embodiments 81 to 84, wherein the disease is associated with overexpression of TMEM106B and/or abnormal levels of TMEM106B.

86. The oligonucleotide for use, or the use or the method according to any one of embodiments 81 to 84, wherein the treatment reduces TMEM106B mRNA levels in the frontal cortex to normal levels.

87. The oligonucleotide for use, or the use or the method according to any one of embodiments 81 to 84, wherein the disease is selected from the group consisting of neurodegeneration, frontotemporal lobar degeneration (FTLD), Parkinson's disease (or parkinsonism), hypomyelinating leukodystrophies, amyotrophic lateral sclerosis and multiple system atrophy, Alzheimer's disease, motor neuron disease, corticobasal syndrome, progressive supranuclear palsy, and neuronal ceroid lipofuscinosis (NCL).

88. The oligonucleotide for use, or the use or the method according to any one of embodiments 81 to 87, wherein the disease is frontotemporal lobar degeneration (FTLD).

89. The oligonucleotide for use, or the use or the method according to any one of embodiments 81 to 88, wherein the subject is a mammal.

90. The oligonucleotide for use, or the use or the method according to embodiment 89, wherein the mammal is human.

EXAMPLES

Materials and Methods
Oligonucleotide Compounds and Motif Sequences

TABLE 7

Compound List
List of oligonucleotide motif sequences (indicated by SEQ ID NO), designs of these, as well as specific oligonucleotide compounds (indicated by CMP ID NO) designed based on the motif sequence.
In the examples, the compounds used have the following structure - Captial letters represents beta-D-oxy LNA nucleosides; all LNA cytosines are 5-methyl cytosine; lower case letters represent DNA nucleosides; all internucleoside linkages are phosphorothioate internucleoside linkages.

| SEQ ID NO | Motif sequence | Design | CMP ID NO | Oligonucleotide Compound |
|---|---|---|---|---|
| 7 | aagctccataaacaacac | 4-11-3 | 7_1 | AAGCtccataaacaaCAC |
| 8 | ctttaaacatttaaacact | 4-11-4 | 8_1 | CTTTaaacatttaaaCACT |
| 9 | ttccatccttaaatttct | 4-12-2 | 9_1 | TTCCatccttaaatttCT |
| 10 | tgataaatacaatcaccac | 3-12-4 | 10_1 | TGAtaaatacaatcaCCAC |
| 11 | tacattctacctttaac | 2-12-4 | 11_1 | TAcattctaccttTAAC |
| 12 | gctttcaaacattaacatt | 4-11-4 | 12_1 | GCTTtcaaacattaaCATT |
| 13 | atgttcaaactacctttt | 3-11-4 | 13_1 | ATGttcaaactaccTTTT |
| 14 | agatatttacactaatta | 4-10-4 | 14_1 | AGATatttacactaATTA |
| 15 | gacttcactattaacca | 3-11-3 | 15_1 | GACttcactattaaCCA |
| 16 | cctgtaaattccacatat | 4-12-2 | 16_1 | CCTGtaaattccacatAT |
| 17 | tgacactatctcttcc | 3-11-2 | 17_1 | TGAcactatctcttCC |
| 18 | caataacacataccccta | 3-12-3 | 18_1 | CAAtaacacatacccCTA |
| 19 | gtttcaactttaattcta | 3-11-4 | 19_1 | GTTtcaactttaatTCTA |
| 20 | agcttccttacacatta | 3-12-2 | 20_1 | AGCttccttacacatTA |
| 21 | atctttattatttctactta | 3-13-4 | 21_1 | ATCtttattatttctaCTTA |
| 22 | atcccttcaactacaata | 4-12-2 | 22_1 | ATCCcttcaactacaaTA |
| 23 | ttcctactttccataatc | 4-12-2 | 23_1 | TTCCtactttccataaTC |
| 24 | cttgatttcctactttcc | 2-14-2 | 24_1 | CTtgatttcctactttCC |
| 25 | gacatatacactcaaataa | 4-11-4 | 25_1 | GACAtatacactcaaATAA |
| 26 | ttcttcacttatcttccat | 1-15-3 | 26_1 | Ttcttcacttatcttccat |
| 27 | tcagtcttcacactacc | 2-13-2 | 27_1 | TCagtcttcacactaCC |
| 28 | cttctcttttattaccaa | 4-11-3 | 28_1 | CTTCtcttttattacCAA |
| 29 | gtgtccatactttacc | 1-11-4 | 29_1 | GtgtccatactttTACC |
| 30 | tcttcgctatcctcat | 2-11-3 | 30_1 | TCttcgctatcctCAT |
| 31 | aatctttaatatcttcttc | 4-11-4 | 31_1 | AATCtttaatatcttCTTC |
| 32 | ccaagaccacaattttat | 3-11-4 | 32_1 | CCAagaccacaattTTAT |
| 33 | ccaagttcatactctca | 3-12-2 | 33_1 | CCAagttcatactctCA |
| 34 | atcatactacatttccca | 4-12-2 | 34_1 | ATCAtactacatttccCA |
| 35 | tgtttacatatctcacc | 2-11-4 | 35_1 | TGtttacatatctCACC |
| 36 | ccatcacacccatatataa | 3-14-2 | 36_1 | CCAtcacacccatatatAA |
| 37 | tcctgaaacctctatca | 3-12-2 | 37_1 | TCCtgaaacctctatCA |

TABLE 7-continued

Compound List
List of oligonucleotide motif sequences (indicated by SEQ ID NO), designs of these, as well as specific oligonucleotide compounds (indicated by CMP ID NO) designed based on the motif sequence.
In the examples, the compounds used have the following structure - Captial letters represents beta-D-oxy LNA nucleosides; all LNA cytosines are 5-methyl cytosine; lower case letters represent DNA nucleosides; all internucleoside linkages are phosphorothioate internucleoside linkages.

| SEQ ID NO | Motif sequence | Design | CMP ID NO | Oligonucleotide Compound |
|---|---|---|---|---|
| 38 | ttttcttctaattctttcca | 1-16-3 | 38_1 | TtttcttctaattctttCCA |
| 39 | cctaatttccttcatattc | 2-13-4 | 39_1 | CCtaatttccttcatATTC |
| 40 | tatttgacaactatcct | 3-10-4 | 40_1 | TATttgacaactaTCCT |
| 41 | catcagtcctctattat | 2-11-4 | 41_1 | CAtcagtcctctaTTAT |
| 42 | gtctccattacaaaattaa | 3-12-4 | 42_1 | GTCtccattacaaaaTTAA |
| 43 | tagtatttcattccaaat | 4-10-4 | 43_1 | TAGTatttcattccAAAT |
| 44 | tgaatccatcataatcta | 3-11-4 | 44_1 | TGAatccatcataaTCTA |
| 45 | ttacatgatcccctaa | 3-9-4 | 45_1 | TTAcatgatcccCTAA |
| 46 | atgttaccaaattttcac | 4-10-4 | 46_1 | ATGTtaccaaattttTCAC |
| 47 | aaacacagccaatcca | 4-9-3 | 47_1 | AAACacagccaatCCA |
| 48 | agtttatttaccctcct | 1-15-2 | 48_1 | AgtttatttaccctcCT |
| 49 | gcatcacttcaaactatac | 3-13-3 | 49_1 | GCAtcacttcaaactaTAC |
| 50 | tcccttttcctaattcaa | 3-13-2 | 50_1 | TCCcttttcctaattcAA |
| 51 | aaacaactatcactcttcc | 4-12-3 | 51_1 | AAACaactatcactctTCC |
| 52 | cagacatctctacctcaa | 2-13-3 | 52_1 | CAgacatctctacctCAA |
| 53 | tgattccactttaacata | 3-11-4 | 53_1 | TGAttccactttaaCATA |
| 54 | atacccaacaattcccca | 1-15-2 | 54_1 | AtacccaacaattcccCA |
| 55 | tattcacatttaaatatact | 3-13-4 | 55_1 | TATtcacatttaaataTACT |
| 56 | acaaagaccctaaactac | 4-10-4 | 56_1 | ACAAagaccctaaaCTAC |
| 57 | atatacttcataacttcaaa | 4-12-4 | 57_1 | ATATacttcataacttCAAA |
| 58 | tacataactcatttcctc | 4-14-2 | 58_1 | TACAtataactcatttccTC |
| 59 | tcagaacttactacatat | 4-10-4 | 59_1 | TCAGaacttactacATAT |
| 60 | ttttctatacttcaaacaat | 4-12-4 | 60_1 | TTTTctatacttcaaaCAAT |
| 61 | aacacccaatttacaaacca | 1-16-3 | 61_1 | AacacccaatttacaaaCCA |
| 62 | cttagataacacccaat | 4-9-4 | 62_1 | CTTAgataacaccCAAT |
| 63 | tatttcttctttaaatccat | 2-14-4 | 63_1 | TAtttcttctttaaatCCAT |
| 64 | tccacatacttttaact | 4-9-4 | 64_1 | TCCAcatactttAACT |
| 65 | atgtttatcaccaaaatt | 4-10-4 | 65_1 | ATGTttatcaccaaAATT |
| 66 | ctgaaatactaccatata | 4-10-4 | 66_1 | CTGAaatactaccaTATA |
| 67 | agatttcacaaaactata | 3-11-4 | 67_1 | AGAtttcacaaaacTATA |
| 68 | cgaaattaatctcaaccca | 1-14-4 | 68_1 | CgaaattaatctcaaCCCA |
| 69 | taatacctatcctattccca | 3-15-2 | 69_1 | TAAtacctatcctattccCA |
| 70 | gtaacatatctttaccat | 2-12-4 | 70_1 | GTaacatatctttaCCAT |
| 71 | tttaatcataccaatct | 4-9-4 | 71_1 | TTTAatcataccaATCT |

TABLE 7-continued

Compound List
List of oligonucleotide motif sequences (indicated by SEQ ID NO), designs of these,
as well as specific oligonucleotide compounds (indicated by CMP ID NO)
designed based on the motif sequence.
In the examples, the compounds used have the following structure - Captial
letters represents beta-D-oxy LNA nucleosides; all LNA cytosines are
5-methyl cytosine; lower case letters represent DNA nucleosides;
all internucleoside linkages are phosphorothioate internucleoside linkages.

| SEQ ID NO | Motif sequence | Design | CMP ID NO | Oligonucleotide Compound |
|---|---|---|---|---|
| 72 | atgctaccaaaatctta | 4-9-4 | 72_1 | ATGCtaccaaaatCTTA |
| 73 | ctcaaataaattaatctct | 4-11-4 | 73_1 | CTCAaataaattaatCTCT |
| 74 | ttcttatttcaaatctca | 4-10-4 | 74_1 | TTCTtatttcaaatCTCA |
| 75 | tcttatttcaaatctca | 4-9-4 | 75_1 | TCTTatttcaaatCTCA |
| 76 | atactattcttatttcaaat | 4-12-4 | 76_1 | ATACtattcttatttcAAAT |
| 77 | gtatctaatattttcata | 4-10-4 | 77_1 | GTATctaatattttCATA |
| 78 | ttttactccaccatctcaa | 1-15-3 | 78_1 | TtttactccaccatctCAA |
| 79 | taacagtcttttactc | 4-9-4 | 79_1 | TAACagtcttttACTC |
| 80 | tagtaactttaatcactt | 4-10-4 | 80_1 | TAGTaactttaatcACTT |
| 81 | tagtaatattacctt | 4-8-4 | 81_1 | TAGTaatattacCTTT |
| 82 | actataacagtctac | 4-7-4 | 82_1 | ACTAtaacagtCTAC |
| 83 | tgcccaaacatattca | 2-12-4 | 83_1 | TGcccaaacatattTTCA |
| 84 | ctactacataatataaaca | 4-11-4 | 84_1 | CTACtacataatataAACA |
| 85 | gtcatacacaactacaa | 4-9-4 | 85_1 | GTCAtacacaactACAA |
| 86 | tcgttttccatattat | 4-9-4 | 86_1 | TCGTttttccataTTAT |
| 87 | atactacttttaatttaata | 4-12-4 | 87_1 | ATACtactttaatttAATA |
| 88 | ctcatttcactcacttaaat | 4-14-2 | 88_1 | CTCAtttcactcacttaaAT |
| 89 | tatgaaaccaaatcct | 3-9-4 | 89_1 | TATgaaaccaaaTCCT |
| 90 | catagccatcttcttta | 2-11-4 | 90_1 | CAtagccatcttcTTTA |
| 91 | caacacgtacccta | 1-10-4 | 91_1 | CaacacgtaccCCTA |
| 92 | agtcacttctattact | 1-11-4 | 92_1 | AgtcacttctatTACT |
| 93 | cttttcttcatacactata | 1-14-4 | 93_1 | CttttcttcatacacTATA |
| 94 | accccacttaacccaa | 2-11-3 | 94_1 | ACcccacttaaccCAA |
| 95 | acagaaatcctattccca | 3-13-2 | 95_1 | ACAgaaatcctattccCA |
| 96 | ctacttgccacaatccc | 1-14-2 | 96_1 | CtacttgccacaatcCC |
| 97 | attcagacccttacaa | 4-9-3 | 97_1 | ATTCagacccttaCAA |
| 98 | cattactcacacctt | 3-9-4 | 98_1 | CATtactcacacCTTT |
| 99 | cccataagtacccatct | 1-14-2 | 99_1 | CccataagtacccatCT |
| 100 | atctatttgctcccat | 3-10-3 | 100_1 | ATCtatttgctccCAT |
| 101 | ctctgtaccatctatt | 1-11-4 | 101_1 | CtctgtaccatcTATT |
| 102 | gcaaataacaaaatctct | 4-10-4 | 102_1 | GCAAataacaaaatCTCT |
| 103 | ccttttatcttcattct | 3-12-2 | 103_1 | CCTtttatcttcattCT |
| 104 | tgacaatttcaaaactca | 2-12-4 | 104_1 | TGacaatttcaaaaCTCA |
| 105 | cctagtttacaccct | 3-10-2 | 105_1 | CCTagtttacaccCT |

TABLE 7-continued

Compound List
List of oligonucleotide motif sequences (indicated by SEQ ID NO), designs of these, as well as specific oligonucleotide compounds (indicated by CMP ID NO) designed based on the motif sequence.
In the examples, the compounds used have the following structure - Capital letters represents beta-D-oxy LNA nucleosides; all LNA cytosines are 5-methyl cytosine; lower case letters represent DNA nucleosides; all internucleoside linkages are phosphorothioate internucleoside linkages.

| SEQ ID NO | Motif sequence | Design | CMP ID NO | Oligonucleotide Compound |
|---|---|---|---|---|
| 106 | tttcctagttcacatt | 4-8-4 | 106_1 | TTTCctagttcaCATT |
| 107 | aactgcaatcactcat | 3-9-4 | 107_1 | AACtgcaatcacTCAT |
| 108 | atctacagttttccac | 4-9-3 | 108_1 | ATCTacagttttcCAC |
| 109 | gcttctctcatctaca | 2-12-2 | 109_1 | GCttctctcatctaCA |
| 110 | agaatacttctctcctt | 1-12-4 | 110_1 | Agaatacttctctccttt |
| 111 | tcacatacgttcttc | 4-7-4 | 111_1 | TCACatacgttCTTC |
| 112 | taaaatgtccacatatc | 4-9-4 | 112_1 | TAAAatgtccacaTATC |
| 113 | gatttctaaacccttcaat | 3-12-4 | 113_1 | GATttctaaacccttCAAT |
| 114 | tacatttccaattttata | 4-10-4 | 114_1 | TACAtttccaatttTATA |
| 115 | tagcttctttattttc | 3-10-4 | 115_1 | TAGctttctttatTTTC |
| 116 | tagtctactctcctaa | 2-10-4 | 116_1 | TAgtctactctcCTAA |
| 117 | tatgcctacaatatac | 4-8-4 | 117_1 | TATGcctacaatATAC |
| 118 | atgaacaacaactcccatt | 2-13-4 | 118_1 | ATgaacaacaactccCATT |
| 119 | ccatctaccttataacat | 3-12-3 | 119_1 | CCAtctaccttataaCAT |
| 120 | cctgcatttactatcca | 2-13-2 | 120_1 | CCtgcatttactatcCA |
| 121 | attagaacccttaca | 3-9-4 | 121_1 | ATTagaacccttTACA |
| 122 | atagaatccttacata | 4-8-4 | 122_1 | ATAGaatccttaCATA |
| 123 | ctgatttactccaat | 4-8-4 | 123_1 | CTGAttttactcCAAT |
| 124 | ctaaatgattcccaat | 4-8-4 | 124_1 | CTAAatgattccCAAT |
| 125 | tacttgatcttcctaca | 4-11-2 | 125_1 | TACTtgatcttcctaCA |
| 126 | tcatcatataaactccat | 3-11-4 | 126_1 | TCAtcatataaactCCAT |
| 127 | caccatgttctttaca | 4-10-2 | 127_1 | CACCatgttctttaCA |
| 128 | ctactcttcatctcaaca | 1-13-4 | 128_1 | Ctactcttcatctcaaca |
| 129 | caacaactcatttcat | 4-8-4 | 129_1 | CAACaactcattTCAT |
| 130 | cctctttgaacaaacca | 2-12-3 | 130_1 | CCtctttgaacaaaCCA |
| 131 | cctttttactctaccttt | 1-11-4 | 131_1 | CcttttactctaCCTT |
| 132 | tcagcttatttacatta | 4-9-4 | 132_1 | TCAGcttatttacATTA |
| 133 | tgctttacattcacaac | 3-10-4 | 133_1 | TGCtttacattcaCAAC |
| 134 | ggcttttaccttacat | 4-10-2 | 134_1 | GGCTtttaccttacAT |
| 135 | acacgatttcatacaatc | 4-10-4 | 135_1 | ACACgatttcatacAATC |
| 136 | atgttttcaacttcaac | 4-9-4 | 136_1 | ATGTtttcaacttCAAC |
| 137 | gaatacccatttcaccc | 3-12-2 | 137_1 | GAAtacccatttcacCC |
| 138 | cctatgtctaaattttc | 4-9-4 | 138_1 | CCTAtgtctaaatTTTC |
| 139 | tttatctatctatcttat | 4-10-4 | 139_1 | TTTAtctatctatcTTAT |

TABLE 7-continued

Compound List
List of oligonucleotide motif sequences (indicated by SEQ ID NO), designs of these, as well as specific oligonucleotide compounds (indicated by CMP ID NO) designed based on the motif sequence.
In the examples, the compounds used have the following structure - Captial letters represents beta-D-oxy LNA nucleosides; all LNA cytosines are 5-methyl cytosine; lower case letters represent DNA nucleosides; all internucleoside linkages are phosphorothioate internucleoside linkages.

| SEQ ID NO | Motif sequence | Design | CMP ID NO | Oligonucleotide Compound |
|---|---|---|---|---|
| 140 | cactgtcattacatta | 4-8-4 | 140_1 | CACTgtcattacATTA |
| 141 | cctgaactcctacaatc | 2-11-4 | 141_1 | CCtgaactcctacAATC |
| 142 | tccctaaaattactta | 4-8-4 | 142_1 | TCCCtaaaattaCTTA |
| 143 | attaattccctaaaattac | 4-11-4 | 143_1 | ATTAattccctaaaTTAC |
| 144 | tcggctctaaccaca | 3-9-3 | 144_1 | TCGgctctaaccACA |
| 145 | tacatgaaacacatact | 4-9-4 | 145_1 | TACAtgaaacacaTACT |
| 146 | catttgacctttatcaa | 4-9-4 | 146_1 | CATTtgacctttaTCAA |
| 147 | tccctaaaacattcata | 4-10-3 | 147_1 | TCCCtaaaacattcATA |
| 148 | attttgcacacctcaca | 2-13-2 | 148_1 | ATtttgcacacctcaCA |
| 149 | ttaatacctactcttc | 4-8-4 | 149_1 | TTAAtacctactCTTC |
| 150 | caaagctaccaaaatct | 4-9-4 | 150_1 | CAAAgctaccaaaATCT |
| 151 | tgtatttcaaatctcaaa | 4-10-4 | 151_1 | TGTAtttcaaatctCAAA |
| 152 | ctgtatttcaaatctca | 3-10-4 | 152_1 | CTGtatttcaaatCTCA |
| 153 | cccacatccttttacac | 2-13-2 | 153_1 | CCcacatccttttacAC |
| 154 | cccacatccttttaca | 2-12-2 | 154_1 | CCcacatccttttaCA |
| 155 | atgtactaattttcttt | 4-9-4 | 155_1 | ATGTactaattttCTTT |
| 156 | ccacactgtatcttca | 3-11-2 | 156_1 | CCAcactgtatcttCA |
| 157 | agcatacaaaatatcc | 4-8-4 | 157_1 | AGCAtacaaaatATCC |
| 158 | aaatcattttccaactct | 3-11-4 | 158_1 | AAAtcattttccaaCTCT |
| 159 | aaccatgtttccctaca | 3-12-2 | 159_1 | AACcatgtttccctaCA |
| 160 | ttcctatcataaccat | 4-9-3 | 160_1 | TTCCtatcataacCAT |
| 161 | attcttgttcctatca | 4-10-2 | 161_1 | ATTCttgttcctatCA |
| 162 | ttgaataagtggatgt | 3-10-3 | 162_1 | TTGaataagtggaTGT |
| 163 | ccaaatcttataataactac | 1-1-3-10-2-1-2 | 163_1 | CcAAAtcttataataACtAC |
| 164 | cgtaaactaccctat | 2-10-4 | 164_1 | CGtaaactaccCTAT |

Motif sequences represent the contiguous sequence of nucleobases present in the oligonucleotide.

Designs refer to the oligonucleotide design, e.g. gapmer design, F-G-F'. In classic gapmer design e.g. 3-10-3 all the nucleotides in the flanks (F and F') are constituted of the same 2'-sugar modified nucleoside, e.g. LNA, cET, or MOE, and a stretch of DNA in the middle forming the gap (G). In gapmers with alternating flank designs the flanks of oligonucleotide is annotated as a series of integers, representing a number of 2' sugar modified nucleosides (M) followed by a number of DNA nucleosides (D). For example a flank with a 2-2-1 motif represents 5' $[M]_2$-$[D]_2$-$[M]$ 3' and a 1-1-1-1-1 motif represents 5' $[M]$-$[D]$-$[M]$-$[D]$-$[M]$ 3'. Both flanks have a 2' sugar modified nucleoside at the 5' and 3' terminal. The gap region (G), is constituted of a number of DNA nucleosides (typically between 5 and 16), located between the flanks.

Oligonucleotide compounds represent specific designs of a motif sequence. Capital letters represent beta-D-oxy LNA nucleosides, lowercase letters represent DNA nucleosides, all LNA C are 5-methyl cytosine, all internucleoside linkages are phosphorothioate internucleoside linkages.

TABLE 8

Motif List

List of oligonucleotide motif sequences (indicated by SEQ ID NO), of the compounds used in the examples, and their target sequence and location on their nucleic acid target/target sequence (SEQ ID NO 1-6), as indicated. Motif sequences represent the contiguous sequences of nucleobases present in the oligonucleotide in the 5' to 3' direction. The RNA target sequence is the complementary sequence of the motif sequence, also in the 5' to 3' direction.

| SEQ ID NO | RNA TARGET SEQUENCE Note DNA version is shown (U→T) | RNA SEQ ID | SEQ ID NO 1 start | SEQ ID NO 1 stop | SEQ ID NO 2 start | SEQ ID NO 2 stop | SEQ ID NO 3 start | SEQ ID NO 3 stop | SEQ ID NO 4 start | SEQ ID NO 4 stop | SEQ ID NO 5 start | SEQ ID NO 5 stop | SEQ ID NO 6 start | SEQ ID NO 6 stop |
|---|---|---|---|---|---|---|---|---|---|---|---|---|---|---|
| 7 | aagtccataaacacac | 167 | 546 | 563 | | | 565 | 582 | | | | | | |
| 8 | ctttaaacatttaaacact | 168 | 2122 | 2140 | | | 2186 | 2204 | | | | | | |
| 9 | ttccatcctaaatttct | 169 | 2143 | 2160 | | | 2207 | 2224 | | | | | | |
| 10 | tgataaatacaatcaccac | 170 | 2165 | 2183 | | | 2227 | 2245 | | | | | | |
| 11 | tacattctaccttttaac | 171 | 2300 | 2317 | | | 2362 | 2379 | | | | | | |
| 12 | gctttcaaacattaacatt | 172 | 2392 | 2410 | | | 2454 | 2472 | | | | | | |
| 13 | atgttcaaactacctttt | 173 | 2548 | 2565 | | | 2596 | 2613 | | | | | | |
| 14 | agatatttacactaatta | 174 | 3507 | 3524 | | | 3564 | 3581 | | | | | | |
| 15 | gacttcactattaacca | 175 | 3678 | 3694 | 489 | 505 | 3735 | 3751 | 314 | 330 | | | | |
| 16 | cctgtaaattccacatat | 176 | 3736 | 3753 | 547 | 564 | 3793 | 3810 | 372 | 389 | | | | |
| 17 | tgacactactcctcc | 177 | 3752 | 3767 | 563 | 578 | 3809 | 3824 | 388 | 403 | | | | |
| 18 | caataacacataccccta | 178 | 3802 | 3819 | | | 3859 | 3876 | | | | | | |
| 19 | gttcaacttaattcta | 179 | 3908 | 3925 | | | 3968 | 3985 | | | | | | |
| 20 | agcttccttacacatta | 180 | 4321 | 4337 | | | 4382 | 4398 | | | | | | |
| 21 | atctttatttctactta | 181 | 4701 | 4720 | | | 4772 | 4791 | | | | | | |
| 22 | atcccttcaactacaata | 182 | 4948 | 4965 | | | 4999 | 5016 | | | | | | |
| 23 | ttcctactttccataatc | 183 | 5063 | 5080 | | | 5114 | 5131 | | | | | | |
| 24 | cttgattcctactttcc | 184 | 5069 | 5086 | | | 5120 | 5137 | | | | | | |
| 25 | gacatatacactcaaataa | 185 | 5172 | 5190 | | | 5226 | 5244 | | | | | | |
| 26 | ttcttcacttatcttccat | 186 | 5512 | 5530 | | | 5563 | 5581 | | | 2166 | 2181 | 477 | 492 |

TABLE 8-continued

Motif List

List of oligonucleotide motif sequences (indicated by SEQ ID NO), of the compounds used in the examples, and their target sequence and location on their nucleic acid target/target sequence (SEQ ID NO 1-6), as indicated. Motif sequences represent the contiguous sequences of nucleobases present in the oligonucleotide in the 5' to 3' direction. The RNA target sequence is the complementary sequence of the motif sequence, also in the 5' to 3' direction.

| SEQ ID NO | RNA TARGET SEQUENCE Note DNA version is shown (U→T) | RNA SEQ ID | SEQ ID NO 1 start | SEQ ID NO 1 stop | SEQ ID NO 2 start | SEQ ID NO 2 stop | SEQ ID NO 3 start | SEQ ID NO 3 stop | SEQ ID NO 4 start | SEQ ID NO 4 stop | SEQ ID NO 5 start | SEQ ID NO 5 stop | SEQ ID NO 6 start | SEQ ID NO 6 stop |
|---|---|---|---|---|---|---|---|---|---|---|---|---|---|---|
| 27 | tcagtcttcacactacc | 187 | 5583 | 5599 | | | 5634 | 5650 | | | | | | |
| 28 | cttctcttttattaccaa | 188 | 6015 | 6032 | | | 6070 | 6087 | | | | | | |
| 29 | gtgtccatatcttacc | 189 | 6032 | 6047 | | | 6087 | 6102 | | | | | | |
| 30 | tcttcgtatcctcat | 190 | 6125 | 6140 | | | 6179 | 6194 | | | | | | |
| 31 | aatctttaatatctcttc | 191 | 6136 | 6154 | | | 6190 | 6208 | | | | | | |
| 32 | ccaagaccacaatttat | 192 | 6172 | 6189 | | | 6226 | 6243 | | | | | | |
| 33 | ccaagttcatactctca | 193 | 6200 | 6216 | | | 6254 | 6270 | | | | | | |
| 34 | atcatactacatttccca | 194 | 6214 | 6231 | | | 6268 | 6285 | | | | | | |
| 35 | tgtttacatatctcacc | 195 | 6401 | 6417 | | | 6446 | 6462 | | | | | | |
| 36 | ccatcacaccccatataa | 196 | 6458 | 6476 | | | 6513 | 6531 | | | | | | |
| 37 | tcctgaaacctctatca | 197 | 6837 | 6853 | | | 6885 | 6901 | | | | | | |
| 38 | tttctctaattcttcca | 198 | 8453 | 8472 | | | 8520 | 8539 | | | | | | |
| 39 | cctaattccttcatattc | 199 | 8983 | 9001 | | | 9054 | 9072 | | | | | | |
| 40 | tatttgacaactatcct | 200 | 9533 | 9549 | | | 9604 | 9620 | | | | | | |
| 41 | catcagtcctctattat | 201 | 9628 | 9644 | | | 9699 | 9715 | | | | | | |
| 42 | gtctccattacaaaattaa | 202 | 11065 | 11083 | | | 11221 | 11239 | | | | | | |
| 43 | tagtatttcattccaaat | 203 | 11117 | 11134 | | | 11273 | 11290 | | | | | | |
| 44 | tgaatccatcataatcta | 204 | 11264 | 11281 | | | | | | | | | | |
| 45 | ttacatgatcccctaa | 205 | 12310 | 12325 | | | 9869 | 9886 | | | | | | |
| 46 | atgttaccaaatttcac | 206 | 12870 | 12887 | | | 13084 | 13101 | | | | | | |

TABLE 8-continued

Motif List

List of oligonucleotide motif sequences (indicated by SEQ ID NO), of the compounds used in the examples, and their target sequence and location on their nucleic acid target/target sequence (SEQ ID NO 1-6), as indicated. Motif sequences represent the contiguous sequences of nucleobases present in the oligonucleotide in the 5' to 3' direction. The RNA target sequence is the complementary sequence of the motif sequence, also in the 5' to 3' direction.

| SEQ ID NO | RNA TARGET SEQUENCE Note DNA version is shown (U→T) | RNA SEQ ID | SEQ ID NO 1 start | SEQ ID NO 1 stop | SEQ ID NO 2 start | SEQ ID NO 2 stop | SEQ ID NO 3 start | SEQ ID NO 3 stop | SEQ ID NO 4 start | SEQ ID NO 4 stop | SEQ ID NO 5 start | SEQ ID NO 5 stop | SEQ ID NO 6 start | SEQ ID NO 6 stop |
|---|---|---|---|---|---|---|---|---|---|---|---|---|---|---|
| 47 | aaacacagcaatca | tggatggctgtgtt | 207 | 13050 | 13065 | | | | | | | 8394 | 8409 | 641 | 656 |
| 48 | agtttattttaccccct | aggaggtaaataaact | 208 | 13397 | 13414 | | | 13604 | 13621 | | | | | | |
| 49 | gcatcacttcaaactatac | gtatagtttgaagtgatgc | 209 | 15061 | 15079 | | | 15198 | 15216 | | | | | | |
| 50 | tccctttcctaattcaa | ttgaattaggaaaggga | 210 | 15249 | 15266 | | | 15386 | 15403 | | | | | | |
| 51 | aaacaactatcactcttcc | ggaagagtgatagtgttt | 211 | 15318 | 15336 | | | 15455 | 15473 | | | | | | |
| 52 | cagacatctctacctcaa | ttgaggtagagatgtctg | 212 | 15368 | 15385 | | | | | | | | | | |
| 53 | tgattccactttaacata | tatgttaaagtggaatca | 213 | 15440 | 15457 | | | 15577 | 15594 | | | | | | |
| 54 | atacccaacaattcccca | tggggaattgttgggtat | 214 | 15632 | 15649 | | | 15774 | 15791 | | | | | | |
| 55 | tattcacatttaaatatact | agtatattaaatgtgaata | 215 | 15823 | 15842 | | | 15957 | 15976 | | | | | | |
| 56 | acaaagaccctaactac | gtagttagggtcttgt | 216 | 16496 | 16513 | | | 16621 | 16638 | | | | | | |
| 57 | atatacttcataacttcaa | tttgaagttatgaagtatat | 217 | 19090 | 19109 | | | 19322 | 19341 | | | | | | |
| 58 | tacataactaactcatttcctc | gaggaaatgagttatatgta | 218 | 19198 | 19217 | 1013 | 1032 | 19432 | 19451 | 838 | 857 | | | | |
| 59 | tcagaactactacatat | atatgtagtagttctga | 219 | 19211 | 19228 | | | 19445 | 19462 | | | | | | |
| 60 | tttctatacttcaaacaat | attgtttgaagtatagaaaa | 220 | 19699 | 19718 | | | 19935 | 19954 | | | | | | |
| 61 | aacacccaatttacaaacca | tggttgtaaattgggtgtt | 221 | 20217 | 20236 | | | 20470 | 20489 | | | | | | |
| 62 | cttgataacaccccaat | attgggtgtatctaag | 222 | 20227 | 20243 | | | 20480 | 20496 | | | | | | |
| 63 | tatttcttcttaaatccat | atggatttaaagaagaata | 223 | 20767 | 20786 | 1238 | 1257 | 21018 | 21037 | 1063 | 1082 | | | | |
| 64 | tccacatacttttact | agtaaaagtatgtga | 224 | 20880 | 20896 | 1351 | 1367 | 21136 | 21152 | 1181 | 1197 | | | | |
| 65 | atgtttatcaccaaaatt | aatttggtgataaacat | 225 | 21084 | 21101 | 1555 | 1572 | 21340 | 21357 | 1385 | 1402 | | | | |
| 66 | ctgaaatactaccatata | tatatggtagtatttcag | 226 | 21214 | 21231 | 1685 | 1702 | 21467 | 21484 | 1512 | 1529 | | | | |
| 67 | agatttcacaaactata | tatagtttgtgaatct | 227 | 21425 | 21442 | 1896 | 1913 | 21674 | 21691 | 1719 | 1736 | | | | |

TABLE 8-continued

Motif List

List of oligonucleotide motif sequences (indicated by SEQ ID NO), of the compounds used in the examples, and their target sequence and location on their nucleic acid target/target sequence (SEQ ID NO 1-6), as indicated. Motif sequences represent the contiguous sequences of nucleobases present in the oligonucleotide in the 5' to 3' direction. The RNA target sequence is the complementary sequence of the motif sequence, also in the 5' to 3' direction.

| SEQ ID NO | RNA TARGET SEQUENCE Note DNA version is shown (U→T) | RNA SEQ ID | SEQ ID NO 1 start | SEQ ID NO 1 stop | SEQ ID NO 2 start | SEQ ID NO 2 stop | SEQ ID NO 3 start | SEQ ID NO 3 stop | SEQ ID NO 4 start | SEQ ID NO 4 stop | SEQ ID NO 5 start | SEQ ID NO 5 stop | SEQ ID NO 6 start | SEQ ID NO 6 stop |
|---|---|---|---|---|---|---|---|---|---|---|---|---|---|---|
| 68 | cgaaattaatctcaaccca | tgggttgagattaatttcg | 228 | 22110 | 22128 | 2581 | 2599 | | | | | | | | |
| 69 | taatacctatcctattccca | tgggataggataggtatta | 229 | 23374 | 23393 | 3845 | 3864 | 23992 | 24011 | | | | | | |
| 70 | gtaacatatcttaccat | atggtaagatatgttac | 230 | 23435 | 23452 | 3906 | 3923 | 24053 | 24070 | | | | | | |
| 71 | tttaatcataccaatct | agattgtatgattaaa | 231 | 23806 | 23822 | 4277 | 4293 | 24430 | 24446 | | | | | | |
| 72 | atgctaccaaaatttta | taagatttggtagcat | 232 | 23874 | 23890 | 4345 | 4361 | 24498 | 24514 | | | | | | |
| 73 | ctcaaataattaatctct | agagattaatttattgag | 233 | 24045 | 24063 | 4516 | 4534 | | | | | | | | |
| 74 | ttcttattcaaatctca | tgagattgaaataagaa | 234 | 24060 | 24077 | 4531 | 4548 | | | | | | | | |
| 75 | tcttattcaaatctca | tgagattgaaataaga | 235 | 24060 | 24076 | 4531 | 4547 | | | | | | | | |
| 76 | atactattcttatttcaaat | atttgaaataagaatagtat | 236 | 24064 | 24083 | 4535 | 4554 | 24675 | 24694 | | | | | | |
| 77 | gtatctaatattttcata | tatgaaaatattagatac | 237 | 24081 | 24098 | 4552 | 4569 | 24692 | 24709 | | | | | | |
| 78 | ttttactccaccatccaa | ttgagatggtggagtaaaa | 238 | 24801 | 24819 | 5272 | 5290 | 25418 | 25436 | | | | | | |
| 79 | taacagtctttttactc | gagtaaaaagactgtta | 239 | 24812 | 24828 | 5283 | 5299 | 25429 | 25445 | | | | | | |
| 80 | tagtaacttttaatcactt | aagtgattaaaagttacta | 240 | 25050 | 25067 | 5521 | 5538 | 25666 | 25683 | | | | | | |
| 81 | tagtaatattacctt | aaaggtaattacta | 241 | 25372 | 25387 | 5843 | 5858 | 25984 | 25999 | | | 18910 | 18925 | | |
| 82 | actataacagtctac | gtagactgttatagt | 242 | 25392 | 25406 | 5863 | 5877 | | | | | | | | |
| 83 | tgcccaaacatatttca | tgaaaatatgtttgggca | 243 | 25773 | 25790 | 6244 | 6261 | 26388 | 26405 | | | | | | |
| 84 | ctactacataataaaca | tgtttatattatgtagtag | 244 | 25796 | 25814 | 6267 | 6285 | 26411 | 26429 | | | | | | |
| 85 | ggtcatacaaactacaa | ttgtagttgtgtatgac | 245 | 25969 | 25985 | 6440 | 6456 | 26583 | 26599 | | | | | | |
| 86 | tcgttttccatattat | ataatgaaaacga | 246 | 29351 | 29367 | | | | | | | | | | |
| 87 | atactacttttaattaata | tattaaattaaagtagtat | 247 | | | | | | | | | 1336 | 1355 | 5466 | 5481 |

TABLE 8-continued

Motif List

List of oligonucleotide motif sequences (indicated by SEQ ID NO), of the compounds used in the examples, and their target sequence and location on their nucleic acid target/target sequence (SEQ ID NO 1-6), as indicated. Motif sequences represent the contiguous sequences of nucleobases present in the oligonucleotide in the 5' to 3' direction. The RNA target sequence is the complementary sequence of the motif sequence, also in the 5' to 3' direction.

| SEQ ID NO | RNA TARGET SEQUENCE Note DNA version is shown (U→T) | RNA SEQ ID | SEQ ID NO 1 start | SEQ ID NO 1 stop | SEQ ID NO 2 start | SEQ ID NO 2 stop | SEQ ID NO 3 start | SEQ ID NO 3 stop | SEQ ID NO 4 start | SEQ ID NO 4 stop | SEQ ID NO 5 start | SEQ ID NO 5 stop | SEQ ID NO 6 start | SEQ ID NO 6 stop |
|---|---|---|---|---|---|---|---|---|---|---|---|---|---|---|
| 88 | ctcattcactcactaaat atttaagtgagtgaaatgag | 248 | | | | | | | | | 1555 | 1574 | | |
| 89 | tatgaaccaatcct aggattggtttcata | 249 | | | | | | | | | 1795 | 1810 | | |
| 90 | catagccactctctta taaagaagatggctatg | 250 | | | | | | | | | 2039 | 2055 | 350 | 366 |
| 91 | caacacgtacccta taggggtacgtgttg | 251 | | | | | | | | | 2216 | 2230 | | |
| 92 | agtcacttctattact agtaatagaagtgact | 252 | | | | | | | | | 2383 | 2398 | | |
| 93 | ctttctttcatacactata tatagtgtatgaagaaaag | 253 | | | | | | | | | 2606 | 2624 | | |
| 94 | accccacttaaccaa ttgggttaagtggggt | 254 | | | | | | | | | 2851 | 2866 | | |
| 95 | acagaaatcctattccca tgggataggattctgt | 255 | | | | | | | | | 2961 | 2978 | | |
| 96 | ctacttgcacaatccc gggattgtgcaagtag | 256 | | | | | | | | | 3033 | 3049 | | |
| 97 | attcagacccttacaa ttgtaagggtctgaat | 257 | | | | | | | | | 3242 | 3257 | | |
| 98 | cattactcacacctt aaaggtgtgagtaatg | 258 | | | | | | | | | 3918 | 3933 | | |
| 99 | cccataagtaccacct agatgggtacttatggg | 259 | | | | | | | | | 4076 | 4092 | | |
| 100 | atctatttgctcccat atgggacaaatagat | 260 | | | | | | | | | 4088 | 4103 | | |
| 101 | ctctgtaccatctatt aatagatggtacagag | 261 | | | | | | | | | 4097 | 4112 | | |
| 102 | gcaaataacaaaatctct agagattttgttatttgc | 262 | | | | | | | | | 4481 | 4498 | | |
| 103 | cctttatcttcattct agaatgaagataaaagg | 263 | | | | | | | | | 4734 | 4750 | | |
| 104 | tgacaattcaaaactca tgagttttgaaattgtca | 264 | | | | | | | | | 4778 | 4795 | | |
| 105 | cctagttacaccct agggtgtaaactagg | 265 | | | | | | | | | 4800 | 4814 | | |
| 106 | tttcctagttcacatt aatgtgaactaggaaa | 266 | | | | | | | | | 4816 | 4831 | | |
| 107 | aactgcaatcactcat atgagtgattgcagtt | 267 | | | | | | | | | 4831 | 4846 | | |
| 108 | atctacagtttccac gtggaaactgcagat | 268 | | | | | | | | | 4978 | 4993 | | |

TABLE 8-continued

Motif List

List of oligonucleotide motif sequences (indicated by SEQ ID NO), of the compounds used in the examples, and their target sequence and location on their nucleic acid target/target sequence (SEQ ID NO 1-6), as indicated. Motif sequences represent the contiguous sequences of nucleobases present in the oligonucleotide in the 5' to 3' direction. The RNA target sequence is the complementary sequence of the motif sequence, also in the 5' to 3' direction.

| SEQ ID NO | RNA TARGET SEQUENCE Note DNA version is shown (U→T) | RNA SEQ ID | SEQ ID NO 1 start | SEQ ID NO 1 stop | SEQ ID NO 2 start | SEQ ID NO 2 stop | SEQ ID NO 3 start | SEQ ID NO 3 stop | SEQ ID NO 4 start | SEQ ID NO 4 stop | SEQ ID NO 5 start | SEQ ID NO 5 stop | SEQ ID NO 6 start | SEQ ID NO 6 stop |
|---|---|---|---|---|---|---|---|---|---|---|---|---|---|---|
| 109 | gctctctcatctaca | tgtagatgagagaagc | 269 | | | | | | | | | 4987 | 5002 | | |
| 110 | agaatacttctctcctt | aaggagagaagtattct | 270 | | | | | | | | | 5186 | 5202 | | |
| 111 | tcacatacgttcttc | gaagaacgtatgtga | 271 | | | | | | | | | 5350 | 5364 | | |
| 112 | taaaatgtccacatatc | gatatgtggacatttta | 272 | | | | | | | | | 5508 | 5524 | | |
| 113 | gattctaaccctcaat | attgaggggtttagaaatc | 273 | | | | | | | | | 5877 | 5895 | | |
| 114 | tacattccaatttata | tataaattggaaatgta | 274 | | | | | | | | | 5965 | 5982 | | |
| 115 | tagcttctttattttc | gaaaataaagaaagcta | 275 | | | | | | | | | 6439 | 6455 | | |
| 116 | tagtctactcctaa | ttaggagtagacta | 276 | | | | | | | | | 6901 | 6916 | | |
| 117 | tatgcctacaatatac | gtatattgtaggcata | 277 | | | | | | | | | 7356 | 7371 | | |
| 118 | atgaacaacaactcccatt | aatgggagtgtgttcat | 278 | | | | | | | | | 7375 | 7393 | | |
| 119 | ccatctacctataacat | atgttataaggtagatgg | 279 | | | | | | | | | 7602 | 7619 | | |
| 120 | cctgcatttactatcca | tggatgtaaatgcagg | 280 | | | | | | | | | 7823 | 7839 | | |
| 121 | attagaacccttaca | tgtaagggttctaat | 281 | | | | | | | | | 8051 | 8066 | | |
| 122 | atagatcctacata | tatgtaaggattctat | 282 | | | | | | | | | 8322 | 8337 | | |
| 123 | ctgatttactccaat | attggagtaaatcag | 283 | | | | | | | | | 8443 | 8458 | 690 | 705 |
| 124 | ctaaatgattcccaat | attgggaatcattag | 284 | | | | | | | | | 8695 | 8710 | | |
| 125 | tacttgacttcctaca | tgtaggaagatcaagta | 285 | | | | | | | | | 8727 | 8743 | | |
| 126 | tcatcatataaactccat | atggagtttatgatga | 286 | | | | | | | | | 8925 | 8942 | | |
| 127 | caccatgtcctttaca | tgtaaagaacatggtg | 287 | | | | | | | | | 9075 | 9090 | | |
| 128 | ctactcctcatctcaaca | tgttgagatgaagagtag | 288 | | | | | | | | | 9348 | 9365 | | |

TABLE 8-continued

Motif List

List of oligonucleotide motif sequences (indicated by SEQ ID NO), of the compounds used in the examples, and their target sequence and location on their nucleic acid target/target sequence (SEQ ID NO 1-6), as indicated. Motif sequences represent the contiguous sequences of nucleobases present in the oligonucleotide in the 5' to 3' direction. The RNA target sequence is the complementary sequence of the motif sequence, also in the 5' to 3' direction.

| SEQ ID NO | | RNA TARGET SEQUENCE Note DNA version is shown (U→T) | RNA SEQ ID | SEQ ID NO 1 | | SEQ ID NO 2 | | SEQ ID NO 3 | | SEQ ID NO 4 | | SEQ ID NO 5 | | SEQ ID NO 6 | |
|---|---|---|---|---|---|---|---|---|---|---|---|---|---|---|---|
| | | | | start | stop | start | stop | start | stop | start | stop | start | stop | start | stop |
| 129 | caacaactcattcat | atgaatgagtgttg | 289 | | | | | | | | | 9584 | 9599 | | |
| 130 | cctcttgaacaacca | tggttgttcaaagagg | 290 | | | | | | | | | 10182 | 10198 | | |
| 131 | cctttacctcacctt | aaggtagagtaaaagg | 291 | | | | | | | | | 10234 | 10249 | | |
| 132 | tcagcttattacatta | taatgtaaataagctga | 292 | | | | | | | | | 10413 | 10429 | | |
| 133 | tgcttacattcacaac | gttgtgaatgtaaagca | 293 | | | | | | | | | 10775 | 10791 | | |
| 134 | ggctttacctacat | atgtaaggtaaaagcc | 294 | | | | | | | | | 11179 | 11194 | | |
| 135 | acacgattcatacaatc | gattgtatgaaatcgt | 295 | | | | | | | | | 11393 | 11410 | | |
| 136 | atgtttcaacttcaaac | gtttgaagttgaaaacat | 296 | | | | | | | | | 11833 | 11849 | 792 | 808 |
| 137 | gaataccattcaccc | gggtgaaatgggtattc | 297 | | | | | | | | | 11961 | 11977 | | |
| 138 | cctatgtctaaatttc | gaaaatttagacatagg | 298 | | | | | | | | | 12579 | 12595 | | |
| 139 | tttatctatctatcttat | ataagatagatagataaa | 299 | | | | | | | | | 12871 | 12888 | | |
| 140 | cactgtcattacatta | taatgtaatgacagtg | 300 | | | | | | | | | 13583 | 13598 | | |
| 141 | cctgaactcctacaatc | gattgtaggagttcagg | 301 | | | | | | | | | 13875 | 13891 | | |
| 142 | tccctaaaattactta | taagtaattttaggga | 302 | | | | | | | | | 14319 | 14334 | | |
| 143 | attaattccctaaaattac | gtaattttagggaattaat | 303 | | | | | | | | | 14322 | 14340 | | |
| 144 | tcggtctaaccaca | tgtggtctagagccga | 304 | | | | | | | | | 14597 | 14611 | 1153 | 1167 |
| 145 | tacatgaacacatact | agtatgtgttcatgta | 305 | | | | | | | | | 15223 | 15239 | 1779 | 1795 |
| 146 | catttgactttatcaa | ttgataaaggtcaaatg | 306 | | | | | | | | | 15326 | 15342 | 1882 | 1898 |
| 147 | tccctaaaacattcata | tatgaatgttttaggga | 307 | | | | | | | | | 15544 | 15560 | 2100 | 2116 |
| 148 | atttgcacacctcaca | tgtgaggtgtgcaaat | 308 | | | | | | | | | 16363 | 16379 | 2919 | 2935 |
| 149 | ttaatacctactcttc | gaagagtaggtattaa | 309 | | | | | | | | | 16841 | 16856 | 3397 | 3412 |

TABLE 8-continued

Motif List

List of oligonucleotide motif sequences (indicated by SEQ ID NO), of the compounds used in the examples, and their target sequence and location on their nucleic acid target/target sequence (SEQ ID NO 1-6), as indicated. Motif sequences represent the contiguous sequences of nucleobases present in the oligonucleotide in the 5' to 3' direction. The RNA target sequence is the complementary sequence of the motif sequence, also in the 5' to 3' direction.

| SEQ ID NO | RNA TARGET SEQUENCE Note DNA version is shown (U→T) | RNA SEQ ID | SEQ ID NO 1 start stop | SEQ ID NO 2 start stop | SEQ ID NO 3 start stop | SEQ ID NO 4 start stop | SEQ ID NO 5 start stop | SEQ ID NO 6 start stop |
|---|---|---|---|---|---|---|---|---|
| 150 | caaagctaccaaaatct | 310 | | | | | 17465 17481 | 4021 4037 |
| 151 | tgtatttcaaatctcaaa | 311 | | | | | 17649 17666 | 4205 4222 |
| 152 | ctgtatttgaaatacag | 312 | | | | | 17651 17667 | 4207 4223 |
| 153 | cccacatcctttacac | 313 | | | | | 17892 17908 | 4448 4464 |
| 154 | tgtaaaggatgtggg | 314 | | | | | 17893 17908 | 4449 4464 |
| 155 | atgtactaattttcttt | 315 | | | | | 18346 18362 | 4902 4918 |
| 156 | ccacactgtatcttca | 316 | | | | | 18698 18713 | 5254 5269 |
| 157 | agcatacaaaatatcc | 317 | | | | | 18858 18873 | 5414 5429 |
| 158 | aaatcatttccaactct | 318 | | | | | 19193 19210 | 5749 5766 |
| 159 | aaccatgtttccctaca | 319 | | | | | 19369 19385 | 5925 5941 |
| 160 | ttcctatcataaccat | 320 | | | | | 19380 19395 | 5936 5951 |
| 161 | attctgttcctatca | 321 | | | | | 19387 19402 | 5943 5958 |
| 162 | ttgataagtggatgt | None - negative control | | | | | | |
| 163 | ccaaatcttataataactac | None - negative control | | | | | | |
| 164 | cgtaaactaccctat | None - negative control | | | | | | |
| 165 | tgaggtcctgcactgg* | SOD1 | | | | | | |
| 166 | gtcagtatcccagtgt* | FXI | | | | | | |

*Corresponds to ASO ID 569721 and 569720 in Burel et al 2016 Nucleic Acid Res 44(5); 2093-109-they be used as positive controls for hepatotoxicity.

Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 µmol scale. At the end of the synthesis, the oligonucleotides are cleaved from the solid support using aqueous ammonia for 5-16 hours at 60° C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphordiester linkages can be introduced using 0.02 M iodine in THF/Pyridine/water 7:2:1. The rest of the reagents are the ones typically used for oligonucleotide synthesis.

For post solid phase synthesis conjugation a commercially available C6 aminolinker phorphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

Purification by RP-HPLC:

The crude compounds are purified by preparative RP-HPLC on a Phenomenex Jupiter C18 10µ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations

DCI: 4,5-Dicyanoimidazole
DCM: Dichloromethane
DMF: Dimethylformamide
DMT: 4,4'-Dimethoxytrityl
THF: Tetrahydrofurane
Bz: Benzoyl
Ibu: Isobutyryl
RP-HPLC: Reverse phase high performance liquid chromatography $T_m$ Assay:

Oligonucleotide and RNA target (phosphate linked, PO) duplexes are diluted to 3 mM in 500 ml RNase-free water and mixed with 500 ml $2 \times T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 209C to 95° C. and then down to 25° C., recording absorption at 260 nm. First derivative and the local maximums of both the melting and annealing are used to assess the duplex $T_m$.

Example 1: In Vitro Reduction of TMEM106b in Neuro2a Mouse Cell Line Using Oligonucleotides LNA modified oligonucleotides targeting mouse Tmem106b were tested for its ability to reduce Tmem106b mRNA expression in mouse Neuro-2a neuroblastoma cell acquired from ATCC (CCL-131).

Neuro2a cells were grown in cell culturing media (DMEM AQ media [Sigma, cat. D0819] supplemented with 10% fetal bovine serum [Sigma, cat. no F7524], 1× Glutamax™ [Sigma, cat. no 3050-038], 1 mM Na-pyruvate and 25 µg/ml gentamicin) in a cell incubator at 37° C. in atmosphere with 5% $CO_2$. Cells were trypsinized upon reaching 80% confluency, by washing with Phosphate Buffered Saline (PBS), [Sigma cat. no 14190-094] followed by addition of 0.25% Trypsin-EDTA solution (Sigma, T3924), 2-3 minutes incubation at 37° C., and trituration before cell seeding. Cells were maintained in culture for up to 15 passages.

For experimental use, 2400 cells per well were seeded in 96 well plates (Nunc cat. no 167008) in 95 µL growth media. Oligonucleotides were prepared from a 500 µM stock. 5 µl of ASOs dissolved in PBS were added approximately 24 hours after the cells were seeded to a final concentration in cell media of 5 µM or 25 µM. Cells were incubated for 3 or 6 days without any media change. Cells used for 3 days and for 6 days long incubation with ASOs were derived from different frozen stock and were at a different passage number during the experiment.

Figure 2:
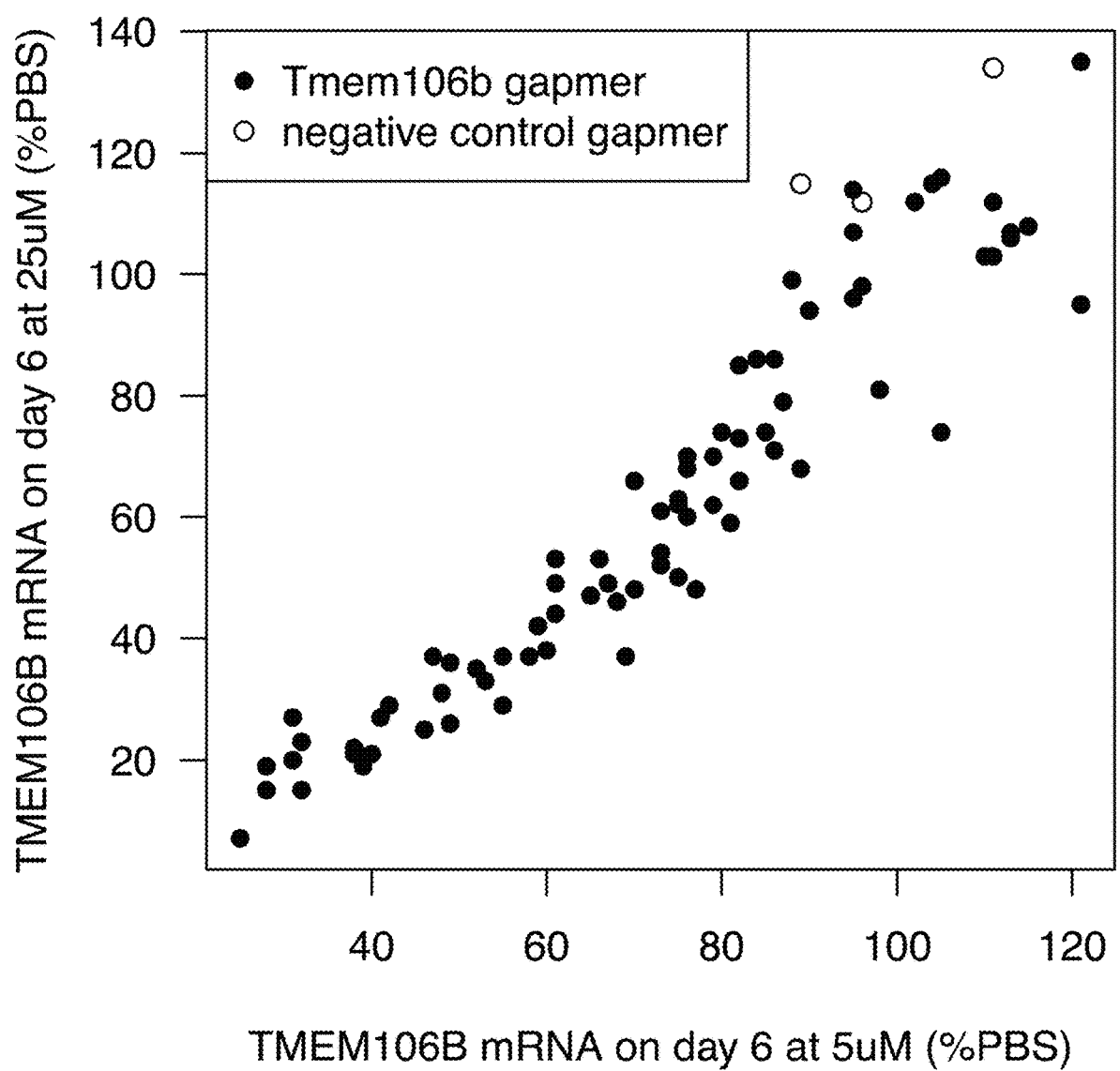
FIG. 2: Target inhibition after 6 days of incubation in mouse Neuro-2a cells at 5 µM vs 25 µM compared to PBS-treated control (mean of two biological replicates).

After incubation, cells were harvested by removal of media followed by cell lysis and RNA purification using QIAGEN RNeasy 96 Kit (cat 74181), following manufacturers protocol. RNA was diluted 10 fold in water prior to the one-step qPCR reaction. For one-step qPCR reaction qPCR-mix (qScript™ XLT One-Step RT-qPCR ToughMix® Low ROX from QuantaBio, cat. no 95134-500) was mixed with two Taqman probes in a ratio 10:1:1 (qPCR mix: probe1: probe2) to generate the mastermix. Taqman probes were acquired from LifeTechnologies: Mm00510952_m1, Mm00510954_m1, Mm01134666_m1 (Thermo Fisher Scientific, cat. 4351368, 4351368 and 4351370, respectively); GAPDH (cat. 4352339E) and ACTB (cat. 4352341E). Each experiment with Neuro2a cells included measurement of both GAPDH and ACTB and one (Mm00510952_m1) or all three of the Tmem106b specific probes, in such a way that in a given well one Tmem106b and one control probe set was included. Mastermix (6 µL) and RNA (4 µL) were then mixed in a qPCR plate (MICROAMP® optical 384 well, 4309849). After sealing, the plate was given a quick spin, 1000 g for 1 minute at RT, and transferred to a Viia™ 7 system (Applied Biosystems, Thermo), and the following PCR conditions used: 50° C. for 15 minutes; 95° C. for 3 minutes; 40 cycles of: 95° C. for 5 sec followed by a temperature decrease of 1.6° C./sec followed by 60° C. for 45 sec. The data was analyzed using the QuantStudio™ Real_time PCR Software. Presented results are normalized to the different housekeeping genes. The results are shown in Table 9 below as control samples (PBS-treated cells) i.e.

the lower the value the larger the inhibition. The results are also plotted in FIG. 1 and FIG. 2. Almost all of the tested compounds (black dots) were found to inhibit target expression at 5 µM and 25 µM as compared to the negative control gapmers (white dots), highlighting that TMEM106B is surprisingly susceptible to oligonucleotide directed inhibition.

TABLE 9 in vitro efficacy of oligonucleotides targeting TMEM106B mRNA in Neuro2a mouse cells. The experiment was performed in duplex for day 3 (replicate A and B) and as a single experiment on day 6.

| | Day 3 | | | | | | Day 6 | |
|---|---|---|---|---|---|---|---|---|
| | mRNA (% PBS) 5 uM | | | mRNA (% PBS) 25 uM | | | mRNA (% PBS) 5 uM | mRNA (% PBS) 25 uM |
| | Replicate | | | | | | | |
| CMP ID NO | A | B | AVG | A | B | AVG | | |
| 17_1 | 66 | 75 | 71 | 39 | 50 | 44 | 25 | 7 |
| 47_1 | 78 | 78 | 78 | 57 | 65 | 61 | 46 | 25 |
| 81_1 | 92 | 95 | 93 | 99 | 101 | 100 | 79 | 70 |
| 87_1 | 102 | 100 | 101 | 102 | 104 | 103 | 95 | 96 |
| 88_1 | 89 | 89 | 89 | 61 | 68 | 65 | 32 | 23 |
| 89_1 | 96 | 94 | 95 | 91 | 85 | 88 | 70 | 48 |
| 90_1 | 89 | 82 | 86 | 80 | 79 | 79 | 75 | 50 |
| 91_1 | 101 | 109 | 105 | 102 | 104 | 103 | 110 | 103 |
| 92_1 | 94 | 99 | 97 | 94 | 97 | 96 | 70 | 66 |
| 93_1 | 108 | 96 | 102 | 105 | 94 | 100 | 111 | 103 |
| 94_1 | 103 | 97 | 100 | 105 | 99 | 102 | 105 | 116 |
| 95_1 | 105 | 104 | 104 | 101 | 95 | 98 | 104 | 115 |
| 96_1 | 108 | 93 | 100 | 105 | 105 | 105 | 102 | 112 |
| 97_1 | 89 | 92 | 91 | 74 | 78 | 76 | 58 | 37 |
| 98_1 | 91 | 89 | 90 | 80 | 92 | 86 | 52 | 35 |
| 99_1 | 100 | 108 | 104 | 102 | 99 | 100 | 111 | 112 |
| 100_1 | 98 | 90 | 94 | 90 | 88 | 89 | 89 | 68 |
| 101_1 | 100 | 98 | 99 | 104 | 100 | 102 | 84 | 86 |
| 102_1 | 92 | 96 | 94 | 90 | 71 | 80 | 48 | 31 |
| 103_1 | 108 | 95 | 101 | 99 | 99 | 99 | 115 | 108 |
| 104_1 | 93 | 103 | 98 | 95 | 101 | 98 | 121 | 95 |
| 105_1 | 92 | 99 | 96 | 95 | 87 | 91 | 81 | 59 |
| 106_1 | 102 | 105 | 104 | 101 | 105 | 103 | 76 | 68 |
| 107_1 | 95 | 99 | 97 | 89 | 91 | 90 | 55 | 37 |
| 108_1 | 103 | 89 | 96 | 94 | 92 | 93 | 86 | 71 |
| 109_1 | 88 | 85 | 87 | 72 | 77 | 74 | 61 | 44 |
| 110_1 | 97 | 97 | 97 | 91 | 89 | 90 | 82 | 66 |
| 111_1 | 103 | 111 | 107 | 97 | 104 | 100 | 90 | 94 |
| 112_1 | 86 | 92 | 89 | 84 | 78 | 81 | 77 | 48 |
| 113_1 | 99 | 99 | 99 | 93 | 87 | 90 | 67 | 49 |
| 114_1 | 74 | 91 | 82 | 63 | 69 | 66 | 47 | 37 |
| 115_1 | 70 | 76 | 73 | 49 | 58 | 53 | 28 | 15 |
| 116_1 | 101 | 104 | 102 | 104 | 101 | 102 | 96 | 98 |
| 117_1 | 100 | 104 | 102 | 98 | 97 | 97 | 113 | 107 |
| 118_1 | 102 | 99 | 101 | 105 | 99 | 102 | 98 | 81 |
| 119_1 | 104 | 106 | 105 | 99 | 87 | 93 | 95 | 107 |
| 120_1 | 103 | 94 | 98 | 104 | 96 | 100 | 87 | 79 |
| 121_1 | 101 | 94 | 97 | 102 | 90 | 96 | 82 | 73 |
| 122_1 | 103 | 113 | 108 | 104 | 108 | 106 | 95 | 114 |
| 123_1 | 80 | 72 | 76 | 58 | 56 | 57 | 40 | 21 |
| 124_1 | 93 | 90 | 91 | 79 | 79 | 79 | 68 | 46 |
| 125_1 | 79 | 97 | 88 | 65 | 72 | 69 | 49 | 36 |
| 126_1 | 93 | 98 | 95 | 77 | 95 | 86 | 49 | 26 |
| 127_1 | 98 | 85 | 91 | 94 | 86 | 90 | 80 | 74 |
| 128_1 | 102 | 97 | 100 | 92 | 102 | 97 | 76 | 60 |
| 129_1 | 81 | 87 | 84 | 64 | 67 | 66 | 38 | 21 |
| 130_1 | 93 | 93 | 93 | 91 | 85 | 88 | 73 | 54 |
| 131_1 | 88 | 97 | 92 | 74 | 74 | 74 | 69 | 37 |
| 132_1 | 95 | 101 | 98 | 81 | 91 | 86 | 60 | 38 |
| 133_1 | 78 | 84 | 81 | 56 | 60 | 58 | 32 | 15 |
| 134_1 | 94 | 103 | 99 | 90 | 94 | 92 | 66 | 53 |
| 135_1 | 95 | 101 | 98 | 87 | 92 | 90 | 61 | 53 |
| 136_1 | 88 | | 88 | 71 | 80 | 75 | 53 | 33 |
| 137_1 | 99 | 105 | 102 | 107 | 96 | 102 | 113 | 106 |
| 138_1 | 95 | 97 | 96 | 91 | 96 | 93 | 75 | 62 |
| 139_1 | 105 | 105 | 105 | 101 | NA | 101 | 105 | 74 |
| 140_1 | 93 | 99 | 96 | 93 | 101 | 97 | 82 | 85 |
| 141_1 | 95 | 112 | 103 | 99 | 97 | 98 | 79 | 62 |
| 142_1 | 112 | 95 | 103 | 101 | 111 | 106 | 88 | 99 |
| 143_1 | 109 | 97 | 103 | 113 | 94 | 104 | 121 | 135 |
| 144_1 | 65 | 77 | 71 | 58 | 64 | 61 | 55 | 29 |
| 145_1 | 70 | 80 | 75 | 58 | 64 | 61 | 39 | 19 |

TABLE 9-continued in vitro efficacy of oligonucleotides targeting TMEM106B mRNA in
Neuro2a mouse cells. The experiment was performed in duplex for
day 3 (replicate A and B) and as a single experiment on day 6.

| | Day 3 | | | | | | Day 6 | |
|---|---|---|---|---|---|---|---|---|
| | mRNA (% PBS) 5 uM | | | mRNA (% PBS) 25 uM | | | mRNA (% PBS) | mRNA (% PBS) |
| | Replicate | | | | | | 5 uM | 25 uM |
| CMP ID NO | A | B | AVG | A | B | AVG | | |
| 146_1 | 82 | 96 | 89 | 72 | 75 | 73 | 76 | 70 |
| 147_1 | 105 | 112 | 109 | 104 | 95 | 100 | 86 | 86 |
| 148_1 | 100 | 98 | 99 | 101 | 92 | 97 | 61 | 49 |
| 149_1 | 91 | 98 | 94 | 90 | 91 | 91 | 73 | NA |
| 150_1 | 100 | 99 | 99 | 90 | 85 | 87 | 59 | 42 |
| 151_1 | 71 | 78 | 75 | 57 | 59 | 58 | 42 | 29 |
| 152_1 | 58 | 59 | 59 | 35 | 40 | 37 | 38 | 22 |
| 153_1 | 98 | 101 | 100 | 94 | 97 | 95 | 85 | 74 |
| 154_1 | 95 | 102 | 99 | 87 | 93 | 90 | 73 | 52 |
| 155_1 | 63 | 69 | 66 | 42 | 47 | 45 | 31 | 20 |
| 156_1 | 59 | 56 | 58 | 38 | 42 | 40 | 28 | 19 |
| 157_1 | 72 | 82 | 77 | 57 | 62 | 59 | 41 | 27 |
| 158_1 | 88 | 84 | 86 | 71 | 75 | 73 | 65 | 47 |
| 159_1 | 98 | 87 | 92 | 86 | 91 | 89 | 73 | 61 |
| 160_1 | 88 | 99 | 94 | 84 | 92 | 88 | 75 | 63 |
| 161_1 | 70 | 78 | 74 | 53 | 57 | 55 | 31 | 27 |
| 162_1 | 102 | 103 | 102 | 110 | 100 | 105 | 89 | 115 |
| 163_1 | 103 | 103 | 103 | 104 | 98 | 101 | 111 | 134 |
| 164_1 | 99 | 100 | 100 | 107 | 103 | 105 | 96 | 112 |

Example 2: In Vitro Reduction of TMEM106B in a Human SK-N-BE(2) Cells Using Oligonucleotides Oligonucleotides targeting TMEM106B was tested for its ability to reduce TMEM106B mRNA expression in human SK-N-BE(2) neuroblastoma cell acquired from ATCC (CRL-2271).

SK-N-BE(2) cells were grown in cell culturing media (MEM [Sigma, cat. no M2279] supplemented with 10% Fetal Bovine Serum [Sigma, cat. no F7524], 1× Glutamax™ [Sigma, cat. no 3050-038] 1×MEM Non-essential amino acid solution [Sigma, cat. no M7145] and 0.025 mg/ml Gentamycin [Sigma, cat. no G1397]). Cells were trypsinized every 5 days, by washing with Phosphate Buffered Saline (PBS), [Sigma cat. no 14190-094] followed by addition of 0.25% Trypsin-EDTA solution (Sigma, T3924), 2-3 minutes incubation at 37° C., and trituration before cell seeding. Cells were maintained in culture for up to 15 passages.

For experimental use, 15,000 (day 3) or 25,000 (day 6) cells per well were seeded in 96 well plates (Nunc cat. no 167008) in 100 µL growth media. Oligonucleotides were prepared from a 750 µM stock. Oligonucleotide dissolved in PBS was added approximately 24 hours after the cells were seeded to a final concentration of 5 µM or 25 µM. Cells were incubated for 3 or 6 days without any media change.

After incubation, cells were harvested by removal of media followed by addition of 125 µL PureLink©Pro 96 Lysis buffer (Invitrogen 12173.001A) and 125 µL 70% ethanol. RNA was purified according to the manufacture's instruction and eluted in a final volume of 50 µL water resulting in an RNA concentration of 10-20 ng/µl. RNA was diluted 10 fold in water prior to the one-step qPCR reaction. For one-step qPCR reaction qPCR-mix (qScriptTMXLE 1-step RT-qPCR TOUGHMIX® Low ROX from Qaunt-aBio, cat. no 95134-500) was mixed with two Taqman probes in a ratio 10:1:1 (qPCR mix: probe1:probe2) to generate the mastermix. Taqman probes were acquired from LifeTechnologies: TMEM_Hs00998849_m1; GAPDH 4325792. Mastermix (6 µL) and RNA (4 µL, 1-2 ng/µL) were then mixed in a qPCR plate (MICROAMP® optical 384 well, 4309849). After sealing, the plate was given a quick spin, 1000 g for 1 minute at RT, and transferred to a Viia™ 7 system (Applied Biosystems, Thermo), and the following PCR conditions used: 50° C. for 15 minutes; 95° C. for 3 minutes; 40 cycles of: 95° C. for 5 sec followed by a temperature decrease of 1.6° C./sec followed by 60° C. for 45 sec.

Figure 4:
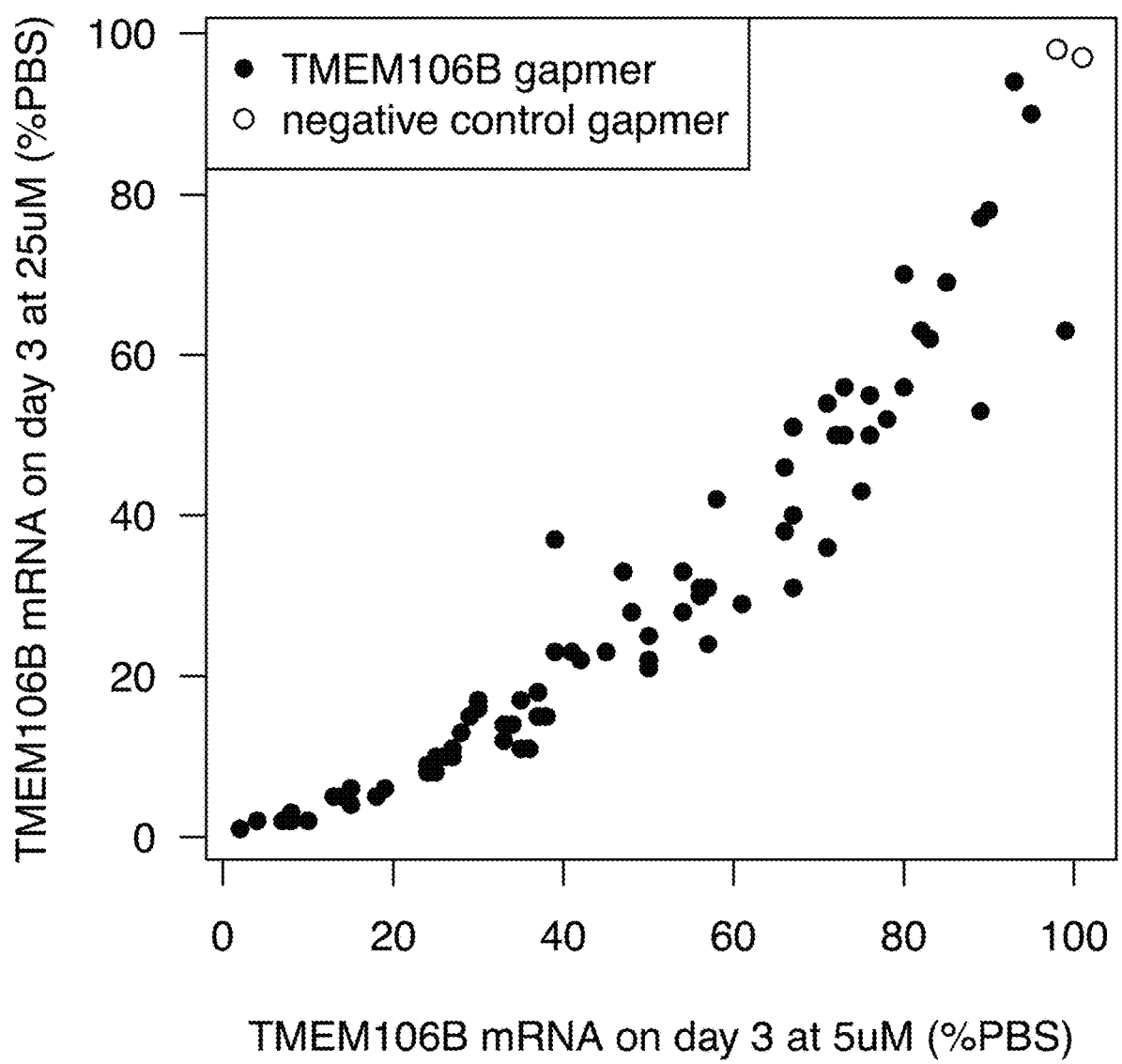
FIG. 4: Target inhibition after 3 days of incubation in human SK-N-BE(2) cells at 5 µM vs 25 µM (mean of two biological replicates).
Figure 5:
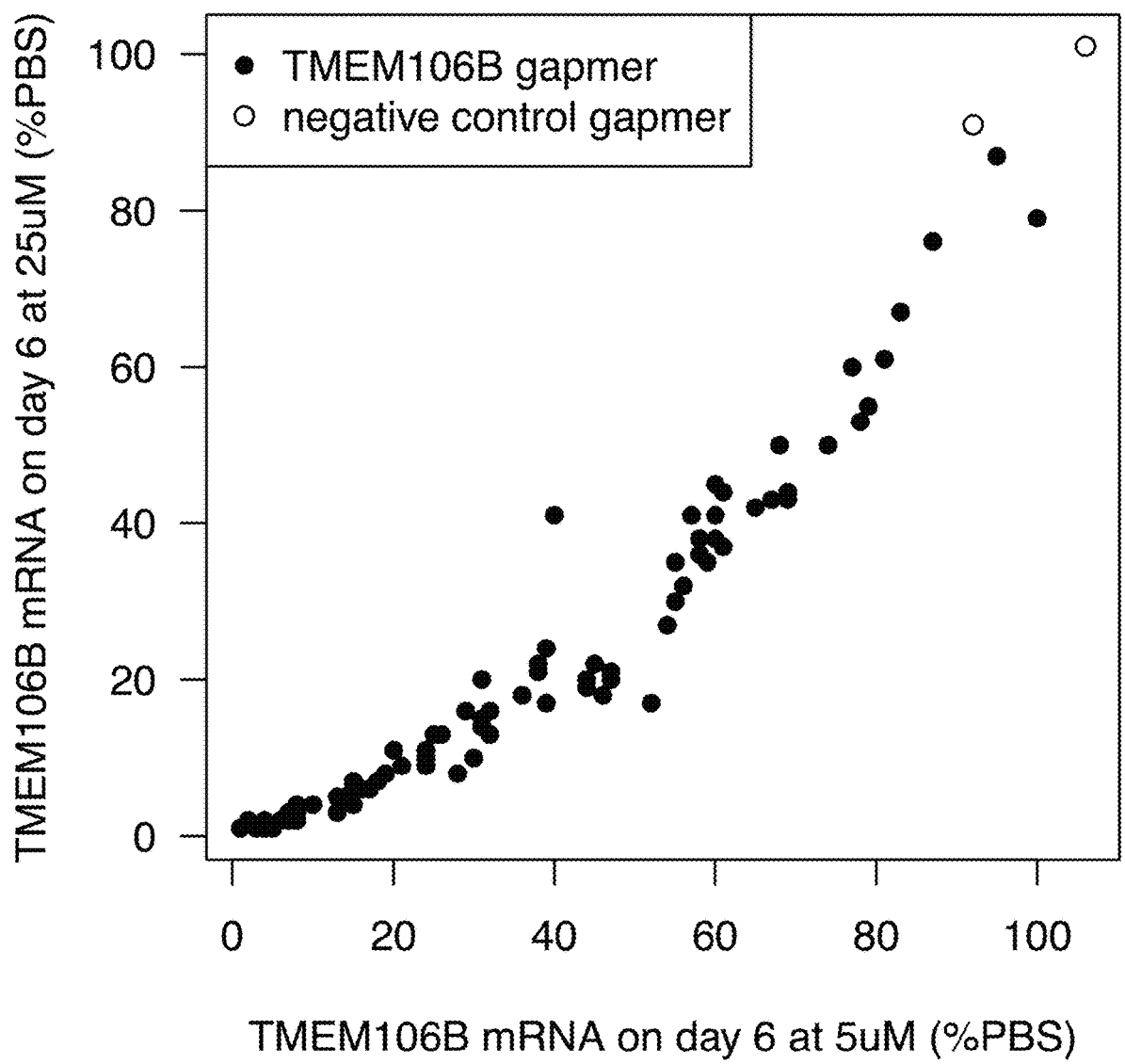
FIG. 5: Target inhibition after 6 days of incubation in human SK-N-BE(2) cells at 5 µM vs 25 µM (mean of two biological replicates).
Figure 6:
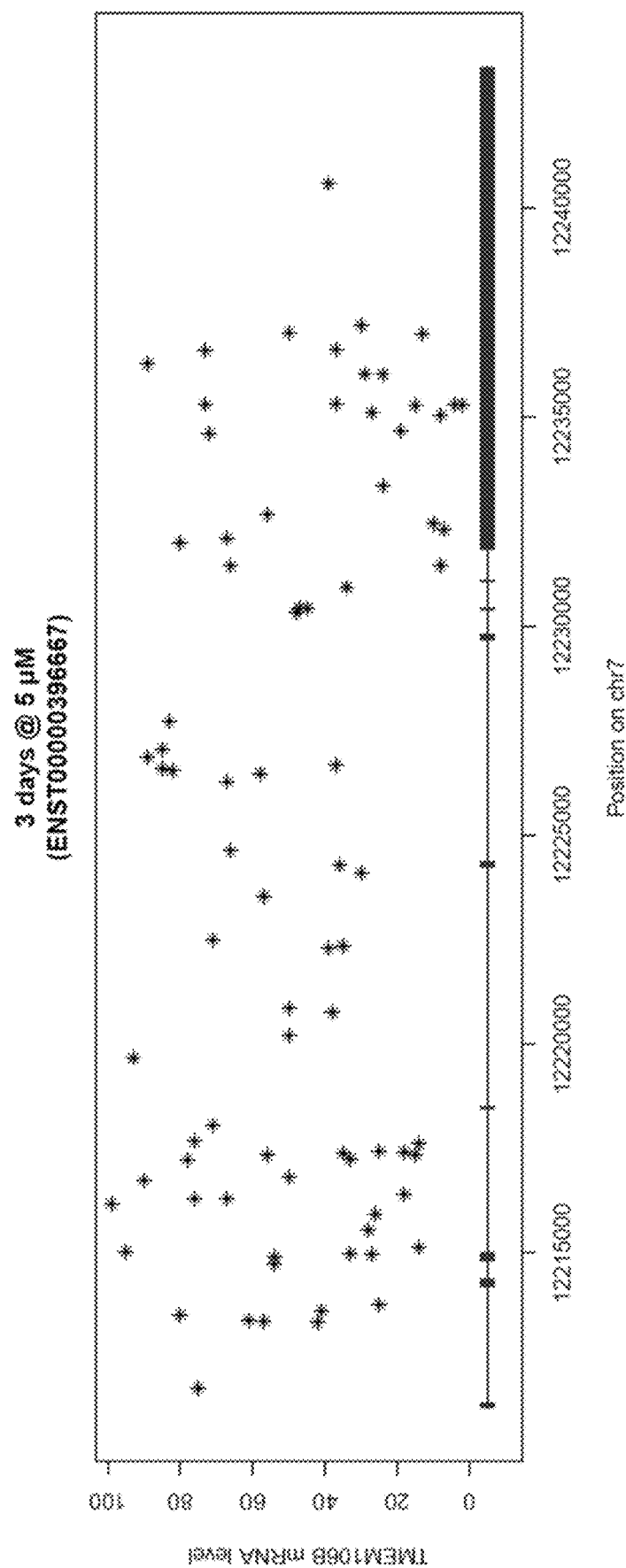
FIG. 6: Target inhibition after 3 days of incubation in human SK-N-BE(2) cells at 5 µM, illustrated vs. the position of the target sequence on Chromosome 7.

The data was analyzed using the QuantStudio™ Real_time PCR Software. Presented results are normalized to GAPDH. The results are shown in Table 10 below as % of control samples (PBS-treated cells) i.e. the lower the value the larger the inhibition. The results are also plotted in FIG. 4 and FIG. 5. Almost all of the tested compounds (black dots) were found to inhibit target expression at 5 µM and 25 µM as compared to the negative control gapmers (white dots), highlighting that TMEM106B is surprisingly susceptible to oligonucleotide directed inhibition. Notably compounds targeting the 3'UTR were found to be particularly effective, for example compounds 68_1, 73_1, 741, 79_1 and 82_1.

TABLE 10 in vitro efficacy of oligonucleotides targeting TMEM106B mRNA in SK-N-BE(2) human cells. The experiment was performed in duplex (sample A and B)

| | Day 3 | | | | | | Day 6 | | | | | |
|---|---|---|---|---|---|---|---|---|---|---|---|---|
| | mRNA (% PBS) 5 uM | | | mRNA (% PBS) 25 uM | | | mRNA (% PBS) 5 uM | | | mRNA (% PBS) 25 uM | | |
| | | | | | Replicate | | | | | | | |
| CMP ID NO | A | B | AVG | A | B | AVG | A | B | AVG | A | B | AVG |
| 7_1 | 82 | 67 | 75 | 59 | 43 | 51 | 57 | 59 | 58 | 34 | 36 | 35 |
| 8_1 | 40 | 44 | 42 | 20 | 22 | 21 | 28 | 31 | 29 | 16 | 16 | 16 |
| 9_1 | 57 | 57 | 57 | 21 | 24 | 22 | 48 | 56 | 52 | 16 | 17 | 16 |
| 10_1 | 68 | 54 | 61 | 27 | 29 | 28 | 42 | 45 | 44 | 19 | 19 | 19 |
| 11_1 | 80 | 79 | 80 | 58 | 56 | 57 | 70 | 68 | 69 | 46 | 44 | 45 |
| 12_1 | 40 | 43 | 41 | 20 | 23 | 22 | 31 | 31 | 31 | 16 | 15 | 16 |
| 13_1 | 25 | 25 | 25 | 10 | 10 | 10 | 14 | 13 | 14 | 5 | 5 | 5 |
| 14_1 | 53 | 54 | 54 | 33 | 33 | 33 | 44 | 46 | 45 | 23 | 22 | 22 |
| 15_1 | 53 | 55 | 54 | 27 | 28 | 27 | 56 | 55 | 56 | 34 | 32 | 33 |
| 16_1 | 28 | 26 | 27 | 12 | 10 | 11 | 17 | 17 | 17 | 6 | 6 | 6 |
| 17_1 | 34 | 33 | 33 | 13 | 12 | 12 | 24 | 25 | 24 | 8 | 9 | 9 |
| 18_1 | 88 | 103 | 95 | 85 | 90 | 88 | 104 | 97 | 100 | 81 | 79 | 80 |
| 19_1 | 15 | 14 | 14 | 5 | 5 | 5 | 7 | 7 | 7 | 2 | 3 | 2 |
| 20_1 | 30 | 27 | 28 | 14 | 13 | 13 | 19 | 17 | 18 | 7 | 7 | 7 |
| 21_1 | 25 | 26 | 26 | 10 | 10 | 10 | 16 | 16 | 16 | 5 | 6 | 6 |
| 22_1 | 112 | 85 | 99 | 81 | 63 | 72 | 75 | 74 | 74 | 49 | 50 | 49 |
| 23_1 | 74 | 60 | 67 | 40 | 31 | 36 | 45 | 47 | 46 | 18 | 18 | 18 |
| 24_1 | 75 | 77 | 76 | 52 | 55 | 53 | 66 | 72 | 69 | 42 | 43 | 42 |
| 25_1 | 18 | 18 | 18 | 4 | 5 | 4 | 8 | 8 | 8 | 2 | 2 | 2 |
| 26_1 | 91 | 89 | 90 | 85 | 78 | 81 | 85 | 88 | 87 | 77 | 76 | 77 |
| 27_1 | 55 | 45 | 50 | 30 | 21 | 25 | 37 | 35 | 36 | 18 | 18 | 18 |
| 28_1 | 87 | 69 | 78 | 59 | 52 | 55 | 60 | 60 | 60 | 38 | 45 | 42 |
| 29_1 | 32 | 34 | 33 | 13 | 14 | 13 | 23 | 25 | 24 | 9 | 10 | 9 |
| 30_1 | 53 | 58 | 56 | 27 | 30 | 28 | 47 | 47 | 47 | 21 | 21 | 21 |
| 31_1 | 15 | 15 | 15 | 4 | 4 | 4 | 6 | 7 | 7 | 2 | 2 | 2 |
| 32_1 | 39 | 31 | 35 | 14 | 11 | 13 | 19 | 19 | 19 | 8 | 8 | 8 |
| 33_1 | 18 | 18 | 18 | 5 | 5 | 5 | 13 | 13 | 13 | 3 | 3 | 3 |
| 34_1 | 26 | 25 | 25 | 7 | 8 | 8 | 15 | 15 | 15 | 4 | 4 | 4 |
| 35_1 | 14 | 15 | 14 | 5 | 5 | 5 | 6 | 7 | 6 | 2 | 2 | 2 |
| 36_1 | 74 | 77 | 76 | 47 | 50 | 49 | 60 | 60 | 60 | 44 | 41 | 43 |
| 37_1 | 76 | 67 | 71 | 34 | 36 | 35 | 53 | 58 | 55 | 27 | 30 | 29 |
| 38_1 | 95 | 91 | 93 | 84 | 94 | 89 | 93 | 97 | 95 | 88 | 87 | 87 |
| 39_1 | 48 | 52 | 50 | 25 | 25 | 25 | 37 | 38 | 38 | 18 | 22 | 20 |
| 40_1 | 38 | 37 | 38 | 15 | 15 | 15 | 30 | 30 | 30 | 8 | 10 | 9 |
| 41_1 | 51 | 50 | 50 | 20 | 22 | 21 | 32 | 33 | 32 | 12 | 13 | 12 |
| 42_1 | 36 | 42 | 39 | 22 | 23 | 23 | 29 | 33 | 31 | 20 | 20 | 20 |
| 43_1 | 33 | 36 | 35 | 15 | 17 | 16 | 23 | 25 | 24 | 12 | 11 | 12 |
| 44_1 | 73 | 69 | 71 | 52 | 54 | 53 | 61 | 60 | 60 | 36 | 38 | 37 |
| 45_1 | 59 | 56 | 57 | 30 | 31 | 30 | 46 | 43 | 44 | 20 | 20 | 20 |
| 46_1 | 29 | 32 | 30 | 20 | 17 | 19 | 20 | 22 | 21 | 9 | 9 | 9 |
| 47_1 | 36 | 37 | 36 | 11 | 11 | 11 | 29 | 28 | 28 | 8 | 8 | 8 |
| 48_1 | 65 | 67 | 66 | 42 | 46 | 44 | 59 | 58 | 58 | 37 | 38 | 38 |
| 49_1 | 66 | 67 | 67 | 47 | 51 | 49 | 56 | 59 | 57 | 42 | 41 | 42 |
| 50_1 | 53 | 64 | 58 | 40 | 42 | 41 | 54 | 55 | 55 | 34 | 35 | 35 |
| 51_1 | 82 | 82 | 82 | 61 | 63 | 62 | 66 | 69 | 68 | 48 | 50 | 49 |
| 52_1 | 85 | 85 | 85 | 69 | 69 | 69 | 83 | 75 | 79 | 59 | 55 | 57 |
| 53_1 | 42 | 32 | 37 | 20 | 15 | 17 | 24 | 25 | 25 | 12 | 13 | 13 |
| 54_1 | 100 | 78 | 89 | 44 | 53 | 49 | 66 | 68 | 67 | 41 | 43 | 42 |
| 55_1 | 82 | 87 | 85 | 64 | 69 | 67 | 77 | 77 | 77 | 60 | 60 | 60 |
| 56_1 | 82 | 84 | 83 | 63 | 62 | 63 | 80 | 77 | 78 | 50 | 53 | 52 |
| 57_1 | 48 | 48 | 48 | 28 | 28 | 28 | 37 | 38 | 38 | 22 | 21 | 22 |
| 58_1 | 42 | 48 | 45 | 22 | 23 | 23 | 33 | 31 | 32 | 15 | 16 | 15 |
| 59_1 | 45 | 49 | 47 | 29 | 33 | 31 | 40 | 37 | 39 | 24 | 24 | 24 |
| 60_1 | 35 | 33 | 34 | 13 | 14 | 14 | 26 | 23 | 24 | 9 | 9 | 9 |
| 61_1 | 64 | 69 | 66 | 34 | 38 | 36 | 53 | 55 | 54 | 26 | 27 | 27 |
| 62_1 | 8 | 8 | 8 | 2 | 2 | 2 | 4 | 5 | 5 | 1 | 1 | 1 |
| 63_1 | 76 | 85 | 80 | 65 | 70 | 68 | 78 | 83 | 81 | 59 | 61 | 60 |
| 64_1 | 68 | 67 | 67 | 42 | 40 | 41 | 58 | 60 | 59 | 36 | 35 | 35 |
| 65_1 | 7 | 7 | 7 | 2 | 2 | 2 | 3 | 3 | 3 | 1 | 1 | 1 |
| 66_1 | 10 | 9 | 10 | 2 | 2 | 2 | 4 | 4 | 4 | 1 | 1 | 1 |
| 67_1 | 54 | 59 | 56 | 29 | 31 | 30 | 48 | 46 | 47 | 20 | 20 | 20 |
| 68_1 | 24 | 23 | 24 | 8 | 8 | 8 | 12 | 13 | 13 | 4 | 5 | 4 |
| 69_1 | 73 | 71 | 72 | 52 | 50 | 51 | 61 | 62 | 61 | 38 | 37 | 38 |
| 70_1 | 20 | 17 | 19 | 6 | 6 | 6 | 8 | 8 | 8 | 3 | 3 | 3 |
| 71_1 | 7 | 9 | 8 | 3 | 3 | 3 | 4 | 4 | 4 | 1 | 2 | 1 |
| 72_1 | 26 | 28 | 27 | 10 | 11 | 11 | 14 | 16 | 15 | 6 | 7 | 6 |
| 73_1 | 14 | 15 | 15 | 5 | 6 | 5 | 9 | 10 | 10 | 4 | 4 | 4 |
| 74_1 | 2 | 2 | 2 | 1 | 1 | 1 | 1 | 1 | 1 | 2 | 1 | 1 |
| 75_1 | 4 | 4 | 4 | 2 | 2 | 2 | 2 | 2 | 2 | 3 | 2 | 3 |

TABLE 10-continued in vitro efficacy of oligonucleotides targeting TMEM106B mRNA in SK-N-BE(2) human cells. The experiment was performed in duplex (sample A and B)

| | Day 3 | | | | | | Day 6 | | | | | |
|---|---|---|---|---|---|---|---|---|---|---|---|---|
| | mRNA (% PBS) 5 uM | | | mRNA (% PBS) 25 uM | | | mRNA (% PBS) 5 uM | | | mRNA (% PBS) 25 uM | | |
| | Replicate | | | | | | | | | | | |
| CMP ID NO | A | B | AVG | A | B | AVG | A | B | AVG | A | B | AVG |
| 76_1 | 75 | 71 | 73 | 56 | 50 | 53 | 64 | 65 | 65 | 42 | 42 | 42 |
| 77_1 | 35 | 38 | 37 | 18 | 18 | 18 | 25 | 25 | 25 | 11 | 13 | 12 |
| 78_1 | 25 | 24 | 24 | 9 | 9 | 9 | 15 | 15 | 15 | 7 | 6 | 6 |
| 79_1 | 26 | 31 | 29 | 14 | 15 | 14 | 25 | 26 | 26 | 13 | 13 | 13 |
| 80_1 | 89 | 89 | 89 | 75 | 77 | 76 | 83 | 83 | 83 | 52 | 67 | 60 |
| 81_1 | 74 | 71 | 73 | 56 | 56 | 56 | 59 | 63 | 61 | 44 | 44 | 44 |
| 82_1 | 36 | 39 | 37 | 18 | 18 | 18 | 30 | 31 | 31 | 15 | 14 | 14 |
| 83_1 | 12 | 14 | 13 | 5 | 5 | 5 | 8 | 8 | 8 | 4 | 4 | 4 |
| 84_1 | 47 | 53 | 50 | 26 | 25 | 26 | 39 | 40 | 39 | 17 | 17 | 17 |
| 85_1 | 30 | 30 | 30 | 15 | 16 | 15 | 21 | 20 | 20 | 10 | 11 | 11 |
| 86_1 | 40 | 38 | 39 | 36 | 37 | 36 | 40 | 41 | 40 | 41 | 41 | 41 |
| 162_1 | 98 | 98 | 98 | 94 | 98 | 96 | 91 | 93 | 92 | 90 | 91 | 90 |
| 163_1 | 98 | 105 | 101 | 95 | 97 | 96 | 110 | 103 | 106 | 100 | 101 | 101 |

Example 3: Cellular Toxicity of Oligonucleotides

To measure if LNA modified oligonucleotides induce apoptosis of the cells a caspase assay was applied as described here. NIH 3T3 cells (ECACC cat. 93061524) were transfected with 100 nM or 30 nM LNA oligonucleotides using Lipofectamine™ 2000 and Caspase 3 and Caspase 7 activation was measured after 24 hours, following protocol described below, adapted from Dieckmann et al. (Molecular Therapy: Nucleic Acids Vol. 10 Mar. 2018). The experiment was performed in two replicates with slightly different protocols. Each replicate was performed in two 96 well plate. Each LNA oligonucleotide at a given transfection concentration was measured in total four times in each replicate.

For the first replicate, mouse embryo fibroblasts cell line NIH 3T3 were grown in m3T3 media (DMEM AQ (Sigma: D0819) supplemented with 10% FBS and 25 µg/ml gentamicin) at 37° C. with 5% $CO_2$. Cells were trypsinized and seeded in 96-well plates (ViewPlate-96, PerkinElmer, cat 6005181), at a density of 4000 cells per well in 100 µl of m3T3 media and grown for 24 hours. LNA oligonucleotides were diluted with DPBS (Thermo Fisher Scientific, cat. 14190250) to a final concentration of 5 µM or 1.5 µM (also included negative controls with 0 µM concentration of oligonucleotide). Each diluted LNA oligonucleotide was mixed with Opti-MEM (Thermo Fisher Scientific cat. 31985047) in a ratio of 1 to 24 (volume), and to 30 µl of such a mixture 30 µl of LOM solution (Lipofectamine™ 2000 (Thermo Fisher Scientific cat. 11668019) mixed with Opti-MEM (Thermo Fisher Scientific cat. 31985047) in a ratio of 1 to 99 (volume), used immediately after preparation) was added followed by 20 min incubation. Media was removed from the NIH 3T3 cell culture and 50 µl of LNA oligonucleotide in LOM solution was added. After four hours, 50 µl of m20F media (mix 800 ml DMEM AQ (Sigma: D0819) with 200 ml FBS and 10 ml 200 mM L-alanyl-L-glutamine and 500 µl 50 mg/ml gentamicin) was added to each well. After 24 hours from adding LNA oligonucleotide to cells 100 µl of the Caspase-Glo® 3/7 reagent (Promega, cat. G8093, prepared as prescribed by the manufacturer) was added to the cells, plates were shaken 500 rpm for 30 seconds and incubated 1 hour at room temperature, followed by blocking back of the plates with BackSeal (PerkinElmer cat. 6005199) and measurement of luminescence with EnSight Multimode Plate Reader (PerkinElmer cat. HH34000000).

For the second replicate similar protocol was followed with following modifications: (1) diluted LNA oligonucleotides were mixed with Opti-MEM in a ratio of 2 to 23 instead of 1 to 24; (2) immediately prior to addition of 50 µl of a mixture of LNA oligonucleotides with opti-MEM and LOM solution to cells, 50 µl of Opti-MEM was added to cells; (3) instead of m20F, 50 µl of m30F (mix 700 ml DMEM AQ (Sigma: D0819) with 300 ml FBS and 10 ml 200 mM L-alanyl-L-glutamine and 500 µl 50 mg/ml gentamicin) was added; (4) immediately prior to addition of Caspase-Glo® 3/7 reagent, 50 µl of media from cells was removed.

Figure 3:
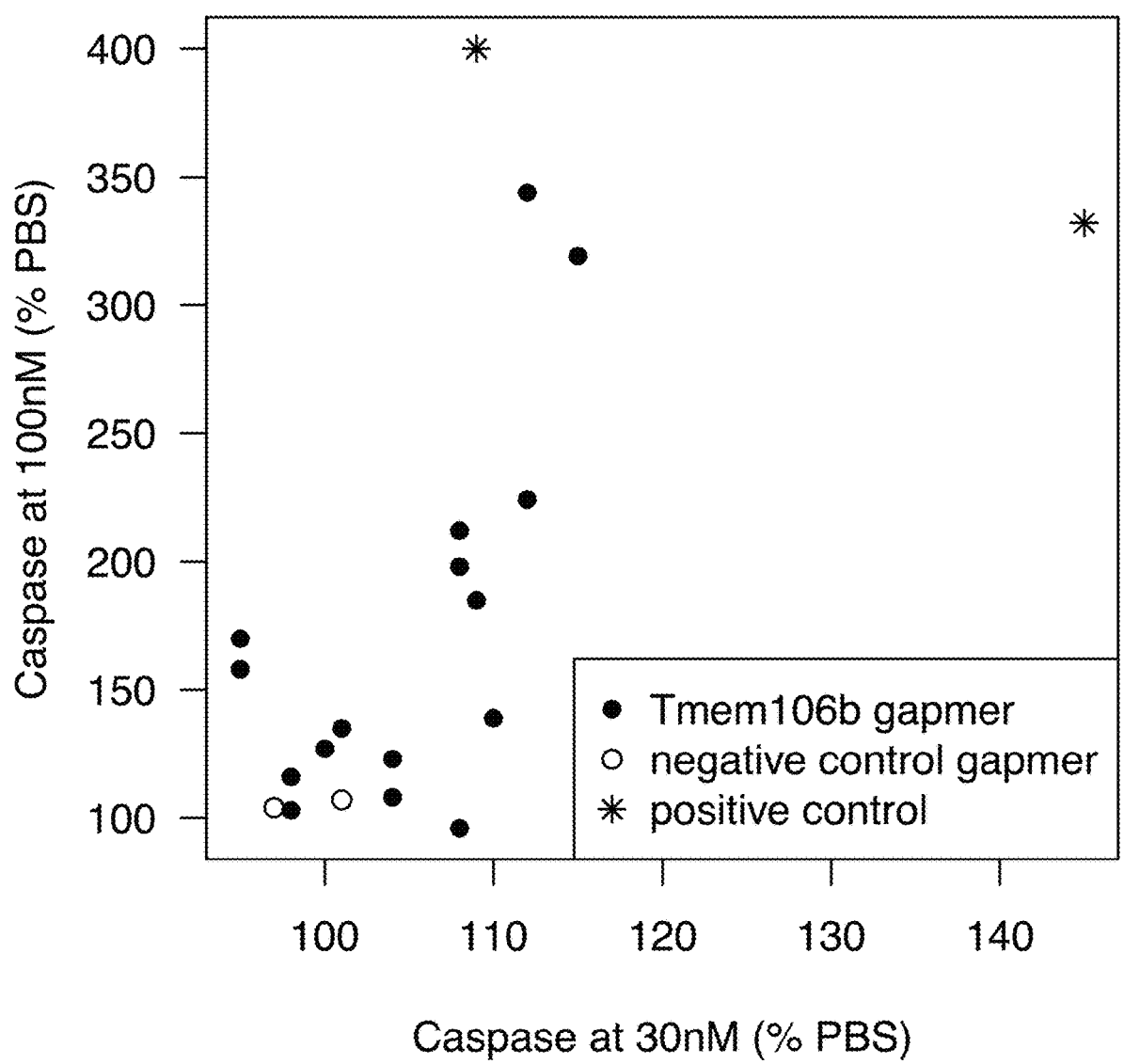
FIG. 3: Caspase activation 24 hours after transfection of gapmers compared to PBS-treated controls (mean of biological replicates).

Luminescence signal as measured by the EnSight reader was divided by the average luminescence signal of the negative control wells within given 96 well plate. Signal for different compounds at a given concentration was averaged across plates and across replicates (outliers, defined as data points that are more or less than 1.5 interquartile ranges from the mean signal within a replicate, were removed). The results are shown in Table 11, and illustrated in FIG. 3.

TABLE 11

Caspase activation in NIH 3T3 cells treated with oligonucleotides (replicates of 4)

| CMP ID NO | 30 nM, average, replicate 1 | 30 nM, st dev, replicate 1 | 30 nM, average, replicate 2 | 30 nM, st dev, replicate 2 | 30 nM, average of replicate1 and 2 avg | 100 nM, average, replicate 1 | 100 nM, st dev, replicate 1 | 100 nM, average, replicate 2 | 100 nM, st dev, replicate 2 | 100 nM, average of replicate1 and 2 avg |
|---|---|---|---|---|---|---|---|---|---|---|
| 017_1 | 102% | 7% | 115% | 4% | 109% | 171% | 25% | 199% | 31% | 185% |
| 047_1 | 113% | 1% | 103% | 6% | 108% | 229% | 48% | 166% | 30% | 198% |
| 088_1 | 113% | 7% | 103% | 2% | 108% | 236% | 7% | 188% | 49% | 212% |
| 114_1 | 105% | 9% | 124% | 13% | 115% | 232% | 4% | 405% | 55% | 319% |
| 115_1 | 108% | 10% | 116% | 14% | 112% | 240% | 52% | 447% | 24% | 344% |
| 123_1 | 105% | 9% | 119% | 19% | 112% | 204% | 15% | 245% | 74% | 224% |
| 129_1 | 88% | 18% | 108% | 10% | 98% | 102% | 2% | 105% | 11% | 103% |
| 133_1 | 96% | 19% | 105% | 2% | 101% | 139% | 26% | 131% | 4% | 135% |
| 144_1 | 105% | 8% | 111% | 8% | 108% | 98% | 2% | 94% | 1% | 96% |
| 145_1 | 98% | 2% | 92% | 4% | 95% | 179% | 52% | 161% | 37% | 170% |
| 151_1 | 102% | 1% | 94% | 4% | 98% | 121% | 13% | 110% | 20% | 116% |
| 152_1 | 94% | 8% | 105% | 11% | 100% | 111% | 12% | 142% | 15% | 127% |
| 155_1 | 102% | 6% | 106% | 10% | 104% | 110% | 6% | 106% | 4% | 108% |
| 156_1 | 106% | 2% | 102% | 15% | 104% | 121% | 0% | 125% | 10% | 123% |
| 157_1 | 106% | 4% | 114% | 2% | 110% | 139% | 21% | 138% | 23% | 139% |
| 161_1 | 89% | 4% | 101% | 15% | 95% | 141% | 21% | 174% | 11% | 158% |
| 162_1 | 96% | 0% | 106% | 4% | 101% | 107% | 8% | 106% | 9% | 107% |
| 163_1 | 100% | 4% | 94% | 7% | 97% | 107% | 11% | 101% | 9% | 104% |
| 165_1 | 113% | 16% | 105% | 4% | 109% | 344% | 15% | 457% | 63% | 400% |
| 166_1 | 116% | 15% | 174% | 48% | 145% | 188% | 42% | 476% | 11% | 332% |

Example 4: In Vivo Reduction of TMEM106B in Mice

The present example tests the ability of selected oligonucleotides from Example 1 to reduce TMEM106B in vivo in mouse brain as well as the acute and non-acute toxicity potential of the oligonucleotides.

C57BL/6J male mice (23-32 g) were freehand injected with 5 µl of 20 mg/ml saline formulated LNA oligonucleotides into right lateral ventricles (0.3 AP, 1.0 ML, 3.0 DV; six animals per group for TMEM106B reactive compounds; fifteen saline treated animals; fifteen animals treated with MAPT reactive compound and six animals treated with a negative control oligo) under isoflurane anesthesia.

After the administration the acute response was scored in four levels: (1) normal behavior, (2) mild response (slight change in activity/posture/gait for 30 min-1 hr), (3) moderate response (prolonged pronounced change in activity/posture for 2-4 hrs), (4) severe (no activity, shallow breathing, moribund). The weight of the mice was measured immediately prior to administration of an oligonucleotide and six days after the administration. Significant loss of body mass is an indicator of potential non-acute toxicity. The results are shown in Table 13 below.

Seven days after the injection, mice were sacrificed with isoflurane overdose followed by rapid decapitation, and the brain was placed in an ice-cold mouse brain slicer matrix (Stoelting) and sectioned into two (2 mm) coronal sections (starting at 0.26 mm from Bregma) weighing approximately 30-40 mg. The tissue was immersed in RNALater solution (ThermoFisher Scientific, cat. AM7021) and stored at 4° C. RNA was isolated using RNeasy Mini Kit (Qiagen, cat. 74116) using QIAcube robotic workstation (Qiagen). Briefly, brain fragment was transferred from the RNALater solution to 1 mL RLT buffer in 1.5 mL Eppendorf tube containing 3 mm tungsten carbide bead (Qiagen, cat 69997). Tissue was lysed using TissueLyser II (Qiagen) (3 min at 30 Hz) and centrifuged 3 minutes at 20000 g. 550 µl of the lysate (no foam, no sediment) was transferred to 2 mL Eppendorf tube and placed in QIAcube pre-filled with all the required reagents. RNA was purified according to a program "RNeasy Mini—Animal tissues and cells—Large samples (version 2)" with elution with 50 µl of $H_2O$. RNA concentration was measured using NanoDrop 8000 (ThermoFisher Scientific) spectrophotometer and the concentration was adjusted with $H_2O$ to 2 ng/µl.

Expression levels on sections from the right hemisphere were essentially measured as described in Example 1, using TMEM106B Mm00510952_m1 (Thermo Fisher Scientific, cat. 4351370) as probe and a GAPDH probe (cat. 4352339E, Thermo Fisher Scientific) for normalization. The data was analyzed using the QuantStudio™ Real_time PCR Software, and the readouts of the technical duplicates were averaged. The results are shown in Table 12 as % of average control samples (PBS-treated mice) i.e. the lower the value the larger the inhibition.

TABLE 12

In vivo efficacy of oligonucleotides targeting TMEM106B.

| CMP ID NO | TMEM106B mRNA (% saline) | SD |
|---|---|---|
| 156_1 | 34% | 10% |
| 152_1 | 34% | 13% |
| 155_1 | 53% | 14% |
| 17_1 | 59% | 18% |
| 144_1 | 67% | 27% |
| 157_1 | 67% | 11% |
| 133_1 | 49% | 17% |
| 151_1 | 63% | 8% |
| 163_1 | 96% | 3% |

TABLE 13

Acute response and body mass change observed in mice injected with oligonucleotides targeting TMEM106B.

| CMP | Acute response | | | | Body mass Average | |
|---|---|---|---|---|---|---|
| ID NO | Normal | Mild | Moderate | Severe | change [g] | SD |
| 156_1 |  | 5 | 1 |  | −0.03 | 0.90 |
| 152_1 | 1 | 5 |  |  | 0.08 | 0.51 |
| 155_1 | 6 |  |  |  | 0.82 | 1.06 |
| 17_1 | 2 | 4 |  |  | −0.40 | 0.74 |
| 144_1 | 6 |  |  |  | −2.27 | 2.33 |
| 157_1 | 6 |  |  |  | 0.83 | 0.40 |
| 133_1 | 6 |  |  |  | 0.63 | 0.54 |
| 151_1 | 6 |  |  |  | 0.67 | 0.45 |
| 161_1 |  |  |  | 3 | 0.22 | 0.18 |
| 163_1 | 6 |  |  |  | 0.65 | 0.74 |
| Saline | 14 | 1 |  |  |  |  |

From Table 12 and 13 it can be seen that all the TMEM106B targeting oligonucleotides were capable of reducing TMEM106B mRNA after a single injection. Of the 10 oligonucleotides tested one was found to cause severe acute toxicity. Compound ID NO 161 was administered to only three animals, which were euthanized immediately following observation of severe response, consequently there is not TMTM106B reduction measured for this compound. Some animals administered with compound 144_1 showed signs of significant body mass loss, which could be due to non-acute toxicity of this compound. All the remaining oligonucleotide compounds seemed to be well tolerated 7 days after treatment.

Example 5: Treatment of Human iPSC Neurons and Astrocytes Mix Culture

In Example 2, human TMEM106b were initially screened in the human neuroblastoma cell line. To assess the ability of these ASO's to reduce the target in human neurons, the efficacy of five human TMEM106b ASOs: CMP ID 74_1, 65_1, 75_1, 71_1, 66_1, were evaluated in a cell culture mixture of human iPSC neurons and astrocytes.

Human iPSC-derived neural stem cells (MTI-Global-Stem, GSC-4311) were maintained in NSC Maintenance Medium (DMEM/F12 (Genentech)/Neurobasal (ThermoFisher Scientific, 21103049), 1×GS22 (MTI-Global STEM, GSM-3200), 20 ng/ml BDNF (Peprotech, 450-02), 20 ng/ml FGF-basic (Peprotech, 100-18b), 20 ng/ml EGF (Peprotech, AF-100-15), 0.5 mM Glutamax (Gibco, 35050061), 0.11 mM β-Mercaptoethanol (Sigma-Aldrich CHECKCAT), 1× Normocin (InvivoGen, ant-nr-1), 50 U/ml Penicillin-Streptomycin (ThermoFisher 15160122)) in a 37° C. $CO_2$ cell culture incubator; NSC Maintenance Medium was changed every 3-4 days until cells were confluent. For neuronal differentiation, the cells were plated onto a 50 µg/ml PDL (Sigma-Aldrich, P6407) and 10 µg/ml Recombinant Human Laminin (Sigma-Aldrich, St Louis, Mo., USA) T-650 cell culture flask at an approximate concentration of $0.7×10^6$-$1.0×10^6$ cells/ml. Cells were plated in Neuron Differentiation Media ((DMEM/F12 (Genentech)/Neurobasal (ThermoFisher Scientific 21103049), 1×GS21 (MTI-Global STEM GSM3300), 1×N2 (MTI-GlobalStem GSM3300), 5 µg/ml Cholesterol (Sigma-Aldrich C3045), 1 mM Creatine (Sigma-Aldrich C0780), 100 µM Ascorbic Acid (Sigma-Aldrich A8960), 0.5 mM cAMP (Sigma-Aldrich D0627), 20 ng/ml BDNF (Peprotech, 450-02), 20 ng/ml GDNF (Peprotech, 450-10), 1 µg/ml Mouse Laminin (Invitrogen, 23017-015), 0.5 mM Glutamax (Gibco, 35050061), 1× Normocin (InvivoGen, ant-nr-1), 50 U/ml Penicillin-Streptomycin (ThermoFisher, 15160122)) supplemented with Y27632 (Tocris, 1254), SU9516 (Tocris, 2907), and Cumate (System Biosciences AM100A-1). The plated cells were differentiated for 1 week; one half volume differentiation media was changed every 3-4 days. After differentiation, cells were plated onto 384-well or 96-well, PDL-Laminin coated plates at an approximate concentration of $2.5×10^5$-$5.5×10^5$ in pre-warmed differentiation medium supplemented with Y27632 Rock inhibitor (Tocris, 1254) and 1× RevitaCell (Gibco, A2644501) and maintained for 1 week; one half volume differentiation media was changed every 3-4 days.

Primary human astrocytes (LifeTechnologies, N7805100) were maintained in Astrocyte Medium (DMEM High Glucose (Genentech), 10% FBS (VWR, 89510-198), 1×N2 (MTI-GlobalStem GSM3300), 1× Normocin (InvivoGen, ant-nr-1), 50 U/ml Penicillin-Streptomycin (ThermoFisher, 15160122)) in a 37° C. $CO_2$ cell culture incubator; medium was change every 3-4 days until cells were confluent. Astrocytes were subsequently added to the human iPSC neurons (described in the previous paragraph) in 384-well or 96-well plates at an approximate concentration of $3.0×10^4$-$8.0×10^4$ cells/ml in BrainPhys Maintenance Medium (BrainPhys Basal (STEMCELL Technologies, 05790), 1×GS21 (MTI-Global STEM GSM-3100), 1×N2 (MTI-GlobalStem GSM3300), 5 µg/ml Cholesterol (Sigma-Aldrich C3045), 1 mM Creatine (Sigma-Aldrich C0780), 10 nM β-estradiol (Sigma-Aldrich E2758), 200 nM Ascorbic Acid (Sigma-Aldrich A8960), 1 mM cAMP (Sigma-Aldrich D0627), 20 ng/ml BDNF (Peprotech, 450-02), 20 ng/ml GDNF (Peprotech, 450-10), 1 µg/ml Mouse Laminin (Invitrogen, 23017-015), 0.5 mM Glutamax (Gibco, 35050061), 1× Normocin (InvivoGen, ant-nr-1), 50 U/ml Penicillin-Streptomycin (ThermoFisher, 15160122), 1 ng/ml TGFβ1 (Peprotech, 100-21); one half volume of the BrainPhus Maintenance Medium was changed every 3-4 days for 6-8 weeks.

For ASO treatment of the human iPSC neurons CMP ID 74_1, 65_1, 75_1, 71_1, 66_1 were diluted from stock in an intermediate 96 well plate in a 9 point 3 fold serial dilution (10 µM, 3.3 µM, 1.1 µM, 0.37 µM, 0.12 µM, 0.04 µM, 0.0137 µM, 0.0045 µM, 0.0015 µM) or a 5 point 10 fold serial dilution (10 µM, 1 µM, 0.1 µM, 0.01 µM, 0.001 µM).

In a continuous 10 days incubation experiment, the ASO's were added the human iPSC neurons and astrocytes mix after 2 months of culture at the ASO concentrations indicated above (5 point 10 fold). On day 3 and day 7, 50% of media were changed to maintain optimal cell health (no additional ASO was added). 10 days after ASO treatment was initiated, cells were harvested for Taqman assay following the manufacturer's instructions from TaqMan Gene Expression Cells-to-Ct Kit (ThermoFisher Scientific, AM1728). The human neuron TMEM106b Taqman assay was performed following the manufacturer's instruction with specific gene expression assay probes for human TMEM106b and POL2RB as housekeeping gene normalizer (assay ID Hs00998849_m1 and Hs00946293_m1, respectively). The TMEM106b expression levels were normalized to the POL2RB housekeeping gene and the relative expression in relation to the media control (100%) was calculated (i.e. lower numbers indicate high TMEM106b reduction). Graph Pad Prism software was used to conduct the IC50 analysis using the software curve fit option. The results are shown in Tables 14 and 15, and FIGS. 7A and 7B. The structural formulas of CMP IDs 74_1, 65_1, 75_1, 71_1, 66_1 are shown in FIGS. 9-13.

TABLE 14

% TMEM106b mRNA reduction in relation to saline in human iPSC neurons and astrocytes mix culture following 10 days consecutive treatment with serial dilution of ASOs (n = 3).

| | ASO Conc | | | | | | | | | |
|---|---|---|---|---|---|---|---|---|---|---|
| | CMP ID 74_1 | | CMP ID 65_1 | | CMP ID 75_1 | | CMP ID 71_1 | | CMP ID 66_1 | |
| µM | Avg | SD | Avg | SD | Avg | SD | Avg | SD | Avg | SD |
| 10.0000 | 2 | 0.0 | 1 | 0.6 | 2 | 1.0 | 5 | 0.6 | 6 | 2.0 |
| 3.3333 | 2 | 0.0 | 3 | 0.6 | 4 | 1.0 | 8 | 5.3 | 10 | 2.9 |
| 1.1111 | 2 | 0.6 | 5 | 1.0 | 7 | 2.6 | 14 | 6.0 | 18 | 3.5 |
| 0.3704 | 5 | 0.6 | 11 | 0.6 | 11 | 1.5 | 19 | 7.9 | 32 | 12.1 |
| 0.1235 | 8 | 0.0 | 21 | 2.5 | 17 | 2.6 | 27 | 10.0 | 50 | 3.0 |
| 0.0412 | 16 | 1.5 | 46 | 5.1 | 32 | 1.5 | 44 | 14.2 | 61 | 12.5 |
| 0.0137 | 29 | 7.0 | 68 | 4.6 | 60 | 16.1 | 59 | 6.4 | 83 | 10.6 |
| 0.0046 | 61 | 12.5 | 79 | 11.4 | 76 | 7.9 | 77 | 1.7 | 111 | 11.4 |
| 0.0015 | 100 | 0.0 | 100 | 0.0 | 110 | 7.0 | 96 | 4.0 | 112 | 14.4 |
| IC50/nM | 7.6 | | 31.4 | | 21.6 | | 30.7 | | 128.7 | |

Figure 7A:
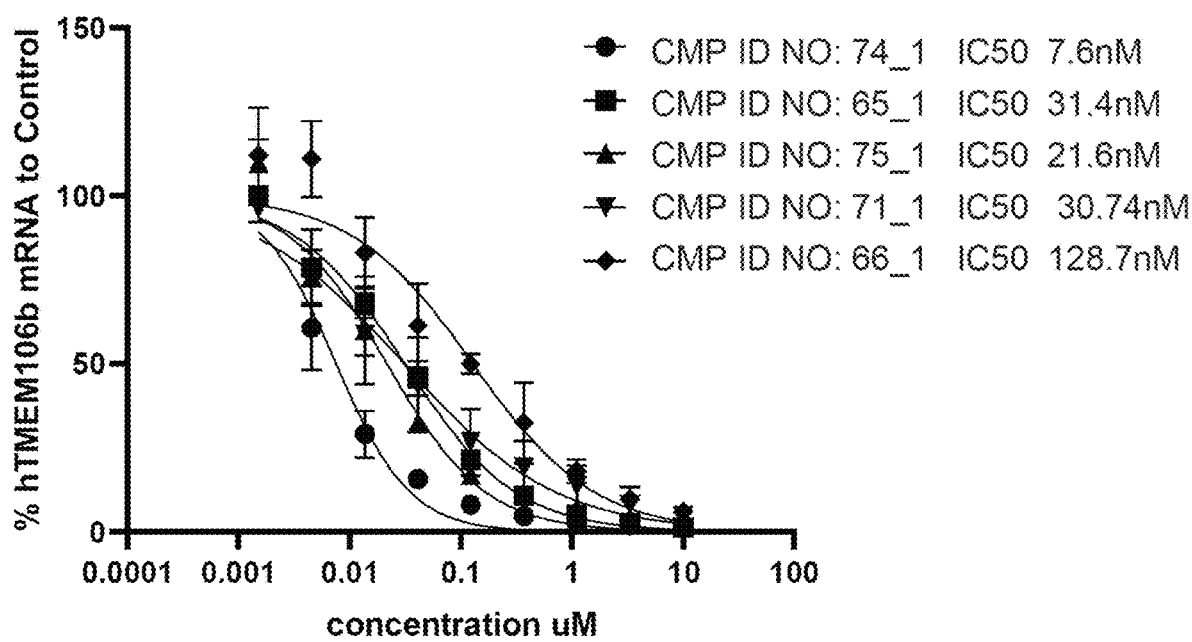
FIG. 7A: Target inhibition after continuous 10 days treatment with ASOs in human iPSC neurons and astrocytes mix culture at increasing concentration for five human ASOs.
Figure 7B:
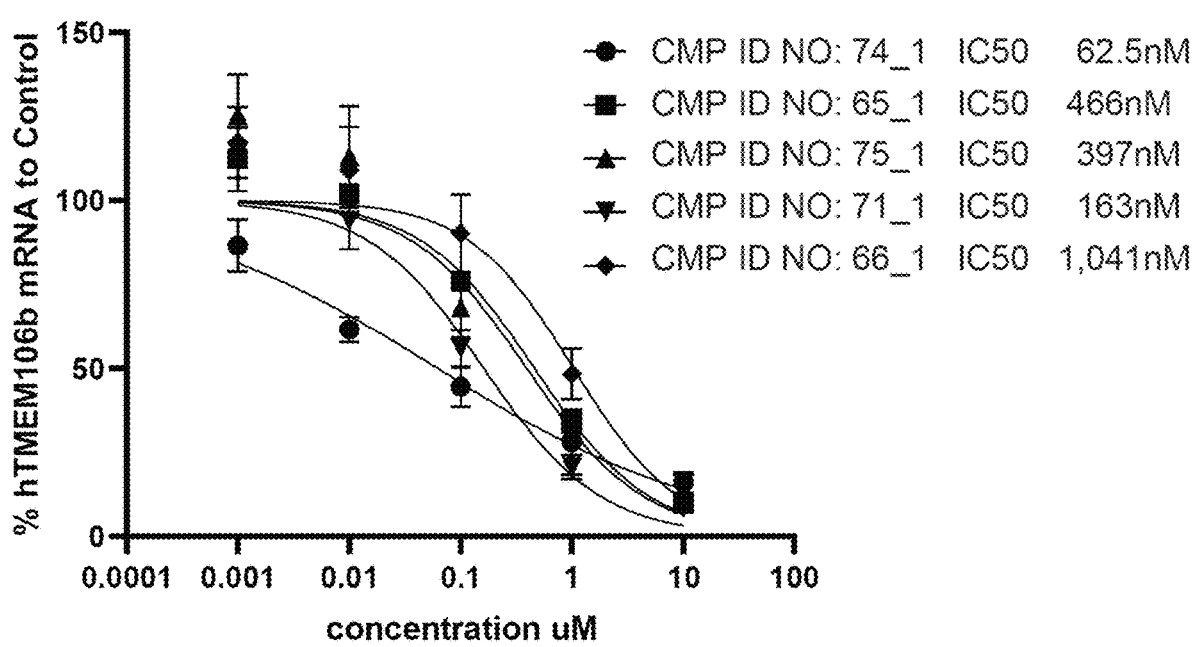
FIG. 7B: Target inhibition after 10 days with 24 hrs pulse treatment with ASOs in human iPSC neurons and astrocytes mix culture at increasing concentration for five human ASOs.

It can be taken from the data that the ASOs show high potency in the range of 7.6 nM to 128.7 nM (Table 14, FIG. 7A). Furthermore, it can be seen that the near complete elimination of human neuronal TMEM106b mRNA.

The ASOs were furthermore evaluated in a 24 hour pulse experiment to assess whether short term ASO treatment can have a long-lasting effect. The five human TMEM106b ASOs CMP ID 74_1, 65_1, 75_1, 71_1, 66_1, were added to human iPSC neurons and astrocytes mix after 2 months of culture at the ASO concentrations indicated above (9 point 3 fold dilutions). The ASO treatment was only for 24 hrs then cells were washed with neuronal culture media 3×. On day 3 and day 7, 50% of media were changed to maintain optimal cell health. 10 days after ASO treatments, cells were harvest and TMEM106B mRNA were accessed with the Taqman assay described above. The results are shown in Table 15 and FIG. 7B.

It was further investigated if the ASO treatment of the human iPSC neurons and astrocytes results in reduction of TMEM106b protein levels. In a continuous 10 days incubation experiment, the ASO's were added to the human iPSC neurons and astrocytes mix after 2 months of culture at a final ASO concentration of 10 µM. On day 3 and day 7, 50% of media were changed to maintain optimal cell health (no additional ASO was added). 10 days after ASO treatment was initiated, cells were harvested with RIPA buffer (Pierce 89900) with proteinase inhibitors (Roche 11836153001) for protein analysis. BCA micro protein concentration analysis was performed according to the manufacture's instruction on all lysates to measure total protein concentration (Thermo Fisher Scientific, 23235). Protein analysis was performed on the Peggy Sue automated western instrument (Protein Simple) following manufacturer's instruction using Peggy Sue kit (SM-S001). Equal amount of total protein was loaded. Antibody for TMEM106b is from Bethyl (A303-

TABLE 15

% TMEM106b mRNA reduction in relation to saline in human iPSC neurons and astrocytes mix culture after 24 hour pulse treatment with serial dilution of ASOs (n = 3).

| | ASO Conc | | | | | | | | | |
|---|---|---|---|---|---|---|---|---|---|---|
| | CMP ID 74_1 | | CMP ID 65_1 | | CMP ID 75_1 | | CMP ID 71_1 | | CMP ID 66_1 | |
| µM | Avg | SD | Avg | SD | Avg | SD | Avg | SD | Avg | SD |
| 10 | 16 | 3.0 | 10 | 2.5 | 14 | 4.4 | 9 | 0.7 | 15 | 2.1 |
| 1 | 28 | 9.6 | 34 | 3.5 | 32 | 3.6 | 21 | 3.5 | 48 | 7.5 |
| 0.1 | 45 | 6.0 | 76 | 1.0 | 68 | 9.0 | 56 | 5.7 | 90 | 11.5 |
| 0.01 | 62 | 3.8 | 102 | 2.0 | 113 | 15.1 | 94 | 8.5 | 109 | 13.0 |
| 0.001 | 87 | 7.8 | 112 | 9.6 | 126 | 12.0 | 114 | 1.4 | 117 | 10.7 |
| IC50/nM | 62.5 | | 468.9 | | 397.2 | | 163.3 | | 1041 | |

These results show IC50 in the range of 62.5 nM to 1 µM (Table 15, FIG. 7B), and that with only 24 hrs incubation, all five human TMEM106b ASOs at 10 µM can effectively and nearly completely eliminate human TMEM106b mRNA and have a long lasting effect for at least 10 days similar to long term incubation (Table 14, FIG. 7A).

439A) and GAPDH for housekeeping gene normalization is from Norvus (NB100-56875).

Figure 7C:
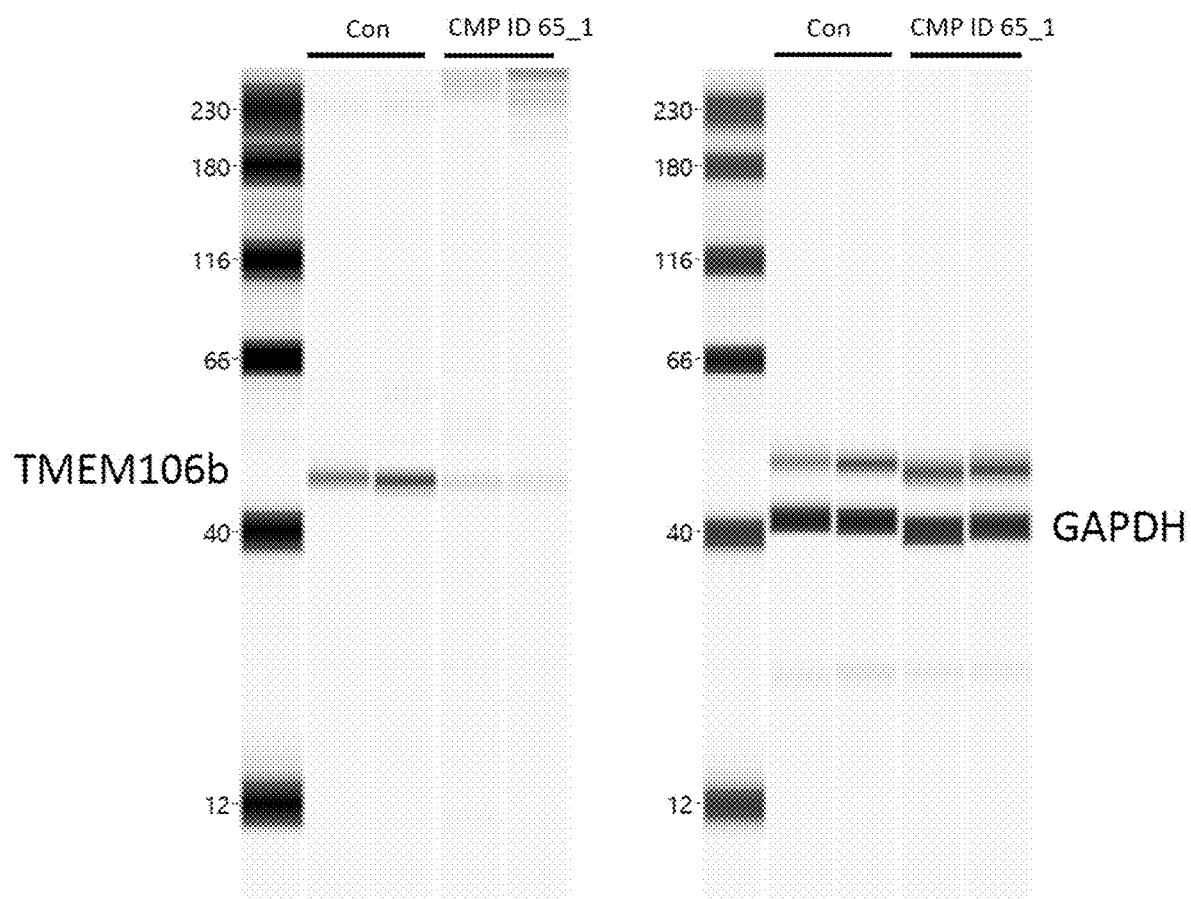
FIG. 7C: Automated western blot on reduction in TMEM106b protein level after continuous 10 days treatment with ASOs in human iPSC neurons and astrocytes mix culture.

FIG. 7C shows the automated western blot result. On the left panel the neuronal lysates after 10 days treatment with control and CMP ID 65_1 ASO 10 µM were load in the indicated lanes. Then the lanes were probed with anti TMEM106b antibodies. The right panel shows the same sample lanes probed with anti GAPDH antibodies. It can be seen that CMP ID 65_1 is able to reduce human TMEM106b protein level after 10 days of treatment.

Example 6: Time Course for In Vivo Reduction in Mice of TMEM106b mRNA and Protein The present example tests the ability of selected mouse ASOs, also used in Example 4 above, for long term reduction of mRNA and protein 1, 2, 4, 8, and 12 weeks after a single ICV injection.

The data generated in Example 4 related to the reduction of mRNA 1 week after a single ICV injection has been taken over in this Example. Additional data were generated on the mRNA and protein reduction 1, 2, 4, 8, and 12 weeks after a single ICV injection.

C57BL/6J males from Jackson Laboratory, age 3-6 months, were used in these experiments. Mice were housed on a regular light/dark cycle (14:10 hours) with adlibitum access to food (LabDiet 5010) and water. All injections and tissue collections were conducted during the light phase. All protocols for mouse experiments were approved by the Institutional Animal Care and Use Committee and were conducted in accordance with the NIH Guide for the Care and Use of Laboratory Animals.

Animals were anesthetized with isoflurane, the hair above the parietal region of the skull was removed by shaving and skin cleaned with either antimicrobial betadine solution and 70% ethanol or Cloraprep solution. A midline incision of the skin was made between the occiput and forehead to identify Bregma. Mice were injected 100 μg of ASO in a volume of 5 μl (saline) into the right lateral ventricle (−0.5 AP, 1.0 ML, 3.0 DV) at a rate of 1 μl/sec, using a 26-gauge 10 μl Hamilton syringe. One minute after the injection the needle was slowly withdrawn. The incision was closed with tissue glue and buprenorphine was given for up to 3 days to reduce any pain caused by the procedure.

At 1 (for mRNA original data from Example 4), 2, 4, 8, and 12 weeks after the injection, mice were euthanized by decapitation under a constant flow of inhalant anesthetic (isoflurane). Brains were placed on an ice cold brain matrix and the right hemibrain was sectioned into two 2 mm sections. One section was immediately place into RNALater (Ambion), and stored at 4° C. for qPCR. The second 2 mm slice was weighed, immediately flash frozen in liquid nitrogen and stored at −80° C. for protein analysis.

For qPCR, tissues were then transferred to RLT Buffer (Qiagen) lysis reagent and lysed using a TissueLyser (Qiagen). RNA was extracted using RNeasy Mini QIAcube Kit (cat. 74116) with QIACUBE workstation. RNA concentrations were checked on Nanodrop (as RNA-40, blank H20) and then each sample was diluted with water to yield 2 ng/μl solutions. RNA was heat denatured at 90° C. for 40 seconds. qPCR assay was performed on Applied Biosystems ViiA7 thermal cycler using qScript™ XLT One-Step RT-qPCR ToughMix® Low ROX (QuantaBio, cat. 95134-02K), using TMEM106b (cat. 4351368, ThermoFisher Scientific) as the probe and GAPDH (cat. 4352339E, ThermoFisher Scientific) probe for normalization. Results are shown in Table 16 and FIG. 8A.

TABLE 16

Long term reduction of TMEM106b mRNA in vivo

| Weeks Post-Injection | CMP ID NO: 152_1 (% saline) | SD | CMP ID NO: 155_1 (% saline) | SD |
|---|---|---|---|---|
| 1 | 34% | 13% | 51% | 14% |
| 2 | 41% | 19% | 46% | 14% |
| 4 | 35% | 7% | 43% | 19% |
| 8 | 57% | 5% | 56% | 6% |
| 12 | 68% | 11% | 67% | 10% |

Figure 8A:
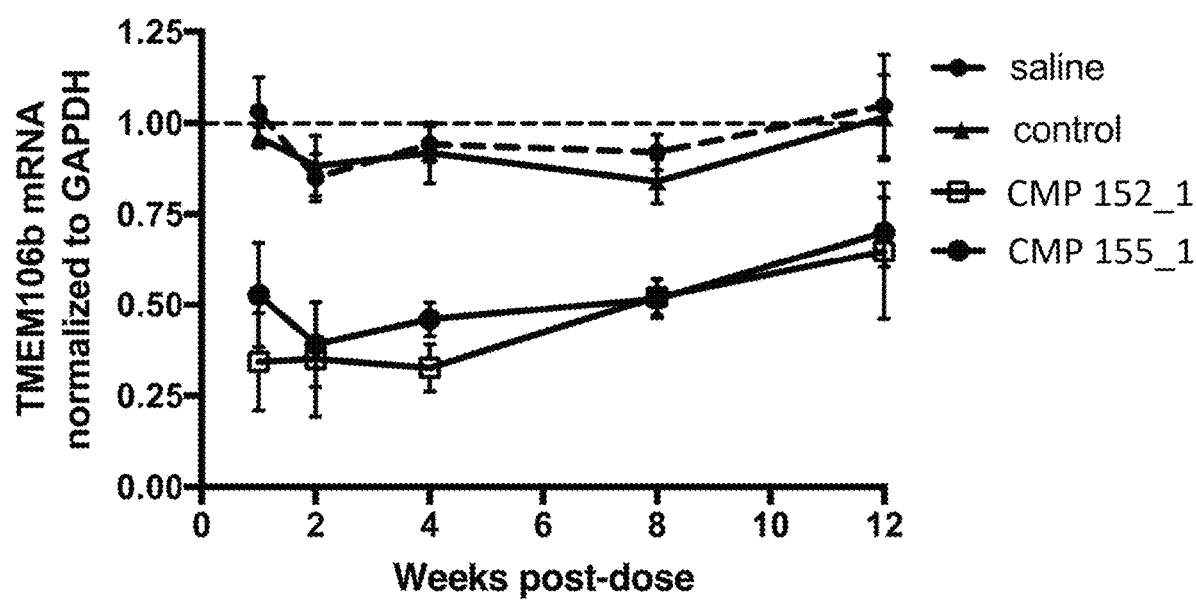
FIG. 8A: Time course for in vivo TMEM106b mRNA reduction after a single ICV injection of 100 µg LNA oligonucleotides in a volume of 5 µl saline into the right lateral ventricle (normalized to GAPDH).

As can be taken from Table 16 and FIG. 8A, reductions of TMEM106b mRNA for both CMP ID NO:152_1 and 155_1 were maximal between 1 and 4 weeks post-injection. Compared to saline controls (n=3-6/group), TMEM106b mRNA in the ASO treated animals did not return to baseline (saline control animals) 12 weeks post-injection, with 30-35% mRNA reduction detected for both CMP ID NO:152_1 and 155_1 (n=6-7/group) after 12 week.

For western blot, the second flash frozen slice was homogenized in 10 volumes of RIPA buffer with Complete Roche protease inhibitor cocktail (Roche) and PhosStop (Roche) using a TissueLyser (Qiagen, 3 min at 30 cycles/s). Samples were then rotated for 20 min at 4° C., then centrifuged at 14,000 rpm (Gs) at 4° C. for 20 min. Supernatants were collected and stored at −80° C. Protein samples were diluted 1/5 in LDS loading buffer (4×, Invitrogen) with Reducing agent (10×, Invitrogen) and heat denatured for 5 min at 95° C. Samples were then kept on ice and stored at −20° C. Equal volumes of sample were separated on a 10% Bis-Tris gel with 1× MOPS running buffer, transferred to nitrocellulose membrane (iBlot2, ThermoFisher) and blocked at room temperature with 5% non-fat dried milk in TBS-Tween. Blots were probed with Rabbit anti-TMEM106b (A303-439; Bethyl, 1:500) or beta-Tubulin in 5% BSA overnight at 4° C. Blots were washed with TBST and incubated with HRP-conjugated secondary antibodies at room temperature for 2 h, then developed using Supersignal West Dura ECL (ThermoFisher) on a ChemiDoc (Bio-Rad). Blots were quantified using Image Lab 5.2 (BioRad) and each lane was normalized to beta-Tubulin, then to control samples. The results are shown in Table 17 and FIG. 8B.

TABLE 17

Long term reduction of TMEM106b protein in vivo

| Weeks Post-Injection | CMP ID NO: 152_1 (% saline) | SD | CMP ID NO: 155_1 (% saline) | SD |
|---|---|---|---|---|
| 1 | 66% | 7% | 64% | 18% |
| 2 | 62% | 9% | 72% | 10% |
| 4 | 53% | 11% | 68% | 20% |
| 8 | 65% | 14% | 67% | 22% |
| 12 | 61% | 7% | 86% | 14% |

Figure 8B:
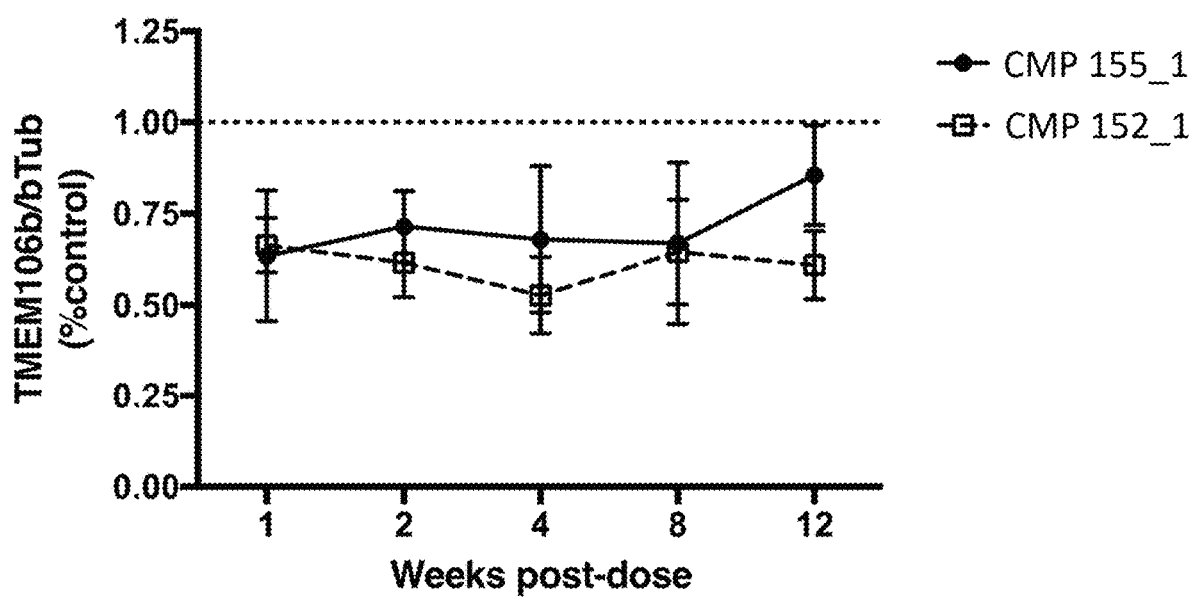
FIG. 8B: In vivo time course for in vivo TMEM106b protein reduction after a single ICV injection of 100 µg LNA oligonucleotides in a volume of 5 µl saline into the right lateral ventricle (normalized to beta-Tubulin).
Figure 9:
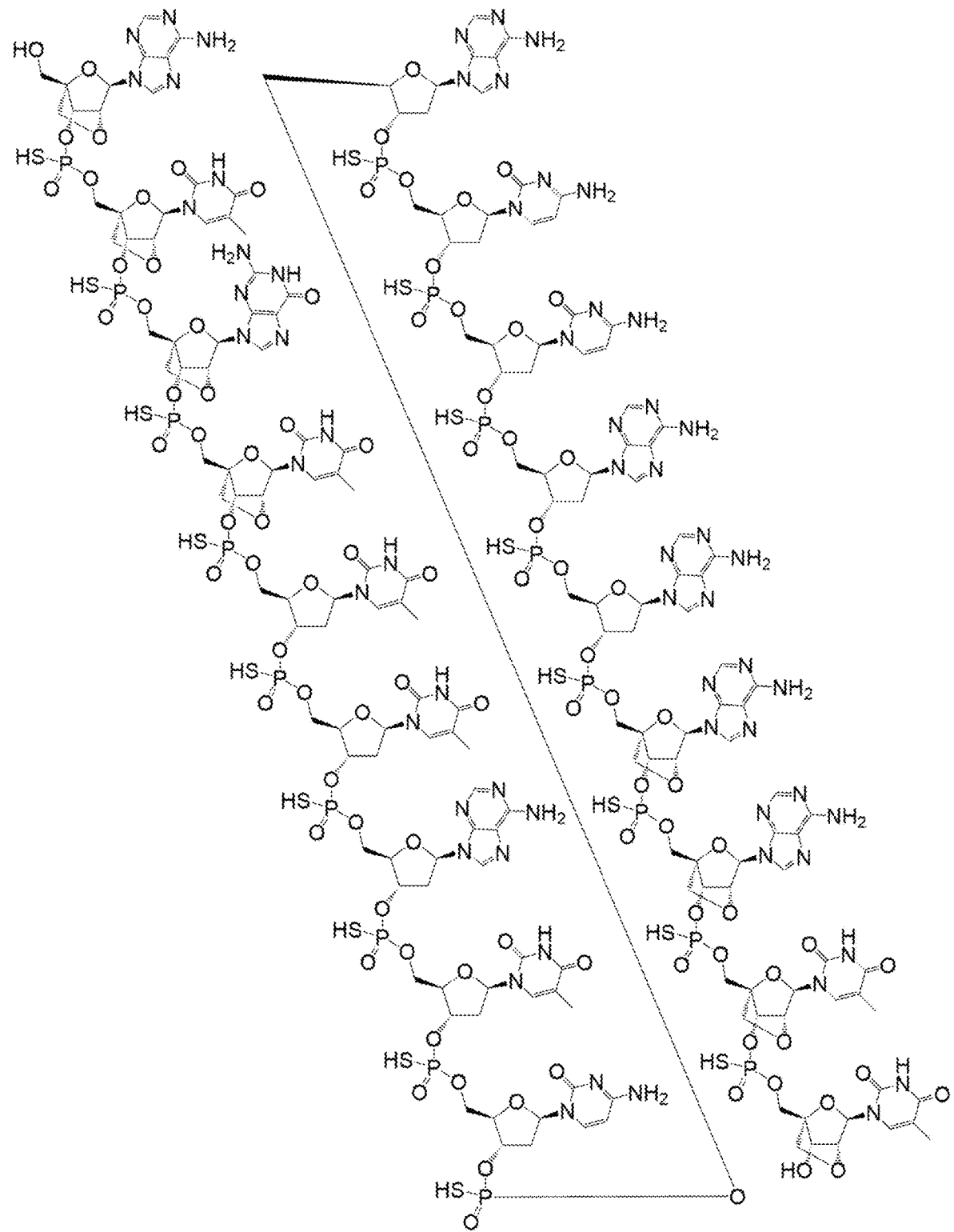
FIG. 9: Structural formula of CMP ID NO: 65_1. Pharmaceutical salts thereof include monovalent or divalent cations, such as $Na^+$, $K^+$, and $Ca^{2+}$ or a mixture of these being associated with the compound.
Figure 10:
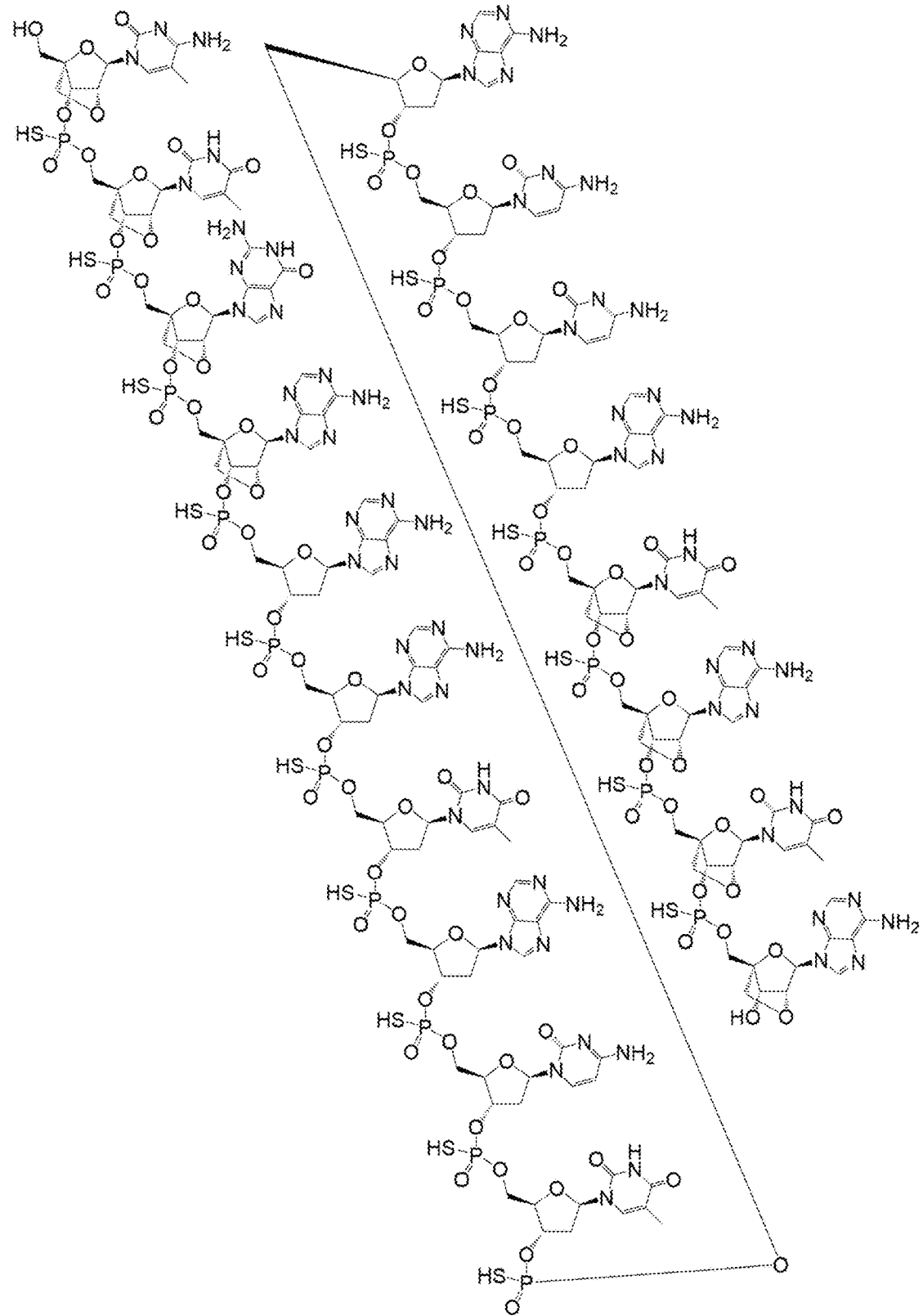
FIG. 10: Structural formula of CMP ID NO: 66_1. Pharmaceutical salts thereof include monovalent or divalent cations, such as $Na^+$, $K^+$, and $Ca^{2+}$ or a mixture of these being associated with the compound.
Figure 11:
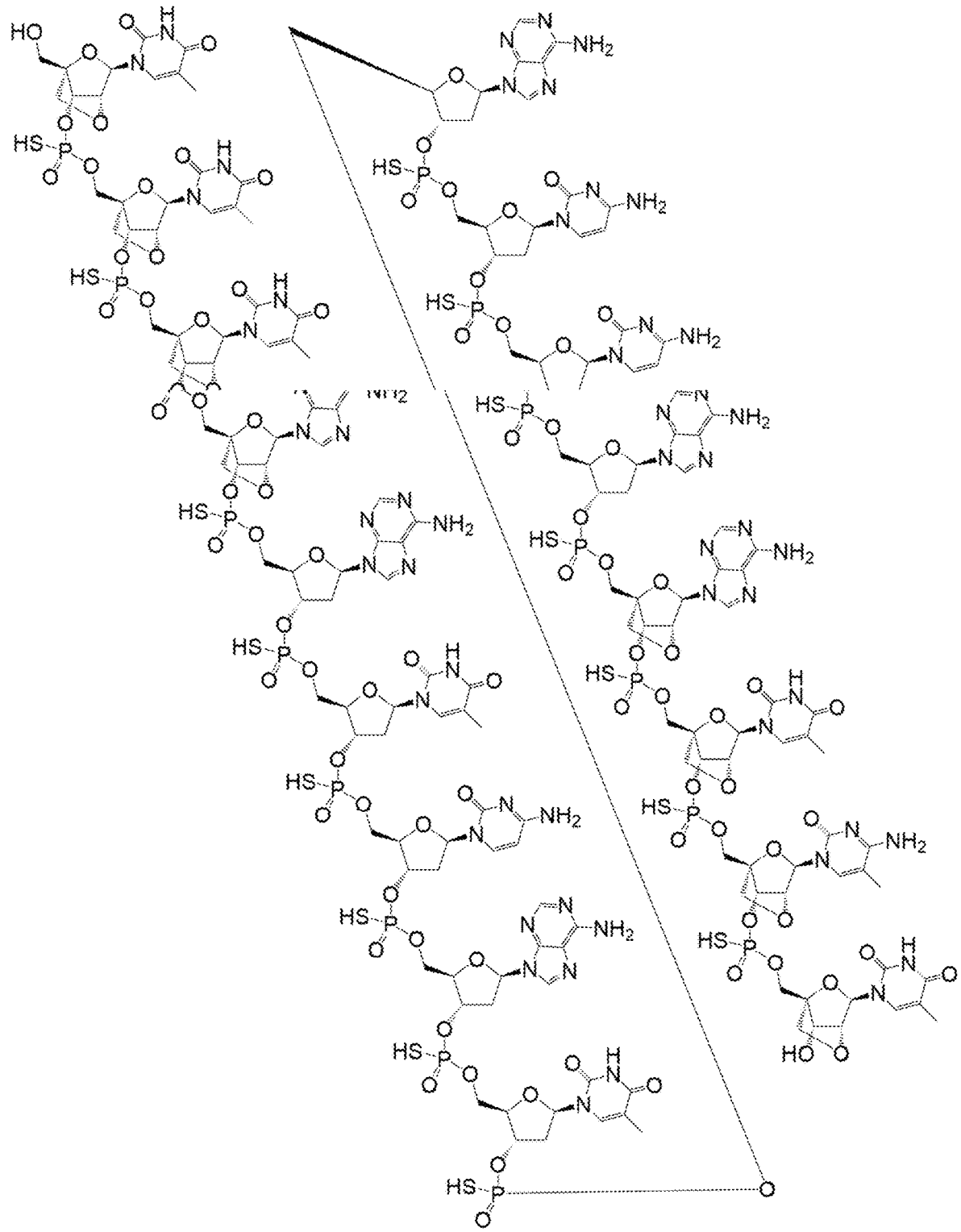
FIG. 11: Structural formula of CMP ID NO: 71_1. Pharmaceutical salts thereof include monovalent or divalent cations, such as $Na^+$, $K^+$, and $Ca^{2+}$ or a mixture of these being associated with the compound.
Figure 12:
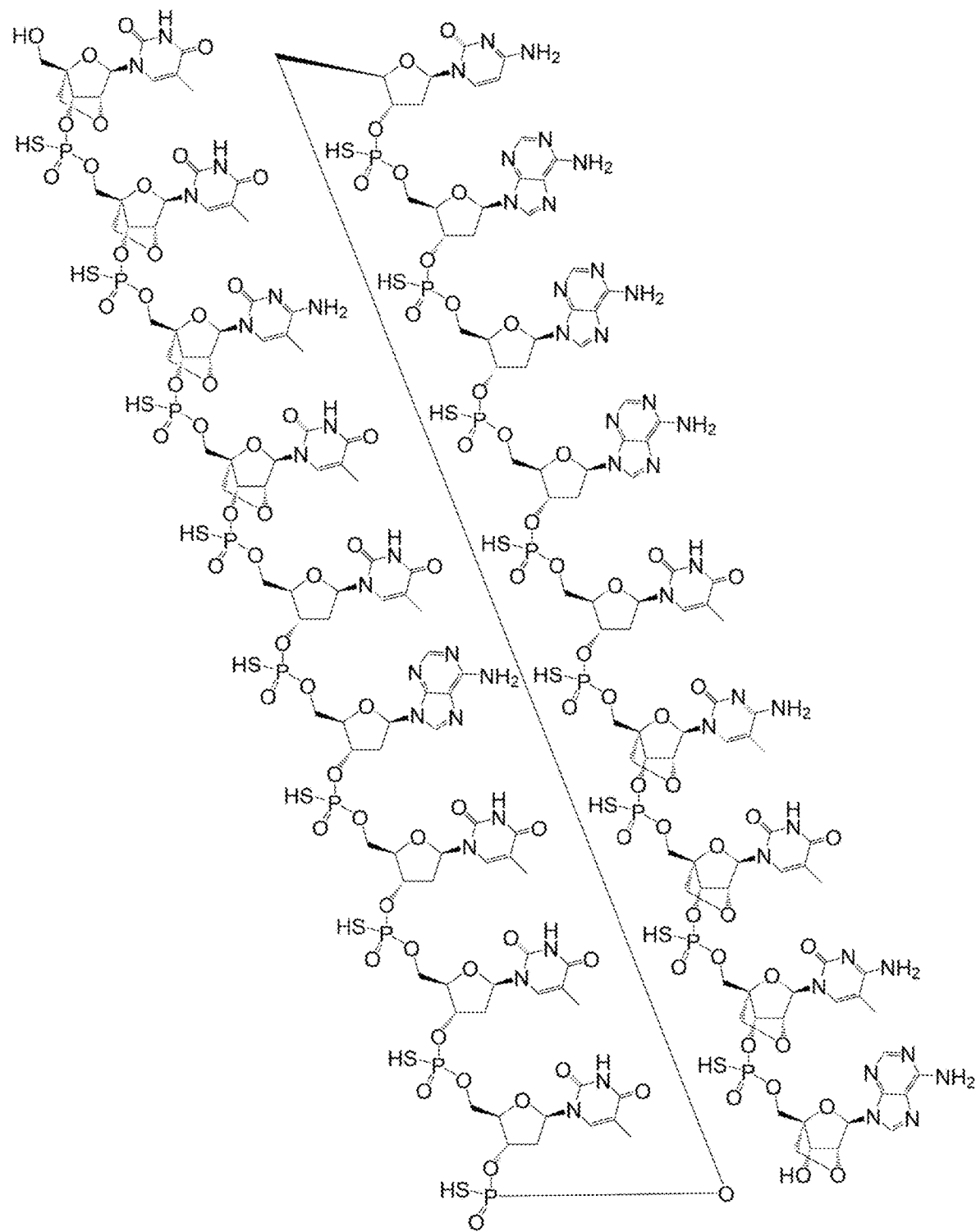
FIG. 12: Structural formula of CMP ID NO: 74_1. Pharmaceutical salts thereof include monovalent or divalent cations, such as $Na^+$, $K^+$, and $Ca^{2+}$ or a mixture of these being associated with the compound.
Figure 13:
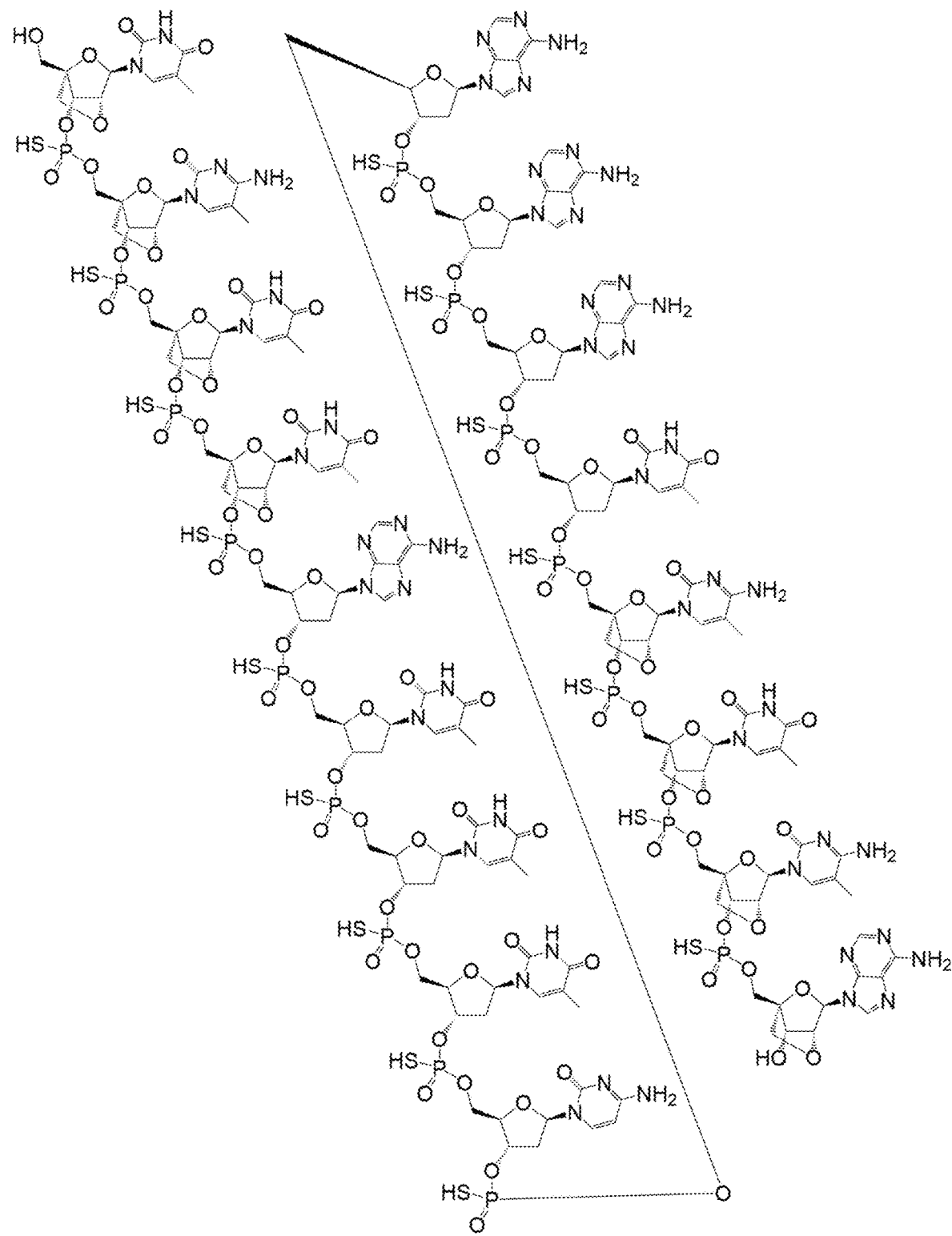
FIG. 13: Structural formula of CMP ID NO: 75_1. Pharmaceutical salts thereof include monovalent or divalent cations, such as $Na^+$, $K^+$, and $Ca^{2+}$ or a mixture of these being associated with the compound.

Similarly, as can be taken from Table 17 and FIG. 8B, TMEM106b protein was maximally reduced by 40-50% between 2-4 weeks post-injection. Compared to saline controls (n=2-6/group), TMEM106b protein did not return to baseline during the 12 weeks post-injection, with 39% reduction in CMP ID NO:152_1-treated animals (n=6-7/group) and 14% reduction in CMP ID NO:155_1-treated (n=5-7/group) animals.

The invention claimed is:

1. A therapeutic single-stranded antisense oligonucleotide of 10 to 50 nucleotides in length, comprising a contiguous nucleotide sequence of 10-30 nucleotides in length, wherein the contiguous nucleotide sequence comprises a sequence selected from the group consisting of SEQ ID NOs: 65, 66, 68, 71, 73, 74, 75, 79, and 82, and wherein the single-stranded antisense oligonucleotide comprises one or more modified nucleosides or nucleotides.

2. The single-stranded antisense oligonucleotide according to claim 1, wherein the contiguous nucleotide sequence comprises or consists of from 12 to 22 nucleotides.

3. The single-stranded antisense oligonucleotide according to claim 1, wherein the single-stranded antisense oligonucleotide comprises one or more 2' sugar modified nucleosides.

4. The single-stranded antisense oligonucleotide according to claim 3, wherein the one or more 2'-sugar modified nucleosides are independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

5. The single-stranded antisense oligonucleotide according to claim 4, wherein at least one of the one or more 2'-sugar modified nucleosides is an LNA nucleoside.

6. The single-stranded antisense oligonucleotide according to claim 1, wherein the contiguous nucleotide sequence comprises at least one modified internucleoside linkage.

7. The single-stranded antisense oligonucleotide according to claim 6, wherein the continuous nucleotide sequence comprises at least one phosphorothioate modified internucleoside linkage.

8. The single-stranded antisense oligonucleotide according to claim 1, wherein at least 75% or all of the internucleoside linkages of the contiguous nucleotide sequence are phosphorothioate internucleoside linkages.

9. The single-stranded antisense oligonucleotide according to claim 1, wherein the single-stranded antisense oligonucleotide is capable of recruiting RNase H1.

10. The single-stranded antisense oligonucleotide according to claim 1, wherein the single-stranded antisense oligonucleotide, or the contiguous nucleotide sequence thereof, consists of or comprises a gapmer of formula 5'-F-G-F'-3', wherein F and F' independently comprise 1-8 nucleosides, of which 1-5 nucleosides independently are 2' sugar modified and define the 5' and 3' end of F and F', and G is between 5 and 18 nucleosides which are capable of recruiting RNaseH.

11. The single-stranded antisense oligonucleotide according to claim 1, wherein the single-stranded antisense oligonucleotide is selected from the group consisting of a 2'-MOE gapmer, a LNA gapmer, a mixed wing gapmer, and an alternating flank gapmer.

12. The single-stranded antisense oligonucleotide according to claim 1, wherein the single-stranded antisense oligonucleotide, or the contiguous nucleotide sequence thereof, is selected from the group consisting of:

ATGTttatcaccaaAATT (SEQ ID NO: 65),
CTGAaatactaccaTATA (SEQ ID NO: 66),
CgaaattaatctcaaCCCA (SEQ ID NO: 68),
TTTAatcataccaATCT (SEQ ID NO: 71),
CTCAaataaattaatCTCT (SEQ ID NO: 73),
TTCTtatttcaaatCTCA (SEQ ID NO: 74),
TCTTatttcaaatCTCA (SEQ ID NO: 75),
TAACagtcttttACTC (SEQ ID NO: 79), and
ACTAtaacagtCTAC (SEQ ID NO: 82), wherein capital letters represent beta-D-oxy LNA nucleosides, lowercase letters represent DNA nucleosides, all LNA C are 5-methyl cytosine, and all internucleoside linkages are phosphorothioate internucleoside linkages.

13. A conjugate comprising the single-stranded antisense oligonucleotide according to claim 1, and at least one conjugate moiety covalently attached to said single-stranded antisense oligonucleotide.

14. A pharmaceutically acceptable salt of the single-stranded antisense oligonucleotide according to claim 1.

15. A pharmaceutical composition comprising the single-stranded antisense oligonucleotide of claim 1, and a pharmaceutically acceptable diluent, solvent, carrier, salt, and/or adjuvant.

16. An in vitro or in vivo method for modulating TMEM106B expression in a target cell expressing TMEM106B, the method comprising administering the pharmaceutical composition of claim 15 in an effective amount to the target cell.

17. A method for treating or preventing a disease comprising administering a therapeutically or prophylactically effective amount of the pharmaceutical composition of claim 15 to a subject suffering from or susceptible to the disease.

18. The method of claim 17, wherein the disease is selected from the group consisting of neurodegeneration, frontotemporal lobar degeneration (FTLD), Parkinson's disease, parkinsonism, hypomyelinating leukodystrophies, amyotrophic lateral sclerosis and multiple system atrophy, Alzheimer's disease, motor neuron disease, corticobasal syndrome, progressive supranuclear palsy, and neuronal ceroid lipofuscinosis (NCL).

19. The method according to claim 18, wherein the disease is FTLD.

20. A pharmaceutically acceptable salt of the conjugate according to claim 13.

21. A pharmaceutical composition comprising the conjugate of claim 13 and a pharmaceutically acceptable diluent, solvent, carrier, salt, and/or adjuvant.

22. The single-stranded antisense oligonucleotide according to claim 12, wherein the single-stranded antisense oligonucleotide, or the contiguous nucleotide sequence thereof, is CMP ID NO: 65_1 (SEQ ID NO: 65).

23. The single-stranded antisense oligonucleotide according to claim 12, wherein the single-stranded antisense oligonucleotide, or the contiguous nucleotide sequence thereof, is CMP ID NO: 66_1 (SEQ ID NO: 66).

24. The single-stranded antisense oligonucleotide according to claim 12, wherein the single-stranded antisense oligonucleotide, or the contiguous nucleotide sequence thereof, is CMP ID NO: 68_1 (SEQ ID NO: 68).

25. The single-stranded antisense oligonucleotide according to claim 12, wherein the single-stranded antisense oligonucleotide, or the contiguous nucleotide sequence thereof, is CMP ID NO: 71_1 (SEQ ID NO: 71).

26. The single-stranded antisense oligonucleotide according to claim 12, wherein the single-stranded antisense oligonucleotide, or the contiguous nucleotide sequence thereof, is CMP ID NO: 73_1 (SEQ ID NO: 73).

27. The single-stranded antisense oligonucleotide according to claim 12, wherein the single-stranded antisense oligonucleotide, or the contiguous nucleotide sequence thereof, is CMP ID NO: 74_1 (SEQ ID NO: 74).

28. The single-stranded antisense oligonucleotide according to claim 12, wherein the single-stranded antisense oligonucleotide, or the contiguous nucleotide sequence thereof, is CMP ID NO: 75_1 (SEQ ID NO: 75).

29. The single-stranded antisense oligonucleotide according to claim 12, wherein the single-stranded antisense oligonucleotide, or the contiguous nucleotide sequence thereof, is CMP ID NO: 79_1 (SEQ ID NO: 79).

30. The single-stranded antisense oligonucleotide according to claim 12, wherein the single-stranded antisense oligonucleotide, or the contiguous nucleotide sequence thereof, is CMP ID NO: 82_1 (SEQ ID NO: 82).

* * * * *

UNITED STATES PATENT AND TRADEMARK OFFICE
CERTIFICATE OF CORRECTION

PATENT NO. : 11,485,975 B2
APPLICATION NO. : 16/987030
DATED : November 1, 2022
INVENTOR(S) : Peter Hagedorn et al.

It is certified that error appears in the above-identified patent and that said Letters Patent is hereby corrected as shown below:

In the Specification

Column 16, Lines 66-67, replace "and 3. Table 2: Genome and assembly information for TMEM106B across species" with --and 3.--.

Column 30, Line 60, replace " 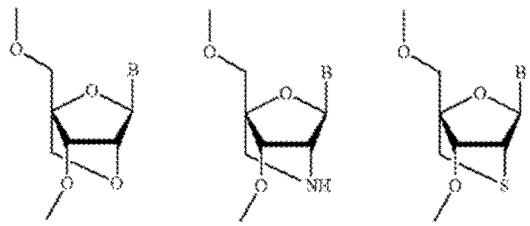 " with

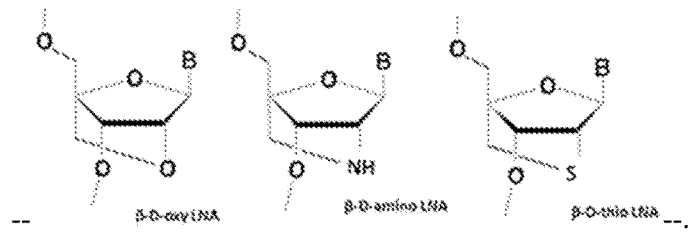 --.

Column 31, Line 22, replace " 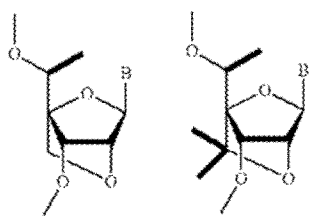 " with

Signed and Sealed this
Twenty-first Day of May, 2024

Katherine Kelly Vidal
*Director of the United States Patent and Trademark Office*

Column 31, Line 33, replace " 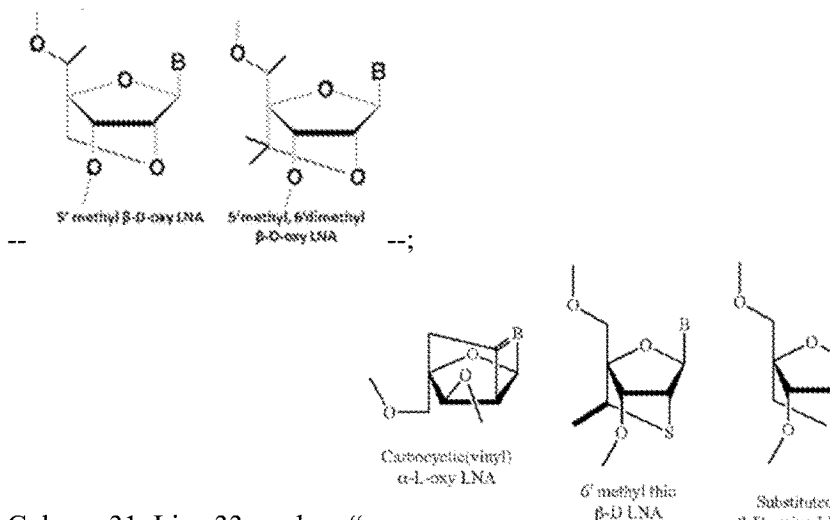 " with " 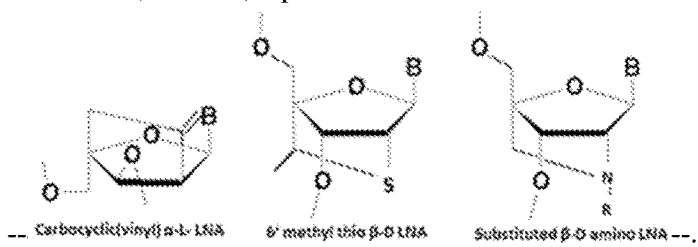 ".

Column 34, Line 9, replace "$E_l$" with --$E_r$--.

Column 36, Line 2, replace "[MOE]$_{3-8}$" with --[MOE]$_{3-6}$--.

Column 53, Line 43, replace "42_1_43_1" with --42_1, 43_1--.

Column 54, Line 12, replace "571" with --57_1--;
    Line 12, replace "601" with --60_1--;
    Line 14, replace "711" with --71_1--;
    Line 24, replace "71-86_1" with --7_1-86_1--.

Column 58, Line 43, replace "Administration The oligonucleotides" with --Administration ¶ The oligonucleotides--.

Column 64, Line 62, replace "301" with --30_1--;
    Line 62, replace "371" with --37_1--.

Column 65, Line 2, replace "931" with --93_1--.

Columns 67-76, Table 7, replace "List of oligonucleotide motif seguences" with --List of oligonucleotide sequences--.

Columns 77-92, Table 8, insert --motif sequence-- as the column header for the second column from the left.

CERTIFICATE OF CORRECTION (continued)

Column 82, Table 8, SEQ ID NO 64, replace "agttaaaagtatgtaga" with --agttaaaagtatgtgga--.

Column 84, Table 8, SEQ ID NO 85, replace "ggtcatacacaactacaa" --gtcatacacaactacaa--.

Column 85, Table 8, SEQ ID NO 89, replace "tatgaaaccaatcct" with --tatgaaaccaaatcct--.

Column 88, Table 8, SEQ ID NO 125, replace "tacttgacttcctaca" with --tacttgatcttcctaca--.

Column 89, Table 8, SEQ ID NO 134, replace "ggctttaccttacat" with --ggcttttaccttacat--.

Column 93, Line 67, replace "209C" with --20° C--.

Columns 95-96, Table 9, replace "..." with

| CMP ID NO | Day 3 | | | | | |
|---|---|---|---|---|---|---|
| | mRNA (%PBS) 5uM | | | mRNA (%PBS) 25uM | | |
| Replicate | A | B | AVG | A | B | AVG |

--.

Column 98, Line 66, replace "741" with --74_1--.

Columns 99-102, Table 10, replace "..." with

| CMP ID NO | Day 3 | | | | | |
|---|---|---|---|---|---|---|
| | mRNA (%PBS) 5uM | | | mRNA (%PBS) 25uM | | |
| Replicate | A | B | AVG | A | B | AVG |

--.

SEQUENCE LISTING

<160> NUMBER OF SEQ ID NOS: 325

<210> SEQ ID NO 1
<211> LENGTH: 32146
<212> TYPE: DNA
<213> ORGANISM: homo sapiens

<400> SEQUENCE: 1

| | | | | | |
|---|---|---|---|---|---|
| aggcgcggac | gcaggttaca | gcagcgcttg | gcctctgctg | atgccgtcgt | tatcctaccc | 60 |
| ctccccgtc | ccagctctac | ggcggccgcg | cgctccaggc | cggtcgctcc | accccccggc | 120 |
| tcccgggact | gtggactcca | cgaccctgtc | ctcggccctg | tccgcgccga | agcagcccgg | 180 |
| gactgcgcag | cgccccgcgt | gccggtgagc | gaccccggac | gtgcagtccc | caggtcccct | 240 |
| tccggagcga | ggctgagcgg | ctgcgccgcg | gcttgagccg | ggcctgacaa | ggaggggagg | 300 |
| ccgctggggt | gctgggccag | ccgcaggtac | ggcggcggtc | agggctggtg | atcgagttgc | 360 |
| tgtgtcgcct | ctaatgaggc | ccagccaggg | aacactcggc | ttcggcccaa | gccctacctc | 420 |
| tgggttgcct | ctaggccctc | acaccttgag | cgccaggtgg | ccctcttcct | tttgctgttg | 480 |
| atgaatgttc | ttgccgtggt | gccgggatct | tattttgcag | ctttacagag | taggctttgt | 540 |
| gctaggtgtt | gtttatggag | cttttcaaag | gcgcttgttt | ccttagttct | caagcccttt | 600 |
| tagaactaaa | accagtgtct | acacagaaga | tcaggagcca | tttaaattgg | agtgctgtga | 660 |
| tatatttttt | ctctccaaac | tgagtctgat | atccatgttg | actttcagta | aactaaggaa | 720 |
| ccgctataat | aaataacact | gagcccacag | aggttgcaga | agagggtcta | gcacccttt | 780 |
| tttaaaccat | tgagtctccc | aagaataaaa | gtggttacac | ttgtcagttc | tctaaggaaa | 840 |
| atctagtaga | gaaggcaagg | gattcccagt | ttctcacaga | gtctggcact | tgtccaaaca | 900 |
| cctaccctaa | agcagaatcg | atcatggcag | ctattagatt | aggacagaaa | acaggctcaa | 960 |
| acggagagcc | acttgagtct | gcctttctgt | gtctttttc | tcaacgcgct | ccagttaaga | 1020 |
| tgcagcttac | agcctggctg | tgttgactga | gatcccagaa | agagtgccct | taaggccttg | 1080 |
| ctgataaggc | ccaatgatcc | caattcatct | agtgttccgc | atagacccca | aggttacagt | 1140 |
| gtgtggggac | agtgatgtta | agtcttccct | atcctacctg | tggctgacag | gtgttgatta | 1200 |
| agacaatgat | ttttagaag | tcataaatca | tttgtatttt | tgatgtgggc | agtgattttt | 1260 |
| ataaatacat | agtttttttt | ttttgaaaga | gtgaaaatct | cattttacat | ttgtttgcat | 1320 |
| accatttgta | tagttttta | aattctgttt | atttgagtga | cagcaacaag | tggatggcat | 1380 |
| gcgaattta | tttattttt | tatctttgta | tttattttgt | gtatattcat | ggagtacaag | 1440 |
| tgccatttgc | tacattgata | cacaacatcc | tggtgaagtc | agagcccta | gtgcatccag | 1500 |
| cactggagca | acacacattg | tacccaccaa | gcaggctcct | atcaggcatg | ccagttctag | 1560 |
| aaagtaaaat | tttcttcata | ctctaggatg | aactgactta | cttggaatgt | ctgttttgtt | 1620 |
| taatcaaata | agtgagaatt | tttgaaagaa | atactatctg | tctgaatgta | tgtaatctat | 1680 |
| ttttaggaac | cgctaaaaga | catatcaaat | ttagaaggag | tataattatg | ttatttttca | 1740 |
| gttttacttt | ttcactttat | ttttttctcag | gatataagca | ggaaaatacc | agcagggtgt | 1800 |
| attatatgac | tgttaagttc | ttttcagctt | taaagggta | tgaccttaag | tataagtta | 1860 |
| cttcattatc | tacctgcaga | agttattttt | gtgtaggcac | tagtactaat | tatttatttc | 1920 |
| tacttagatt | tttacatttg | tattgttatt | ttgatactct | tatcctaaaa | ttttgaagt | 1980 |
| tagtgttcta | aattttgctg | ctttgtattg | gtaacttata | tttaatattt | tggaacattg | 2040 |
| gcttcataat | tttaactgtc | aactgttgaa | tgaaaaaaa | actgtgattt | tggaattttg | 2100 |

```
gggcttttta ttgttgttgc gagtgtttaa atgtttaaag caagaaattt aaggatggaa    2160
aagagtggtg attgtattta tcacaaaggt gcgtgaattt tcagaggctg aaacgtacta    2220
ctttgaagtt acttggtgat atacatcaaa tacctagtta tcgtctaccc aaagcaattt    2280
ttgcctttag tgctaactag ttaaaaggta gaatgtattt ttattttatt ttaagaaaaa    2340
tgaaacctgc atgtttcttt tcagagaacc tgcaggtgta gacttttgtc aaatgttaat    2400
gtttgaaagc ccattctcat cataagcatg ataggacatc atttcacatt atttgtttaa    2460
aaaaacactt ctggactcta gtaaatggct cctttgtttc agacattatt ttgattggat    2520
ataatcctaa tccaaaaggt ataatccaaa aggtagtttg aacattctct taatgtttgt    2580
tctgtaaacc aaaaataaaa ttctgagccc cccaactaag tggaacccgc ttctctgtca    2640
agggcattcc aaagtaaacc taaaaaggta gttcaggcca tgatgaaaag gtgggtggag    2700
gggattgaac atgccccgtt gtaccttcct ctctttggaa ttcaggcaca actgaccagc    2760
atcaattaaa acagagattt gaagactaac aagagtctct ttgtagcaat aagatatcaa    2820
atcccaacct gactctaata tagaatcact cgacagatag caggccctga gagaaattga    2880
aatatcttac cccaaaatat atttctttga aatggccttg caaagctgtc tctcgtgggg    2940
aagatccaca ttctgtacag aatccccttt cctttccaga tcttttccta attcagcagc    3000
gatttaacca agagcctgga atattttaag gagtaataag agacatttac aaactattct    3060
ctctgaagcc tgctacctgg aggcatcatc tagataatca gaaccttggc ttccacatcc    3120
tcctcccttg tcttaactac aaacatttct ttctgctgac ttcaactcct caggtagagt    3180
ttaaccgttt caaccaattg ccattaggaa atctttaaat ccacctatgc acctatgacc    3240
tggacacccc ccagccttcc accctgctt caaaatgtcc tgcttttctg ggctgaatta    3300
atgtatacct tacatctatt gatttatgcc tctgcctgta atttctgtct ccaaaatgta    3360
taatcaagct gtaacccaac taccttgagg acattttctc aggacctgtt gagactgtgc    3420
ctcaggcctt gttcactcat ttttggctcc gaataaatcc cttcaaatat tttacagagt    3480
ttgactgttc cttgactgtt ctaaattaat tagtgtaaat atctcagagt gttcttgaat    3540
gtactttttt ccctgaagtt tactgtaaga ttttttatttt tctttagaca tgggaaagtc    3600
tctttctcat ttgcctttgc attcaagcaa agaagatgct tatgatggag tcacatctga    3660
aaacatgagg aatggactgg ttaatagtga agtccataat gaagatggaa gaaatggaga    3720
tgtctctcag tttccatatg tggaatttac aggaagagat agtgtcacct gccctacttg    3780
tcagggaaca ggaagaattc ctaggggtat gtgttattgt attgttttcc ctttaaatga    3840
ttttaggtat ttgctcaagt attataaaaa ctgtgggtct caggaaccac ctgttttaga    3900
ggactcttag aattaaagtt gaaacatcat atcagttacc ttcagtcaaa aagatgcaaa    3960
agaaacaaat aaagtattaa ttaaggttcc taaagcagta aagaaaacca cctcactacc    4020
tccagtattt tttcattccc acctgctatt atagcagata ttcactgtct tgtaaatgaa    4080 aactttagt cctatttggc atctgtagag atgacatcat agttacttgc tactttgcta    4140
tatcagatgt tagaagcaat ttaagtaatt tgttgaccta ttttttttttt tttttttaaga    4200 gatgagatct cgcaattgtt ggccaggctg gtcttgaact cctgtcctca agcaatcctc    4260
ccacctcggc ttcccagagt gctaggatta tagcagtaag ccaccatgcc cagccagagt    4320
taatgtgtaa ggaagcttat tctttcatgt tatttttaaa attttatttt tttaataata    4380
aggatggagt ttccccatgt ttcccaggat gatgtcgaat tcttgggctc aagcgatcat    4440
```

-continued

```
ccagccttgg cctcccaaag tgttagaatt acagctgtga gccaccacgc ctggccaacc    4500 taatatttt  aattcattat ctaaagaaga agaataagct ggctgtgccc taatgagtta    4560
aagaaactct gtgaagaggg atggtacgtg aaaatgagcc aaattgaaaa aaaaaaattg    4620
tttgtgatat atcatagggg acgtcagaag gaaataatcc cctgtgtgct gcttgtaagc    4680
tactttagga acagtggcaa taagtagaaa taataaagat actttatgct gttctcatta    4740
tcttcttggt gaaagttgat gtgtgaccct ggagataccc agagggaaga aggtcaaagt    4800
ataaagtata ctttgtgtac ctttttaaga tgcttaaaat gtatcttaaa atgctgtggg    4860
tttgaattga agtttacatt tgcgttggcc tttgagtatg atggttttat tttcacaagg    4920
atagtagcta tttaagaata aaataattat tgtagttgaa gggattaatg caccaggctc    4980 aggggggtagg ggagtactgt tttagcagtc tggttacatt tttgaggtat gaccagtaaa    5040
cttttttggc cgcctggata cagattatgg aaagtaggaa atcaaggatg actccagagt    5100
ttttttgggg gggtttgttt gagcaactga agaatgtag tagcaattta ttaaaattga     5160
aaaaaaaaag attatttgag tgtatatgtc acaggagagt tcaggagctc aagtttagac    5220
atggatattt ggagatgcct atttgacgtg gaagtggata tgttcattag gcagttagtt    5280
atcataaggg tcaggaattc aattgcgcg cccagcctca agttaccaat gtatagatga     5340
cacttaaagc tcagctggat gacagcagca agctagtcag tgcagatggc aaaaatgaga    5400
ccctagcgaa tcctgagaca ctgtagcata tcaaggtcag tgaaagaatt aacaaaggac    5460
cctgagaaag aaaagttaga atgagaggag gaaatcattg tgtgtggtat catggaagat    5520
aagtgaagaa agtgtaccaa ggaggaaaga gtgaccaact gtcatatgct actgatagat    5580
tgggtagtgt gaagactgag aactggccat tggatttggt tatatggagg ccacagaaga    5640
gtttaaaaga gcggttttgg taagacgtg tagcatgtat agagtgggct caagagtgca     5700
taggagatgt tacatagaga gaaaatagat tttctgaggg gtttggctcc atagcagaga    5760
gaagagaggt agtcattaga aggggctgtg aggtcaggag agggatttt ttttttcttt     5820 gtaagataga gtgaataata gacagttgta tactgatgag aattatctgt agagaaaaca    5880
ttggtaattc gggagataag agaattattg gagcaatgtt cttgaataga cagaagggca    5940
gatctactgc acaagaacaa agagctgctc ttttttttcta taaaggtaa gttataagca    6000 caggtggttt attcttggta ataaaagaga aggtaaagta tggacacaga agcaggtagg    6060
tggatagatc tgataataga agcttgtaga aattatcttc catttatcac ataatgaact    6120
aagaatgagg atagcgaaga agatattaaa gatttgaaga gagttgaagt tataaaattg    6180
tggtcttgga gagtcagctt gagagtatga acttgggaaa tgtagtatga ttgttgacat    6240
cattaagtgc tacttgacat gagtgatcaa aaatgaaacc agtgagtgta gttgtgtgtt    6300
tttctgtgtc catgtttagc tctgttgata tatgcatagg agccagaggg ttggttttaa    6360
ccagggttgt agttttagcc agatgaatac cactaaacaa ggtgagatat gtaaacacac    6420
aaagatacag atatccatgt tatatgtatt tgtataatta tatatgggtg tgatggggga    6480
gcacagatga gaggaagagt atagatgtgt cgggggaaat aacagaagca ttttagaaag    6540
cttttaaaga gaacttgact atctgatacc ttaatagtta atatgataag ccaacttcta    6600
ataagattat aaaattggca tttaaaggtc catttatcct ttaaacttat ggatatagct    6660
caacccaaga aagaaatcac ggattttgaa gtgactttaa catggattgg ggtgagacct    6720
gaaagggccc tggaaggctc attatgtagg gggctcttaa agcttgagac ttctacttca    6780
gaggccggtt ttggttttca aggggacaa tgtcagaagc tctgcagtga tagagatgat    6840
```

```
agaggtttca ggaaagggcg ataccaatat gtttcttctt ttatcatcca gacaaccaaa    6900
tcagagtctt aatggacacc agtgaagctg aaggaaggcc tggtaaattt agctcttctg    6960
aaagctagga cttagatttt ttttagtgga agaaaaagta agccctcatt tgttatactt    7020
tttttttttt tttttttagct agacatttac gtgtgaaaaa acacgctgtc ttctctagaa    7080
cttctgctgg atactttctg aagacttagc aatttactaa aggaaagaga tgagtgccag    7140
atgatattct ggtcttttcca aaccagattg tgatggggag ccattatatt tttaactaat    7200
catagtaatt tctgaactta cttctttcac atttagggca agaaaaccaa ctggtggcat    7260
tgattccata tagtgatcag agattaaggc caagaagaac gtaagtgatt ctaagaatat    7320
ggcagtgttt tatgttttat ttttgttttt tgtattttt caaattatgt ataataacta     7380
gttaaaacta ttaaaagaaa aaatgctgtc acgtagttaa attatgtcat catatgcttt    7440
gtatccttaa acagacaaga aaggattttc tggttgggt aaggtcttga aagcagtatg     7500
gtatctttat cttctcaaat ctatggaaat agatctagaa tagcagtaca acacacaca     7560 cacataaaat tttcattaaa aattggataa taaggtgtac tccacaaccc caggataaaa    7620
attggtattt aaacatggtg acagcaggga ccccaacggc cttagcagct gtgtggaggt    7680
tgtgaaggaa agcaaaaaga gttactaagg atcatatgag ccctgataca caaagcaaat    7740
actttgtccc aaaagaagag gacacccagc aaatatttcc aagaataatc tgtaaaaatg    7800
acaagatttg catgctctag cttggagaaa gtgcaaaaag accacaagag acctgctaag    7860
tatcttcgag atcagaagga actgaccat cctaaatcct cagagacgtt aggaaatgtg      7920
gaagcaaaaa ttattgcaaa aggatacaaa tacatatcct caagaaaaaa gttgagtaga    7980
atccaatgtt tacaggacag gagttaggaa ggaaggagag aacagattga catattaggg    8040
agatcatctc aaaactgtgg agataaatat acatggaggc catattttca aatactttgt    8100
atatcaacag aggatggagc ccttgaacag tgaagctagc aaagcaacgc tggcatattc    8160
catcaccgca aatgaaacct ttcttgaaa gtacaaaagc tcttttcatt taaacatgag     8220
cacctggaaa ggattgcaac aaagcattat acaaatatac tttttaagaa gttgaagaaa    8280
gtaagctaag caaaatactg acactttaat aaaggcatgt gaaagagca gatgaacact     8340 ttaacttaat actataaaag ctataacagg acagcataag gcagaaattg agaagctcag    8400
aaatgagata actaaacaat gggagtatgt gcaaagagaa tttacagacc tctgaaaga    8460 attagaagaa aaacatttcc acaaaactgg aagaacacaa gtacaaatac attggaaata    8520
cagtcaggga aatagaacat aaacgggagg aatgaaaaca tcaacaacaa attgtgtaaa    8580
ggatttgaga gaaaatgtct aaaagtcaca taaagaaaac taaacatgta tgtaattgga    8640
gcatctgaag aagaaaacca aaggaataga actggacaaa tgcaaaacat taaatcaaga    8700
acacagggac ctgcatattg aaaagacacc acaatcctga aaaaatcaa cccaggttag     8760 tgaaattctt gaacttttaag aaaacaacaa aactcctaaa tacctaggca aaaggatcaa    8820
ttaatttata aatgttagaa atcagattg acatgctgct tcttgactac agtgcctcaa     8880
acggataagc aatggtgtga catatttaaa tcaggaaaat aaaacaaacc aaggatttta    8940
taaacagtct gaccttttat tacaaaatgt atagacagat atgaatatga aggaaattag    9000
gattaatccc tttataacct aaaagtggga gaacttttta aactatgatt ttgaatgcag    9060
aaaagataaa tttgacagat gaacttttac aggatgaaga caaaaccta actgaagtca    9120 aaatacaaat agcaaactaa gtagtaaagt ttacaaatca tatcacagac agagggccaa    9180
```

```
tatccttact ctataaagag cttcagaatt tgagaagaaa aaggccaacc tccaaagcaa    9240
aatagaagct atgaacagct agttcacaaa aaagaaatgc aaatgacctt taaacatttg    9300
aaaagatgtc caatcttgct cataatagaa atgcaaatta aagctacact tagatgccat    9360
ttctatcaca gtggcaaaaa tccaaaatgt tgacaacata ctttgttggc agtagtgact    9420
gaaaacaagt atattcattc cttgctagtg aatgaaaatt tggcattatt tgccaaatta    9480
catctgcatt tactttttgg ctcagaaatc ctactttgaa aaatttattc tcaggatagt    9540
tgtcaaatat agtaaatggt atttgcgcaa attatttatt gtgccaatgt ttgcagaagc    9600
aaacaactgg aaacaatgta aataccaata atagaggact gatggaataa gatactatgt    9660
gtacacaatg gtaaaatgga aggagaacta tattttacca cagtgtgata ttgacaatat    9720
gttttttcttt gaaacaccca cacactcaaa cccacacata tacacacaaa gagacaaaca    9780
atgggatgat aaaccaaatc taatacaatt ggttcacctc tgagtttggg aaggaatttg    9840
gaagagggag tggataagca agtaaagtgt gtgtgtgtgt gtgtgtgtgt ctgtatctgt    9900
gtacattttt tttacataac ttaaaagatg aaatcaaaag taactgccaa aaattgagac    9960
aaaaggaaac attattctaa ctgtatatga agttggtgac actaacaaaa ctgaaataat    10020
tattttaagt gacttgaaaa cattgtgctg tgactataaa tgtcgggagt tgtgttccaa    10080
atggcaaaga gaatcacaac aaattttaaa ctgtacttaa tagttgcatt attaggagta    10140
cctttgatgt agtttggaaa ttttatactt aaataagtta ttatgtaaat gccttaggga    10200
gcaagagttt tagcaataag accaaagaga tacaaaatca agaaaattga attttccact    10260
tttgacccaa atagaataat gcctgaaata ccccacctga aatcactgta aaactggaca    10320
aatatagtaa acaatatttt cagacattgg acatcagcca gcacagggca gtgattcctg    10380
agaaagcaaa aacaaggag ataagcccta tgattgcacc agcaagccct gtgattgtac    10440
cagcttactg tctgagaaag gttccagcct gcagcacaag gaaggaacca acccaggcag    10500
agctcagtgg tcttcctcaa tggagatgga actgggtgtc cagaaagcca aaatgactag    10560
agttagcagg gcagagtacc agaaggtaga gagctggaga gggtgctctt aagcctgcag    10620
ctgtgtcctg atcaacatat atgtgtgagg aacatacctg aggctgagga aagaccaccc    10680
aataggagca gagagaatag tcctcagagc tcacacaagg ccaagaacag ttgttgtttc    10740
tcaatttgta ataaaattat aatattttgg gaacaacttt gggtctttat ttctttacaa    10800
attgagtgat ttgtaagatt attagaaaat tatatttatc aattgctttt gtctgtatac    10860
tttagctatg tcatttaatc ctcaaacatg gattttaaag aggaagaaaa gtaaattgca    10920
ttaaatactg caggtaggaa atggcaaaaa tggaattcta acttgattgc agatataccc    10980
cacaactttc ataacttcat tagcacctta taactcccag gatttggttg ctatcactag    11040
agccataaga aaaatcatta ctagttaatt ttgtaatgga gacatatatt ttgtcagtaa    11100
actagccaac ttttcaattt ggaatgaaat actagatgga atgttgtttt attgtcccac    11160
caggttcagt aatgttcgtt atggctacaa acgtggtata cagagtaatt tagaaacatga    11220
ttcatttatt cacaactagg actgacttat aagccctaag gactagatta tgatggattc    11280
acccgcccat aagtaattaa aaataaaacg ctgaagtgta gaaaatccaa caaagttcag    11340
attttattat gatgatgtta aacacttctt atgccttttt atgtatttttg gtgtgttata    11400
gatactataa acgtgtttaa atttcctatt aggtaatcca gtgggatca ctaccccctac    11460
tcaggttgag agagtccaaa atgagtgagt gggaactgtt tgattgctc aagacaacag    11520
catggactta gtagcagtga cttagcaaat ttgtgtttgc ttgtattatt tgttttttta    11580
```

```
ataaaccagt tgctctgtt cttaacttgg gcaacttaaa acactaagaa atatttataa    11640
aatatctgca ggaggcactt taattgctct tgtaatacat acaaagatta aatccatcag    11700
agcatttaga aaggaaatgg tggcggagag tggaagaaac aataaaatgg aaaattttg     11760 tataagtaga ttgtaaggaa aataagtaat tgtcatgcaa gactcaaaaa caaaaaaagg    11820
atgttgtggg catccaatag aggacttgta tgttagagag aacaggaaat agttatttga    11880
actctggttt tgaggttaac cttgaaaaga ggaagttttt acctacaaat ttttccttgt    11940
cttatacctg catgaaatat cttttcttga ttagaaaaag aaatgtaaca acaccttcaa    12000
agcagagttg atcaatgtaa aaaaaatctt aaaaactgag tatgtaagta ctttgagatg    12060
agaatactca aaaaaagact aattatagta agaatcattg atgagccatg tggttgtgtc    12120 atttttttt aattttaaaa atatggagga tgtgcaggtt tgttacatag gtaaatgtgt     12180
gccatggtgg tttattgtac ccatcaaccc atcccctagg tattaagctc agcatgatta    12240 gctattttc ctaatgctct cccttcccca tcattattat ttctaagatg gttctgatga    12300
gcagtcactt tagggggatca tgtaatggca aaacttaaca tgtgaaaatt ctgcttcagt   12360
gaattcagag ggagttttga aatgtgcgtt tgtatgaagc tcctcagctt gaatctaatg    12420
tgaaaactgc tctggcagtc aaaaaagtaa atgttctatt gttttttaagc ccaaaatttc   12480 agtgtccaaa aatgtgattc cttttttttt ttttttttggt acagagtctc gctctctcgt   12540
ccaggcagga gtgcggtggt gcgatctcag ttcactccaa cctctgcctc ccgggttcaa    12600
actattctcc tgcctcagcc tcctgagtag ctgggattac aggcgcacac caccacacct    12660
ggctaatttt tgtgttttta gtagagatgg ttttcactg tgttggtcag gctggtctcg     12720
aactcctgac ctcttgatac gcccgcctca gcctctcaaa gtgctgggat tacaggcgtg    12780
agccaccgca tcccgccgat ttcatctttt aaagagaaca tcttaacact taatagactc    12840
agactcaacc atacccaata cttttcagatg tgaaaatttg gtaacattta gcatcttata   12900
tatgttgctg ctgatatatg gggggaaattg aacataccctt ctctaatgtt gtgttatata  12960
atttctgatg cacatgtact taaataccct cttttccttt tcagaaagct gtatgtgatg    13020
gcttctgtgt ttgtctgtct actcctttct ggattggctg tgttttttcct tttccctcgc   13080 tctatcgacg tgaaatacat tggtgtaaaa tcagcctatg tcagttatga tgttcagaag    13140
cgtacaattt atttaaatat cacagtgagt ataaatttat atgaaaaatg tttaacttca    13200
ttcttttatc ctattaagca gcacctttgt ccccattgag aagagatgtt tgttaaatgt    13260
gacactggtc agtgtgctt ctgtatgtct tttctgtatt gacgttctct accatttctg     13320
gttctgctaa aaatagcaat aataaatact ggcaattctg tatatacaga atgatttagc    13380
atttgaaaat gtcttttagga gggtaaaata aactaaaaaa agaaaaaagg tattacaatt   13440 tactttttcag catatgactc tgaataactt ctagcaaagt gttgacatag ttgatttgat   13500 agatttata aatgtaacat tttgatttca ttgtatttgg gaaatacagt ttttgccacg     13560
tttaatagac cattccttta tcagctttaa agatgaaata caggtgactg gtttctcttt    13620
tgtaaattag catatgtgaa aatgccgtgt tttttttttt ttaattatta agttctaggg    13680
tacatgtgca cagcatgcag gtttgttaca tatgtataca ggtgccatgt tggtgtgctg    13740 caccccattaa ctcatcattt actttaggta tttctcctaa tgctatccct cccccatccc   13800
tccacctcac gacaggcctc ggtgtgtgat gttccctcc ctgtatccaa gtattctcat     13860
tgttcaattc ccacctatga gtgagaacac gtggtgtttg gttttctgtc cttgtgatag    13920
```

-continued

| | | | | | |
|---|---|---|---|---|---|
| tttgcttaga | atgatggttt | ccagcttcat | ccacgtccct | acaaaggaca | tgaactcatc | 13980 |
| cttttttatg | gctgtatagt | attccatggt | gtatatgtgc | cacgttttct | taatccagtc | 14040 |
| tataattgat | ggacatttcg | gttgtttcca | agtctttact | attgtgaata | gtgctgcaat | 14100 |
| aaacataacg | tgttaatgtg | tctttatagc | agcatgattt | ataatccttt | gggtatatac | 14160 |
| ccagtaatgg | gattgctggg | tcaaatggta | tttctagttc | tagatccttg | aagaatcacc | 14220 |
| acactgtctt | ccacaatggt | tgaactagtt | tacagtccct | ccaacagtgt | aaaagtgttc | 14280 |
| ctatttctcc | acatcctctc | taccatctgt | tgtttcctga | acttttaat | aatcgccatt | 14340 |
| ctaattggtg | tgagatgata | tctcattgtg | gttttgattt | gcattttct | gatggccagt | 14400 |
| gatgatgagc | atttttcat | gtgtctgttg | gctgcataaa | tgtcttcttt | tgagaagtgt | 14460 |
| ccgttcatat | ccttcgccca | cttttgatg | gggttgtttg | atttttttaa | gttcttgta | 14520 |
| gatcctggat | attagccatt | tgtcagatgg | gtagatagca | aaaattttct | cccattcttt | 14580 |
| aggttgcctg | ttccctctga | tgatagtttc | ttttgctatg | cagaagcttt | ttactttaat | 14640 |
| tagatcacat | ttgtcaattt | tggcttttgt | tgccattgct | tttggtgttt | tagtcatgaa | 14700 |
| gtccttgccc | atgcctacat | cctgaatggt | attgcctagg | ttttcttcta | gggttttat | 14760 |
| ggttttaggt | tttttaaata | ttaggtctaa | catttaagtc | tttactccat | cttgagttaa | 14820 |
| tttttgtaca | aggtgtaagg | aagggatcca | gtttcagctt | tctacttatg | acaagccagt | 14880 |
| tttcccagga | ccatttatta | aatagggaat | cctttcccca | ttcttgtttt | tgtcaggttt | 14940 |
| gtcaaagatc | agatggttgt | agatgtgtgg | tattatttct | gagggctgtg | ttctgttcca | 15000 |
| ttggtctgta | tctctgtttt | ggtaccagta | ccatgctgtt | ttggttactg | tagccttgta | 15060 |
| gtatagtttg | aagtgatgcc | tccagctttg | ttcttttgc | aaacaatgtg | tgtttcttag | 15120 |
| gacattgttt | ttgaaaggac | cgtgtagcct | tgccactcat | gaaaacaaaa | caaacaaaaa | 15180 |
| ccttagagag | gttttctacc | tgttttacat | gttaacgttt | gtttgaaaag | agcacggttt | 15240 |
| gctaactatt | gaattaggaa | aagggataat | atttattggc | cagccatgag | atatatgtga | 15300 |
| gtgacagtga | tctgccagga | agagtgatag | ttgttttttc | ttgcagaggt | taatggtgtg | 15360 |
| gttaaggttg | aggtagagat | gtctgtggtg | gtggttggaa | agagggaggt | ttgtcaggac | 15420 |
| agtgagtgaa | atggaatggt | atgttaaagt | ggaatcacta | cttaattaca | gagaaaaaat | 15480 |
| ggatcccgtg | gatccattta | ttcttattgc | tttctgtcaa | aagttgccgg | tttaagggct | 15540 |
| ttttctttaa | aaacaacaat | ataggaaaat | atacgtatat | gtgaataaaa | cgtttgtaac | 15600 |
| acaatgctaa | ttgtaaattg | ttttatgcaa | ctggggaatt | gttgggtatt | ttctcactta | 15660 |
| gcccttgga | acaaggaaca | tatttctctt | tttatacact | gtttaaaaca | ttggccagac | 15720 |
| ttttttggc | ctacctccaa | agactttttt | catgtcaaat | aacataaata | tgtactaata | 15780 |
| aataataaaa | aaccctgtga | tgttttcttt | taagtaccag | caagtatatt | taaatgtgaa | 15840 |
| tatcatactc | tattttaagt | aattatgcag | aaattctcac | attttggaat | actgccactt | 15900 |
| aaactgagac | agactgaaca | ttaaatgaaa | aataagatta | tttggatgaa | cattaactag | 15960 |
| atgacaatga | gataagaggc | tgaattttct | gtacattatc | tataagtatg | ttgaaaatgg | 16020 |
| aactgctttg | cttccttaaa | atgattagta | tatattagta | gtactacttt | ttagtaacat | 16080 |
| ttgtctttct | acttatgaaa | atatttgtca | ttataagaca | tttgagaact | ataatgtata | 16140 |
| aagatttta | cttctgctac | ctaggtcgaa | ctattaccat | atacatatat | ttacgaacaa | 16200 |
| tgcatataca | tttacaaatg | taatcattct | catgtgtaaa | ggatacacac | attcattcac | 16260 |
| atatatacaa | atgcacattt | caactgaggt | cacagtacat | tttcccatgt | taaatggtct | 16320 |

```
tgtgtagtct tttacatgat catattataa ttaattcaac cattttctta atgaatgttt     16380
aattttacta ttacaaatat taggaaaaca tctttgtgct taaactttgt ttccatttca     16440
ggttatttct ttaggataaa ttcctgaaag tacatttgcc aattaaagat cataggtagt     16500
ttagggtctt tgttaacaat tatggtgatc tcttttcatc ttttaaatta aatggattct     16560
cactactctg agcaacaaat gtctaacctt tattactaaa ttttattta ttctgtctta     16620 ttttttcttt gtcttaattc tcataaggat ttgtattctc aacctgtatt acatcattga     16680
tcccttaaat attctaatga aactgtggac agtacagaaa aagacatgta ccagcataat     16740
tttgcatata caaagacttc caagattctt ctaaatttca atccttggtc ttatcagaag     16800
atccattgac ctcaaattaa ctatctcttt cctatcatgt ctagaaatga aattgacatg     16860
aacattaaga gccaaataga taaaatgttt atatatttaa agattatttt tactgtgttt     16920
gagaacattt ttgaaatttc tttacatttg tgactatacc aatgtaaatg actccataaa     16980
tgtaatcata taattgctga ctctagcata ttctttcatc cttttttta ctaaaactat     17040 tttctctcct tcaactcatc ccatattgca tcttttcata tctttctaca tattcctatt     17100
aacatttatg tatactcaca tattcagctt tataaaaatc agtatttta aaaaatatta     17160 tttagtactt atttatgtgc atcttggttt tcacatttgt taataccttg taaaaatctt     17220
tcctaattat ctgacttaat tgattctttt tgatggcttc ataatattcc atataaggac     17280
ttaatataat ttattctttc ttttatgaa tagaattcat tttattgtca ggatttttt     17340 tcccattcca ataacactg tcattagcat cctaatgttt ttatttctgt ggaatcggtg     17400
ctcagaagta ggattgcccg atcaaagtct atacataatt ctaattttaa tgtatataac     17460
taaattactg atgaaatggc tgtaacactt cacatatttg ctagcagtat gaaaatatac     17520
cctttcccca tatctgtgcc aggaatagaa tttggtgctt tctataaatt gtactagttt     17580
gaggaattta aagcaatatt ccatttttac ttaaataaac gttttcctaa ctataaatga     17640
atttgagcat tgtaaaatat ttttggccat ttagctttgt acctttttga tttgtttatg     17700
tatgtccttt gttctttttt catttcctgt tagagttttg tcttttttctt ttcaatttgt     17760 aagggctctt tgcatgttat agattataac cgatgcttac aaatatttct tttatttatc     17820
atttagtgtc tatggatttt gtttatgtta cctttggta tgactgttac agatctttta     17880
tatatctgtt atttttatt taacattttt aaattttta atgactgttt tctacagtaa     17940
tttgagacaa cagttgtaaa ttagaaatgt agaaggtgat cccagctatt agttgttact     18000
taagcatgtg aatgatgcaa ccacatttct ccccaaccaa ccagacttga atctagccca     18060
tttcttcttc atagtgagct gttgtaaatc tctactagtg tacaagttga aatagcaatt     18120
tcttttaaac aaaaaagatt atttttaggta ctgttgaaca tttaaatgg tcatctttgt     18180 atttaataga ataggaaaca gcttactaat gtccatattc tgaagctata cattttgttt     18240
tttttaaata ctgaattatg ttttttattct tggcatatta catacatagt actcgtgcat     18300
aaaaccaaat aattggttta atttctcttg acattttggt attactttct ttttcttaat     18360
aaatgaagca tagctacagc tgaagttact ttaattttaa atacatattt gtatattttt     18420
agctaacttg taaatttct gtgtcctttt tttgtagaac acactaaata taacaaacaa     18480
taactattac tctgtcgaag ttgaaaacat cactgcccaa gttcaatttt caaaaacagt     18540
tattggaaag gcacgcttaa acaacataac cattattggt ccacttgata tgaaacaagt     18600
aagaatcaat catgaaatac tttgtaagag ttaaatgaat gtcagctttg tatatcatat     18660
```

```
aacttgaagg aggtggggga tttcctcaaa aacttgattt agaaatgtgt ctctgctggg    18720
tacagtggct catgcctgtg atccccgcac cttgggaggc tgagctcagt ggactgcttg    18780
agcccaggaa ttcgagacca gcctgggcaa catggtgaaa cctcatctct acaaaaaaat    18840
acaaaaatgt gctgagtgtg gtagtgtgca cctctcttcc cacctactgg ggaggctgag    18900
gtgggaggat cactggagcc cagtaggtcg aggctcgcga gccgtgatca caccgccgta    18960
ctccaaactg ggtgacacag tgagatcctg tctcaaaaaa gaaaaaaaag aaaaagaaat    19020
gtgtcttata cacatacaag atgaaatctt tgagaatcaa gcttgtaaaa ggagaaaaat    19080
ttctaattat ttgaagttat gaagtatatc tgaaatgttt gatgttttga tcttgttctc    19140
tatcgaattt ctccttttgc ctttcagatt gattacacag tacctaccgt tatagcagag    19200
gaaatgagtt atatgtagta agttctgatt tataataact ttttattgtc aaataatgaa    19260
gtgtataaaa taaagtataa agagtataca tatttttttaa tttccgttat cagtcaaaaa    19320
gagtacatta tgtagtattc tggcttctgg tcctctctgt tcctcttttt caacatatat    19380
aatattcatg tatatataca cataaaattt gttttttttat ttattttttca gaattagggt    19440 tataccatgt cactttattt ttcattacta tgttactgtg ttaaacttgt tactatgtta    19500
aaataattat aaattttcat catcttttga ataagcgtag atacagactt ttagggtaaa    19560
taacaaccta gttatcaaaa tttcagaaga tgagcaaaat atataagtaa tttatagcct    19620
gcatttaaac aaccctgcaa ctgcagtggc atgaatacat acatgttttt cgagtaagaa    19680
gtcatgaata tatcagtcat tgtttgaagt atagaaaatt ctcaaccaac aaatgcttat    19740
tatatttctt agcatctctg ttagcttaaa gataggaggg agaattttta atttataatg    19800
tagtaacttg catttgttca catttttaatt tctttaacag tgatttctgt actctgatat    19860
ccatcaaagt gcataacata gtactcatga tgcagtaagt acaaatcttt tttgaaagag    19920
attttgcttg ttaacatttt ggatttataa cattggctta taatatacac aacatcttta    19980
taaatgccac ctcagttggg ttttaagcct tacaagagtg ctatgagtaa atatcaccca    20040
cttaaaaaat tacgaaatgg ttgttcagag aagtagtgaa agactacgtg actgctaagt    20100
agtgaatctg gatgtcacaa gagttcagga aaatggaaag gatacaggga actgagcccc    20160
acatccaatt ccttactccc ttgacaaata gtcattaaca gtaataagaa tattattggt    20220
ttgtaaattg ggtgttatct aagccaataa aacattgttg attataggtt tggtgttttg    20280
accattagct gacatttgat taaccttttt ttctatgata agagaaccat ggtcactttt    20340
aagcatataa tgaacttttta tatttttaac agaagataat tgttttaaaa tattacactt    20400
attatgtgta attatgtcta cagggctcac tcagctatcc attttttgttg tctgttgggg    20460 aaatactcct taagaggatt gtgtgcacaa tattaagtta tcattaatca aatattctct    20520
tctgggagat aattttttatg tgttaaagta gtctcactat ggaaaaactt ctaatataac    20580
tattaaatgt ctctcctcac ttacattatt tttagagtta ctgtgacaac aacatacttt    20640
ggccactctg aacagatatc ccaggagagg tatcagtatg tcgactgtgg aagaaacaca    20700
acttatcagt tggggcagtc tgaatattta aatgtacttc agccacaaca gtaaaaactg    20760
gaagagatgg atttaaagaa gaaatatcta ttgatatttc ctatactctc aatgaagagg    20820
tatttcctaa taggagacct taaattgaac aaacctaaag tttacacttc taagagtaca    20880
gttaaaagta tgtggacctg cagttcttgt aactctccac tctgtgttaa tgatatattt    20940
gtactaggat cttttacttg aatctaaatt tactggttga tttccttctc cagcctatcc    21000
cctacaggga aaagctgata cttcccctat agtacaataa ataattattt aaaagtcata    21060
```

```
gctccagtca ctactgaaaa cataattttg gtgataaaca taatttgaga aacttaattt   21120
ctgaatgttt ttatagaaaa ttactgaaag tctattactc atggaagact tttaaagaat   21180 aaccttttt  cctgttttat aaattcccat tgttatatgg tagtatttca gctacacaat   21240
attttagctt ttagctagac atttatagct tttcatttgt tgaaatggta atcatctgca   21300 tgttttgtc  acttatttca ggttagtgat tgcctaacac ttataagcca aaataatctt   21360
tgcaaaattc catcctaaa  attttgaaag cccctaatgt tttcacacat ctttctgtat   21420
tagttatagt tttgtgaaat ctttgtgtga tcttcaaaca ttatcattta atgtacaata   21480
ctgtaaataa actgtgcatg gcttttatac agctttagta aatgtcaaat aaagtggtac   21540
agactcatta caacaagttt ctcataaaaa tacaataaat aggaaaatga aattcagaaa   21600
cccatagact gggaataggt tccagttaca gcttggatct ggcataaaat aaatttgaaa   21660
taaaatattt tgatgctcca ttttttttatg ttgcttttca tactaaagaa tggtgtagac   21720
atgttttgca actgttaggt acccagttat caattttatc aatgttttag aggaggaaat   21780
tatttttttg gtagaaattg ttcaagaaat ccttaattga atgtcattaa atgatggtgg   21840
ccaaaataaa acctatttag aaatttaatc actttgcaca tcacttggaa tatgatgcct   21900
ctagtagtta cttttttata gttttctact tttggtttta tttaaaattg ttttcaaata   21960
tagattattg acttattcaa ctttgctgtt ttatattttc agtatcattt ttcatttttt   22020 ttttttttg  tcttttcact taccaagttc tagggacatt taaaatatgt actaagtgta   22080
ggagtggtta tgataccaaa aaatgtagct gggttgagat taatttcgtt ctgttttctc   22140
atgacagaaa tcaggtttcc ctttccccac ccctaagtgc ctaacttagg tctgaaacag   22200
cctgtttatt agtctgactc tctcaaccat aaaacataag ctttatttaa ttctgccttt   22260
aaacacactc aggtttcccc ttaattttca tattattttc tgcaagtttt cttgagtatc   22320
ttcaattcgt tgaatgtggt tttggttt   tttttgtttt aacactagtc ttcccttaat   22380
tcattgctaa ctcaagccat ccttactatt aaacccaaat cagtccttta agttcattat   22440
ggccttctta gtatttaaaa aaaaaaaat cattttcatt tttcttctgc tacgtttcct   22500
gactactact gcatacttct ctgatacagg ttctgtttgt attttttata tcattctcat   22560
tttctcattt gacatgatct atgtctatat atgatatagg tccccttttg tctcaaaatt   22620
tttaattatg tgacttcaaa aatcacctgt atctgtagta gggcttccaa atctgcttct   22680
ccatatgtga ccagtcacct gtctgctttc acatttagct agtgaactac acatttacta   22740
aaatgtgtaa attttacaca tttagtgact gtgtaaaata aaaaaaagt tatttttatca   22800 tatcctttct attatgttcc catcctgtcc tcatgtccca tttactttat tatcaccatt   22860
catttcttca aaattatctt ttagatacgc tcatacaaaa atcaatcctt gttttcttgc   22920 ttgtgtctt  taaccttgga aaattacatc gtgtaaatta aacagatttt tctgatgatc   22980
tgtgcttctt atatactatt agagtgcatg atagtatctc ctgaaaagga tggaaagtag   23040
aagcatttgc ttttagtcac ttaattttga atctttttc  ttcatcttt  gaattaattt   23100 tttttattat atctactttt agtggagttt gagtcagaaa aaaacaagaa tttgaaacaa   23160 gtaaaagat  agaagagaaa taagatggt  atgtgactac tttcagagag agttaagtaa   23220
ctgtcagaat aagcctggaa caaaacaggc tgtaaattaa taaaactaca aacacacatt   23280
caggtgaagc agaagtatag ccataaaaca tctagaaaga gtgaatgagg cttttagctt   23340
ttcttaggtc aatgtccagt gtgcttttt  ccatgggaat aggataggta ttaatacgct   23400
```

```
tttctaaact gctctcagac cttatccaga ggacatggta aagatatgtt acagaaattt    23460
ttctgatact tcctggaata actttaagtt acaccctagt agactggtca ttctaataaa    23520
atccagtact ataacaaacc tctgtatgtt gatagcacat tggccctttt tagagttctt    23580
tcctatgttt ttcttacgtg atttcccaca gttccatgag tccaacaaag gagagtgata    23640
ggctccttat cttttagaag aggaaggaaa ggcatgaaga agttgaggga ctggctgaag    23700
atcacgtact tactaagtag tacaactgga gcaagatcaa gtatctctgt ctcccatatc    23760
tgtgttctat catttaaaat atatattgga aatccctgct gactcagatt ggtatgatta    23820
aaaatgagag gaaagttcaa atagttagta gtgacaaact aatactgctg gactaagatt    23880
ttggtagcat tgttttctaa aatattttaa atggagaatg aacacttata aaatgctttg    23940
gaacataatc tttagcttaa ttttctgtta aaatttagta cccttcatc attccaataa    24000 agataagact gatccattgt ctaaggaaat tatttataaa taatagagat taatttattt    24060
gagatttgaa ataagaatag tatgaaaata ttagatacca cataaattgt ttgaaattac    24120
tgaataacca tcttaagtat ggaacattta aatggctata ttttatttgt gtacagtttt    24180
tctgtgcctt gttaggccag tgaagcaatt attttctcta agaaaatgac aataaaatat    24240
aacacacttc agattgtctg atttacagtt tggaaaggac accgcaatgt tcaaataggt    24300
aggagaccat caaaaacaca attaaagtaa catattagga gacttgaaac ttcagcctaa    24360
taaatccttc atggttctta gccttattat tgtgatataa ttctagatat tttcttggag    24420
ggcatgtgcc caactctccc gcaccccatt ttgtttgtct tttaaagttc ttagaataaa    24480
cagttcttta tataataatt atattttatt taagaaaata gtttgttagg tacttttaa    24540 aagatgtaaa ttttaaaatt tacaaataca tatgggtctt tgataagcaa taggaattga    24600
attacaagtt actagggtta taagcaaaag gttgcttacc ataatgtcat taggtcacga    24660
tttttagctc acatctggaa gcagcaacta cttggctcaa gtacatataa gagtaattag    24720
ttttattctc tcttttttat aaaatcgggt ttcagatgag atgtttatct tagactattt    24780
tagggaaaaa ttttacatgt ttgagatggt ggagtaaaaa gactgttaaa catttctttt    24840
aaaaaattat ttttacatta caacaatata tttatgatgt gttcagatca aaaatttaac    24900
ttctgtgtcc cagatctact ttcaaagtga gattttcact tgtcagctta aatttctgac    24960
tagaactaac atttgtgtat ttttgtgctt agtcggaata caaatttcac agtggatttt    25020
tgaagtttgt ccttaaattg gataaaatca agtgattaaa gttactaaag agataaaaat    25080
ggtaatttcc attttaaaa gtaatttggt tgtgtttata gttatttgta caagtattta    25140
tcacagactc taaattgaaa aatgtagtat gatctatatt tgaccctaaa aatgttggat    25200
taatttaaca aatatggcag attttttcata actaagtctt aagtcttcta aaaggaagct    25260
gttacccttc tgttttaat tacattaatt gaaatgtgtt ttaagagata caatttcagc    25320
atattttata tattaaaaaa caaaaaagga ttagtattga gccagtggcc aaaaggtaat    25380
attactacca tgtagactgt tatagttcaa attgtcccac ttcacccaga attttagaaa    25440
ctagaagtct gggaggtact atatcagctg tagttgggta attccaagtg ctgatagtac    25500
tattcatctt ttttattatt gtgtcagatg aaacaaatgc caagttgcaa aatatgcaga    25560
tttttattat ataatggttt taggcataaa ttattaacaa gccatgcctt atgtgtttca    25620
tcttatattt ttcttagaa ctaaactata acagattttg gaaaatgatt tgacgtgctt    25680
gctcacttga ttgacttggt cagatatttg aatgatggta ttacctagat tctaatcctt    25740
gattctagtt atataataaa taatatagaa tatgaaaata tgtttgggca tttactgttt    25800
```

-continued

```
atattatgta gtagcctcca tcatgacaca cttactacat ttatgaattg agcagttctg    25860
taattgtaat tattattgct gttcatgtaa caaaacatgc ttataatagc aaacaaatag    25920
aaatgccccc aaaatgctat ttttttaatt cagttataac tgttactctt gtagttgtgt    25980
atgacgcaat aaaatttgta aaaaatttc agcatgaaaa ataaaatttg tatcacttat     26040
gtattttggc tatgcttttg aaatttcctt aacataaaca aatcagtgta gatattcaaa    26100
atcttttacc tttaatcctt ttcatccttta tagtccttac ctgaactcta ctttagcatt   26160
atctttgatt tctttttttc attcacttaa cttccaatca gtactcaagc tttatccatt    26220
ctacctctgt aatgtctctg gaatttatct catacgtgaa atttcccttg atattataga    26280
cataccttgg atatattgca ggtttggttc cacaccatat cgataaagtg atataatcaa    26340
gcaagttaca cacctttttt tggtttccca gtgcatatga aagttatgtt tacatcatac    26400
tgtagtctat taagtgtgca atagcattat gtcgaaaaac acaatatata tgccttaata    26460
aaaaataggc tgtgtgcagt ggctcacacc tgtaatccca gcactttcgg aggccaaggt    26520
gggaggatca cctgagccca gaagttcaag accaaattgg tcaacatggc gagacccat    26580 ataaaatata tacatacaca cacacacaca cacacacaca cacacacaca cacactattg    26640
ctaaaaaatg ttaacgatca tctgaatgtt cagaagttta tactccttt gccggcacag     26700 gatcttgtct ggatgttgtt tgctgataga tccatgtagt ggttactaaa gttggggtgg    26760
ctatggcaat ttcttaagac aacaatgaag tttatcacat ctattgcctt gtcctttcat    26820
gaaagatgtc tctagcatgt gatgctgttt tgatagcatt ttaccaatgg taggtctttt    26880
ttcaaaattg gagccagtcc tctcaaaccc tgcctctgct ttatcgacca tgtttaaata    26940
attttctaaa ttcttttattg tcatttcagc agtggtctca gcatcttcac caggagtaga   27000
ttccaactca agaaaccact ttcttagctc attcataaga aacaattcct catctgttca    27060
agttttggca tcaagttgta gcaattcagt cacatctaca gactccattg ctaaattta     27120 gttctcttgc tatttccaca tctgctgtga cttccttcac tgaagtcatg aacccctcaa    27180
aattatccat gagagttgaa atcaatttct ttcaaactcc tgttaatgtt catatttaga    27240
cctcttcccc tgaatcacaa atgttgttaa tggcatctag aatggcaaat cctttctgga    27300
aggtttcaat ttactttgcc cagatccatc agaggaatca ctacctatga cagctatggt    27360
cttacaaaat gtatttctta tatagtaaga ttcaaaagtc aaatttactc cctgatccat    27420
ggctgcagaa tgcacgttgt gttaagaggc atgaaaacaa cattaatcta tttgtacatc    27480
atcagagctg ttgggtgacc aggtacattg tcaatgagta gtaatacttt gaaggaatt    27540 ttttttttcca agcaggtctc aacaatgggc ttaaaatatt cagtgaaccg tgttgtaaac   27600
agatgtcata ttatccagac tgttccattt attgaacaca ggcagagtag gtaaaagttt    27660
taagggtcct aggattttca ggatggcaaa tgagcattgg cttcaactta aagtcaccag    27720
ctacattcac cactaaagag agtcagcctg tcctttaaag ctttaaaggc aagcattgac    27780
ttctctttag ctatgaaagt tttagatggc accttttttgt aaaagaaggt tgttttatct   27840
acattgaaaa tatattgttc attgtaacca ctttcatcaa tgatcttagc tagatattct    27900
gggtaactta ctgcaggttc tccatcagca cttactgctt caccttgcac ttttatatta    27960
tggaaacaac ttatctcctt aaacatcatt aaccaacctc ttggtagctt ccaacttttc    28020
ttcaatagct tcctcatctc tctcagcctt catagaattg aagcgtgtta gggctttgtt    28080
caggattagg cttttcactta aggcaatgtt gtggctggtt tgatctattg aaaccactaa   28140
```

```
aacattccca tatcggcaat aaggctgttt gattttctta tcattcatgt tttctggaac   28200
acttttcaat tacttacagt aaggaaatag cacttttaat ttccttcaag aacttttcct   28260
ttgccttcac aacttgtgca agagacctag ctttcagcct atcttgactt tccaagattg   28320
tccttggtga gaaatgcttg attactaggt gtaattattt ctagcttttg attgaaagtg   28380
agagatatgt gactcttcct tttacttgaa cagttagagg ctattgtagg attattaatt   28440
ggcctaattt caatgttatt ttgtctcaag gagagaggga tgtgggaaca gctggttagg   28500
agagcagtcc gaacacacac ttttttttat tactttcact gccttacatg ggtatggttc   28560
atgctgcctc caaatactta caaaaacatc aaagatcact gattacagat cattaaaata   28620
ggtttaataa taatggaaac atttgaaata ttgcaaaaat taccaaaatg cgacagagac   28680
atgaaatgag aacatgctgt tgaaaaaaat ggcactcata gacttgttgg acacaggatt   28740
gaaagaaacc aattcatcaa aaccacaata tctgcaaaac gcaataaggt gatgcacaat   28800
aaaaggaagt atatctgcac ttccttcttt tttactgaaa aagcccaagt tcttactctg   28860
gtgttgagaa cctttcatta gctggctaca atctcagttc acaatcattt cttattgccc   28920
ttcaacaatg tcctgaccaa atcgagttct ttctcattgg gaacagttca ttcctttatc   28980
ccttcgctca ttctgttcct ttttttcttag aaaaattatt tgcccatgtt ttttatcccc   29040
caattctatc tttttcaatg cccacttcgt gtccaacccc tctctacttt ccctctaaac   29100
ttactcaaac acttggtgaa cttttttctga atgtttttttc tgaatgttta cttttaaagg   29160
agttgcccag tcacaaagtt tgagccaagt ttttttgttt taaacttgtt ttaaacttttt   29220 gttttcatca acttttttca aacaattttt gtcagcttag aggttgtgtt ttaattacta   29280
tttttaaaat cttgtatgag gtagtatgat ttgaaattag atggaatgtg cccaaaatta   29340
tctctgtaga ataatatgga aaaacgaaaa tgaaagatg tattacctga atgtgctcct   29400
cctagccagt ttctcaaggg agaagaatca ttaataagtt tgtgaggctt ttttttttttt   29460 tctggtagat ttctgtttcc ttgatcagtg gttttcaga atttttaaa gcttgtgaaa   29520 tacttatttg taaatagcat cttatgagga accttgatat gtgacaaaac agatgctttg   29580
atttgagagc agaagacctg cagcccctga ctgctcacct ttccagggac ccctgaacat   29640
tggcctagag ggtagtgtac agtcacttct tcagtgataa cttactgagt gtgattcaac   29700
aaaactgctt tggtttatgg gtgaaacata atttataact aggcaaatgt cagcttaaat   29760
ttatattttc taaatagcac tgaaaatgac aatagacaaa tgtaatttct gattttttaag   29820 aaatgatttt ccattttaac atacatttta aatgttttgt cttcaaaggg aatccttaaa   29880
aatgatatat tggaaaccac tgatttctta ttttcatttc atgaatttca gattcatgaa   29940
tggaatatat tgataatagc attttttaag ttgccccaaa aagatgaaat acaaataatt   30000
ttaatcccaa atctatttca gacacctaac tttttttttta tttttatac tttaagttct   30060 aggatacatg tgcagaacgt gcaggttttgt tacataggta tacacgtgcc atgttggttt   30120
gctgcaccca tcaacccgtc atctacatta gatatttcta ctaatgctat ccctccccta   30180
gccccctacc ccacaaaagg ccccagtgtg tgatgttccc ctccctgtgt ccatctgttc   30240
tcattgttca actcccactt atgagtggca acatgtgctg tttggttttc tgttcctgtg   30300
tgtgtttgct gagaatgatg gtttccagct tcatccatat ccctgaaaag gacatgaact   30360
catccttttt tatggctgca tagtattcca tggtgtatat atgccacatt ttctttatcc   30420
agtctatcat tgatggacat ttgggttggt tccaagtctt tactattgtg aacagtgctg   30480
caataaacat atgtgtgtat gtgtctttac agtaaaatga tttataatct tttgggtata   30540
```

```
cacccagtaa tgggattgct gggtcaaatg gtatttctgg ttctagatcc ttgaggaatc    30600
accacactgt cttccacaat ggttgcaatt tacactccca ccaacagtgt gtaaaagctt    30660
cctatttctc tacattctct ccagcatctg ttgtttcctg acttaatgat tgccattcta    30720
actggcgtga gatggtttct cactgtggtt ttgatttgca tttctgtaat gacccgtgat    30780
gatgagcttt ttttcatgtt tgttggctgc ataaatgtct tcttttgaga agtgtaaggt    30840
acttaattct taaattaaaa aaaaatacccc ggccgggcac ggtggctcac gcctgtaatc    30900
ccagcacttt gggaggccga ggcgggtgga tcatgaggtc aagagatcga gaccatcctg    30960
gctaacaagg tgaaaccccg tctctactaa aaatacaaaa aattagccgg gcgcggtggc    31020
gggcgcctgt agtcccagct actcgggagg ctgaggcagg agaatggcgt gaacccggga    31080
agcgggcctt gcagcgagcc gagattgcgc cactgcagtc cgcagtccgg cctgggcgac    31140
agagcgagac tccgtctcaa aaaaaaaaa aaaaaaaaa aaaaaatacc cttctttaac    31200
aaaatcaagt ttcaagtttt ctgccttgtt gataacttgt taacatttttt ttatttttaga    31260 ataaatctaa acagagacca cactgatatc tgtaacaacc tatgtaaagt taagattaag    31320
gttaaatcac attttttcaca gagagtgttt tactgaaata taaacttttta tgcatctgat    31380 attatctaat tgtgtcctta ctgggtaact tgtgtatttt tcaagttaaa ggatttccta    31440
aaaatgctta tttgaatatt tatgtcattt gtcacacata ctttcaaaac ataaccttct    31500
tcaacgagta tcttcttttc cttcctaaaa tactgttaat agctggctat tttgtaagcc    31560
tgtatctggt ttaaaaaaaa gaagtgaata ttttcaatac ttatgaacca tagaattctg    31620
tattcttttc ataactttta acttttccat aggacctatc actatgtaaa atattataca    31680
tatctactga tttatttatt gcctatgtac ctatactaga acatagtaaa catgagaaca    31740
gggaatcttg gttattaatt cctgcaggac tcaactactt atcactcaaa catttgttct    31800
tgaaaagaac ttcgtataac atcattagat ttttacagaa tctttaaaaa agctttaata    31860
ttttcaaggt tttttattta tataaatatt gttactttac cactagtgat ttcaatagtg    31920
gcattgtcac atgattcaag aagaggaggc cattacatta ctgttgtatt aaaaagtcag    31980
ttcaggctta atatatatga ctactataag tcaacctcac attttaatgt atgaagaaga    32040
ttgtatgaac gatcacatta attcatttaa atagtatgta ttttgatact aattttttaag    32100 aagaaatgta tcattctcat ggaaataaaa gataatttga aaagca              32146

<210> SEQ ID NO 2
<211> LENGTH: 6514
<212> TYPE: DNA
<213> ORGANISM: homo sapiens

<400> SEQUENCE: 2
aggcgcggac gcaggttaca gcagcgcttg gcctctgctg atgccgtcgt tatcctaccc      60
ctcccccgtc ccagctctac ggcggccgcg cgctccaggc cggtcgctcc accccccggc     120
tcccgggact gtggactcca cgaccctgtc ctcggccctg tccgcgccga agcagcccgg     180
gactgcgcag cgccccgcgt gccgatcttt tcctaattca gcagcgattt aaccaagagc     240
ctggaatatt ttaaggagta ataagagaca tttacaaact attctctctg aagcctgcta     300
cctggaggca tcatctagat aatcagaacc ttggcttcca catcctcctc ccttgtctta     360
actacaaaca tttctttctg ctgacttcaa ctccctcagac atgggaaagt ctcttttctca    420 tttgcctttg cattcaagca aagaagatgc ttatgatgga gtcacatctg aaaacatgag     480
```

```
gaatggactg gttaatagtg aagtccataa tgaagatgga agaaatggag atgtctctca    540
gtttccatat gtggaattta caggaagaga tagtgtcacc tgccctactt gtcagggaac    600
aggaagaatt cctagggggc aagaaaacca actggtggca ttgattccat atagtgatca    660
gagattaagg ccaagaagaa caaagctgta tgtgatggct tctgtgtttg tctgtctact    720
cctttctgga ttggctgtgt ttttcctttt ccctcgctct atcgacgtga atacattgg     780 tgtaaaatca gcctatgtca gttatgatgt tcagaagcgt acaatttatt taaatatcac    840
aaacacacta aatataacaa acaataacta ttactctgtc gaagttgaaa acatcactgc    900
ccaagttcaa ttttcaaaaa cagttattgg aaaggcacgc ttaaacaaca taaccattat    960
tggtccactt gatatgaaac aaattgatta cacagtacct accgttatag cagaggaaat   1020
gagttatatg tatgatttct gtactctgat atccatcaaa gtgcataaca tagtactcat   1080
gatgcaagtt actgtgacaa caacatactt tggccactct gaacagatat cccaggagag   1140
gtatcagtat gtcgactgtg aagaaacac aacttatcag ttggggcagt ctgaatattt    1200
aaatgtactt cagccacaac agtaaaaact ggaagagatg gatttaaaga agaaatatct   1260
attgatattt cctatactct caatgaagag gtatttccta ataggagacc ttaaattgaa   1320
caaacctaaa gttacactt ctaagagtac agttaaaagt atgtggacct gcagttcttg    1380
taactctcca ctctgtgtta atgatatatt tgtactagga tcttttactt gaatctaaat   1440
ttactggttg atttccttct ccagcctatc ccctacaggg aaaagctgat acttcccta    1500 tagtacaata aataattatt taaaagtcat agctccagtc actactgaaa acataatttt   1560
ggtgataaac ataatttgag aaacttaatt tctgaatgtt tttatagaaa attactgaaa   1620
gtctattact catggaagac ttttaaagaa taaccttttt tcctgtttta taaattccca   1680
ttgttatatg gtagtatttc agctacacaa tattttagct tttagctaga catttatagc   1740
ttttcatttg ttgaaatggt aatcatctgc atgttttgt cacttatttc aggttagtga    1800
ttgcctaaca cttataagcc aaaataatct ttgcaaaatt ccatacctaa aattttgaaa   1860
gcccctaatg ttttcacaca tctttctgta ttagttatag ttttgtgaaa tctttgtgtg   1920
atcttcaaac attatcattt aatgtacaat actgtaaata aactgtgcat ggcttttata   1980
cagctttagt aaatgtcaaa taaagtggta cagactcatt acaacaagtt tctcataaaa   2040
atacaataaa taggaaaatg aaattcagaa acccatagac tgggaatagg ttccagttac   2100
agcttggatc tggcataaaa taaatttgaa ataaaatatt ttgatgctcc attttttat    2160 gttgctttc atactaaaga atggtgtaga catgttttgc aactgttagg tacccagtta    2220
tcaattttat caatgtttta gaggaggaaa ttatttttt ggtagaaatt gttcaagaaa    2280
tccttaattg aatgtcatta aatgatggtg gccaaaataa aacctattta gaaatttaat   2340
cactttgcac atcacttgga atatgatgcc tctagtagtt acttttttat agttttctac   2400
ttttggtttt atttaaaatt gttttcaaat atagattatt gacttattca actttgctgt   2460
tttatatttt cagtatcatt tttcattttt tttttttttt gtcttttcac ttaccaagtt   2520
ctagggacat ttaaaatatg tactaagtgt aggagtggtt atgataccaa aaaatgtagc   2580
tgggttgaga ttaatttcgt tctgtttct catgacagaa atcaggtttc cctttcccca    2640
cccctaagtg cctaacttag gtctgaaaca gcctgtttat tagtctgact ctctcaacca   2700
taaaacataa gctttatta attctgcctt taaacacact caggtttccc cttaatttc     2760 atattatttt ctgcaagttt tcttgagtat cttcaattcg ttgaatgtgg ttttggtttt   2820
ttttttgttt taacactagt cttcccttaa ttcattgcta actcaagcca tccttactat   2880
```

```
taaacccaaa tcagtccttt aagttcatta tggcctttct agtatttaaa aaaaaaaaaa    2940
tcattttcat ttttcttctg ctacgttticc tgactactac tgcatacttc tctgatacag    3000
gttctgtttg tatttttat atcattctca ttttctcatt tgacatgatc tatgtctata    3060
tatgatatag gtccccttttt gtctcaaaat ttttaattat gtgacttcaa aaatcacctg    3120
tatctgtagt agggcttcca aatctgcttc tccatatgtg accagtcacc tgtctgctttt    3180 cacatttagc tagtgaacta cacatttact aaaatgtgta aatttacac atttagtgac    3240 tgtgtaaaat aaaaaaaaag ttattttatc atatcctttc tattatgttc ccatcctgtc    3300
ctcatgtccc atttacttta ttatcaccat tcatttcttc aaaattatct tttagatacg    3360
ctcatacaaa aatcaatcct tgttttcttg cttgtgtctt ttaaccttgg aaaattacat    3420
cgtgtaaatt aaacagattt ttctgatgat ctgtgcttct tatatactat tagagtgcat    3480
gatagtatct cctgaaaagg atggaaagta gaagcatttg cttttagtca cttaattttg    3540
aatctttttt cttcatcttt tgaattaatt tttttatta tatctacttt tagtggagtt    3600
tgagtcagaa aaaacaaga atttgaaaca agtaaaaaga tagaagagaa ataaagatgg    3660
tatgtgacta ctttcagaga gagttaagta actgtcagaa taagcctgga acaaaacagg    3720
ctgtaaatta ataaaactac aaacacacat tcaggtgaag cagaagtata gccataaaac    3780
atctagaaag agtgaatgag gcttttagct tttcttaggt caatgtccag tgtgctttt    3840 tccatgggaa taggataggt attaatacgc ttttctaaac tgctctcaga ccttatccag    3900
aggacatggt aaagatatgt tacagaaatt tttctgatac ttcctggaat aactttaagt    3960
tacaccctag tagactggtc attctaataa aatccagtac tataacaaac ctctgtatgt    4020
tgatagcaca ttggccctttt ttagagttct ttcctatgtt tttcttacgt gatttcccac    4080
agttccatga gtccaacaaa ggagagtgat aggctcctta tcttttagaa gaggaaggaa    4140
aggcatgaag aagttgaggg actggctgaa gatcacgtac ttactaagta gtacaactgg    4200
agcaagatca agtatctctg tctcccatat ctgtgttcta tcatttaaaa tatatattgg    4260
aaatccctgc tgactcagat tggtatgatt aaaaatgaga ggaaagttca aatagttagt    4320
agtgacaaac taatactgct ggactaagat tttggtagca ttgttttcta aaatatttta    4380
aatggagaat gaacacttat aaaatgcttt ggaacataat ctttagctta attttctgtt    4440
aaaatttagt acccctttcat cattccaata aagataagac tgatccattg tctaaggaaa    4500
ttatttataa ataatagaga ttaatttatt tgagatttga aataagaata gtatgaaaat    4560
attagatacc acataaattg tttgaaatta ctgaataacc atcttaagta tggaacattt    4620
aaatggctat attttatttg tgtacagttt ttctgtgcct tgttaggcca gtgaagcaat    4680
tattttctct aagaaaatga caataaaata taacacactt cagattgtct gatttacagt    4740
ttggaaagga caccgcaatg ttcaaatagg taggagacca tcaaaaacac aattaaagta    4800
acatattagg agacttgaaa cttcagccta ataaatcctt catggttctt agccttatta    4860
ttgtgatata attctagata ttttcttgga gggcatgtgc ccaactctcc cgcacccccat    4920 tttgttttgtc tttttaaagtt cttagaataa acagttcttt atataataat tatattttat    4980
ttaagaaaat agtttgttag gtactttta aagatgtaa attttaaat ttacaaatac    5040 atatgggtct ttgataagca ataggaattg aattacaagt tactagggtt ataagcaaaa    5100
ggttgcttac cataatgtca ttaggtcacg attttagct cacatctgga agcagcaact    5160
acttggctca agtacatata agagtaatta gttttattct ctctttttta taaaatcggg    5220
```

| | |
|---|---|
| tttcagatga gatgtttatc ttagactatt ttagggaaaa attttacatg tttgagatgg | 5280 |
| tggagtaaaa agactgttaa acatttcttt taaaaaatta ttttttacatt acaacaatat | 5340 |
| atttatgatg tgttcagatc aaaaatttaa cttctgtgtc ccagatctac tttcaaagtg | 5400 |
| agattttcac ttgtcagctt aaatttctga ctagaactaa catttgtgta ttttttgtgct | 5460 |
| tagtcggaat acaaatttca cagtggattt ttgaagtttg tccttaaatt ggataaaatc | 5520 |
| aagtgattaa agttactaaa gagataaaaa tggtaatttc catttttaaa agtaatttgg | 5580 |
| ttgtgtttat agttatttgt acaagtattt atcacagact ctaaattgaa aaatgtagta | 5640 |
| tgatctatat ttgaccctaa aaatgttgga ttaatttaac aaatatgcca gatttttcat | 5700 |
| aactaagtct taagtcttct aaaaggaagc tgttacccctt ctgttttttaa ttacattaat | 5760 |
| tgaaatgtgt tttaagagat acaatttcag catattttat atattaaaaa acaaaaaagg | 5820 |
| attagtattg agccagtggc caaaaggtaa tattactacc atgtagactg ttatagttca | 5880 |
| aattgtccca cttcacccag aattttagaa actagaagtc tgggaggtac tatatcagct | 5940 |
| gtagttgggt aattccaagt gctgatagta ctattcatct ttttattat tgtgtcagat | 6000 |
| gaaacaaatg ccaagttgca aaatatgcag attttttatta tataatggtt ttaggcataa | 6060 |
| attattaaca agccatgcct tatgtgtttc atcttatatt tttctttaga actaaactat | 6120 |
| aacagatttt ggaaaatgat ttgacgtgct tgctcacttg attgacttgg tcagatattt | 6180 |
| gaatgatggt attacctaga ttctaatcct tgattctagt tatataataa ataatataga | 6240 |
| atatgaaaat atgtttgggc atttactgtt tatattatgt agtagcctcc atcatgacac | 6300 |
| acttactaca tttatgaatt gagcagttct gtaattgtaa ttattattgc tgttcatgta | 6360 |
| acaaaacatg cttataatag caaacaaata gaaatgcccc caaaatgcta tttttttaat | 6420 |
| tcagttataa ctgttactct tgtagttgtg tatgacgcaa taaatttgt aaaaaaattt | 6480 |
| cagcatgaaa aataaaattt gtatcactta tgta | 6514 |

<210> SEQ ID NO 3
<211> LENGTH: 32695
<212> TYPE: DNA
<213> ORGANISM: Macaca fascicularis

<400> SEQUENCE: 3

| | |
|---|---|
| ctccgggagc actgtgcgca ggcgcgggag caggttacgg cggcgcttgg cctctgctga | 60 |
| tgccgtcgtt gttctacccc tcccccatcc cagctctgcg gcggccgcgc gctccaggcc | 120 |
| ggtcgctcca ccccccggct cccgggactg tggactccgt gaccctgtcc tcggccctgt | 180 |
| ccgcgccgaa gcagcccggg actgcgcagc gccccgcgtg ccggtgagcg accccggacg | 240 |
| tgcagtcccc aggtccccctt ccggagcggg gctgagcggc tgcgctgcgg cttcagccgg | 300 |
| gcctgacgag gaggggaggc cgcctgggtg ttgggcctgc cgcaggtacg gcggcgctca | 360 |
| gggctcgaga tcgaggtgct gtttcgcctc ttttgaggcc cagccaggga acaccggcct | 420 |
| tcggcccaag cccggcctct gggttgcctc taggcccctca ccccttgagc gccaggtggc | 480 |
| cctcttgatt ttgctgttga tgaatttttct tgccgtggtg ccgggatgtt atttttcagc | 540 |
| tttacagagt agactttgtg ctaggtgttg tttatggagc ttttttaaagg cgctggtttc | 600 |
| cttcgttctc aagcccttttt agaactaaaa ccagtgtctg cacagacgat caggagccat | 660 |
| ttaaattgga gtgctgtgat atattttttc tctccaaatt gagtctgata tccatgttgg | 720 |
| ctttcagtaa aggaaggaac cgctataata acattgagca ccgagaggtt ggagaagagg | 780 |
| gtctagcacc ccttttttaa accattgagt ctccaagaat aaaagtggtt aaacttgtca | 840 |

```
gttctctaag gaaaatctag tagagaaggc aagggattcc cagattttga caaagtctgg     900
cacttgtcca aacacctacc taaaacaatc gatcacggca gctgttagat taggacagaa     960
aacaggccca aacggagagc cacttgagtt ttcctttctg tgtcttttct ctcaacgccc    1020
tccagtaaga tgcagcttac accctggctg tgttgactga gatcccagaa agggtgcctc    1080
taaggctgaa agggtgccct taagaccttg ctggtaaggc ccagtgatcc cagttcatct    1140
agtgttccgc atagacccca aggtcactgt gtggggacag tgatgttaag tcttctctaa    1200
cctacctgtg gctggcaggt gttgatttga ccagggtatt gtgtcattga gccaaattaa    1260
gacaatgatt ttttagaagt cataaatcat ttgtattttt aatgtgggca attatttta    1320
taaatacata gttttttttt ttttaaaga gtgaaaatcg cattttacag tttcgtttgc    1380
acaccatttg tatatttttt ttattctgtt tgacagcaac aagtggatgg catgcgagtt    1440
ttttttttt ttatctttgt atttattttg tatatatatt catgggcaat tgctacaag    1500
tgcaatttgc tacattgata tacgacctcc tagtgaagtc agggccctca gtgcatccaa    1560
cactggagca acacacattg tacccaccaa gcaacctccc atcaggcatg ccaattctaa    1620
aaagtaaaag ttcttcata ctctaggatg aattgactta tttggagtat ctgttttgtt    1680
taatcaaata agtgagaatt tttgaaagaa atactatctg tcttaatgtc tgtaatctat    1740
ttttaggaac cgataaaaga catatcaaat ttagaaggag tagaattatg ttacttctaa    1800
gttttacttt ttcactttat tttttctcaa gttataagca ggaaaatgcc agcagggtgt    1860
attgtatgac tattaagttc ttttcagctt taaaagggta tgaccttaag tataaagtta    1920
cttcattatc tacttgcaga agttattttt gtgtaggcac tagtcctaat tatttctact    1980
tagatttta catgtgtatt taattttccc atgttatttg gatactctca tcctaaaagt    2040
ttgaagttag tattctaaat tttgctgctt tgtaaattat atttaatatt ttggaacact    2100
ggcttcataa ttttaactct gtcaactgct gaatgaaaaa aacttgcatg attttggaat    2160
ttcgggcctt tttattgttg ttgcaagtgt ttaaatgttt aaagcaagaa atttaaggat    2220
ggaagagtgg tgattgtatt tatcacaaag gtgcatgaat tttcagaggc tgaaacgtac    2280
tgttttgaag ttacttggac atatacatca aatacctagc tatcatctac ccaaagcaat    2340
ttttgccttt agtgccgact ggttaaaagg tagaatgtat ttttatttta ttctaaggaa    2400
aatgaaacct gcatgtttct tttcagagaa cctgcagatg tagactttg tcaaatgtta    2460
atgtttgaaa gcccattctc atcataagca tggtaggata tcatttcaca ttatttctt    2520
taaaaaacac ttctggactc tagtaaatga ctcctttgtt tcagacatta ttttgattgg    2580
atattatcct aatccaaaag gtagtttgaa cattctctta agtttgttc tgtaaaccaa    2640
aaataaaatt ctgagccccc caactgactg agtggaccct gcttctctgt caagggcatt    2700
ccaaagtaaa cctaataatg tggttttggc catgatgaaa aggtgggcgg aggggattga    2760
acataccta ttataccttc ctctctttag aattcaggca caactgacca gcattgatga    2820
aaacagagat tttaaaacta acaaaagagt ctctttgtag cagtaagata tcaaatccca    2880
acctgactct aatatagaat cacttgacag atagcaggcc ctgaaagaaa tcaaaatatc    2940
ttaccccaaa atatatttat ttgaaatggc cttgcaaagc tgtctcttgt ggggaagatc    3000
cacattctgt acagaatccc ctttcctttc cagatctttt ccttaatcca gcagagattt    3060
aaccaagagc ctggaatatt ttaaggtgta ataagacaca tttacaaact gttctctctc    3120
aagcctgcta cctggaggca tcatctacat aataagaacc ttggcttcca caacctcctc    3180
```

-continued

```
ccttgtctta actataagca tttctttctg ctgacttcaa ctcctcaggt agagtttaac     3240
cccctttcaac caattgccat tagaaaatct ttaaatccac ctttgcacct atgacctgga    3300
tacccccccaa ccttccaccc ctgcttcaaa ctgttctgct tttctgggct gaattaatgt    3360
ataccttaca tgtattgatt tatgcctctg cctgtaattt ctgtctccaa aatgtataaa    3420
tcaagctgta acccaactac cttgaggaca ttttctcagg acctgttgag actgtgcctc    3480
aggccttggt cactcatatt tggctcagaa taagtccctt cagatatttt acagagttta    3540
actcttcctt tactgttcta aattaattag tgtaaatatc tcatagagtt cttgaatgta    3600
cttttttcct tgaagtttac tgtaagattt ttattttttct ttagacatgg gaaagtctct   3660
ttctcatttg cctttgcatt caagcaaaga agatgcttat gatggagtca catctgaaaa    3720
tatgagaaat ggattggtta atagtgaagt ccataatgaa gatggaagaa atggagatgt    3780
ctctcagttt ccatatgtgg aatttacagg aagagatagt gtcacctgcc ctacttgtca    3840
gggaacagga agaattccta ggggtatgtg ttattgcatt gctttcccctt taaataatga   3900
tttcaggaat ttgctcaaat attataaaaa ctatgggtct caggaaccac ctgttttaga    3960
agactgttag aattaaagtt gaaacatcat atcagttatc ttcaggcaaa agatgcaaa     4020
agaaacaaat aaaaaaatat taattaaggt tcctaaagca gtgaagaaaa ccacctcact    4080
acctccaata tttttttcatt cccttctact attataacag atattcactg tcttgtgaac   4140
aaaaacttttt agtcctattt ggcatctata gagatgacat catagttatt tgctactttg   4200
ctatatctga tgttagaagc aatttaagta atttgttgac ctaatttttt ttttttttaag   4260
agatgagatc tcgcaattgt tggccaggct ggtcttgaac tcctgtcctc aagcaatcct    4320
cccatcttgg cctcccagag tgctaggatt atagcagttg agccccatgc ccagccagaa    4380
ttaatgtgta aggaagctta ttcttttcatg ttattttaaa aattttatta ttttttaataa  4440
taaggataga atttccccat gtttcccagg atgatgatga gttcttgggc tcaagccatc    4500
atccagcctt ggcctctcaa agtgttagaa ttacagctgt gagccaccac gcctggccaa    4560
cctaatatttt ttaattcatt atctaaagaa gaagaataag ctgcctgtgc tgtaatcagt   4620
tatttctaaa agaaactcta tgaagaggga tggtatgtga aaacaagcca aattgaaaaa    4680
aaaaaaaatt gtttgtgata tatcacaggg gacgtcagaa ggaaataatc ccctatgtgc    4740
tgcttgtaag ttactttagg aacagtggca ataagtagaa ataataaaga taccttatgc    4800
tgttctcatt atcttcttgg tgaaagttga tatgtgaccc tggagacacc cagagggaaa    4860
aaggacaaaa tgaaagtata aagtatacca gagtcttaaa aatgctgtgg gttggaattg    4920
aagtttacat ttgcattggc ctttgagtat gatggtttta tcttcacagg gataatagct    4980
gtttaagaat aaaataatta ttgtagttga agggattaat gcaccagact caggggttag    5040
gggagtactg ttttaccagt ctggttacat ttttgaggtg tgactagtaa acttttttgg    5100
ccacctggat acagattatg gaaagtagga aatcaaggat gactgcagag ttttttgttt    5160
tttaggtcg tttgtttgag caactgaaag aatgtagtaa caatttatta aaattgaaaa     5220
aaatattatt tgagtgtata tgtcacagga gagttcagga gctcaagttt acacatgtaa    5280
atttggagat acctatttga catggaaatg ggtatgttca ttaggcagtt agttatcata    5340
agggtcagga attcaattgc agggcccagc ctcaagttat caatgtatag atgacactta    5400
aagctcagct ggatgacagc accaagctaa tcagtgcaga tagcaaaatg agaccctagc    5460
actgaatcct gagacactgt ggcatatcaa ggtcagtgaa agaattaaca aaggaccctg    5520
agaaagaaca gcgagagagg aggaatcact gtgtctggta tcatggaaga taagtgaaga    5580
```

```
aagcgtacca aggagaaaag agttaccaaa tgttggatgc tactgataga ttaggtagtg   5640
tgaagactga gaactgacca ttggatttgg tgacatggag gccacaggag agtttaaaag   5700
agcagttttg gtaaaggcat gtgtagcatg tatagggtgg gctcaagagt gcatagaaga   5760
tgttacatag agagaaaaca gattttctga ggagtttggc tccatagcag agagaagaga   5820
ggtggtcctt agaaggcgct gtgaggtcag gagaggattt ttttaaatat atgtatatat   5880
ataagatgga gtgaataata gacacttgta tgctgatgag aattatctgt aaacattggt   5940
aattcaggag ataagaggaa ttattggagt aatgttcttg aacagatgaa agggcagatc   6000
tgctgcacag gagcaaagag ctgctctttt ttctataaaa ggtaagttgt aaacacgggt   6060
agtttattct tggtaataaa agagaaggta agtatggac acagaagcag ctacgtggat    6120
agatctgata gtaaatcttg tagaaattat cttctgttta tcatataatg aactaagaat   6180
gaggatagcg aagaagatat taaagatttg aagagagttg aagttataaa attgtggtct   6240
tggagagtca gcttgagagt atgaacttgg gaaatgtagt atgattgttg acttcattga   6300
gtgctacttg acatgagtga tcaaaaatga aaccagttgt gtatttttct gtgtccatgt   6360
ttagctgtgt tgatatacgc acaggagcca gagggctggt tttaaccagg gttgtagttt   6420
tagccaaatg aataccgcta aacaaggtga gatatgtaaa cacacaaaaa cgcagatatc   6480
catattgtat gtatttgtat aattttgtat aattatatat gggtgtgatg ggggagcaca   6540
gacgagagga agagtataga agtgttggag ggaataacag aagcatttta gaaagctttt   6600
aaagataact tgactatctg gtaccttaat agtaatata ataggccaac ttctaataag    6660
cttataaaat tggcatttaa aggtccgttt atcctttaaa aacttatgga tttagctcaa   6720
cccaagaaag aaataatgga ttttgaagtg actttaatat gaattggggt gagacctgaa   6780
agggccctgg aagactcatt atgtagggg ctcttaaagc ttgagacttc tacttcaaaa    6840
gccagttttg gttttgagg gggacaatgt cagaagctct gcagtgatag aggtttcagg    6900
aaagggagat agcaatatgt tcttcttttt atcatccaga caaccaaatc agagtcttaa   6960
tggacaacag tgaagcagaa ggaagacctg gtaaatttag ctcttctgaa agctgagact   7020
ttttaaattt tttttcagta gagaaaaagt aatggagccc tcatttgtta caattttttt   7080
ttttaagctc gacatctagg tatgaaaaaa cacactgtct tctctagaac ttctgctgtg   7140
tactttctga agacttagca atttactaaa ggaaagagat gagtgccaga tgatattctg   7200
gtctttccaa accagattgt gatggggagc cattgtattt ttaactaatc atagtaattt   7260
ctaaacctac ttctttcacg tttagggcaa gaaaaccagc tggtggcatt gattccatat   7320
agtgatcaga gattaaggcc aagaagaacg taagtgattc taagaacatg gcagtgtttt   7380
atgttttatt tttgtttttt gtattttttc aaattatgta taaacaactc tagttaaaac   7440
tattaaaagg aaaaatgctg tcacgttgtt aaattatgtc atcatatgct ttgtatcctt   7500
aaacagacaa acaaaaaagg aatttctgtt tagggtaagg tcttgaaagc agtatggtat   7560
ctttatcttc tcaaatctat ggaaatagat ctagaatagc agtaggaaac acatacactc   7620
acataaaatt ttcattaaaa attggataag gtatgctcca caaccccgga ataaaaattg   7680
gtatttaaac atgatgacaa cagggacccc agctggctta gcagctgtgt ggaggttgtg   7740
aaggaaagca aaaagagagt tactgaggat cctatgagcc ctgatacaca aagcaaatac   7800
tttgtcccaa aagaaaagga cacccagcaa atatttccaa gaataatctg caaaaatgac   7860
aaggtttgca tgctgtagct tggagaaagt acaaaaatac cacagagatg tactaagcat   7920
```

```
cttcgagaag atcagaagga actggaccat cctaaatcct cagcgacctt aggaaatgtc   7980
aaaacaaaaa ttcttggaaa aggatacaga tacatatcct caagaaaaaa gttgttgagt   8040
agaaaacagt gtctacagga caggagttag gaatgaagga gagaacagat tcagatatta   8100
gggagatcat ctcaaaactg tggagataaa tacacatgga ggccatgttt tcaaatactt   8160
tgtatgtcaa cagaggatgt atcccttgaa cagtgaagct agcaaatgga cgctggcata   8220
ttccatcacc aaaaatggaa ccttttctta aaagtacaaa agctcttttc atttaaacat   8280
gagcaactgg aaaggatcgc aacaaagcat tatacaaata tacttttttaa gaaattgaag   8340
aaagtaagct gagcaaaata ctgacacttt aataaaggca tgtgagaaga gcagatgaac   8400
actttaactt aatactatat atagaagcta caacaggaca gcataaggca gaaattgaga   8460
agctcagaaa tgagataact aaacaatcag agtatgtgaa aagagaattt acagacctct   8520
ggaaagaatt agaagaaaaa cacatccaca aaactggaag aacacaagta caaatacgtt   8580
ggaagtacag tcagggaaat agaacataaa caggaggaat gaagacatac acaacaaatt   8640
aatgtaaacg atttgagaac aaatgtctaa aagtcaaata aactgaacat gtgtgtaatt   8700
ggagcatctg aagaagaaaa ccaaaggaat agaactgaac aaatgcaaaa cattaaatca   8760
agaacacaga gacctacata ttgaaaagac atcacaatcc tgaaaaaaat caacccatgt   8820
tagtgaaatt cttgaacttt aaggttaaga aacaacagc aaaactccta aatacccagg   8880
caaaaggatc agttaattta taaaggttag aaaatcagat tgcatgctg ctgcttgact   8940
acagtgcctc aaacagataa gcagtggagt gatgtattta atcaggaaaa taaaacgaac   9000
caaggatttt ataaatagtc tgacctttta ttacaaaacg tataaacaga tatgaatatg   9060
aaggaaatta ggatgaatcc cttcaaaacc tacaagtggg agaacttttt aaactatgat   9120
tttaaatgca gaaaaggtaa atttgataag taaacttttta cagaatgaag acaaaacctt   9180
aactgaagtc aaaatacaaa tagcaaactg agtagtaatg tttacaaatc atatcacaga   9240
cagagggcca atatccttac tctaaaaaga gcttcagaat ttgagaagaa aaaggccaac   9300
ctccaaagca aagtagaagc tatgaacagc tagttcacaa aaaagaaatg caaatgacct   9360
ttaaacatttt gaaagatgt ccaatcttgc tcataaataga aatgcaaatt aaaactacac   9420
ttagttgcca tttctgtcac attggcaaaa atccaaaatg ttgacaacat actttgttgg   9480
cagtagtgac tgaaaacaag tatattcatt ccttgctagt gaatgaaaat gtggcgttat   9540
ttgccaaatt acatctgcat ttactttttg gctcaggaat cctactttga aaaatttatt   9600
ctaaggatag ttgtcaaata tagtaaattg tatttgcaca aattattcat tgtgccaatg   9660
tttgcagaag caaacaactg gaaacaatgt aaatacccat aatagaggac tgatggaatg   9720
agatattaca tgtacacaat gataaaatgg aagaagtatt ttactacagt gcgatattga   9780
gaatatgttt ttctttgaaa acaccacaca ctcacaccca cacacatata cacacaaaca   9840
gactgactta taagccctaa ggactaaata gattatgatg gattcacccg cccataagta   9900
attaaaaata aaacactaaa gtgtagaaaa tcggataaaa ccaaatcaaa taaaacaatg   9960
ggatgataaa ccaaatctaa agaattggtt cccctcagag tttgggaagg aatttgaaag  10020
agggagtgga taagcaagag tgtgtgtgtg tgtgtgtctg tgtacatatt tttttacatt  10080
aaagatgaaa tcaaaagtga agtaactgc caaatattga gataaaagga aacattattc  10140
taactgtata tgaaattggt gacactaaca aaactgaaag attttaagtg acttgaaaac  10200
attgtgctat gattgtagat gtttagtaag ttgtgttcca aatggcaaag aaaatcacaa  10260
taaattttaa actgtactta atagttgtat tattaggagt acctttggtg taatttggaa  10320
```

```
attttatatg taaataagta attatgtaaa tcccttagga agcaagattt ttagcgttaa    10380
gagcaaagag atacaaaatc aaagaaattg aattttccac ttttgaccca aatagaataa    10440
tgcctgaaat acttccacct gaaatcacta aaaaaatgga caaatatagt aaacaatatt    10500
ttccaacatt ggacatcagc cagcacaggg cagtgattcc tgagaaagca aaaacaaagg    10560
agatacgccc tataattgca ccagcaagcc ctgtgattgt accagcttac tgtctgagga    10620
aggttccaag ctgcagcaca aggaaggaac caacccaggc agagctcaga ggtcgtcttc    10680
aattgaggag gtggatctga gtgtccagaa aaccaagctg actagagttt gcagggccga    10740
gtaccagatg gtagagagct gcagagggtg ctcttaagac tgcagctgtg tcctggtcaa    10800
catatatgtg tggggaacat acttgaggct gaggaaagac tacccaatag gagcagaggg    10860
aatagtcctc agagctcaca caaggccaag aacagttgtt tctcaatttg taataaaatt    10920
ataatatttt aggaacaact ctgggtcctt attcctttac aaattaagtg agttgtggtg    10980
agattagaaa attatcagtt gcttttgtct gtatacttta gctatgtcat ttaatcctca    11040
aacatggatt ttaaagtgga agagaagtaa actgcgttaa atactgtggg taggaaatgg    11100
caaaaatgga attctaactt gattgcacat ataccacaca actttcataa ctttatcagc    11160
accttataac tcccaggatt tgggtgctat cgctagagcc gtaagaaaaa tcattgctaa    11220
ttaatttgt aatggagaca tatattttgt cagtaaacta gccaattttt caatttggaa    11280
tgaaatacta catgaaatgt tgttgtattg tcctactcag gttcaataat gtttgttatg    11340
gctacaacct tgatatacag agtaatttag aacatgattc atttattcac aactaggact    11400
gactcataag ccctaaggac taaatagatt atgatggatt cacccaccta aagtaatta    11460
aaaataaaac cctaacgtgt agaaaatcca acaaagttca gattttatta tgatgttaaa    11520
ttcttcttat gctttttat gtattttggt gtattgtaga tactataaac gtgtttaaat    11580
ttcctattag gtaattcagt ggggatcact accctactca ggttgagaga gtccagaatg    11640
agtaagtggg aactactttg tttgctcaag acaacagtat gggcttcata gcagtgattt    11700
agcaaatttg tgtttgctta tattattttg tttttttaata aaccagtgtg ctctgttctt    11760
aacttgggcg gcttaaaaca ctaagaaata tttaaaaat atctgcagga ggcactttaa    11820
tagttgttgt aatacataca aagattaaat ccatcagagc atttagaaag gaattggtgg    11880
cgaagagaga gtggaagaaa caataaaatg gaaaatttt gtataagtag aatgtaagga    11940
aaataagaaa taattgtcat gcaagactca aataaaaaag gatgttgtag gcatccagta    12000
aagggcttgt atattagaga ggacaggaaa tagtcctttg gaactctggg tttgaggtta    12060
accttgaaaa gaggaaattt ttacctacac atattggaaa gagcaagaaa aggaagaaat    12120
acatttcagg agagttagaa gaatgtcaaa ggcatgtaag gcttagtttc ttccttgtct    12180
tatacctgtg taatatatct tttgattaaa aaagaaatg taacaacacc ttcaaagcag    12240
agttgatcaa tgtaaaaaat atttaaaaa ctgagtacat aagtactttg agatgagaat    12300
actcaaaaaa gagactatag taagaatcat ttattaggca tgtggttatg tcattttttt    12360
tttttttaata tggaggatgt gcaggtttgt tagataggta aatgtgtgcc atggtggttt    12420
gttgtacctg tcaacccatc ccctaggttt ttaagcccag catgattagc tatttgtcct    12480
catgctctcc cttccccatc attattttta agatggttct gatgagcagt cactttaggg    12540
gatcatgcaa tggcaaaact catgtaaaaa ttccgcttca gtgaattcag agggagtttt    12600
gaaatgtgta tttgtatgaa gcgcctcaac ttgattctaa tgtgaaaact gctctggcag    12660
```

```
tcactaaagt aaatgttcta ttgcttttaa gcgcaaaatt tcagtgttca aaaatgtgat    12720 tccattttt  tttgagatgg agtctcgctg tcttgtctag gcaggagtgc ggtggcacga    12780
tctcggctca ctccaacctc tagctcccgg gttcaagcta ttctcctgcc tcagcctcct    12840
gagtacctgg gatatcaggc acacatcacc acgcctggct aattttttgtg ttttagtag    12900 agacggggct tcactatgtt ggtcagactg gtctcgaact cctgacctcg tgatccaccc    12960
acctcagcct ctcaaagtgc tgggattaca ggcatgagcc acagcgtgcc gccgatttca    13020
tcttttgaag ggaacatctt aacacttagt actcagactc aatgataccc aatactttca    13080
aatgtgaaaa tttggtaaca tttaatgtat gttgctgcta atatacgggg gaaattgaac    13140
atatcctctc tagtgttaca ttatataatt cttgatgcac atgtacttaa ataccctctt    13200
ttccttttca gaaagctgta tgtgatggct tctgtgtttg tctgtctgct cctttccgga    13260
ttggctgtgt ttttcctttt ccctcgctct atcgacgtga aatacattgg tgtaaaatca    13320
gcatatgtca gttatgatgt tcagaagcgt acaatttatt taaatatcac agtgagtata    13380
aatttatatg aaaaatgttt aacttcattc ttttatccta ttaagcagca cctttgtccc    13440
cattgagaag aggtgtttgc taaatgtgac actggtcagt gtgctttctg tatgcctttg    13500
ctgtattgac cttcagtacc atttctggtt ctgctaaaaa tagcaataat aaatactggc    13560
aattctgtat atgcagaatc atttagcatt tgaaaatgtc tttaggaggg taaaataaac    13620 taaaagaga aaaggtatta caatttactt ttcaacattt gactctgaat aacttctagc    13680
aaagtgttga catagttgat ttcatagatt ttataaatgt aacattttca tttcattgta    13740
tttgggaaat gcagttttg  ccacctttaa cagaccattc ctttatcagc tttaaagatt    13800
acatacaagt gactggtttc tcttttgtaa attagcatag gtgaaaatgc cctgtggttt    13860
tttttaatta tactttaagt tctagggtac atgtgcacaa cgtgcaggtt tgttatatat    13920
gtatacaggt gccatgatgg tgttctgcac ccattaactt gtcatttaca ttagatattt    13980
ctcctaatgc tatcccccta ccccaccaca gaccccggtg tgtgatgttc cccaccctgt    14040
gtccagatgt tctcactgtt cagtttgttc agaatgatgg tttccaactt catccatgtc    14100
cctgcaaagg acatgaactc atcctttttt atggctgcat ggtattccat ggtatatgtg    14160
tgccacattt tcttaatcca gtctatcatt gatggacatt tcggttggtt ccaagtcttt    14220
gctattgtga atagagccgc aataaacata catgttcatg tgtctttata gcagcatgat    14280
ttataatcct ttgggtatat acccagtaat gggatggctg gatcaaatga tatttctagt    14340
tctagatcct tgaggaatcg ccacactgtc ttccatagtg gttgaactag tttacactcc    14400
caccaacagt gtagaagtgt tcctatttct ccacatcctc tccagcatct gttgtttccc    14460
gaacttttta atgactgcca ttctaactgg tgtgagatga tatctcattg tggttttgat    14520
ttgaatttct ctgatggcca gtgacgatga gcatttttttc atgtgtctct ggctgcata    14580 aatgtcttct tttgagaagt gtctgttcct atcctttgcc cactttttga tggggttttt    14640 taatttttt  cttgtagatt tatttaagtt cttttgtagat tctggatatt agccattgt    14700 cagatatgta ggttacaaac attttctccc attctgtagg ttgcctgttc actctgatgg    14760
tagtttattt tgctgtagag cagctcttta attagatccc attttttcaat tttggcttt    14820 gttgccattg cttttggtgt tttagtcatg aagaccttgc ccatgcctat gtcctgaatg    14880
gtattgtcta ggttttcttc taggattttt atggtttta  gtctaacagt taagtcttta    14940
atccatcttg aattaatttt tgtataaggt ataaggaagg gatccagttt cagctttcta    15000
catatggcta gccagttttc ccagcaccat ttattaaata gggaatcctt tccccattta    15060
```

```
ttgtttttgt caggtttgtc aaagatcaga tggttgtaga tgtgtggtat tatttctgag   15120
ggctctgttc tgttccattg gtgtatatct ctgttttgat accagtacca tgctgttttg   15180
attactgtag ccttgtagta tagtttgaag tgatgcctcc agctttgttt tttttgcaaa   15240
caatgtgtgt ttcttagaac attgtttttg gaaggactgt gtagccttgc cactcatgaa   15300
aataaaacaa acaaaaagct cagagaggtt ttctacctgt tttacatgtt aacatttgtt   15360
tgaaagagc atggtttgct aactgttgaa ttaggaaaag ggatgatgta tattggccag    15420
ccgtgaaata tatctgagtg acagtgatct gccaggaaga gtgatagttg ttttttcttg   15480
cagaggtgag tggtatgatt aaggttgagg tagagatgtc tatagtggtg gttggaaaga   15540
gggaggtttg tcgggacagt gagtgagacg gaatgttatg ttaaagtgga atcactactt   15600
aattgcagag aaaaagtaac tcccgtggat ccatttatcc ttattgcttt ctgtcaaaag   15660
ttgccagttt aagggctttt tctttaaaaa caatatagga aaatatatat atatatatat   15720
atgtgaataa acatttata acacaatgct aattgtaaat tgttttacac aactggggaa   15780
ttgttgggta tattctcagc cctttggaac aaggaacata ttttcttttt tgtacactgt   15840
ttaaaacatt gaccagactt tttttggcct acctccaaag ccttttttag tgtcaaagaa   15900
cataaatatg tactactaat aaaaagccat gtgatgtttt cttttaagta ccagaaagta   15960
tatttaaatg tgaatatcat actctgtttt aattatgcag aaattctcac attttggaat   16020
actgccactt aaactgagac agattgaaca ttaaatgaaa aataagatta ttatttggat   16080
gaacattaag tttaactaga cgacaataag atgctgaatt ttctgtacat tatcagtatt   16140
ttgaaaatgg aactgctttg ctttcttaaa attagtacat attagtagta ctactcttta   16200
gtaacatttg tctttctact tacaaaaata tttgtcatta taagacattt gaaaactata   16260
atgtataaag attttttactt ctatctaggt cgaactatta ccacatacat atatttatga   16320
gcaatgcata tacatttaca aatgtaatca ttatcatgtg taaaggatac acacacactc   16380
attcacatat atacaaatgc acatttcaac taggtcacag tacatttttcc cgtgtcaaat   16440
ggtcttgtgt agtcgtttcc gtgatcatat tgtaattaat tcaaccattt tcttaatgga   16500
tgtttaattt tgctattaca aatattcaga aaacacctat atgcttaaac tttgtttcca   16560
tttcaggtta tttctttagg ataaattcct gaaagtatat ttgccaatta aagatgatag   16620
gtagtttagg gtctttgtta ataattacag tgacctcttt tcatctttta agttaaatga   16680
attctcacta ctctgagcaa caaatgtcta acctttatta ctaaattttt atttattgtc   16740
ttattttttc tttgtcttaa ttctcataag catttgtatt ctcaacctgt tttatgtcat   16800
tgatccttta aatattctaa tgaaacttat ggacagtaca gaaaaagaca ggtaccagca   16860
taattttgca tatacaaaga cttccaagat ttttctaaat ttcaatcctt ggtcttatca   16920
ggagatccat tgacctcaaa ttaactatat cttttcctatc atgtctagaa atgaaattga   16980
catgaacatt aagaaccagc taaaacgtttt atatatttag ataaaggtta tttttactat   17040
gtttgagaac tgttttgaaa tttctttaca tttgtgacta taccaacgta aatgactcca   17100
taaatgtaat catataattg ctgactctag catattcgtt catccttttt tactaaaact   17160
attttctctc cttcaactca tcccatattg catcttttca tatctttctc catattcctg   17220
ttaacatgta tatatatact cacatattca gctttataaa aatcagtatt ttaaaaaaat   17280
attattaagt acttacttat gtacatcttg gttttcacat ttgttaatac cttgtaaaaa   17340
tctttcctga ttatctggct tggttctttt tgatggctcc ataattttcc atataaggac   17400
```

```
ttaatataat ttattcattg ttttatgaat agaattcatt ttattttcag gattttttt    17460 cccatttcaa ataacactgt cattagcatc ctaatgtttt catttctgtg aatagttgc    17520 tcagaagtag gattgctaga tcaaagtctg tacatagttc taattttaat gtatatgact   17580
gaattactga tgaaatggct gtaatacttc acatatttgc tagcagtata aaaatatacc   17640
cttttcccat atctgccagg aatagaattt gttgctttct ataaattata ctagttcaag   17700
gaatttaaag caatattcca tttttactta aattaccttt ttcttaactg taaatgaagt   17760
tgagcattgt gaaatatttt tggccattta gctttgtacc tttttgattt gtttatgtat   17820 attcttgtt cttttttcat tttctgttac agttttgtct tttcaatttg taagggccct    17880
ttccatattc tagattataa ctgatgctta caaatatttc ttctatttat catttagtgt   17940
ctactgattt tgtttatgat accttttggt atgactgttt tagatttttt atatatctgt   18000 tatttttat ttaacatttt taaatttttt aatgactgtt ttctacagta atttaagacg    18060
ataattgtaa attagaaatg tctaaggtga tcccagctat tagttcttac ttaagcatgt   18120
gaatgatgta accacatttc tccccaacca accagacttg aatctagccc atttcttctt   18180
cataatgagc tggtgtaaat ctctactaat gtataagttg aaatagcagt ttcttttaaa   18240
caaaaaagat gattttaggt actattgaac attttaaatg accatcttta tatttaatag   18300
aatagcaaac agcttactaa taaagtttgt ggagacatgt atatatattg agttagtaaa   18360
aatgtagatt aaatcttaaa attattttta ttaaacattt gctaaggcca caaataaatt   18420
ttctgacatt aatttgtcca tattctgaaa ctatacattt tctgtttttt taaatgttga   18480
atcatgtgtt tattcttggc atattacata catagtactc atgcataaaa ccaaataatt   18540
ggtttaattt tctttgacat tttggtatta ctttctttt cttaattaat gaagcatagc    18600
cacagctgaa gttactttct ttaattttaa atacatattt gtatgtttat ttttagctaa   18660
cttgtacatt ttctgtctcc ttttttgtag aacacactaa atataacgaa caataactat   18720
tattctgtcg aagttgaaaa catcactgcc caagttcaat ttgcgaaaac agttattgga   18780
aaggcacgct taaacaacat aacccatatt ggtccacttg atatgaaaca agtaagactc   18840
aatcatgaaa taccttgtaa gagtgaaatg aatatcaact ttgtatatca tataacttga   18900
aggaggtggg ggatttcctc aaaaacttga tttaaaaatg tgtctccgct gggtatagtg   18960
gctcatgcct gtgatactag caccccttggg aagctgagct tggtggactg cttgagccca   19020
ggaattcaag accagcctgg gcaacatggt gaaacctcat ctctacaaaa aatacaaaaa    19080
tgtgctgagt gtggtggtgt gcacctctcg tcccacctac tggggaggct gatgtgggag   19140
gatcacttga acccagtagg tcgaggcttg caagccgtga ttgcactgct gtactccaaa   19200
ctgggtgaca cagtgagatc ctgtctcaaa gaaaaaaaa agaaaaagaa aagtgtcttg    19260
tagacttaca agatgaaatc tttgagaatc aagcttgtaa agggagaaaa ttttctaatt   19320
ctttgaagtt atgaagtata tctgaaatat ttgatgtttt gatcctgttc tctattgatt   19380
tttttccctt ttgccttaca gattgattac acagtaccta ccgttatagc agaggaaatg   19440
agttatatgt agtaagttct gatttataac ttttttattat caagtaatga aatgtataaa   19500
ataaggtatt aagaatatac atattttta atttccataa tcagtcaaaa agagtacatt    19560
atgcagtatt ctggtttctg gtcctctctg ttcttttca acatatataa tattcatgta    19620
tatatacaca taaaatttgt ttttttattt ttcagaatta gggtcatata taccatgtca   19680
cttatttttt agttactatg ttaactatgt tactatgtta aacttagtta ctatattaaa   19740
ataattataa atttcatca tcttttgaaa gcttagatat agaatttag ggtaaataac     19800
```

```
aacccagtta tcaaaatttc agaagatgag caaaatatgt aagtaattta tagcctgcat   19860
ttaaacaacc ctgcagctgc agtggtgtga atacatacat gttttctag taagaaggca   19920 tgaatatatc agtcattgtt tgaagtatag aaaatgctca accaataaat gcttattata   19980
tattcttagg taacatctgt tagctttaat ataggaagga gaatttataa tttataatgt   20040
aataacttgt atttgttcac gttttaattt cttttaacag tgatttctgt actctgatat   20100
ccatcaaagt gcataacata gtactcatga tgcagtaagt acgaatcttt tttgaaagag   20160
atatttcttg tcaaaattct agatttataa cattggctta taatatacac aacatcttta   20220
taaatgccac ctcagttggg ttttaagcct tacaagagtg ctgtgaggtt gagtaaatat   20280
cacccacttt aaaaatcagg aaatggttgg tcacagaagt agtgaaatac tacattactg   20340
ctaaatagtg aatctggatg tcacaagagt tcaggaaaat ggaaaggata cggtgaactg   20400
agccccacat ccaattcctt actcccttga taaatagtca ttaacagtaa taagaagtag   20460
taatattatt ggtttgtaaa ttgggtgtta tctaagccaa taaaacattg ttggttacag   20520
gtttggtgtt ttgaccatta gctgacattt gattaacctt ttttctatg ataagagaac   20580 catggtcact tttaagcata taatgaactt ttatatttttt aacaagataa ttgtcttaaa   20640
atattacatt tattatgtgt aattatatca acagggttca ctcagctatc cattttttgtt   20700 gtctgttggg gaaatgttcc ttaagaggac tgtgtgcaca atattaagtt atcattaatc   20760
aaatattctc ttctaggaga taattttttat atgtaaaagt agtctcatta tggaaaaact   20820
tctaatataa ctattaaatg tctctcccca ctaacattat ttttagagtt actgtgacaa   20880
caacatactt tggccactct gaacagatat cccaggagag atatcagtat gtcgactgtg   20940
gaagaaacac aacttatcag ttagggcagt ctgaatatt aaatgtactt cagccacaac   21000
agtaaaaact ggaagagatg gatttaaaga agaaatatct attgatattt cctacactct   21060
cagtgaagag gtatttccta ataggagatc ttaaattgaa ccaacctaaa gtttacactt   21120 ctatttaag agtacagtta aaagtatgtg gacctgcagt tcttgtaact ctccactctg   21180
tgttaatgat gtatttgtac taggatcttt tacttgaatc taaatttact gtttgacttc   21240
cttctccaac ctatccccta cagggaaaag ctgatacttc ccctatagta caataaataa   21300
ttatttaaaa gtcatcgctc cagtcactac tgaaaacata attttggtga taaacataat   21360
ttgagaaact tagtttctga atgtttttat agaaaattac tgaaagtcta ttattcatgg   21420
aagactttta aataaccttt tttcctgttt tataaattcc cgttgttata tggtagtatt   21480
tcagctacac aatatttag ctttcagcta aacatttata gcttttcatt tgttgacgct   21540
gtaatcatct gcatgttttt gttacttgct tcaagttagt gattgcctaa cacttgtaag   21600
ccaaaataat ctttgcaaaa ttccatacct aaaattttga aagctcctga tgttttcaca   21660
tgtctttctg tattatagtt ttgtgaaatc tttgtgtgat cttcaaacat tatcatttaa   21720
tgtacaatac tgtaaataaa ctgtgcatgg cttttgtaca gctttagtaa atgtcaaata   21780
aagtggtaca gattcattac aacaagtttc tcgtaaaaat acaataaata ggaaaacgaa   21840
attcagaaac ccatagattg ggaataggtt ccaattacat gttggatctg gcataaaata   21900
aatttgaact attttgatgc tccattttttt ttatgttgct tttcatgcta gagaatggtg   21960
tatacatatt ttccaactgt taggtaccca gttatcaatt ttatcaatgt tttacagaag   22020
gaaacttttt tttgatagat actgttcaag aaatcctgtc attaaatgat ggtggctata   22080
tcaaaataaa acctatttag aaatttaatc actttgcaca tcacttggaa tatgatgcct   22140
```

```
ctagtagtta cttttttata gttttctact tttagtttta attttattta aaattgtatt    22200
caaatataga ttattgactt actttgctgt tttatatttt caatatcatt tttcatttaa    22260
tttttttttt cacttaccaa gttctaggga catttaaaat atgtatcact aagtgtagga    22320
gtgatgatac caaaaaatgt aggtgggtta agattaattt cattctgttt tctcgtgaca    22380
gaaatcaggt ttccctttcc ccatcccta agtgcctaac ttaggtctga aacagcctgt     22440
ttgtttatta gtctgactct ctcaagcata aacgtaagc tttatttgtt taattctgcc     22500
tttaaacaca ctcaggtttc cccttaattt tcatattatt ttctccaagt tttcctgagt    22560
gaatatctta aattcgttga atgtgctttt tctttctttt tacactagtc ttcccttaat    22620
tcattgctaa ctcaggccat ccttactatt aaacccaaat cagtccttta agttcattat    22680
ggcctttcct agtataaata aataaataaa taaatacaaa aaaaaccttc attttcattt    22740
ttcttctgct atattttctg actactactg catacttctt taatacattg attctgtttg    22800
tttttttttt tttttttttt tgagaaggag tctggctctg tcacccgtgc tggagtacag    22860
tggctggatc tcagctcact gcaagctcca cctcccgggt tcacgccatt ctcctggctc    22920
agcctcctga gtagctggga ctacaggtgc ccaccacctc gcccagctag ttttttgtat    22980
ttttttttag tagagacgag gtttcactgt gttagccagg atggtctcga tctcctgacc    23040
tcgtgatccg cccgtctcgg cctcccaaag tgctgggatt acaggcttga gccatcgcgc    23100
ccggcctctg tttgtattt ttatatcatt ctcattttct catttgacat gatctatgtc     23160
tatatatgat ataggtcccc ttttgtctca acatttttaa ttatgtgact tcaaaaatca    23220
cctgtatctc tagtagggct tccaaatctg cttctccata tgtgaccagt cacctgtctg    23280
ctttcacatt tagctagtga gctacacatt tactaaaatg tgtaaatttt acacatttag    23340
tgactgtata aaatcaaaaa aatgttaaag catttatc atatcctttc tattatgttc      23400
ccaccctgtc ctcatgtccc gtttacttca ttatcaccat tcatttaaaa ttatctttta    23460
gatatgctca tacaaaaatc aatccttgtt ttcttgcttg tgtcttttaa ccttagaaaa    23520
tttcttgctt atgtctttta accttggaaa attacattgt gtaaattaaa cagattttcc    23580
tgatgatctg tgcttcttat atcctattag agtgtatgca tagtatctcc tgaaaaggat    23640
ggaaagtaga aaaaacattt gctttttaagt cacttaattt tgaatcttt tcattttttt     23700
gaattaaatt ttttttttt ttactacatc tagtttcact ggagtttgag tcagaaaaaa     23760
acaagaattt gcaacaagta aaaagatag aagagaaatt aagatggcat gtgactactt     23820
tcagagagaa ttaagtaact gtcagaataa gcctggaaca aaacaggctg tcaattaata    23880
aaactacaaa cacacattca ggtgaagcag aagtatagcc ataaaacatc tagaaagagt    23940
gaatgaggct tttagctttt cttaggtcag tgtccaatgt gcttttcc atgggaatag      24000
gataggtatt aatacactt tctaaactgc tctcagacct tatccagagg acatggtaaa     24060
gatatgttac agaaatttt ctgatacttc ctgtaactta aatcttttaa gttcacccct     24120
agtagactgg tcattctaat aaaatccggt actgtaacaa acgtctgtat gttgatagca    24180
cattggccct ttttagagtt ctttcctatg ttttttcttac atgatttccc acagttccgt   24240
gagtccaaca aaggagagtg ataggctcct tatatttag aaggggaagg aaaggcatgg     24300
agaagttgag ggactggctg aagatcccat acttaactaa gtagtataat tggagccaga    24360
ccaagtctct ctgtctccca tatctgtgtt ctgtcgttta aaatatatat tggaaatccc    24420
tgctgactca gattggtatg attaaaaatg agaggaaagt tcaaatagta gtgacaatca    24480
aactagtact gctggactaa gattttggta gcatctaaaa tgttttaagt ggagaatgaa    24540
```

```
cacttataaa atgctttaga acataatctt tagcttaatt ttctgttaaa atttagtacc   24600
ccttcatcat tccaataaag actgatccat tgtctaagga aattatttat aaataagaga   24660
ttaatgtatt tgtgatttga aataagaata gtatgaaaat attagatacc acataaattg   24720
tttgaaatta ctaaataacc atcttaagta tgggaacatt taaatggcta tattttgtgt   24780
acagttttcc tgtgcctttt ttgttaggcc aatgaagcaa ttattttctc taagaaaatg   24840
acaataaaat atagcacact tcagattgtc tgatttacag tttggaaagg acactgcaat   24900
gttcaaatag gtaggagacc atcaaaaaca caattaaaat aatgtgttag gagacttgaa   24960
actttagtcc aataaatcct tcatggttct tagccttatt attgtgatat aattctagat   25020 attttttttgg agggcatgtg cccaactctc ccccacccca ttttgtttgt cttttaaagt   25080
tcttagaata aacagttatt tatataataa ttatatttta tttaagaaaa taatttgtta   25140 gatactttttt aaaagatgta aattttttaaa tttacaaata catatgggtc tttgataagc   25200
aatatgaatt gaatttcagg ttactagggt tataagcaaa aggttgctta ccataatgtc   25260
attaggtcat gattttttagc tcacatctgg aagcagcaac tacttggctc aagtacatat   25320
aaaagtaatt agtttttattc tctcttttttt ataaaattgg gtttcagata agatgtttat   25380
cttacactat tttcttttag ggaaaaattt tacatgtttg agatggtgga gtaaaaagac   25440
tgttaaacat ttcttttaaa aaattattttt tacattataa caatatattt atgatgtgtt   25500
tagatcaaaa atttaacttc tgtgtcccag atctactttc aaagtgaaat tttcatttgt   25560
cagctgaaat ttctgactag aactaacatt tgtgtatttt tgtgcttagt cagaatacaa   25620
atttcacagt gaattttttga agtttgtcct taaattggaa aaatcaagtg attaaagtta   25680
ctaaagagat aaaaatggta atttccatttt ttaaaactaa tttggttgtg tttatagtta   25740
ctcgtacaag tatttatcac agactctaaa ttgaaaaata tagtatgatc tatatttgac   25800
cctaaaattg ttccataaat taacaaagat atggcaaatt tttcataact aaatctaagt   25860
cttctaaaag gaagctgtta cccttctgtt tttaattaca ttaattgaaa tgtgtttaag   25920
agatgatttc agcatatttt gtatattaaa aaaaaaaaag gattagtatt gggccaatgg   25980
ccaaaaggta atattactac catgtagatt gttatagttc aaattgtccc acttccccca   26040 gaatttttaga aactagaatt ctgggagata ctgtatcagc tgtagttggg taattccaag   26100
tgctgatagt actattcatc tttttttatta ctgtgtcaga tgaaacaaat accaagttgc   26160
aaaagatgca gatttttattt atataatggt tttaggcata aattattaac aagccatgcc   26220
ttgtatgttt catcttacat ttttctttag aactaaacta taatagattt tggaaaacga   26280
tttgatgtgc ttgctcactt gattcacttg gtcagatatt tgaatgatgg tattacctag   26340
attctaatcc ttgattctag ttatataata aataataata tagaatgtga aaatatgttt   26400
gggcacttac tgtttatatt atgtagtagc ctccatcatg atacactaca tttatgaatt   26460
gagcagttgt gtaattgtaa ttattattgc tgttcatgta acaaacatg cttatgatag   26520 tagcaaacaa atagaaatgc ccccaaaatg ctattttttt aattcagttg taactattac   26580
tcttgtagtt gtgtatgaca caataaaatt tgtaaaaaaa atttagcatg aaaaataaaa   26640
tttgtatcac tgatgtattt tggctatgct tttgaaattt ccttgacata aacaaatcag   26700
tgtagatatt gaaaatcttt tacctttaat cttttttcatc cttatagtcc ttacctgaac   26760
tccactttag cattctcttt gatttctttc attcatttaa cttccagtca gtgctcaagc   26820
tttatccctt ctacctctgt aatgtctctg gaatttatct catacatgaa atatccttg    26880
```

```
atattatgga catacccttgg agatactaca ggtttggttc caccccatat caataaagtg    26940
atgtaataaa gcaagttaca cacctatttt tggttttcca gtacatacaa aagttaggtt    27000
tatatcatac tatagtctat taagtgtaca atagcatgtc aaaaaacaca atatacatgc    27060
cttaataaaa aaatagtctc tgtgcagtgg ctcccacctg taatcccagc actttcagag    27120
gccaaggtgg gaggatcacc tgagcccaga agttcaagac caaactggtc aacatggcga    27180
gaccctatat aaaatacaca tgcacacaca cacacccaca cacacacatt attgctaaaa    27240
aatgttaaca atcatctgaa tgtacagaag tttgtattac ttttgctggc agaggatctt    27300
gtctggatgt cgtttgctga catccatgca gtggttacta aagttggagt ggctatggca    27360
atttcttaag acagcaatga agtttatcac atctattgtc ctttcatgaa agatttctct    27420
agcatgtgat gctgttttga tagcatttta ccaatgatat gtcttttttc aaaattggag    27480
ccagtcctct caaaccctgc cactgcttta tcaaccatgt caaccatgtt taaataattt    27540
tctaagttct ttattgtcat ttcagcaatg gtctcagcat cttcaccagg agtagattcc    27600
aactcaagaa accactttct ttgctcattc ataagaaaat tcctcgtctg ttcaagtttt    27660
gtcatcaagt tgtagcaaac agattccatt gctaaatttt agttcccttg ctatttccac    27720
atctgctgtg acttccttca ctgaagtcgt gaattttgag ggcaaaatta tccatgagag    27780
ttgaagtcaa cttcttttcaa actcctgtta atattcatat ttagacctcc tcccctgaat    27840
cacaaatgtt cttaatggca tctagaatgg caaatctttt ctggaaggtt tcaatttact    27900
ttgtccagat ccatcagagg aatcactacc tatgaagcta tggtcttaca aaatgtattt    27960
cttatatagt aagattcaaa agtcaaattt actccctgat ccatggctgc agaatgcatg    28020
ttgtgttaag aggcatgaaa acaacattaa tctacttgta catcatcaga gttgttgggt    28080
gagtagtaat attttgaaag gaattctttt ttccaagcag taggtctcaa caatgggctt    28140
aaaatattca gcgaaccgtg ttgtaaacag atgtgctact atccagactg ttccatttat    28200
tgaacacagg cagagtaggt aaaagtttta agggtcctag gattttcagg atggcaaatg    28260
agcattggct tcaacttaaa gtcaccagct acattcacca ctaaagagac tcagtctgtc    28320
cttttaaagct ttaaaggcaa gcactaactt ttctttagct atgaaagttt tagatggcac    28380
ctttttgtaa aagaaggttg ttttatctaa attgaaaata tgttgtttag tgtaaccact    28440
ttcatcagtg atcttggcta gatattctgg ataacttact gcaggttctc catcagcact    28500
tactgcttca ccttgcactt ttatattatg gaaacaactt atttccttaa acatcattaa    28560
ccaacctctt ggtagcttcc aacttttctt cgatagcttc ctcgtctctc tcagccttca    28620
tagaattgaa gcgtgttagg gcttcggtca ggattaggct ttcacttaag gcaacgttgt    28680
ggctggtttg atctatccag atcactaaaa cattcccata tcaacaataa ggctgtttca    28740
ttttcttatt attcatgttt tctggaacac ttttcaatta cttctagtaa ggaaatagca    28800
cttttaattt cattcaagaa ctttttccttt gcattcacaa cttgtgcaag agacctagct    28860
ttcagcctat cgtggctttc caagatagtc ctttgtgaga aatgcttgat cactaggtat    28920
aattatttct agcttttaat tgaaagtgag agatatgtga ctcttccttt tacctgaaga    28980
tttagaggcc attgtaggat tattaattgg cctaatttca atgttatttt gtctcaagga    29040
gagagggata tgggaacagc tggttattag agcagtccgg acacacactt ttttttttact    29100
acgttcactg ccttacatgg gtgtggttca tgctgtctcc aaatacttaa aaaacataaa    29160
gatcacggat tacagatcat taaaatagtt ttaataataa tggaaccttt tgaaatattg    29220
caaaaattac caaaatgcag agagacatga agtgagaaca tgctgttgaa aaaatggcac    29280
```

```
tgatagactt gctggacaca ggattgaaag aaaccaattt atcaaaacca caatatctgc   29340
aaagcacaat aaggtgatgc acaataaaaa gaggtatgtc tgcatttcct tctttttac    29400 tgaaaaaagc caaagttctt actctggtgt taaccttca ttagctggct acaatctcag    29460
ttcacaatca tttcttattt tccttcaact atgtcctgac caaatagagt tctttctcat   29520
tgggaatagt tcattccttt atcccttgc tcattccatt ccttttcct tagaaaatta    29580 tttgcccatg ttttttatcc cccaattcac atgtccaacc cctctctact tgtctccctc   29640
caaacttact caaacacttg gtgaattttt ttctgaatgt ttttctgaa catttactt     29700 taaaggagtt gcccagtcac aaagtttgaa ctcaagtttt ttttgtttt gaactcaaaa    29760 cttgttttaa acttttgttt tcatcaactt ctttatttaa acaattttg tcagcttaga    29820 gtttgtgttt taattactat ctttaaaata gtaattatca gatagtatga tttgaaatta   29880
tatggaatgt gcccaaaatt atctctgaag aataatatgg aaaaatgaaa attaaaagat   29940
gtattacctg aatgtgctcc tcctagccag tttctcaagg gagaagaatc attaacaagt   30000
ttgtgaggct ttttttttct ggtagatttc tgtttctttg atcaatggtt ttttcagaat   30060 tttttttaagg ttgtgaaata catatttgta aatagcatct tgtgtagaat cttgatatat  30120
gacaaaacag ctgctttgat ttgagagcag aagacctgca gacccagact gctcaccttt   30180
ccagggaccc ctgaatcatt ggcctagagg gtagtgtaca gtcacttctt caatgataac   30240
ttactgagtg tgattcaaca aaactgcttt gtttatgggt aaaacaattt ataactaggc   30300
aaatgtaggc ttaaatttat attttataaa tagcactgaa aatgataata gacaaatgta   30360
atttctgtaa tttctgattt ttaagaaatg attttctgtt ttaacatata ttttaaatgt   30420
tttgtcttca aagggaatcc ttaaaacata tactggaaac cattgatttc ttattttcat   30480
ttcatgaatt tcagattcat gaatggaata tattaatagc atttttaag ttaccccaaa    30540 aagatgaaat acaaataatt ttaatcccaa atctatttca gatacttaac tcttattttt   30600
tatactttaa gttctgggat acatgtgcag aacatggttt gtcacatagg tatacacatg   30660
ccatgttggt ttactgcacc catcaaccca tcatctacat taggtattta tcctaatgct   30720
atccctcccc taggatccca ccccacgaca ggccccagtg tgtgatgttc ccctccctgt   30780
gtccatgtgt tctcattgtt cagctcccac ttatgagaac gtgtgatgtt tggttttccg   30840
ttcctgtgtt agtttgctga gaataatggt ttctagcttc atcaatgtcc ctgcaaagga   30900
catgaactca ccttttttta tggctgcatc gtattccatg gtgtatatgt gctacatttt   30960
ctttatctag tctatcattg atgggcattt ggggttggtc tgagtctta ctattgtgaa    31020 cagtgctgca gtaaacatac atgtgcatgt gtctttatag aagaatgatt tataatcctt   31080
tgggcatata cccagtaatg ggattgctgg gtcagatggt atttctggtt ctagatcttt   31140
gaggaatcac cacactgtct tccacaatgg ttgaactaat ttacactccc accaacagtg   31200
tgtaatttct ctacattctc tacagcatct gttgttcct gagttaatga ttgccattct    31260
aactggtgtg agatggtata tcattgtggt tttgatttgc atttctctaa tgatcagtga   31320
tgatgagctt ttttttcatgt ttgttggctg cataaatgtc ttcttttgag aagtgtaaga  31380
tacttaattc tttaatttaa aaaaatacc ctccccaaact aacaaaatca gttttctgc    31440 cttgttaata acttgttaac atttttaat tttagaataa atctaaacag agaccccatt    31500
catatccgta acaacctatg taaagtaaga ttaaggttaa atcacatttt tcacagagag   31560
tgttttactg acatacaaac ttttatgatc tgatattatc taattgtgtc cttactggat   31620
```

| | |
|---|---|
| aacttgtgta tttttcaagt taaaagattt cctaaaagtg cattacttga atgtttatgt | 31680 |
| catttatcac acatactttc aaaacataac cttcttcaac cagtatcttc cttcctaaaa | 31740 |
| tactgttaat agctggctat tttgtaagcc tgtgtctggt taaaaaaaag aaatgaatat | 31800 |
| tttcaatact tatgaaccat agaattctgt attcttttcg taacttttac cttttccata | 31860 |
| ggacctatca ccatgtaaaa tattatacat atttatttgt ttattgtcta cgtacctata | 31920 |
| ctagaacata gtaaacatga gaacagggaa tcttggttat taattcctgc agcactcagc | 31980 |
| tacttatcac tcaaacattt gttcttgaaa agaacttcaa ataacatcat tagatttta | 32040 |
| cagaatcttt aaaaaagctt taatattttc aaggttttt tatttatata aacattgtta | 32100 |
| cttcactact agtgatttta atagtggcat tgtcacatga ttcaaaaaga ggaggccaat | 32160 |
| acattactgt tgtattaaga agtcagttca ggcttaatat atgtgactac tgtaggtcaa | 32220 |
| cctcacattt taatgtatga agaagattgt atgaacgatc acatcaattc atttaaatag | 32280 |
| tatgtatttt gatactaatt aagttttaag aagaaatgta tcattatctt gaaaataaaa | 32340 |
| gataatttga aaagcatgtc atgctatta tatcagggaa aatttgttca gctcacacaa | 32400 |
| agccatacat tgacatttt tttttaaact ttgtggcact ctatagtctt tgaatttatt | 32460 |
| taatacctgt taagagatat aacaaactga aagttatttc aggagtgttt aatgtattta | 32520 |
| atggaatgac gttgacgtac taagtaatag ataaaatgtt aagagctttc tcggtgtcag | 32580 |
| gcactataac aagcattctt taggcattat tttgtataat atgtacagcc ttatgaggta | 32640 |
| tgtactctta ttgctatttt ccttttaca gtttaaaaac tgaggcatag ttcaa | 32695 |

<210> SEQ ID NO 4
<211> LENGTH: 2740
<212> TYPE: DNA
<213> ORGANISM: Macaca fascicularis

<400> SEQUENCE: 4

| | |
|---|---|
| ctccgggagc actgtgcgca ggcgcgggag caggttacgg cggcgcttgg cctctgctga | 60 |
| tgccgtcgtt gttctacccc tcccccatcc cagctctgcg gcggccgcgc gctccaggcc | 120 |
| ggtcgctcca ccccccggct cccgggactg tggactccgt gaccctgtcc tcggccctgt | 180 |
| ccgcgccgaa gcagcccggg actgcgcagc gccccgcgtg ccgacatggg aaagtctctt | 240 |
| tctcatttgc ctttgcattc aagcaaagaa gatgcttatg atggagtcac atctgaaaat | 300 |
| atgagaaatg gattggttaa tagtgaagtc cataatgaag atggaagaaa tggagatgtc | 360 |
| tctcagtttc catatgtgga atttacagga agagatagtg tcacctgccc tacttgtcag | 420 |
| ggaacaggaa gaattcctag ggggcaagaa aaccagctgg tggcattgat tccatatagt | 480 |
| gatcagagat taaggccaag aagaacaaag ctgtatgtga tggcttctgt gtttgtctgt | 540 |
| ctgctccttt ccggattggc tgtgtttttc cttttccctc gctctatcga cgtgaaatac | 600 |
| attggtgtaa aatcagcata tgtcagttat gatgttcaga agcgtacaat ttatttaaat | 660 |
| atcacaaaca cactaaatat aacgaacaat aactattatt ctgtcgaagt tgaaaacatc | 720 |
| actgcccaag ttcaatttgc gaaaacagtt attggaaagg cacgcttaaa caacataacc | 780 |
| catattggtc cacttgatat gaaacaaatt gattacacag tacctaccgt tatagcagag | 840 |
| gaaatgagtt atatgtatga tttctgtact ctgatatcca tcaaagtgca taacatagta | 900 |
| ctcatgatgc aagttactgt gacaacaaca tactttggcc actctgaaca gatatcccag | 960 |
| gagagatatc agtatgtcga ctgtggaaga aacacaactt atcagttagg gcagtctgaa | 1020 |
| tatttaaatg tacttcagcc acaacagtaa aaactggaag agatggattt aaagaagaaa | 1080 |

```
tatctattga tatttcctac actctcagtg aagaggtatt tcctaatagg agatcttaaa   1140
ttgaaccaac ctaaagttta cacttctatt ttaagagtac agttaaaagt atgtggacct   1200
gcagttcttg taactctcca ctctgtgtta atgatgtatt tgtactagga tcttttactt   1260
gaatctaaat ttactgtttg acttccttct ccaacctatc ccctacaggg aaaagctgat   1320 acttcccta tagtacaata ataattatt taaaagtcat cgctccagtc actactgaaa    1380
acataatttt ggtgataaac ataatttgag aaacttagtt tctgaatgtt tttatagaaa   1440
attactgaaa gtctattatt catggaagac ttttaaataa cctttttttcc tgttttataa  1500 attcccgttg ttatatggta gtatttcagc tacacaatat tttagctttc agctaaacat   1560
ttatagcttt tcatttgttg acgctgtaat catctgcatg tttttgttac ttgcttcaag   1620
ttagtgattg cctaacactt gtaagccaaa ataatctttg caaaattcca tacctaaaat   1680
tttgaaagct cctgatgttt tcacatgtct ttctgtatta tagttttgtg aaatctttgt   1740
gtgatcttca aacattatca tttaatgtac aatactgtaa ataaactgtg catggctttt   1800
gtacagcttt agtaaatgtc aaataaagtg gtacagattc attacaacaa gtttctcgta   1860
aaaatacaat aaataggaaa acgaaattca gaaacccata gattgggaat aggttccaat   1920
tacatgttgg atctggcata aaataaattt gaactatttt gatgctccat tttttttatg   1980
ttgcttttca tgctagagaa tggtgtatac atattttcca actgttaggt acccagttat   2040
caattttatc aatgttttac agaaggaaac ttttttttga tagatactgt tcaagaaatc   2100
ctgtcattaa atgatggtgg ctatatcaaa ataaaaccta tttagaaatt taatcacttt   2160
gcacatcact tggaatatga tgcctctagt agttacttttt tatagttttt ctactttag   2220 ttttaatttt atttaaaatt gtattcaat atagattatt gacttacttt gctgttttat    2280
attttcaata tcattttca tttaattttt tttttcactt accaagttct agggacattt    2340
aaaatatgta tcactaagtg taggagtgat gataccaaaa aatgtaggtg ggttaagatt   2400
aatttcattc tgttttctcg tgacagaaat caggtttccc tttccccatc ccctaagtgc   2460
ctaacttagg tctgaaacag cctgtttgtt tattagtctg actctctcaa gcataaaacg   2520
taagctttat ttgtttaatt ctgcctttaa acacactcag gttcccctt aattttcata    2580 ttattttctc caagttttcc tgagtgaata tcttaaattc gttgaatgtg ctttttcttt   2640 cttttttacac tagtctcccc ttaattcatt gctaactcag gccatcctta ctattaaacc   2700
caaatcagtc ctttaagttc attatggcct ttcctagtat                         2740
```

<210> SEQ ID NO 5
<211> LENGTH: 19526
<212> TYPE: DNA
<213> ORGANISM: Mus musculus

<400> SEQUENCE: 5

```
tagcccctcc ttcctggggc gaactgcgca agcgcacgcg caggctctcc cggtacggag     60
ctcagctgat gcagttgttg tgctaccct ccccgcagc tctcccggct gcactctacc     120
ggcgctcggc ccggcccgg gaccgggacg ctgtgaccct gtcctgcggc ccgcacgcac     180
cggagcatcc cggaccgcg cagcactccg cgtgcgggtg agcgacccgg gccgtggggc     240
ccacgtcccc tgcccgagcg gtgagggagg ccgcggcgag ccgggtgcgg ggttgtcacc    300 gcggggcct tggcttcgct cccggggtgg ctcgggcggc gccagggccc ttgatctgag    360
cggccgagta gctctggggc ttgacagttg tagttgcaag gtgactcgga tgttgatttc    420
```

| | |
|---|---:|
| ttccgggggt tgtttgcct gtgatgccct tgaaaagcg ctcgtttccg tctcccttga | 480 |
| gccctcaga actaacccca ggtctgcaca caaacaggtg acacatctca gttgcatgcg | 540 |
| ctgctgaatt tatcttttc ccagtttcta gagcatctga gaaccgtgtt gagttacaa | 600 |
| gaccgcggta taaacattga gagcccgggg aggagacgaa ggggatctac cactcccttt | 660 |
| aaaaacctca gtaagtttc caaaatgaca ggggttacac ttgtcaatag cctcaagaaa | 720 |
| agctaagcaa gaaggctagg attcaagtga ctgcttaatc tggtgtgtac ccaaacccac | 780 |
| cttcagcaga atatgtcaag gttactgtgg gtctgagtaa ggcagccagc ggagaccaga | 840 |
| accacttagc tgtccctagc cttttgccat aaaggctccc atttgtggga cacagttttc | 900 |
| accctgtga tgacaccacg tgttgtctag tgtcagctga ttctaaacca ccctgtgtac | 960 |
| tccaaagctt ccaaggtcac agtgtaagga gccggtactg attacaattc acccctgtgc | 1020 |
| acctgtggct gccaagtgtt ggcttggctc tgactcgctg tcattgagcc acagtaagat | 1080 |
| actgtgtgtg tgtaagtcac aatcactgat atttctgagc tatggtacac agtgtgtaca | 1140 |
| cagaacttct gaaagtatat ttattcattt ttttttactc cttttctata tgactcaagt | 1200 |
| ttttaaattt aatattgctg tctacacagt gagtgaattc aacaagtagc attcagattt | 1260 |
| tgaaaagcag atatgaattt ccttcatctg gggtgacctg aatcacttag tatcatttta | 1320 |
| tttttaatg aaaaatatta aattaaaagt agtatctgtg attgtgtagt tcgtattttg | 1380 |
| aatctgataa gtgatggata accgcaggga gaatggaatt gtaccattta aaattttgt | 1440 |
| ttgcttttc tattattttg tctctcagaa accggcatg ttgtattatg tggcttttca | 1500 |
| tgttcttttc agtcatgtac ttctagggtt ttattgacaa ctaaaggagt atgaatttaa | 1560 |
| gtgagtgaaa tgagtcactt tgaagttagc tggtgatata catatctgtt gtaacaggcc | 1620 |
| aacaagttca cctgcagtgc caactggttt atagttaaaa tatgttttc tctacaaaaa | 1680 |
| actaaaacca tatttctgtt ttgaacatgc taagaaagcc tagcatctcc attgacactg | 1740 |
| taaacttttg ccaactgtta ccattttaaa cattgttcac attacaagtc ttacaggatt | 1800 |
| tggtttcata atgttctgtt agaaaagtac tttctgaatg ctacaaatgg tttccttgta | 1860 |
| tcagacatta ctttggttga acataatttt aatcctacaa gtaatttgca tttgcctaac | 1920 |
| cctgtaaata tatcccatag ggtctgagac tctttttttc cacatggaat ttactgtcag | 1980 |
| attttctttt tcattagac atgggaaagt ctctttctca cttacctttg cattcaaata | 2040 |
| aagaagatgg ctatgatggc gttacatcga cagacaatat gagaaatgga ttggttagca | 2100 |
| gtgaagtgca caacgaagac ggaagaaatg gagatgtctc tcagttccca tatgtggaat | 2160 |
| ttactggaag agatagtgtc acttgtccca cttgccaagg aacaggaaga attcctaggg | 2220 |
| gtacgtgttg tagcattggc tgtcctctta aggattcca acatttgct caaacaatgt | 2280 |
| aaaatctata gtcttaagca cttctatttt cagagattca agtttacca gttttgttta | 2340 |
| gtcagaaaca caaagcaaa caattagtac cattcctaaa gcagtaatag aagtgactta | 2400 |
| agcacatata acttttttt gtcttgcttg tctgctgtta tagctcctat gcacctatgc | 2460 |
| accctgagg attttagtca ttttatgtc attggaagcc atatcacagt cattttgcca | 2520 |
| cagtggatgt tagcagctaa gttgttcagt aactcattat ctaaacaata agttgcttcc | 2580 |
| acctcaatat ttctaaaaga aaatctatag tgtatgaaga aaagcaagag gggaaaatga | 2640 |
| gcctgaggtt tgccatggag aagacaggag gaagagtcct atccctgcta tttgtcgggc | 2700 |
| gctagaattc ctctcacaga aaggaaaaat agtgaggtta tgttgtactc ctctccttct | 2760 |
| gtaattggta gaagtcaata ggtgaccctg agagaccct aaagaaggac aaagtgactg | 2820 |

```
catgggaaac tcgagtctct agaaagtgcc ttgggttaag tggggtttgt tgcataggct    2880
actgaatggt ggttttatct ttctgggggt aggagctgct taagaatagt tgaagaaatt    2940
aatacaccaa cgtggaaggg tgggaatagg atttctgtcc atctagccat gtgtttgagg    3000
tgtggccagg aggcttttg gtggcctggg cggggattgt ggcaagtaga taatcaagga     3060
gcactgcaaa gaggttgttg ttgtttgttt ttctatccaa caatttaaag aataaactaa    3120
ccacttatta aaataggcat aaaaaattga gtgcacatgc cagaagtgag atgaagaact    3180
cagtttcaga catgtgtttg aggatgttgg tttccatcaa agtgagtttc taataggcaa    3240
gttgtaaggg tctgaattcg agagcatatc ttagcttctg tcacccatgt atggtggcac    3300
ttgaagtgga acttaagaca ggaaagttct gctcagcaat ttgggtagaa gacaaggaag   3360
agactgtagc gtgacttcat tgtgaactct ggaacagggc agcgttggag ggacaggagc    3420
agaagagggg gcagctcggt ggggaggcgg aagtcttaat tgtggagtcc tagaagataa    3480
gcagagaggg tgcacagaga aagaggaaga gccactgcta gtgctgatga cacatgaagt    3540
tgtgtgggga ctgaggggtg cccattggtt tggtgatgtg gaggccattc cccaatggcc    3600
tctttaagag tacttagagg ggctggagag atggctcagt gggtaagagc actgactgct    3660
cttccaaagg tcatgagttc aaatcccagc aaccacatgg tggctcacaa ccatccttaa    3720
taagatctga cgccctcttc tgatgtgtct gaagacagct ccagtgtact tagatataat    3780
aataaataaa tctttaaaaa aaaagaaga attaaaaaa agagtactt gagtagttgc     3840 aagaacatgt gtagacagtg tcatagtgaa acaaacaaac aaacaaaaaa atccttttat    3900
gagctcttac atgctcaaaa ggtgtgagta atggaacatc ttatagggag aaaggcattt    3960
tgtgcatttt gctctaggac atgagggtga gaggtgatct cttgtaagat ggatgaatac    4020
cagatgtatg catgctgaca gaagtgatcc atagagagcg tcctggtaac agaggagatg    4080
ggtacttatg ggagcaaata gatggtacag agtgcataag tgcagaacag tgccctgcag    4140
agggcacagg gagcttctcc agtagggatg tagaagcagg gaggtaggta gatactgcta    4200
aatcaaactc ttgaggcaga gcaactgtga aatagagggc agatgggct gttacacata     4260 ccagccaaag gtgtaagagc cggtcctatg acaaatctct aagtcaccag cagcattgcc    4320
aaatagcact tagtgaaaaa gtttctgctg ggcctaaggg agcaagatat tcacaatga     4380 aactctagaa aaatgtctat atattatttg catgaactta ttctgtgtct agaaaagttg    4440
gcaggataac agaagcccat gggaagcact ctaggaacaa agagatttg ttatttgctt     4500 gatcggttgg tttcagaaac agaatgcagg gggtgtggcc tcatcgcttc ctcctcaaca    4560
tacaggaaag gaatgtgaga tacttgtacc ccttctttct ttagtgctat gagttaaatg    4620
aacttaactc tttcttccct ctgctttctg tcctgtaact taatgtagga catctgaaaa    4680
ctctattcag ggtctgttag ggacattctc tccatgtgct gcattatgag ccaagaatga    4740
agataaaagg gggcggtcct gagaacatga ggagtgatga gttttgaaat tgtcatttta    4800
gggtgtaaac taggaaatgt gaactaggaa atgagtgatt gcagttgaga acagtgagct    4860
tttgaaagct tgggatttag agtagccgtt ttggtccagc tattgaggat caatgaatgg    4920
gcagcaccaa tgtgtttctt ctacccttag tgaacttagt ctgatgaatg gaaaacagtg    4980
gaaaactgta gatgagagaa gcacgtgtaa gttaaggtcc cccggaagcc agggcttttc    5040 agggttttt tggtttttgt tttttaacca gcagattaaa ggatagtaga gccctcatta    5100
tagtattttt gtttagtatg aaaaaagtgt cttctctaac actgaataat ttctgaagac    5160
```

```
atgaataaca gtttactaaa gggctaagga gagaagtatt ctgctagttt tgaaacaaat    5220
ttctaataaa gtgtcactat attttagtta ttcatgtcaa tgcatttttta aacctgcatc    5280 ttttactttt aggacaagaa aaccaactgg tggcattgat tccatatagt gatcagcggt    5340
tacggccaag aagaacgtat gtgattataa gatttcttcc tttattgttg tttgtatagt    5400
tttactttca aactttatat aagtaattac tctagttagg acatttaaga agaagaatat    5460
gtctggttgt taagttatgc catcctgaat gataatagtc attagcagat atgtggacat    5520
tttaagagaa gcaagggag tcttgaatgt tctactctaa agaagccaaa actcagcgct    5580
cctggcaaat atttttgaga atagcttgtt acaatgaaaa gaacagagat tgcagaaaac    5640
ccacagtggc cttgagaacg tcataaaagg ctgagtattc atgtgggtca aacaaatctg    5700
gaccgtccca ttacttgatg gtagaaccac atgagcaaca tgaatctaca gtaaagtaga    5760
agaacgtgaa ctcaggaaaa tgctgaaaaa atgaaagaca cacaaaaaag catataaaaa    5820
cttaaatata tataaaattt aaactgtaga atgcacagca gtagcttaag tgagacattg    5880
aagggtttag aaatcaagca actgatagga gtctatgaga tccgatttca caggcccta    5940 aaatatctag aaaaatactt gttctataaa attggaaatg tacaataaaa gtaagatacc    6000
ctagaaaata caaggaaagt ggattaaaca ggaggcacgt aaacatggtc tatgttagtc    6060
agtgctcttt tgctgtgaag agacaccatg actatgccac ttcttatgaa agaagacctt    6120
cctttgattg ttgctggctt acagtttcat tttcaggggt gtagtcctt atcagcatgg    6180 cgggaacatc acagcatgga gacaggcact gtggtggagt agctgagagt tctacatctg    6240
aatctacaga gagcaggaag agagcactag gcctgcatg ggcttttttga aacctcaaag    6300 cccaccccta gtgacagagt ctccaacaa ggccacatct actccaacaa ggccacacct    6360
cctaatccat ctcaaataga gtcatttctt attcaaacca tcatacatac ataatgaaaa    6420
gctttgagca aagtagcaga aaataaagaa agctaaacat gtatgtaaca ttctgtattt    6480
tctatcaaac cacataggag tcaatctttt attgaagttt cgtctgttgc tatgtattgt    6540
aatgctaaat cctatacatg aaggtctata cgtacaaggg acttctactg tttataagct    6600
tttgttgttc aaaccctatt ccttgattaa aaaaaaaaaa aactattggt tgaataaaaa    6660
tgtctataag ccagttactg gagggattag aggtaggtgg gttttcagtg acctggttag    6720
agagagaggg gaaagcagga ggaaggacaa gagagagaga aagagaggga gggaaggaaa    6780
gacggagcga gagaaggagg gagggagggg gcagggacgc tgccataaga ggagatgggg    6840
atgagcgcat ggccaggaaa aacagcaggt gcacagctgg ggaggcagcc aggcctgcag    6900
ttaggagagt agactagcgg ttacagctca gtaattgtca aagcgaaata aataaccat    6960 ggtccgagtc tcatttattt gtaagctagt caggggtaag cttaaattgg ttaccatctt    7020
tggctcagga atttcaattt tgaaaaatat atattaaagg tagttatcaa atatagtaag    7080
agcagccagg cattatggta cacacctgta atcccagcac cagaaagtag atgcaaaaag    7140
gtcagaagtt caaggctcta agctcagctc taagtttaag gtctctctag gctttctaag    7200
accctgtatc cagtaacaca aagcaaaaag tgtgtgtgta cacagttaaa taaataaaac    7260
cacctaataa catataggag atctagcaat gttaagatct tgatcacaa tcatttttaa    7320 attccttttg tgcctatggt gttttctgcc tattggtata ttgtaggcat aacaaatggg    7380
agttgttgtt cattggtgac ttggggctca tagctgtaaa gatttaagga accccctcagt    7440 gaaagagtag gaagaagctg gtttgttcca cccaccagca tggactcagt ggtgggattt    7500
ggtgagattc tgttcatttg ctttagttct ttttagcaag ccatttttctt tttcttagga    7560
```

```
agctagaata actagaaaaa ttattaggat attttaaaca gatgttataa ggtagatgga    7620
tgcagttaac ttagttgggg cataggaagt ttgaggggag agagactgg gcaaaatgac     7680
aggtcaccag gaagggcaag gatggaggac tcagaatgaa ataggccttt cacagagcgc    7740
catatgttca cgtgaccaag aaatctgaag ccatagtctt gagtgtaaca ttggagagca    7800
tacacatttc agaggcatta gatggatagt aaatgcaggt tagttgtctt tttgtcttat    7860
atgtgcccaa tactgccact tgtctcaggt aaacagaaca gcgttaggtt gatcagtgta    7920
aacagtatct gtaaaactgc gtgcattagt gcttcgtgac gagcactcag ggtttatcag    7980
ggcagggagt gaggctatcc agagcaaggc ctgctgcagt gaatccagat gaaggggtga    8040
attctgggct tgtaaagggt tctaatttaa aatctggatt gaaaatcact cattataagt    8100
aatgaatcag ttcattataa gtaattgttt cattataagt ctgagatctc attttctaaa    8160
attgacaatt aagcttctaa agagattatt ttaaccctta tctaatagtc ttagagtgaa    8220
tattttgtaa acttaaatgt attttcttgg gggtatatgt ggtaaatttc aaatgaaaat    8280
aatttcctga aatgttgttc tatgtagttt tggatgacac atatgtaagg attctatttt    8340
cctttcagaa agctgtatgt gatggcgtct gtgtttgtct gcctgctcct gtctggattg    8400
gctgtgtttt ttcttttccc tcgatctatt gaggtgaagt acattggagt aaaatcagcc    8460
tatgtcagct acgacgctga aaagcgaacc atatatttaa atatcacggt aagtgcgtgt    8520
ttgcactgaa ggccttgaca ccattcttgc cttgctcagc cgcccagtgg ctctgctgag    8580
agaatgaatg cttgctaatg acccctgctg ctgtagttta catgactctg ccttggcgat    8640
tccactacca tgtctgcttc tgccaaaaat ggaaggaag ctccgttttt gtacattggg     8700
aatcatttag cattgaagat gtcttttgta ggaagatcaa gtaaacattt tctggtaaag    8760
gggaaaaatg ctgtccattt acttttcaac atttgattcc aaataggtaa caaggtgcta    8820
gccgttgact caaaggatgt gatgagtaca acacttttgc tttctaacct tttatgaaag    8880
aaaaattgtc agtcttaaca gacttgtact cgactctatt caagatggag tttatatgat    8940
gacctgattg ttttaatgtg aaaatggcta tgggtttaca acacatgtga ctttgaaaaa    9000
aggattatat atccttccaa ctttgaaact tcacagctct gctccctgca tttacacaca    9060
cattagcctt tggctgtaaa gaacatggtg tgctaaccac tgtattggga cggggaggtg    9120
tgtaaccacc tgtgccatca cggtggctca caccttcaag ttcagagtgt gctgtggtct    9180
cttgggaagt gttcttaaga gtatgtcatt tccttttaaa taacagtgtc atgaaacgag    9240
aatgcctctt tgtattttaa acaatgaagc aaggattatc acaattttag atatttactc    9300
ataatcaaat taaggaatat tgaactttag gttagaaata ggatttctgt tgagatgaag    9360
agtaggcctc actagaagat attgaaggaa aagactgaca aggtcatagg tcagaattgt    9420
attattcctg cccccttgagg taagtgctgt gcattagtga gtgttaatat tgactgtcag   9480
tgtgacagga tctagaacca tcctggtgac aagcctctgg gtatcgctgt gggcattagg    9540
ttgaggtaga atgacctgcc ttaacggtgg gcagtcgtgt tttatgaaat gagttgttga    9600
actgaaccaa caatagagaa ggcaaactaa gcagcagcat tcatcatgct gtgctggcta    9660
actgaggcta tgcattgtga ccagcctcct caagtgtctg ccagcgtgcc ccaccccgc     9720
cgtcatggac tgtagttctt taaactatag taaatgcttt ttatcaagta tttggtcata    9780
ggaatgtata aaataactaa tacttccatt tatagtagct aattacgtat ggggattccc    9840
tggaccaaac caaccagaa acaagctctg ggtctcctgt cccatgagtt ctattatccc     9900
```

```
accttgtaga attttcttct gcagttctac agaagcaatc agctcaggtc ttttttaaact    9960 aactcacttc tgacactgac caactgtcag cagccttcag acttcacagt ttagaggctc   10020
tgtcccaaca ccctcctccc cactttccat gtcagtttca ggttcagacc cccaaaacgt   10080
ctagtagact atcagttggg agtctcatga cctgatccta tgtttgctta acttctctga   10140
acaactcata aaactcaaag gagcaatata cttacattca ctggtttgtt caagaggct    10200 attataaggg ctacaggccc acagatagat gaaaaggtag agtaaaaggc agagggcaga   10260
ggcttctgtc cccgcggaac tgagtgttcc gtcctcccag cacaggtttt ctctgtggca   10320
ttggccccag ccccttttca gctcttatga agcattagct gcatcagcat gactgaagga   10380
tagccaactg cagatagaca aaaatcctgc tctaatgtaa ataagctgag agttgtcagc   10440
caggagccaa tgtgtgtcat agtgccacag tacactcact ggcactgtgc tactgaaata   10500
ctcaatgtct atgactagac ccttgaaaac cccagaatac ataatgattt tgactcttct   10560
gtgaaaactt aattctcaac aatatatata tgcaattgct aacaatgtat atacatcccc   10620
ctacttataa acctttcttt gttttatcaa gcagtctcat tcttatgtct gaaagataca   10680
catatgctcc gtacatttca gctgagttca cactacattt ttctgcatga aagacttttt   10740
cattggctaa ttttcaaagt gatttgctct aagagttgtg aatgtaaagc atataaacat   10800
agcatatgtg tgtgtactgc tatgactaga aggggcaggg cagaagcttg aaaacagaag   10860
acgggcactg acagctctcc cagaggccct gagttcaatt cccagcaacc acatggtggc   10920
tcacaaccat ctgtaatggg atctgatacc ctcttctggt gtgtgtgaag acagcaacag   10980
tgtgctcata caaacaaaca aacaaacaaa cagtgtgctc atataaataa ataaataaac   11040
aaacaaaata cagcaacagt gtgctcatat aaacaaacaa acaattaatt aattaaaaaa   11100
aaagaagtag cagcaaccag ctggaaacct ggagcctttt tatctcttca tatggatcca   11160
gtataaatct ctacaggcat gtaaggtaaa agccattttt tttttacata ggctgctaat   11220
gccactcatt tggtagttgt tcttgcctat catgcacaag ggtctgattt agtccctatt   11280
gtcacacaaa acctagcttc gtgctgtaag cctgtaatag gagctctgta gagctggaga   11340
tgggaaaggt tcaaggtcat ccttagctac atagtgaggt caaagcctgc aggattgtat   11400
gaaatcgtgt ctgaaaaaaa aaaatggact ttcttaaaaa caaaatgtaa gtactgacct   11460
gttgttggta gaggcatgta tataatacat aagaatttaa ataaaaattt aaaatgttta   11520
gtccaacttt tgctaaaact ataaaatata tgttttaaca tttacttttc catattttcc   11580
tgtagtatat tttctgggtc ttgttttcaa taatttgaat catgttcatt atacacatag   11640
ttctctataa atgttcttta acattttatt aatattttct tttcccagta aatgagatat   11700
agttccaagt aaagtccatt tggtttataa ttctgagttc atatttatgt acctatgtaa   11760
acatagtgtg tatttcctgt ctctgttttt ttgcagaaca cactaaatat aacaaataat   11820
aactattatt ctgttgaagt tgaaaacatc actgctcaag tccagttttc aaaaaccgtg   11880
attggaaagg ctcgtttaaa caacataact aacattggcc cacttgatat gaagcaggta   11940
agcctattca ggagttgagg gggtgaaatg ggtattcacc ctgtgtaatg cagaatggag   12000
cggggtcggg ggcctcctca aagacttgac ttggaaatgt gtcccagaaa agtataaacc   12060
agatttatta aaggaaagat tccttttttt ttttaaatta gatattttct ttatttacat   12120
caaatgttat ccccttttcct ggttcccctc tgaaaatccc tcatcctctc cccctcccc    12180 ctgctcacca acccacccac tcacaaatcc tggccctggc attccctat actggggaat    12240 agaaacttca taggaccaag ggcctctcct cccatccgtg accgactagg ccatcctctg   12300
```

```
ctacatatgc agctagagcc aggtgtccca ccatgtgttt tctttggttg gtggtttagt    12360
cccagggagc tttgggggta ctggttagtt catattgttg ttcctcctat gggactgcaa    12420
atcccttcag ctccttgggt cctttctcta gctcctccat tggggaccct gtgctctgtc    12480
cagtggatgg ctgtgagcat ccccttctgt atttgtcagg cactggcaga gcctctcagg    12540
aaacagcttt atcaggcaaa agaaagattt ctaactttga aaatttagac ataggggtaa    12600
catgtttggt gtttggatcc tatcctctgt ttatgtgttt ttcttgatag ttgttgtttt    12660
tgctttcaga ttgattatac ggtacccaca gttattgcag aggaaatgag ttacatgtag    12720
taagttttgg attttagtat ctttacctt ttgttttctt aattttttata agattatcaa     12780 ttaaaaggac cacatattgc aatgcttgcc ctattctcta aacatgcttt tctttataca    12840
gtctacagca tagataacac agatgcatag ataagataga tagataaagc catcaaattc    12900
atctttattt ccataattgt gtgtatgtat gtgtgtgtgt gtgtgtgtgt gtgtgtgtga    12960
gagagagaga gagagagaga gagagagaga gagggagaaa acattatata ttgttattta    13020
gttactatat attcttggtg ctttaatata ggagtactga aatttctaat gtataagaat    13080
actttcccat ggacttgtac ttctgtatat gttgcatttg tgaagacaca cacacacacg    13140
catttgttca aggcgggggtt gaagttgaat tcttcctcta tcagtctcta ccttattctc    13200
taaggcaggc catgtgacta aaaatctaga gctcattgat ttggtgaggc tggctggcaa    13260
gcaagcctct aatagcctgt ttccaactct agtcccaagt ttctgagtgc atcctgcctt    13320
gcctggcttt ctgcctgaag gcttggcacc caaacgcaag ccctcatgcc tacaaagcaa    13380
gtgttttccc gccgaagcca cccccctagc acgactttta atagtgtctc gacaggcaca    13440
gtaacatggc ccagaatccc aggcattaca gaggctgaga tgacgaaggt ttctgcggcc    13500
aacataggga gatttcatct cataggaaaa aacaaaatca ctattcagag tctctattag    13560
gtttaataga actttacatt gataatgtaa tgacagtgct cttctatttt taatttcttt    13620
aacagtgatt tctgtacact gctctccatc aaagtgcaca acatagtact catgatgcag    13680
taagtatggc catgcctgca aaggtagcac ttgctaagac tgtgctcata atgtctgcta    13740
gggtatgtaa acccatgaaa gccatctcag cttggcttac agacttacgg gagtgctatg    13800
taaaatgtag tgttttggaa tttagctacc tagaatgtgt ttgctcagag ccacagagat    13860
taaaagcctg cagagattgt aggagttcag gcaaatggca gggttagctc agaggatggt    13920
cacacagcta ttcctcctg accttgtacg taaacctaca gcaatgaaga gaagtaatgc     13980
tttgggttta taaattggtt attacctatt tacataaaat attattgctt atatttgata    14040
tttttgtcct tggctgacat ttaattttcc attttcctat gaagagagga ccatatgatt    14100
cttttaagca tgtaataaac tttaattaca tttatataaa ttttaataaa tattttatat    14160
attcatataa atatgttatc tgtattgtac aagcagataa ttattggata gggtttgcta    14220
tgttagcatt tttgagtctg ttggaaaaat acttcctaag aatctataat gtcatcttaa    14280
tatcaaatgt tccataactg ataattataa ttcacaatta agtaattta gggaattaat      14340 taacttatga tatataagtt catatttgat tggtattatc cccagataac ccttttggaa    14400 taattttat ataacaaata ttcttttgtc tatttcattt ttagagttac tgtaacaaca      14460
gcatactttg gacactctga gcagatatct caggaaaggt accagtatgt cgactgtgga    14520
aggaacacga cttaccagtt ggcccagtct gagtatctaa atgtccttca gccacaacaa    14580
taaactctaa aggagatgtg gttagagccg atgacacacc tgagacatcg tcagaactgt    14640
```

```
cagtgaggag gtactgccta gaaggacatc tttaattaag cacgtctgaa gttcacactg   14700
ggatgtcgag ggtcagctga cagactgtgg gccttgtgca gttcctgcac tctcactttc   14760
tgtgttgacg atttgctcct accaagagcc tttcgtccag cttaagttaa ctgattggct   14820
ttcttctcac ctttgttccc aaggtgaaaa attgaaactt ccgtagaata caataaataa   14880
ttatataaaa gtcatagatt taatctatat atctattgat aatatagttc attcctgaac   14940
ataatttgaa aaataacttc tgaagatttt tatataaaat tactgaaagc ctattattca   15000
tggagaactt ttaaaaactg acctgtttta taaattccca ttcttacatg gtagtctttc   15060
aactatatga taactagct attagctaaa tgtttttagc ctttaatttc ttgaaattct   15120
```

```
cactgggagg atttggttta aaattatata ttagtaaatc cttcagttgc agccagaagc    17100
tgcttctccg actctcttct tatctgtgcc ctatcaatta caatgtccat tggcaagcca    17160
tggtgactca ggttagtaca attacacatt gaaaaagtgg ccggcaaggt ggggcagcgg    17220
ttgaggatgg tggccaccaa gcttgatgac ctgagttcaa tctttgtacc ccacagaagg    17280
cggagagaac tggcactctt ctcggatgac cgttcacgga cagtacaata ccacatatat    17340
agtgtacaca cacatacaaa tgtgtcgatg cccattcaca aacagtacag tacacgcaca    17400
cacagacaca tacaaatgca tgaaaaaata aagtaaaagt ttttgaagtt aatagtgatg    17460
gctaagattt tggtagcttt gagttgctat ctgaaatatt tctaaaagta aattaaacga    17520
tgtagaatcc ttcagaacca aagctggagc ttaattttta tgtgttaata tttaatactt    17580
cacaatcatt ccaataaaaa taaaactgac attttggtg tgaattattt ataagtaaga    17640
ttattacatt tgagatttga aatacagagc tgaaaatact agacatgaga taaatttctt    17700
gaaattgctt gaaagactat cttgcctgag gtgacatttc atagaacata actgtatttt    17760
gttatcagtt ttcctttgac tcctgtttac ccggtcttaa tgaagtaatt ctttttttctt    17820 aaaacctatt aaaagagtaa aatataactg acttcagatc ttataatttg cacttaggaa    17880
atggtggtga agtgtaaaag gatgtgggag gttgacatcc aaacaccgtc taagtaacat    17940
taggacaatt ggaacttggc cctaatgggc cttgtggttt ttagcctact atggaataat    18000
tttggctatt atgttggcag gtgtgccgac ttttccattc tgccttttaa agtgcttaaa    18060
tcaactggtt gttaacacat tgcgtcttat tttagaagat agtttcattc atatgttttt    18120
aaaataggag tacctttttac attttcaaat acattttgt cttctttgat aagtaataag    18180
agctaaacat ttagccattg gtttataatc aaatggtaaa ccgtgatgcc tgagacacta    18240
aaatgccata gctgcttggc tcaaagtgtg tcttagagtg ggcagcctta ttcctctgac    18300
tttgtgaaac tagatttaa atgaaacatt tatcttaac tttctaaaga aaattagtac    18360
atatcttaga aagctgaata aaaaaaatca ctatttcttc aaagttgtaa ttttagatta    18420
aaataaatgt atttgtgata tacttacttg gctcaaaaat ttaacttcta tatcaaagac    18480
ctatttacat tacagtcttc attcacagtt tctggttgca actactttgt gtggttttta    18540
gcttgcttag agaacaggtt tcacagaaga gctctgacgc ttatctttaa attcgataaa    18600
agcaacagca atgggattac tgtaggaaca caaatagaat ttccatgttt taagctgttc    18660
ttgttccttt ttacatgtgt taacacagac tccaagctga agatacagtg tggttggggt    18720
tcaaccctca aagcagtgca tagacaacgt agcaatatta tgaggagctt catagttaag    18780
tcttaactat tctagaagga agttgttgcc ttctgtttaa ttacattcat gaaatgtgtt    18840
taagtgaaat attttcagga tattttgtat gctgtaaaac aaaaaaggaa ttgtattgtg    18900
ccaatggcca aaggtaatat tactaccatg tagatgatga cagttcaaat tgtcccacgt    18960
cacccagaag tttagaaact agaagtctgg gagacaccac atcagttgta ttgggtgatt    19020
cttaagtgct gtacacgcta ttcatcttgt caatgtccag cacaagaagg agcgatgcca    19080
ggcaagctgc aaagatgcag aatttcatga cgcaggctgg tgtcagacat aagtatcagc    19140
cagtcatgtc cgtgtgtttt atcttagagt ttcacttaga gcttcaccct taagagttgg    19200
aaaatgattt gggatgtgat agtattccta agctctgaca gtcgattcgg atggtggaat    19260
agagaatgta aggtccgttc tgtatgcttg ctctttagcg acctccatta tgttacatct    19320
gttaaattca ttatttgtac agttctgaat tattatgatt gctgttcatg tagggaaaca    19380
```

```
tggttatgat aggaacaaga atagaaatgt ccccaatgct attttttaaa ttcacttgta    19440
actgttactc ttatacttgt gtatgacaaa ataaaatttg taaaaaacac tttagcatga    19500
aaaataaaat ttgtatcaac aaagta                                         19526

<210> SEQ ID NO 6
<211> LENGTH: 6099
<212> TYPE: DNA
<213> ORGANISM: Mus musculus

<400> SEQUENCE: 6
ggggcgaact gcgcaagcgc acgcgcaggc tctcccggta cggagctcag ctgatgcagt       60
tgttgtgcta cccctccccc gcagctctcc cggctgcact ctaccggcgc tcggcccggc      120
cccgggaccg ggacgctgtg accctgtcct gcggcccgca cgcaccggag catcccggga      180
ccgcgcagca ctccgcgtgc ggtttctaga gcatctgaga accgtgttga gttcacaaga      240
ccgcggtata acattgaga gcccggggag gagacgaagg ggatctacca ctcccttttaa      300 aaacctcaaa catgggaaag tctctttctc acttaccttt gcattcaaat aaagaagatg      360
gctatgatgg cgttacatcg acagacaata tgagaaatgg attggttagc agtgaagtgc      420
acaacgaaga cggaagaaat ggagatgtct ctcagttccc atatgtggaa tttactggaa      480
gagatagtgt cacttgtccc acttgccaag gaacaggaag aattcctagg ggacaagaaa      540
accaactggt ggcattgatt ccatatagtg atcagcggtt acggccaaga agaacaaagc      600
tgtatgtgat ggcgtctgtg tttgtctgcc tgctcctgtc tggattggct gtgttttttc      660 ttttcccctcg atctattgag gtgaagtaca ttggagtaaa atcagcctat gtcagctacg      720
acgctgaaaa gcgaaccata tatttaaata tcacgaacac actaaatata acaaataata      780
actattattc tgttgaagtt gaaaacatca ctgctcaagt ccagttttca aaaaccgtga      840
ttggaaaggc tcgtttaaac aacataacta acattggccc acttgatatg aagcagattg      900
attatacggt acccacagtt attgcagagg aaatgagtta catgtatgat ttctgtacac      960
tgctctccat caaagtgcac aacatagtac tcatgatgca agttactgta caacagcat     1020 actttggaca ctctgagcag atatctcagg aaaggtacca gtatgtcgac tgtggaagga     1080
acacgactta ccagttggcc cagtctgagt atctaaatgt ccttcagcca caacaataaa     1140
ctctaaagga gatgtggtta gagccgatga cacacctgag acatcgtcag aactgtcagt     1200
gaggaggtac tgcctagaag gacatctttta attaagcacg tctgaagttc acactgggat     1260
gtcgagggtc agctgacaga ctgtgggcct tgtgcagttc ctgcactctc actttctgtg     1320
ttgacgattt gctcctacca agagcctttc gtccagctta agttaactga ttggctttct     1380
tctcaccttt gttcccaagg tgaaaaattg aaacttccgt agaatacaat aaataattat     1440
ataaaagtca tagatttaat ctatatatct attgataata tagttcattc ctgaacataa     1500
tttgaaaaat aacttctgaa gatttttata taaaattact gaaagcctat tattcatgga     1560 gaactttttaa aaactgacct gttttataaa ttcccattct tacatggtag tctttcaact     1620
atatgataac ttagctatta gctaaatgtt tttagccttt aatttcttga aattctactg     1680
atttgcatgt tttgtcttat ttctagctaa tggttgcata atatttacca accataccat     1740
tcggccacat tctgttctac attttgtaag aacctctcag tatgtgtttc atgtataact     1800
ttgtgagctt tctgtgtgat cttcaaacat attcctttaa tgtacaatat tgtaaataaa     1860
gtgcatggct tttatacagc tttgataaag gtcaaatgaa gtagtacaga ttaagaataa     1920
agcaggttgt tcataaacaa taaggtagga aattgaaatt aagaaaccta taaatatca      1980
```

```
gtaggttccg ctacatgttg gatctgacat aacatagatg cacagtaaaa catttcgatg    2040
ctctactttt tatattaatt atatagatgc ttttcccagc aattaggtat catcaatttt    2100
atgaatgttt tagggaagaa aaccatttct ttctagaaat tagtcaagga ataatttcat    2160
tgaacactgg tgactacatc aaaataaaac ctatagtttg cttaaaaaat ttaatcatta    2220
cccatcatcc tgagtcgatg cttctagcag ttacagtaaa catttatttt ttaattttgt    2280
ctaacatggt tttcaaatat gatggacgta ttcatcttgt tgctttatat ttccagtgtc    2340 attttttgacc aagtattttc cttattcacc cagcaaattt ccagtgcatt ctgttttctt    2400
atgtcagaag ttgggttttc cgtttcccat acccaagtgc ttccgttggt tgtgatgtgt    2460
gctctgttcc tcagcctggc tctcaagtgg aaagcagaaa ctctaacggc ttcaccctgc    2520
ccttgaagca ctcgtcatct ttccttagca gtcacctgca ttcgctgtat gagggagctt    2580
tggggtcacc cgtggtctgt gtgtggccac ccttcccgta cacccagagc accctctgca    2640
gtcattcacg ctctagtcaa gctgggcttt gtttgtttgg ttttttcttt ctgtgcttgc    2700
tggtcacctc cattcttgaa gctgcacagt tggctggttg tgcttacatt tttcaaatca    2760
acctcatttc attatatgca gtctctcctt tttatgtaac tgtctgtgag tcatttgttt    2820 catttcatttt gttttgtcta gaaatgtcta ctcctgttac ttaaaagtta ccactgtctt    2880
tagtttggct actcagctga acactagcca taaatacgtg tgaggtgtgc aaaatcatca    2940
tccatccatc tctgcagaat cgcccttac ctaggcctca tgtagtagcc actttctctg    3000 cccccttccat gtgtatttca gtccaggaga gcactgtgtt ctgccagagt tcgtggacaa    3060
ggcctactga ggcaggacag tacagtcaac tttactccca gtgattcagt ttcaaaaacc    3120
ttttcgtaac tatttacatt gaaatttcta tctcaaccag ttctaatgtc tagctttaat    3180
aatgcctgag tcatttgaaa acccagcctg caactcttca acgaaaatca agtaactcct    3240
gggtaagcca ggctgctaac agctgtaagt taataaaact caaaccaaat gaacaaacag    3300
cagctgaaca atagccatgg agacatctgc aactatgagt gaagctttgt gcttttctta    3360
ggtctggttt agctaggtct gacttcgggc agggaggaag agtaggtatt aatatagttt    3420
tatatgagca ccaccagagc ttagccaggg acatgatgaa gacattacca tgttgcccca    3480
tgctcacagg ggtaaattct gttctacact aacccagcac tgccccaggc tctgtgtgga    3540
caacacactg gctgttgctc ttctgtctgc ttttcttatg taatttctca acaggacact    3600
gggaggattt ggtttaaaat tatatattag taaatccttc agttgcagcc agaagctgct    3660
tctccgactc tcttcttatc tgtgccctat caattacaat gtccattggc aagccatggt    3720
gactcaggtt agtacaatta cacattgaaa aagtggccgg caaggtgggg cagcggttga    3780
ggatggtggc caccaagctt gatgacctga gttcaatctt tgtacccccac agaaggcgga    3840 gagaactggc actcttctcg gatgaccgtt cacggacagt acaataccac atatatagtg    3900
tacacacaca tacaaatgtg tcgatgccca ttcacaaaca gtacagtaca cgcacacaca    3960
gacacataca aatgcatgaa aaaataaagt aaaagttttt gaagttaata gtgatggcta    4020
agattttggt agctttgagt tgctatctga aatatttcta aaagtaaatt aaacgatgta    4080
gaatccttca gaaccaaagc tggagcttaa tttttatgtg ttaatattta atacttcaca    4140
atcattccaa taaaaataaa actgacattt ttggtgtgaa ttatttataa gtaagattat    4200
tacatttgag atttgaaata cagagctgaa aatactagac atgagataaa tttcttgaaa    4260
ttgcttgaaa gactatcttg cctgaggtga catttcatag aacataactg tattttgtta    4320
```

```
tcagttttcc tttgactcct gtttacccgg tcttaatgaa gtaattcttt tttcttaaaa    4380
cctattaaaa gagtaaaata taactgactt cagatcttat aatttgcact taggaaatgg    4440
tggtgaagtg taaaaggatg tgggaggttg acatccaaac accgtctaag taacattagg    4500
acaattggaa cttggcccta atgggccttg tggtttttag cctactatgg ataattttg     4560 gctattatgt tggcaggtgt gccgactttt ccattctgcc ttttaaagtg cttaaatcaa    4620
ctggttgtta acacattgcg tcttatttta gaagatagtt tcattcatat gtttttaaaa    4680
taggagtacc ttttacattt tcaaatacat ttttgtcttc tttgataagt aataagagct    4740
aaacatttag ccattggttt ataatcaaat ggtaaaccgt gatgcctgag acactaaaat    4800
gccatagctg cttggctcaa agtgtgtctt agagtgggca gccttattcc tctgactttg    4860
tgaaactaga ttttaaatga acatttatc tttaactttc taagaaaaat tagtacatat    4920
cttagaaagc tgaataaaaa aaatcactat ttcttcaaag ttgtaatttt agattaaaat    4980
aaatgtattt gtgatatact tacttggctc aaaaatttaa cttctatatc aaagacctat    5040
ttacattaca gtcttcattc acagtttctg gttgcaacta ctttgtgtgg tttttagctt    5100
gcttagagaa caggtttcac agaagagctc tgacgcttat cttaaattc gataaaagca    5160 acagcaatgg gattactgta ggaacacaaa tagaatttcc atgttttaag ctgttcttgt    5220
tcctttttac atgtgttaac acagactcca agctgaagat acagtgtggt tggggttcaa    5280
ccctcaaagc agtgcataga caacgtagca atattatgag gagcttcata gttaagtctt    5340
aactattcta gaaggaagtt gttgccttct gtttaattac attcatgaaa tgtgtttaag    5400
tgaaatattt tcaggatatt ttgtatgctg taaaacaaaa aaggaattgt attgtgccaa    5460
tggccaaagg taatattact accatgtaga tgatgacagt tcaaattgtc ccacgtcacc    5520
cagaagttta gaaactagaa gtctgggaga caccacatca gttgtattgg gtgattctta    5580
agtgctgtac acgctattca tcttgtcaat gtccagcaca agaaggagcg atgccaggca    5640
agctgcaaag atgcagaatt tcatgacgca ggctggtgtc agacataagt atcagccagt    5700
catgtccgtg tgttttatct tagagtttca cttagagctt caccccttaag agttggaaaa    5760 tgatttggga tgtgatagta ttcctaagct ctgacagtcg attcggatgg tggaatagag    5820
aatgtaaggt ccgttctgta tgcttgctct ttagcgacct ccattatgtt acatctgtta    5880
aattcattat ttgtacagtt ctgaattatt atgattgctg ttcatgtagg gaaacatggt    5940
tatgatagga acaagaatag aaatgtcccc aatgctattt tttaaattca cttgtaactg    6000
ttactcttat acttgtgtat gacaaaataa aatttgtaaa aaacacttta gcatgaaaaa    6060
taaaatttgt atcaacaaag taaaaaaaaa aaaaaaaa                            6099
```

<210> SEQ ID NO 7
<211> LENGTH: 18
<212> TYPE: DNA
<213> ORGANISM: Artificial
<220> FEATURE:
<223> OTHER INFORMATION: oligonucleotide motif sequence

<400> SEQUENCE: 7
aagctccata aacaacac                                                  18

<210> SEQ ID NO 8
<211> LENGTH: 19
<212> TYPE: DNA
<213> ORGANISM: Artificial
<220> FEATURE:
<223> OTHER INFORMATION: oligonucleotide motif sequence -continued

```
<400> SEQUENCE: 8
ctttaaacat ttaaacact                                              19

<210> SEQ ID NO 9
<211> LENGTH: 18
<212> TYPE: DNA
<213> ORGANISM: Artificial
<220> FEATURE:
<223> OTHER INFORMATION: oligonucleotide motif sequence

<400> SEQUENCE: 9
ttccatcctt aaatttct                                               18

<210> SEQ ID NO 10
<211> LENGTH: 19
<212> TYPE: DNA
<213> ORGANISM: Artificial
<220> FEATURE:
<223> OTHER INFORMATION: oligonucleotide motif sequence

<400> SEQUENCE: 10
tgataaatac aatcaccac                                              19

<210> SEQ ID NO 11
<211> LENGTH: 18
<212> TYPE: DNA
<213> ORGANISM: Artificial
<220> FEATURE:
<223> OTHER INFORMATION: oligonucleotide motif sequence

<400> SEQUENCE: 11
tacattctac cttttaac                                               18

<210> SEQ ID NO 12
<211> LENGTH: 19
<212> TYPE: DNA
<213> ORGANISM: Artificial
<220> FEATURE:
<223> OTHER INFORMATION: oligonucleotide motif sequence

<400> SEQUENCE: 12
gctttcaaac attaacatt                                              19

<210> SEQ ID NO 13
<211> LENGTH: 18
<212> TYPE: DNA
<213> ORGANISM: Artificial
<220> FEATURE:
<223> OTHER INFORMATION: oligonucleotide motif sequence

<400> SEQUENCE: 13
atgttcaaac tacctttt                                               18

<210> SEQ ID NO 14
<211> LENGTH: 18
<212> TYPE: DNA
<213> ORGANISM: Artificial
<220> FEATURE:
<223> OTHER INFORMATION: oligonucleotide motif sequence

<400> SEQUENCE: 14
agatatttac actaatta                                               18

<210> SEQ ID NO 15
```

```
<211> LENGTH: 17
<212> TYPE: DNA
<213> ORGANISM: Artificial
<220> FEATURE:
<223> OTHER INFORMATION: oligonucleotide motif sequence

<400> SEQUENCE: 15
gacttcacta ttaacca                                                    17

<210> SEQ ID NO 16
<211> LENGTH: 18
<212> TYPE: DNA
<213> ORGANISM: Artificial
<220> FEATURE:
<223> OTHER INFORMATION: oligonucleotide motif sequence

<400> SEQUENCE: 16
cctgtaaatt ccacatat                                                   18

<210> SEQ ID NO 17
<211> LENGTH: 16
<212> TYPE: DNA
<213> ORGANISM: Artificial
<220> FEATURE:
<223> OTHER INFORMATION: oligonucleotide motif sequence

<400> SEQUENCE: 17
tgacactatc tcttcc                                                     16

<210> SEQ ID NO 18
<211> LENGTH: 18
<212> TYPE: DNA
<213> ORGANISM: Artificial
<220> FEATURE:
<223> OTHER INFORMATION: oligonucleotide motif sequence

<400> SEQUENCE: 18
caataacaca taccccta                                                   18

<210> SEQ ID NO 19
<211> LENGTH: 18
<212> TYPE: DNA
<213> ORGANISM: Artificial
<220> FEATURE:
<223> OTHER INFORMATION: oligonucleotide motif sequence

<400> SEQUENCE: 19
gtttcaactt taattcta                                                   18

<210> SEQ ID NO 20
<211> LENGTH: 17
<212> TYPE: DNA
<213> ORGANISM: Artificial
<220> FEATURE:
<223> OTHER INFORMATION: oligonucleotide motif sequence

<400> SEQUENCE: 20
agcttcctta cacatta                                                    17

<210> SEQ ID NO 21
<211> LENGTH: 20
<212> TYPE: DNA
<213> ORGANISM: Artificial
<220> FEATURE:
<223> OTHER INFORMATION: oligonucleotide motif sequence
```

```
<400> SEQUENCE: 21
atctttatta tttctactta                                          20

<210> SEQ ID NO 22
<211> LENGTH: 18
<212> TYPE: DNA
<213> ORGANISM: Artificial
<220> FEATURE:
<223> OTHER INFORMATION: oligonucleotide motif sequence

<400> SEQUENCE: 22
atcccttcaa ctacaata                                            18

<210> SEQ ID NO 23
<211> LENGTH: 18
<212> TYPE: DNA
<213> ORGANISM: Artificial
<220> FEATURE:
<223> OTHER INFORMATION: oligonucleotide motif sequence

<400> SEQUENCE: 23
ttcctacttt ccataatc                                            18

<210> SEQ ID NO 24
<211> LENGTH: 18
<212> TYPE: DNA
<213> ORGANISM: Artificial
<220> FEATURE:
<223> OTHER INFORMATION: oligonucleotide motif sequence

<400> SEQUENCE: 24
cttgatttcc tactttcc                                            18

<210> SEQ ID NO 25
<211> LENGTH: 19
<212> TYPE: DNA
<213> ORGANISM: Artificial
<220> FEATURE:
<223> OTHER INFORMATION: oligonucleotide motif sequence

<400> SEQUENCE: 25
gacatataca ctcaaataa                                           19

<210> SEQ ID NO 26
<211> LENGTH: 19
<212> TYPE: DNA
<213> ORGANISM: Artificial
<220> FEATURE:
<223> OTHER INFORMATION: oligonucleotide motif sequence

<400> SEQUENCE: 26
ttcttcactt atcttccat                                           19

<210> SEQ ID NO 27
<211> LENGTH: 17
<212> TYPE: DNA
<213> ORGANISM: Artificial
<220> FEATURE:
<223> OTHER INFORMATION: oligonucleotide motif sequence

<400> SEQUENCE: 27
tcagtcttca cactacc                                             17

<210> SEQ ID NO 28
```

```
<211> LENGTH: 18
<212> TYPE: DNA
<213> ORGANISM: Artificial
<220> FEATURE:
<223> OTHER INFORMATION: oligonucleotide motif sequence

<400> SEQUENCE: 28
cttctctttt attaccaa                                                 18

<210> SEQ ID NO 29
<211> LENGTH: 16
<212> TYPE: DNA
<213> ORGANISM: Artificial
<220> FEATURE:
<223> OTHER INFORMATION: oligonucleotide motif sequence

<400> SEQUENCE: 29
gtgtccatac tttacc                                                   16

<210> SEQ ID NO 30
<211> LENGTH: 16
<212> TYPE: DNA
<213> ORGANISM: Artificial
<220> FEATURE:
<223> OTHER INFORMATION: oligonucleotide motif sequence

<400> SEQUENCE: 30
tcttcgctat cctcat                                                   16

<210> SEQ ID NO 31
<211> LENGTH: 19
<212> TYPE: DNA
<213> ORGANISM: Artificial
<220> FEATURE:
<223> OTHER INFORMATION: oligonucleotide motif sequence

<400> SEQUENCE: 31
aatctttaat atcttcttc                                                19

<210> SEQ ID NO 32
<211> LENGTH: 18
<212> TYPE: DNA
<213> ORGANISM: Artificial
<220> FEATURE:
<223> OTHER INFORMATION: oligonucleotide motif sequence

<400> SEQUENCE: 32
ccaagaccac aattttat                                                 18

<210> SEQ ID NO 33
<211> LENGTH: 17
<212> TYPE: DNA
<213> ORGANISM: Artificial
<220> FEATURE:
<223> OTHER INFORMATION: oligonucleotide motif sequence

<400> SEQUENCE: 33
ccaagttcat actctca                                                  17

<210> SEQ ID NO 34
<211> LENGTH: 18
<212> TYPE: DNA
<213> ORGANISM: Artificial
<220> FEATURE:
<223> OTHER INFORMATION: oligonucleotide motif sequence
```

```
<400> SEQUENCE: 34
atcatactac atttccca                                                    18

<210> SEQ ID NO 35
<211> LENGTH: 17
<212> TYPE: DNA
<213> ORGANISM: Artificial
<220> FEATURE:
<223> OTHER INFORMATION: oligonucleotide motif sequence

<400> SEQUENCE: 35
tgtttacata tctcacc                                                     17

<210> SEQ ID NO 36
<211> LENGTH: 19
<212> TYPE: DNA
<213> ORGANISM: Artificial
<220> FEATURE:
<223> OTHER INFORMATION: oligonucleotide motif sequence

<400> SEQUENCE: 36
ccatcacacc catatataa                                                   19

<210> SEQ ID NO 37
<211> LENGTH: 17
<212> TYPE: DNA
<213> ORGANISM: Artificial
<220> FEATURE:
<223> OTHER INFORMATION: oligonucleotide motif sequence

<400> SEQUENCE: 37
tcctgaaacc tctatca                                                     17

<210> SEQ ID NO 38
<211> LENGTH: 20
<212> TYPE: DNA
<213> ORGANISM: Artificial
<220> FEATURE:
<223> OTHER INFORMATION: oligonucleotide motif sequence

<400> SEQUENCE: 38
ttttcttcta attctttcca                                                  20

<210> SEQ ID NO 39
<211> LENGTH: 19
<212> TYPE: DNA
<213> ORGANISM: Artificial
<220> FEATURE:
<223> OTHER INFORMATION: oligonucleotide motif sequence

<400> SEQUENCE: 39
cctaatttcc ttcatattc                                                   19

<210> SEQ ID NO 40
<211> LENGTH: 17
<212> TYPE: DNA
<213> ORGANISM: Artificial
<220> FEATURE:
<223> OTHER INFORMATION: oligonucleotide motif sequence

<400> SEQUENCE: 40
tatttgacaa ctatcct                                                     17

<210> SEQ ID NO 41
```

```
<211> LENGTH: 17
<212> TYPE: DNA
<213> ORGANISM: Artificial
<220> FEATURE:
<223> OTHER INFORMATION: oligonucleotide motif sequence

<400> SEQUENCE: 41
catcagtcct ctattat                                                        17

<210> SEQ ID NO 42
<211> LENGTH: 19
<212> TYPE: DNA
<213> ORGANISM: Artificial
<220> FEATURE:
<223> OTHER INFORMATION: oligonucleotide motif sequence

<400> SEQUENCE: 42
gtctccatta caaaattaa                                                      19

<210> SEQ ID NO 43
<211> LENGTH: 18
<212> TYPE: DNA
<213> ORGANISM: Artificial
<220> FEATURE:
<223> OTHER INFORMATION: oligonucleotide motif sequence

<400> SEQUENCE: 43
tagtatttca ttccaaat                                                       18

<210> SEQ ID NO 44
<211> LENGTH: 18
<212> TYPE: DNA
<213> ORGANISM: Artificial
<220> FEATURE:
<223> OTHER INFORMATION: oligonucleotide motif sequence

<400> SEQUENCE: 44
tgaatccatc ataatcta                                                       18

<210> SEQ ID NO 45
<211> LENGTH: 16
<212> TYPE: DNA
<213> ORGANISM: Artificial
<220> FEATURE:
<223> OTHER INFORMATION: oligonucleotide motif sequence

<400> SEQUENCE: 45
ttacatgatc ccctaa                                                         16

<210> SEQ ID NO 46
<211> LENGTH: 18
<212> TYPE: DNA
<213> ORGANISM: Artificial
<220> FEATURE:
<223> OTHER INFORMATION: oligonucleotide motif sequence

<400> SEQUENCE: 46
atgttaccaa attttcac                                                       18

<210> SEQ ID NO 47
<211> LENGTH: 16
<212> TYPE: DNA
<213> ORGANISM: Artificial
<220> FEATURE:
<223> OTHER INFORMATION: oligonucleotide motif sequence
```

<400> SEQUENCE: 47
aaacacagcc aatcca                                                    16

<210> SEQ ID NO 48
<211> LENGTH: 18
<212> TYPE: DNA
<213> ORGANISM: Artificial
<220> FEATURE:
<223> OTHER INFORMATION: oligonucleotide motif sequence

<400> SEQUENCE: 48
agtttatttt accctcct                                                  18

<210> SEQ ID NO 49
<211> LENGTH: 19
<212> TYPE: DNA
<213> ORGANISM: Artificial
<220> FEATURE:
<223> OTHER INFORMATION: oligonucleotide motif sequence

<400> SEQUENCE: 49
gcatcacttc aaactatac                                                 19

<210> SEQ ID NO 50
<211> LENGTH: 18
<212> TYPE: DNA
<213> ORGANISM: Artificial
<220> FEATURE:
<223> OTHER INFORMATION: oligonucleotide motif sequence

<400> SEQUENCE: 50
tcccttttcc taattcaa                                                  18

<210> SEQ ID NO 51
<211> LENGTH: 19
<212> TYPE: DNA
<213> ORGANISM: Artificial
<220> FEATURE:
<223> OTHER INFORMATION: oligonucleotide motif sequence

<400> SEQUENCE: 51
aaacaactat cactcttcc                                                 19

<210> SEQ ID NO 52
<211> LENGTH: 18
<212> TYPE: DNA
<213> ORGANISM: Artificial
<220> FEATURE:
<223> OTHER INFORMATION: oligonucleotide motif sequence

<400> SEQUENCE: 52
cagacatctc tacctcaa                                                  18

<210> SEQ ID NO 53
<211> LENGTH: 18
<212> TYPE: DNA
<213> ORGANISM: Artificial
<220> FEATURE:
<223> OTHER INFORMATION: oligonucleotide motif sequence

<400> SEQUENCE: 53
tgattccact ttaacata                                                  18

<210> SEQ ID NO 54

```
<211> LENGTH: 18
<212> TYPE: DNA
<213> ORGANISM: Artificial
<220> FEATURE:
<223> OTHER INFORMATION: oligonucleotide motif sequence

<400> SEQUENCE: 54
atacccaaca attccca                                                   18

<210> SEQ ID NO 55
<211> LENGTH: 20
<212> TYPE: DNA
<213> ORGANISM: Artificial
<220> FEATURE:
<223> OTHER INFORMATION: oligonucleotide motif sequence

<400> SEQUENCE: 55
tattcacatt taaatatact                                                20

<210> SEQ ID NO 56
<211> LENGTH: 18
<212> TYPE: DNA
<213> ORGANISM: Artificial
<220> FEATURE:
<223> OTHER INFORMATION: oligonucleotide motif sequence

<400> SEQUENCE: 56
acaaagaccc taaactac                                                  18

<210> SEQ ID NO 57
<211> LENGTH: 20
<212> TYPE: DNA
<213> ORGANISM: Artificial
<220> FEATURE:
<223> OTHER INFORMATION: oligonucleotide motif sequence

<400> SEQUENCE: 57
atatacttca taacttcaaa                                                20

<210> SEQ ID NO 58
<211> LENGTH: 20
<212> TYPE: DNA
<213> ORGANISM: Artificial
<220> FEATURE:
<223> OTHER INFORMATION: oligonucleotide motif sequence

<400> SEQUENCE: 58
tacatataac tcatttcctc                                                20

<210> SEQ ID NO 59
<211> LENGTH: 18
<212> TYPE: DNA
<213> ORGANISM: Artificial
<220> FEATURE:
<223> OTHER INFORMATION: oligonucleotide motif sequence

<400> SEQUENCE: 59
tcagaactta ctacatat                                                  18

<210> SEQ ID NO 60
<211> LENGTH: 20
<212> TYPE: DNA
<213> ORGANISM: Artificial
<220> FEATURE:
<223> OTHER INFORMATION: oligonucleotide motif sequence
```

<400> SEQUENCE: 60
ttttctatac ttcaaacaat                                            20

<210> SEQ ID NO 61
<211> LENGTH: 20
<212> TYPE: DNA
<213> ORGANISM: Artificial
<220> FEATURE:
<223> OTHER INFORMATION: oligonucleotide motif sequence

<400> SEQUENCE: 61
aacacccaat ttacaaacca                                            20

<210> SEQ ID NO 62
<211> LENGTH: 17
<212> TYPE: DNA
<213> ORGANISM: Artificial
<220> FEATURE:
<223> OTHER INFORMATION: oligonucleotide motif sequence

<400> SEQUENCE: 62
cttagataac acccaat                                               17

<210> SEQ ID NO 63
<211> LENGTH: 20
<212> TYPE: DNA
<213> ORGANISM: Artificial
<220> FEATURE:
<223> OTHER INFORMATION: oligonucleotide motif sequence

<400> SEQUENCE: 63
tatttcttct ttaaatccat                                            20

<210> SEQ ID NO 64
<211> LENGTH: 17
<212> TYPE: DNA
<213> ORGANISM: Artificial
<220> FEATURE:
<223> OTHER INFORMATION: oligonucleotide motif sequence

<400> SEQUENCE: 64
tccacatact tttaact                                               17

<210> SEQ ID NO 65
<211> LENGTH: 18
<212> TYPE: DNA
<213> ORGANISM: Artificial
<220> FEATURE:
<223> OTHER INFORMATION: oligonucleotide motif sequence

<400> SEQUENCE: 65
atgtttatca ccaaaatt                                              18

<210> SEQ ID NO 66
<211> LENGTH: 18
<212> TYPE: DNA
<213> ORGANISM: Artificial
<220> FEATURE:
<223> OTHER INFORMATION: oligonucleotide motif sequence

<400> SEQUENCE: 66
ctgaaatact accatata                                              18

<210> SEQ ID NO 67

```
<211> LENGTH: 18
<212> TYPE: DNA
<213> ORGANISM: Artificial
<220> FEATURE:
<223> OTHER INFORMATION: oligonucleotide motif sequence

<400> SEQUENCE: 67
agatttcaca aaactata                                                 18

<210> SEQ ID NO 68
<211> LENGTH: 19
<212> TYPE: DNA
<213> ORGANISM: Artificial
<220> FEATURE:
<223> OTHER INFORMATION: oligonucleotide motif sequence

<400> SEQUENCE: 68
cgaaattaat ctcaaccca                                                19

<210> SEQ ID NO 69
<211> LENGTH: 20
<212> TYPE: DNA
<213> ORGANISM: Artificial
<220> FEATURE:
<223> OTHER INFORMATION: oligonucleotide motif sequence

<400> SEQUENCE: 69
taatacctat cctattccca                                               20

<210> SEQ ID NO 70
<211> LENGTH: 18
<212> TYPE: DNA
<213> ORGANISM: Artificial
<220> FEATURE:
<223> OTHER INFORMATION: oligonucleotide motif sequence

<400> SEQUENCE: 70
gtaacatatc tttaccat                                                 18

<210> SEQ ID NO 71
<211> LENGTH: 17
<212> TYPE: DNA
<213> ORGANISM: Artificial
<220> FEATURE:
<223> OTHER INFORMATION: oligonucleotide motif sequence

<400> SEQUENCE: 71
tttaatcata ccaatct                                                  17

<210> SEQ ID NO 72
<211> LENGTH: 17
<212> TYPE: DNA
<213> ORGANISM: Artificial
<220> FEATURE:
<223> OTHER INFORMATION: oligonucleotide motif sequence

<400> SEQUENCE: 72
atgctaccaa aatctta                                                  17

<210> SEQ ID NO 73
<211> LENGTH: 19
<212> TYPE: DNA
<213> ORGANISM: Artificial
<220> FEATURE:
<223> OTHER INFORMATION: oligonucleotide motif sequence
```

```
<400> SEQUENCE: 73
ctcaaataaa ttaatctct                                                19

<210> SEQ ID NO 74
<211> LENGTH: 18
<212> TYPE: DNA
<213> ORGANISM: Artificial
<220> FEATURE:
<223> OTHER INFORMATION: oligonucleotide motif sequence

<400> SEQUENCE: 74
ttcttatttc aaatctca                                                 18

<210> SEQ ID NO 75
<211> LENGTH: 17
<212> TYPE: DNA
<213> ORGANISM: Artificial
<220> FEATURE:
<223> OTHER INFORMATION: oligonucleotide motif sequence

<400> SEQUENCE: 75
tcttatttca aatctca                                                  17

<210> SEQ ID NO 76
<211> LENGTH: 20
<212> TYPE: DNA
<213> ORGANISM: Artificial
<220> FEATURE:
<223> OTHER INFORMATION: oligonucleotide motif sequence

<400> SEQUENCE: 76
atactattct tatttcaaat                                               20

<210> SEQ ID NO 77
<211> LENGTH: 18
<212> TYPE: DNA
<213> ORGANISM: Artificial
<220> FEATURE:
<223> OTHER INFORMATION: oligonucleotide motif sequence

<400> SEQUENCE: 77
gtatctaata ttttcata                                                 18

<210> SEQ ID NO 78
<211> LENGTH: 19
<212> TYPE: DNA
<213> ORGANISM: Artificial
<220> FEATURE:
<223> OTHER INFORMATION: oligonucleotide motif sequence

<400> SEQUENCE: 78
ttttactcca ccatctcaa                                                19

<210> SEQ ID NO 79
<211> LENGTH: 17
<212> TYPE: DNA
<213> ORGANISM: Artificial
<220> FEATURE:
<223> OTHER INFORMATION: oligonucleotide motif sequence

<400> SEQUENCE: 79
taacagtctt tttactc                                                  17

<210> SEQ ID NO 80
```

```
<211> LENGTH: 18
<212> TYPE: DNA
<213> ORGANISM: Artificial
<220> FEATURE:
<223> OTHER INFORMATION: oligonucleotide motif sequence

<400> SEQUENCE: 80
tagtaacttt aatcactt                                             18

<210> SEQ ID NO 81
<211> LENGTH: 16
<212> TYPE: DNA
<213> ORGANISM: Artificial
<220> FEATURE:
<223> OTHER INFORMATION: oligonucleotide motif sequence

<400> SEQUENCE: 81
tagtaatatt accttt                                               16

<210> SEQ ID NO 82
<211> LENGTH: 15
<212> TYPE: DNA
<213> ORGANISM: Artificial
<220> FEATURE:
<223> OTHER INFORMATION: oligonucleotide motif sequence

<400> SEQUENCE: 82
actataacag tctac                                                15

<210> SEQ ID NO 83
<211> LENGTH: 18
<212> TYPE: DNA
<213> ORGANISM: Artificial
<220> FEATURE:
<223> OTHER INFORMATION: oligonucleotide motif sequence

<400> SEQUENCE: 83
tgcccaaaca tattttca                                             18

<210> SEQ ID NO 84
<211> LENGTH: 19
<212> TYPE: DNA
<213> ORGANISM: Artificial
<220> FEATURE:
<223> OTHER INFORMATION: oligonucleotide motif sequence

<400> SEQUENCE: 84
ctactacata atataaaca                                            19

<210> SEQ ID NO 85
<211> LENGTH: 17
<212> TYPE: DNA
<213> ORGANISM: Artificial
<220> FEATURE:
<223> OTHER INFORMATION: oligonucleotide motif sequence

<400> SEQUENCE: 85
gtcatacaca actacaa                                              17

<210> SEQ ID NO 86
<211> LENGTH: 17
<212> TYPE: DNA
<213> ORGANISM: Artificial
<220> FEATURE:
<223> OTHER INFORMATION: oligonucleotide motif sequence
```

```
<400> SEQUENCE: 86
tcgtttttcc atattat                                                    17

<210> SEQ ID NO 87
<211> LENGTH: 20
<212> TYPE: DNA
<213> ORGANISM: Artificial
<220> FEATURE:
<223> OTHER INFORMATION: oligonucleotide motif sequence

<400> SEQUENCE: 87
atactacttt taatttaata                                                 20

<210> SEQ ID NO 88
<211> LENGTH: 20
<212> TYPE: DNA
<213> ORGANISM: Artificial
<220> FEATURE:
<223> OTHER INFORMATION: oligonucleotide motif sequence

<400> SEQUENCE: 88
ctcatttcac tcacttaaat                                                 20

<210> SEQ ID NO 89
<211> LENGTH: 16
<212> TYPE: DNA
<213> ORGANISM: Artificial
<220> FEATURE:
<223> OTHER INFORMATION: oligonucleotide motif sequence

<400> SEQUENCE: 89
tatgaaacca aatcct                                                     16

<210> SEQ ID NO 90
<211> LENGTH: 17
<212> TYPE: DNA
<213> ORGANISM: Artificial
<220> FEATURE:
<223> OTHER INFORMATION: oligonucleotide motif sequence

<400> SEQUENCE: 90
catagccatc ttcttta                                                    17

<210> SEQ ID NO 91
<211> LENGTH: 15
<212> TYPE: DNA
<213> ORGANISM: Artificial
<220> FEATURE:
<223> OTHER INFORMATION: oligonucleotide motif sequence

<400> SEQUENCE: 91
caacacgtac cccta                                                      15

<210> SEQ ID NO 92
<211> LENGTH: 16
<212> TYPE: DNA
<213> ORGANISM: Artificial
<220> FEATURE:
<223> OTHER INFORMATION: oligonucleotide motif sequence

<400> SEQUENCE: 92
agtcacttct attact                                                     16

<210> SEQ ID NO 93
```

```
<211> LENGTH: 19
<212> TYPE: DNA
<213> ORGANISM: Artificial
<220> FEATURE:
<223> OTHER INFORMATION: oligonucleotide motif sequence

<400> SEQUENCE: 93
cttttcttca tacactata                                                  19

<210> SEQ ID NO 94
<211> LENGTH: 16
<212> TYPE: DNA
<213> ORGANISM: Artificial
<220> FEATURE:
<223> OTHER INFORMATION: oligonucleotide motif sequence

<400> SEQUENCE: 94
accccactta acccaa                                                     16

<210> SEQ ID NO 95
<211> LENGTH: 18
<212> TYPE: DNA
<213> ORGANISM: Artificial
<220> FEATURE:
<223> OTHER INFORMATION: oligonucleotide motif sequence

<400> SEQUENCE: 95
acagaaatcc tattccca                                                   18

<210> SEQ ID NO 96
<211> LENGTH: 17
<212> TYPE: DNA
<213> ORGANISM: Artificial
<220> FEATURE:
<223> OTHER INFORMATION: oligonucleotide motif sequence

<400> SEQUENCE: 96
ctacttgcca caatccc                                                    17

<210> SEQ ID NO 97
<211> LENGTH: 16
<212> TYPE: DNA
<213> ORGANISM: Artificial
<220> FEATURE:
<223> OTHER INFORMATION: oligonucleotide motif sequence

<400> SEQUENCE: 97
attcagaccc ttacaa                                                     16

<210> SEQ ID NO 98
<211> LENGTH: 16
<212> TYPE: DNA
<213> ORGANISM: Artificial
<220> FEATURE:
<223> OTHER INFORMATION: oligonucleotide motif sequence

<400> SEQUENCE: 98
cattactcac accttt                                                     16

<210> SEQ ID NO 99
<211> LENGTH: 17
<212> TYPE: DNA
<213> ORGANISM: Artificial
<220> FEATURE:
<223> OTHER INFORMATION: oligonucleotide motif sequence
```

```
<400> SEQUENCE: 99
cccataagta cccatct                                                    17

<210> SEQ ID NO 100
<211> LENGTH: 16
<212> TYPE: DNA
<213> ORGANISM: Artificial
<220> FEATURE:
<223> OTHER INFORMATION: oligonucleotide motif sequence

<400> SEQUENCE: 100
atctatttgc tcccat                                                     16

<210> SEQ ID NO 101
<211> LENGTH: 16
<212> TYPE: DNA
<213> ORGANISM: Artificial
<220> FEATURE:
<223> OTHER INFORMATION: oligonucleotide motif sequence

<400> SEQUENCE: 101
ctctgtacca tctatt                                                     16

<210> SEQ ID NO 102
<211> LENGTH: 18
<212> TYPE: DNA
<213> ORGANISM: Artificial
<220> FEATURE:
<223> OTHER INFORMATION: oligonucleotide motif sequence

<400> SEQUENCE: 102
gcaaataaca aaatctct                                                   18

<210> SEQ ID NO 103
<211> LENGTH: 17
<212> TYPE: DNA
<213> ORGANISM: Artificial
<220> FEATURE:
<223> OTHER INFORMATION: oligonucleotide motif sequence

<400> SEQUENCE: 103 cctttatct tcattct                                                     17

<210> SEQ ID NO 104
<211> LENGTH: 18
<212> TYPE: DNA
<213> ORGANISM: Artificial
<220> FEATURE:
<223> OTHER INFORMATION: oligonucleotide motif sequence

<400> SEQUENCE: 104
tgacaatttc aaaactca                                                   18

<210> SEQ ID NO 105
<211> LENGTH: 15
<212> TYPE: DNA
<213> ORGANISM: Artificial
<220> FEATURE:
<223> OTHER INFORMATION: oligonucleotide motif sequence

<400> SEQUENCE: 105
cctagtttac accct                                                      15

<210> SEQ ID NO 106
```

```
<211> LENGTH: 16
<212> TYPE: DNA
<213> ORGANISM: Artificial
<220> FEATURE:
<223> OTHER INFORMATION: oligonucleotide motif sequence

<400> SEQUENCE: 106
tttcctagtt cacatt                                                       16

<210> SEQ ID NO 107
<211> LENGTH: 16
<212> TYPE: DNA
<213> ORGANISM: Artificial
<220> FEATURE:
<223> OTHER INFORMATION: oligonucleotide motif sequence

<400> SEQUENCE: 107
aactgcaatc actcat                                                       16

<210> SEQ ID NO 108
<211> LENGTH: 16
<212> TYPE: DNA
<213> ORGANISM: Artificial
<220> FEATURE:
<223> OTHER INFORMATION: oligonucleotide motif sequence

<400> SEQUENCE: 108
atctacagtt ttccac                                                       16

<210> SEQ ID NO 109
<211> LENGTH: 16
<212> TYPE: DNA
<213> ORGANISM: Artificial
<220> FEATURE:
<223> OTHER INFORMATION: oligonucleotide motif sequence

<400> SEQUENCE: 109
gcttctctca tctaca                                                       16

<210> SEQ ID NO 110
<211> LENGTH: 17
<212> TYPE: DNA
<213> ORGANISM: Artificial
<220> FEATURE:
<223> OTHER INFORMATION: oligonucleotide motif sequence

<400> SEQUENCE: 110
agaatacttc tctcctt                                                      17

<210> SEQ ID NO 111
<211> LENGTH: 15
<212> TYPE: DNA
<213> ORGANISM: Artificial
<220> FEATURE:
<223> OTHER INFORMATION: oligonucleotide motif sequence

<400> SEQUENCE: 111
tcacatacgt tcttc                                                        15

<210> SEQ ID NO 112
<211> LENGTH: 17
<212> TYPE: DNA
<213> ORGANISM: Artificial
<220> FEATURE:
<223> OTHER INFORMATION: oligonucleotide motif sequence
```

```
<400> SEQUENCE: 112
taaaatgtcc acatatc                                                    17

<210> SEQ ID NO 113
<211> LENGTH: 19
<212> TYPE: DNA
<213> ORGANISM: Artificial
<220> FEATURE:
<223> OTHER INFORMATION: oligonucleotide motif sequence

<400> SEQUENCE: 113
gatttctaaa cccttcaat                                                  19

<210> SEQ ID NO 114
<211> LENGTH: 18
<212> TYPE: DNA
<213> ORGANISM: Artificial
<220> FEATURE:
<223> OTHER INFORMATION: oligonucleotide motif sequence

<400> SEQUENCE: 114
tacatttcca attttata                                                   18

<210> SEQ ID NO 115
<211> LENGTH: 17
<212> TYPE: DNA
<213> ORGANISM: Artificial
<220> FEATURE:
<223> OTHER INFORMATION: oligonucleotide motif sequence

<400> SEQUENCE: 115
tagctttctt tattttc                                                    17

<210> SEQ ID NO 116
<211> LENGTH: 16
<212> TYPE: DNA
<213> ORGANISM: Artificial
<220> FEATURE:
<223> OTHER INFORMATION: oligonucleotide motif sequence

<400> SEQUENCE: 116
tagtctactc tcctaa                                                     16

<210> SEQ ID NO 117
<211> LENGTH: 16
<212> TYPE: DNA
<213> ORGANISM: Artificial
<220> FEATURE:
<223> OTHER INFORMATION: oligonucleotide motif sequence

<400> SEQUENCE: 117
tatgcctaca atatac                                                     16

<210> SEQ ID NO 118
<211> LENGTH: 19
<212> TYPE: DNA
<213> ORGANISM: Artificial
<220> FEATURE:
<223> OTHER INFORMATION: oligonucleotide motif sequence

<400> SEQUENCE: 118
atgaacaaca actcccatt                                                  19

<210> SEQ ID NO 119
```

```
<211> LENGTH: 18
<212> TYPE: DNA
<213> ORGANISM: Artificial
<220> FEATURE:
<223> OTHER INFORMATION: oligonucleotide motif sequence

<400> SEQUENCE: 119
ccatctacct tataacat                                              18

<210> SEQ ID NO 120
<211> LENGTH: 17
<212> TYPE: DNA
<213> ORGANISM: Artificial
<220> FEATURE:
<223> OTHER INFORMATION: oligonucleotide motif sequence

<400> SEQUENCE: 120
cctgcattta ctatcca                                               17

<210> SEQ ID NO 121
<211> LENGTH: 16
<212> TYPE: DNA
<213> ORGANISM: Artificial
<220> FEATURE:
<223> OTHER INFORMATION: oligonucleotide motif sequence

<400> SEQUENCE: 121
attagaaccc tttaca                                                16

<210> SEQ ID NO 122
<211> LENGTH: 16
<212> TYPE: DNA
<213> ORGANISM: Artificial
<220> FEATURE:
<223> OTHER INFORMATION: oligonucleotide motif sequence

<400> SEQUENCE: 122
atagaatcct tacata                                                16

<210> SEQ ID NO 123
<211> LENGTH: 16
<212> TYPE: DNA
<213> ORGANISM: Artificial
<220> FEATURE:
<223> OTHER INFORMATION: oligonucleotide motif sequence

<400> SEQUENCE: 123
ctgattttac tccaat                                                16

<210> SEQ ID NO 124
<211> LENGTH: 16
<212> TYPE: DNA
<213> ORGANISM: Artificial
<220> FEATURE:
<223> OTHER INFORMATION: oligonucleotide motif sequence

<400> SEQUENCE: 124
ctaaatgatt cccaat                                                16

<210> SEQ ID NO 125
<211> LENGTH: 17
<212> TYPE: DNA
<213> ORGANISM: Artificial
<220> FEATURE:
<223> OTHER INFORMATION: oligonucleotide motif sequence
```

```
<400> SEQUENCE: 125
tacttgatct tcctaca                                                 17

<210> SEQ ID NO 126
<211> LENGTH: 18
<212> TYPE: DNA
<213> ORGANISM: Artificial
<220> FEATURE:
<223> OTHER INFORMATION: oligonucleotide motif sequence

<400> SEQUENCE: 126
tcatcatata aactccat                                                18

<210> SEQ ID NO 127
<211> LENGTH: 16
<212> TYPE: DNA
<213> ORGANISM: Artificial
<220> FEATURE:
<223> OTHER INFORMATION: oligonucleotide motif sequence

<400> SEQUENCE: 127
caccatgttc tttaca                                                  16

<210> SEQ ID NO 128
<211> LENGTH: 18
<212> TYPE: DNA
<213> ORGANISM: Artificial
<220> FEATURE:
<223> OTHER INFORMATION: oligonucleotide motif sequence

<400> SEQUENCE: 128
ctactcttca tctcaaca                                                18

<210> SEQ ID NO 129
<211> LENGTH: 16
<212> TYPE: DNA
<213> ORGANISM: Artificial
<220> FEATURE:
<223> OTHER INFORMATION: oligonucleotide motif sequence

<400> SEQUENCE: 129
caacaactca tttcat                                                  16

<210> SEQ ID NO 130
<211> LENGTH: 17
<212> TYPE: DNA
<213> ORGANISM: Artificial
<220> FEATURE:
<223> OTHER INFORMATION: oligonucleotide motif sequence

<400> SEQUENCE: 130
cctctttgaa caaacca                                                 17

<210> SEQ ID NO 131
<211> LENGTH: 16
<212> TYPE: DNA
<213> ORGANISM: Artificial
<220> FEATURE:
<223> OTHER INFORMATION: oligonucleotide motif sequence

<400> SEQUENCE: 131 cctttactc tacctt                                                   16

<210> SEQ ID NO 132
```

```
<211> LENGTH: 17
<212> TYPE: DNA
<213> ORGANISM: Artificial
<220> FEATURE:
<223> OTHER INFORMATION: oligonucleotide motif sequence

<400> SEQUENCE: 132
tcagcttatt tacatta                                                    17

<210> SEQ ID NO 133
<211> LENGTH: 17
<212> TYPE: DNA
<213> ORGANISM: Artificial
<220> FEATURE:
<223> OTHER INFORMATION: oligonucleotide motif sequence

<400> SEQUENCE: 133
tgctttacat tcacaac                                                    17

<210> SEQ ID NO 134
<211> LENGTH: 16
<212> TYPE: DNA
<213> ORGANISM: Artificial
<220> FEATURE:
<223> OTHER INFORMATION: oligonucleotide motif sequence

<400> SEQUENCE: 134
ggcttttacc ttacat                                                     16

<210> SEQ ID NO 135
<211> LENGTH: 18
<212> TYPE: DNA
<213> ORGANISM: Artificial
<220> FEATURE:
<223> OTHER INFORMATION: oligonucleotide motif sequence

<400> SEQUENCE: 135
acacgatttc atacaatc                                                   18

<210> SEQ ID NO 136
<211> LENGTH: 17
<212> TYPE: DNA
<213> ORGANISM: Artificial
<220> FEATURE:
<223> OTHER INFORMATION: oligonucleotide motif sequence

<400> SEQUENCE: 136
atgttttcaa cttcaac                                                    17

<210> SEQ ID NO 137
<211> LENGTH: 17
<212> TYPE: DNA
<213> ORGANISM: Artificial
<220> FEATURE:
<223> OTHER INFORMATION: oligonucleotide motif sequence

<400> SEQUENCE: 137
gaatacccat ttcaccc                                                    17

<210> SEQ ID NO 138
<211> LENGTH: 17
<212> TYPE: DNA
<213> ORGANISM: Artificial
<220> FEATURE:
<223> OTHER INFORMATION: oligonucleotide motif sequence
```

<400> SEQUENCE: 138
cctatgtcta aattttc                                                      17

<210> SEQ ID NO 139
<211> LENGTH: 18
<212> TYPE: DNA
<213> ORGANISM: Artificial
<220> FEATURE:
<223> OTHER INFORMATION: oligonucleotide motif sequence

<400> SEQUENCE: 139
tttatctatc tatcttat                                                     18

<210> SEQ ID NO 140
<211> LENGTH: 16
<212> TYPE: DNA
<213> ORGANISM: Artificial
<220> FEATURE:
<223> OTHER INFORMATION: oligonucleotide motif sequence

<400> SEQUENCE: 140
cactgtcatt acatta                                                       16

<210> SEQ ID NO 141
<211> LENGTH: 17
<212> TYPE: DNA
<213> ORGANISM: Artificial
<220> FEATURE:
<223> OTHER INFORMATION: oligonucleotide motif sequence

<400> SEQUENCE: 141
cctgaactcc tacaatc                                                      17

<210> SEQ ID NO 142
<211> LENGTH: 16
<212> TYPE: DNA
<213> ORGANISM: Artificial
<220> FEATURE:
<223> OTHER INFORMATION: oligonucleotide motif sequence

<400> SEQUENCE: 142
tccctaaaat tactta                                                       16

<210> SEQ ID NO 143
<211> LENGTH: 19
<212> TYPE: DNA
<213> ORGANISM: Artificial
<220> FEATURE:
<223> OTHER INFORMATION: oligonucleotide motif sequence

<400> SEQUENCE: 143
attaattccc taaaattac                                                    19

<210> SEQ ID NO 144
<211> LENGTH: 15
<212> TYPE: DNA
<213> ORGANISM: Artificial
<220> FEATURE:
<223> OTHER INFORMATION: oligonucleotide motif sequence

<400> SEQUENCE: 144
tcggctctaa ccaca                                                        15

<210> SEQ ID NO 145

```
<211> LENGTH: 17
<212> TYPE: DNA
<213> ORGANISM: Artificial
<220> FEATURE:
<223> OTHER INFORMATION: oligonucleotide motif sequence

<400> SEQUENCE: 145
tacatgaaac acatact                                                    17

<210> SEQ ID NO 146
<211> LENGTH: 17
<212> TYPE: DNA
<213> ORGANISM: Artificial
<220> FEATURE:
<223> OTHER INFORMATION: oligonucleotide motif sequence

<400> SEQUENCE: 146
catttgacct ttatcaa                                                    17

<210> SEQ ID NO 147
<211> LENGTH: 17
<212> TYPE: DNA
<213> ORGANISM: Artificial
<220> FEATURE:
<223> OTHER INFORMATION: oligonucleotide motif sequence

<400> SEQUENCE: 147
tccctaaaac attcata                                                    17

<210> SEQ ID NO 148
<211> LENGTH: 17
<212> TYPE: DNA
<213> ORGANISM: Artificial
<220> FEATURE:
<223> OTHER INFORMATION: oligonucleotide motif sequence

<400> SEQUENCE: 148
attttgcaca cctcaca                                                    17

<210> SEQ ID NO 149
<211> LENGTH: 16
<212> TYPE: DNA
<213> ORGANISM: Artificial
<220> FEATURE:
<223> OTHER INFORMATION: oligonucleotide motif sequence

<400> SEQUENCE: 149
ttaataccta ctcttc                                                     16

<210> SEQ ID NO 150
<211> LENGTH: 17
<212> TYPE: DNA
<213> ORGANISM: Artificial
<220> FEATURE:
<223> OTHER INFORMATION: oligonucleotide motif sequence

<400> SEQUENCE: 150
caaagctacc aaaatct                                                    17

<210> SEQ ID NO 151
<211> LENGTH: 18
<212> TYPE: DNA
<213> ORGANISM: Artificial
<220> FEATURE:
<223> OTHER INFORMATION: oligonucleotide motif sequence
```

```
<400> SEQUENCE: 151
tgtatttcaa atctcaaa                                          18

<210> SEQ ID NO 152
<211> LENGTH: 17
<212> TYPE: DNA
<213> ORGANISM: Artificial
<220> FEATURE:
<223> OTHER INFORMATION: oligonucleotide motif sequence

<400> SEQUENCE: 152
ctgtatttca aatctca                                           17

<210> SEQ ID NO 153
<211> LENGTH: 17
<212> TYPE: DNA
<213> ORGANISM: Artificial
<220> FEATURE:
<223> OTHER INFORMATION: oligonucleotide motif sequence

<400> SEQUENCE: 153
cccacatcct tttacac                                           17

<210> SEQ ID NO 154
<211> LENGTH: 16
<212> TYPE: DNA
<213> ORGANISM: Artificial
<220> FEATURE:
<223> OTHER INFORMATION: oligonucleotide motif sequence

<400> SEQUENCE: 154
cccacatcct tttaca                                            16

<210> SEQ ID NO 155
<211> LENGTH: 17
<212> TYPE: DNA
<213> ORGANISM: Artificial
<220> FEATURE:
<223> OTHER INFORMATION: oligonucleotide motif sequence

<400> SEQUENCE: 155
atgtactaat tttcttt                                           17

<210> SEQ ID NO 156
<211> LENGTH: 16
<212> TYPE: DNA
<213> ORGANISM: Artificial
<220> FEATURE:
<223> OTHER INFORMATION: oligonucleotide motif sequence

<400> SEQUENCE: 156
ccacactgta tcttca                                            16

<210> SEQ ID NO 157
<211> LENGTH: 16
<212> TYPE: DNA
<213> ORGANISM: Artificial
<220> FEATURE:
<223> OTHER INFORMATION: oligonucleotide motif sequence

<400> SEQUENCE: 157
agcatacaaa atatcc                                            16

<210> SEQ ID NO 158
```

```
<211> LENGTH: 18
<212> TYPE: DNA
<213> ORGANISM: Artificial
<220> FEATURE:
<223> OTHER INFORMATION: oligonucleotide motif sequence

<400> SEQUENCE: 158 aaatcattttt ccaactct                                                    18

<210> SEQ ID NO 159
<211> LENGTH: 17
<212> TYPE: DNA
<213> ORGANISM: Artificial
<220> FEATURE:
<223> OTHER INFORMATION: oligonucleotide motif sequence

<400> SEQUENCE: 159
aaccatgttt ccctaca                                                      17

<210> SEQ ID NO 160
<211> LENGTH: 16
<212> TYPE: DNA
<213> ORGANISM: Artificial
<220> FEATURE:
<223> OTHER INFORMATION: oligonucleotide motif sequence

<400> SEQUENCE: 160
ttcctatcat aaccat                                                       16

<210> SEQ ID NO 161
<211> LENGTH: 16
<212> TYPE: DNA
<213> ORGANISM: Artificial
<220> FEATURE:
<223> OTHER INFORMATION: oligonucleotide motif sequence

<400> SEQUENCE: 161
attcttgttc ctatca                                                       16

<210> SEQ ID NO 162
<211> LENGTH: 16
<212> TYPE: DNA
<213> ORGANISM: Artificial
<220> FEATURE:
<223> OTHER INFORMATION: oligonucleotide motif sequence

<400> SEQUENCE: 162
ttgaataagt ggatgt                                                       16

<210> SEQ ID NO 163
<211> LENGTH: 20
<212> TYPE: DNA
<213> ORGANISM: Artificial
<220> FEATURE:
<223> OTHER INFORMATION: oligonucleotide motif sequence

<400> SEQUENCE: 163
ccaaatctta taataactac                                                   20

<210> SEQ ID NO 164
<211> LENGTH: 16
<212> TYPE: DNA
<213> ORGANISM: Artificial
<220> FEATURE:
<223> OTHER INFORMATION: oligonucleotide motif sequence
```

```
<400> SEQUENCE: 164
cgtaaactac ccctat                                                    16

<210> SEQ ID NO 165
<211> LENGTH: 16
<212> TYPE: DNA
<213> ORGANISM: Artificial
<220> FEATURE:
<223> OTHER INFORMATION: oligonucleotide motif sequence

<400> SEQUENCE: 165
tgaggtcctg cactgg                                                    16

<210> SEQ ID NO 166
<211> LENGTH: 16
<212> TYPE: DNA
<213> ORGANISM: Artificial
<220> FEATURE:
<223> OTHER INFORMATION: oligonucleotide motif sequence

<400> SEQUENCE: 166
gtcagtatcc cagtgt                                                    16

<210> SEQ ID NO 167
<211> LENGTH: 18
<212> TYPE: DNA
<213> ORGANISM: homo sapiens

<400> SEQUENCE: 167
gtgttgttta tggagctt                                                  18

<210> SEQ ID NO 168
<211> LENGTH: 19
<212> TYPE: DNA
<213> ORGANISM: homo sapiens

<400> SEQUENCE: 168 agtgttttaaa tgtttaaag                                                19

<210> SEQ ID NO 169
<211> LENGTH: 18
<212> TYPE: DNA
<213> ORGANISM: homo sapiens

<400> SEQUENCE: 169
agaaatttaa ggatggaa                                                  18

<210> SEQ ID NO 170
<211> LENGTH: 19
<212> TYPE: DNA
<213> ORGANISM: homo sapiens

<400> SEQUENCE: 170
gtggtgattg tatttatca                                                 19

<210> SEQ ID NO 171
<211> LENGTH: 18
<212> TYPE: DNA
<213> ORGANISM: homo sapiens

<400> SEQUENCE: 171
gttaaaaggt agaatgta                                                  18
```

```
<210> SEQ ID NO 172
<211> LENGTH: 19
<212> TYPE: DNA
<213> ORGANISM: homo sapiens

<400> SEQUENCE: 172
aatgttaatg tttgaaagc                                                  19

<210> SEQ ID NO 173
<211> LENGTH: 18
<212> TYPE: DNA
<213> ORGANISM: homo sapiens

<400> SEQUENCE: 173
aaaaggtagt ttgaacat                                                   18

<210> SEQ ID NO 174
<211> LENGTH: 18
<212> TYPE: DNA
<213> ORGANISM: homo sapiens

<400> SEQUENCE: 174
taattagtgt aaatatct                                                   18

<210> SEQ ID NO 175
<211> LENGTH: 17
<212> TYPE: DNA
<213> ORGANISM: homo sapiens

<400> SEQUENCE: 175
tggttaatag tgaagtc                                                    17

<210> SEQ ID NO 176
<211> LENGTH: 18
<212> TYPE: DNA
<213> ORGANISM: homo sapiens

<400> SEQUENCE: 176
atatgtggaa tttacagg                                                   18

<210> SEQ ID NO 177
<211> LENGTH: 16
<212> TYPE: DNA
<213> ORGANISM: homo sapiens

<400> SEQUENCE: 177
ggaagagata gtgtca                                                     16

<210> SEQ ID NO 178
<211> LENGTH: 18
<212> TYPE: DNA
<213> ORGANISM: homo sapiens

<400> SEQUENCE: 178 tagggggtatg tgttattg                                                  18

<210> SEQ ID NO 179
<211> LENGTH: 18
<212> TYPE: DNA
<213> ORGANISM: homo sapiens

<400> SEQUENCE: 179
tagaattaaa gttgaaac                                                   18
```

<210> SEQ ID NO 180
<211> LENGTH: 17
<212> TYPE: DNA
<213> ORGANISM: homo sapiens

<400> SEQUENCE: 180
taatgtgtaa ggaagct                                                    17

<210> SEQ ID NO 181
<211> LENGTH: 20
<212> TYPE: DNA
<213> ORGANISM: homo sapiens

<400> SEQUENCE: 181
taagtagaaa taataaagat                                                 20

<210> SEQ ID NO 182
<211> LENGTH: 18
<212> TYPE: DNA
<213> ORGANISM: homo sapiens

<400> SEQUENCE: 182
tattgtagtt gaagggat                                                   18

<210> SEQ ID NO 183
<211> LENGTH: 18
<212> TYPE: DNA
<213> ORGANISM: homo sapiens

<400> SEQUENCE: 183
gattatggaa agtaggaa                                                   18

<210> SEQ ID NO 184
<211> LENGTH: 18
<212> TYPE: DNA
<213> ORGANISM: homo sapiens

<400> SEQUENCE: 184
ggaaagtagg aaatcaag                                                   18

<210> SEQ ID NO 185
<211> LENGTH: 19
<212> TYPE: DNA
<213> ORGANISM: homo sapiens

<400> SEQUENCE: 185
ttatttgagt gtatatgtc                                                  19

<210> SEQ ID NO 186
<211> LENGTH: 19
<212> TYPE: DNA
<213> ORGANISM: homo sapiens

<400> SEQUENCE: 186
atggaagata agtgaagaa                                                  19

<210> SEQ ID NO 187
<211> LENGTH: 17
<212> TYPE: DNA
<213> ORGANISM: homo sapiens

<400> SEQUENCE: 187
ggtagtgtga agactga                                                  17

<210> SEQ ID NO 188
<211> LENGTH: 18
<212> TYPE: DNA
<213> ORGANISM: homo sapiens

<400> SEQUENCE: 188
ttggtaataa aagagaag                                                 18

<210> SEQ ID NO 189
<211> LENGTH: 16
<212> TYPE: DNA
<213> ORGANISM: homo sapiens

<400> SEQUENCE: 189
ggtaaagtat ggacac                                                   16

<210> SEQ ID NO 190
<211> LENGTH: 16
<212> TYPE: DNA
<213> ORGANISM: homo sapiens

<400> SEQUENCE: 190
atgaggatag cgaaga                                                   16

<210> SEQ ID NO 191
<211> LENGTH: 19
<212> TYPE: DNA
<213> ORGANISM: homo sapiens

<400> SEQUENCE: 191
gaagaagata ttaaagatt                                                19

<210> SEQ ID NO 192
<211> LENGTH: 18
<212> TYPE: DNA
<213> ORGANISM: homo sapiens

<400> SEQUENCE: 192
ataaaattgt ggtcttgg                                                 18

<210> SEQ ID NO 193
<211> LENGTH: 17
<212> TYPE: DNA
<213> ORGANISM: homo sapiens

<400> SEQUENCE: 193
tgagagtatg aacttgg                                                  17

<210> SEQ ID NO 194
<211> LENGTH: 18
<212> TYPE: DNA
<213> ORGANISM: homo sapiens

<400> SEQUENCE: 194
tgggaaatgt agtatgat                                                 18

<210> SEQ ID NO 195
<211> LENGTH: 17
<212> TYPE: DNA

```
<213> ORGANISM: homo sapiens

<400> SEQUENCE: 195
ggtgagatat gtaaaca                                                 17

<210> SEQ ID NO 196
<211> LENGTH: 19
<212> TYPE: DNA
<213> ORGANISM: homo sapiens

<400> SEQUENCE: 196
ttatatatgg gtgtgatgg                                               19

<210> SEQ ID NO 197
<211> LENGTH: 17
<212> TYPE: DNA
<213> ORGANISM: homo sapiens

<400> SEQUENCE: 197
tgatagaggt ttcagga                                                 17

<210> SEQ ID NO 198
<211> LENGTH: 20
<212> TYPE: DNA
<213> ORGANISM: homo sapiens

<400> SEQUENCE: 198
tggaaagaat tagaagaaaa                                              20

<210> SEQ ID NO 199
<211> LENGTH: 19
<212> TYPE: DNA
<213> ORGANISM: homo sapiens

<400> SEQUENCE: 199
gaatatgaag gaaattagg                                               19

<210> SEQ ID NO 200
<211> LENGTH: 17
<212> TYPE: DNA
<213> ORGANISM: homo sapiens

<400> SEQUENCE: 200
aggatagttg tcaaata                                                 17

<210> SEQ ID NO 201
<211> LENGTH: 17
<212> TYPE: DNA
<213> ORGANISM: homo sapiens

<400> SEQUENCE: 201
ataatagagg actgatg                                                 17

<210> SEQ ID NO 202
<211> LENGTH: 19
<212> TYPE: DNA
<213> ORGANISM: homo sapiens

<400> SEQUENCE: 202
ttaattttgt aatggagac                                               19

<210> SEQ ID NO 203
<211> LENGTH: 18
```

```
<212> TYPE: DNA
<213> ORGANISM: homo sapiens

<400> SEQUENCE: 203
atttggaatg aaatacta                                                  18

<210> SEQ ID NO 204
<211> LENGTH: 18
<212> TYPE: DNA
<213> ORGANISM: homo sapiens

<400> SEQUENCE: 204
tagattatga tggattca                                                  18

<210> SEQ ID NO 205
<211> LENGTH: 16
<212> TYPE: DNA
<213> ORGANISM: homo sapiens

<400> SEQUENCE: 205
ttaggggatc atgtaa                                                    16

<210> SEQ ID NO 206
<211> LENGTH: 18
<212> TYPE: DNA
<213> ORGANISM: homo sapiens

<400> SEQUENCE: 206
gtgaaaattt ggtaacat                                                  18

<210> SEQ ID NO 207
<211> LENGTH: 16
<212> TYPE: DNA
<213> ORGANISM: homo sapiens

<400> SEQUENCE: 207
tggattggct gtgttt                                                    16

<210> SEQ ID NO 208
<211> LENGTH: 18
<212> TYPE: DNA
<213> ORGANISM: homo sapiens

<400> SEQUENCE: 208
aggagggtaa aataaact                                                  18

<210> SEQ ID NO 209
<211> LENGTH: 19
<212> TYPE: DNA
<213> ORGANISM: homo sapiens

<400> SEQUENCE: 209
gtatagtttg aagtgatgc                                                 19

<210> SEQ ID NO 210
<211> LENGTH: 18
<212> TYPE: DNA
<213> ORGANISM: homo sapiens

<400> SEQUENCE: 210
ttgaattagg aaaaggga                                                  18

<210> SEQ ID NO 211
```

```
<211> LENGTH: 19
<212> TYPE: DNA
<213> ORGANISM: homo sapiens

<400> SEQUENCE: 211
ggaagagtga tagttgttt                                                  19

<210> SEQ ID NO 212
<211> LENGTH: 18
<212> TYPE: DNA
<213> ORGANISM: homo sapiens

<400> SEQUENCE: 212
ttgaggtaga gatgtctg                                                   18

<210> SEQ ID NO 213
<211> LENGTH: 18
<212> TYPE: DNA
<213> ORGANISM: homo sapiens

<400> SEQUENCE: 213
tatgttaaag tggaatca                                                   18

<210> SEQ ID NO 214
<211> LENGTH: 18
<212> TYPE: DNA
<213> ORGANISM: homo sapiens

<400> SEQUENCE: 214
tggggaattg ttgggtat                                                   18

<210> SEQ ID NO 215
<211> LENGTH: 20
<212> TYPE: DNA
<213> ORGANISM: homo sapiens

<400> SEQUENCE: 215
agtatattta aatgtgaata                                                 20

<210> SEQ ID NO 216
<211> LENGTH: 18
<212> TYPE: DNA
<213> ORGANISM: homo sapiens

<400> SEQUENCE: 216
gtagtttagg gtctttgt                                                   18

<210> SEQ ID NO 217
<211> LENGTH: 20
<212> TYPE: DNA
<213> ORGANISM: homo sapiens

<400> SEQUENCE: 217
tttgaagtta tgaagtatat                                                 20

<210> SEQ ID NO 218
<211> LENGTH: 20
<212> TYPE: DNA
<213> ORGANISM: homo sapiens

<400> SEQUENCE: 218
gaggaaatga gttatatgta                                                 20
```

```
<210> SEQ ID NO 219
<211> LENGTH: 18
<212> TYPE: DNA
<213> ORGANISM: homo sapiens

<400> SEQUENCE: 219
atatgtagta agttctga                                                 18

<210> SEQ ID NO 220
<211> LENGTH: 20
<212> TYPE: DNA
<213> ORGANISM: homo sapiens

<400> SEQUENCE: 220
attgtttgaa gtatagaaaa                                               20

<210> SEQ ID NO 221
<211> LENGTH: 20
<212> TYPE: DNA
<213> ORGANISM: homo sapiens

<400> SEQUENCE: 221
tggtttgtaa attgggtgtt                                               20

<210> SEQ ID NO 222
<211> LENGTH: 17
<212> TYPE: DNA
<213> ORGANISM: homo sapiens

<400> SEQUENCE: 222
attgggtgtt atctaag                                                  17

<210> SEQ ID NO 223
<211> LENGTH: 20
<212> TYPE: DNA
<213> ORGANISM: homo sapiens

<400> SEQUENCE: 223
atggatttaa agaagaaata                                               20

<210> SEQ ID NO 224
<211> LENGTH: 17
<212> TYPE: DNA
<213> ORGANISM: homo sapiens

<400> SEQUENCE: 224
agttaaaagt atgtgga                                                  17

<210> SEQ ID NO 225
<211> LENGTH: 18
<212> TYPE: DNA
<213> ORGANISM: homo sapiens

<400> SEQUENCE: 225
aattttggtg ataaacat                                                 18

<210> SEQ ID NO 226
<211> LENGTH: 18
<212> TYPE: DNA
<213> ORGANISM: homo sapiens

<400> SEQUENCE: 226
tatatggtag tatttcag                                                 18
```

```
<210> SEQ ID NO 227
<211> LENGTH: 18
<212> TYPE: DNA
<213> ORGANISM: homo sapiens

<400> SEQUENCE: 227
tatagttttg tgaaatct                                                 18

<210> SEQ ID NO 228
<211> LENGTH: 19
<212> TYPE: DNA
<213> ORGANISM: homo sapiens

<400> SEQUENCE: 228
tgggttgaga ttaatttcg                                                19

<210> SEQ ID NO 229
<211> LENGTH: 20
<212> TYPE: DNA
<213> ORGANISM: homo sapiens

<400> SEQUENCE: 229
tgggaatagg ataggtatta                                               20

<210> SEQ ID NO 230
<211> LENGTH: 18
<212> TYPE: DNA
<213> ORGANISM: homo sapiens

<400> SEQUENCE: 230
atggtaaaga tatgttac                                                 18

<210> SEQ ID NO 231
<211> LENGTH: 17
<212> TYPE: DNA
<213> ORGANISM: homo sapiens

<400> SEQUENCE: 231
agattggtat gattaaa                                                  17

<210> SEQ ID NO 232
<211> LENGTH: 17
<212> TYPE: DNA
<213> ORGANISM: homo sapiens

<400> SEQUENCE: 232
taagattttg gtagcat                                                  17

<210> SEQ ID NO 233
<211> LENGTH: 19
<212> TYPE: DNA
<213> ORGANISM: homo sapiens

<400> SEQUENCE: 233
agagattaat ttatttgag                                                19

<210> SEQ ID NO 234
<211> LENGTH: 18
<212> TYPE: DNA
<213> ORGANISM: homo sapiens

<400> SEQUENCE: 234
tgagatttga aataagaa                                                 18
```

```
<210> SEQ ID NO 235
<211> LENGTH: 17
<212> TYPE: DNA
<213> ORGANISM: homo sapiens

<400> SEQUENCE: 235
tgagatttga aataaga                                                  17

<210> SEQ ID NO 236
<211> LENGTH: 20
<212> TYPE: DNA
<213> ORGANISM: homo sapiens

<400> SEQUENCE: 236
atttgaaata agaatagtat                                               20

<210> SEQ ID NO 237
<211> LENGTH: 18
<212> TYPE: DNA
<213> ORGANISM: homo sapiens

<400> SEQUENCE: 237
tatgaaaata ttagatac                                                 18

<210> SEQ ID NO 238
<211> LENGTH: 19
<212> TYPE: DNA
<213> ORGANISM: homo sapiens

<400> SEQUENCE: 238
ttgagatggt ggagtaaaa                                                19

<210> SEQ ID NO 239
<211> LENGTH: 17
<212> TYPE: DNA
<213> ORGANISM: homo sapiens

<400> SEQUENCE: 239
gagtaaaaag actgtta                                                  17

<210> SEQ ID NO 240
<211> LENGTH: 18
<212> TYPE: DNA
<213> ORGANISM: homo sapiens

<400> SEQUENCE: 240
aagtgattaa agttacta                                                 18

<210> SEQ ID NO 241
<211> LENGTH: 16
<212> TYPE: DNA
<213> ORGANISM: homo sapiens

<400> SEQUENCE: 241
aaaggtaata ttacta                                                   16

<210> SEQ ID NO 242
<211> LENGTH: 15
<212> TYPE: DNA
<213> ORGANISM: homo sapiens
```

```
<400> SEQUENCE: 242
gtagactgtt atagt                                            15

<210> SEQ ID NO 243
<211> LENGTH: 18
<212> TYPE: DNA
<213> ORGANISM: homo sapiens

<400> SEQUENCE: 243
tgaaaatatg tttgggca                                         18

<210> SEQ ID NO 244
<211> LENGTH: 19
<212> TYPE: DNA
<213> ORGANISM: homo sapiens

<400> SEQUENCE: 244
tgtttatatt atgtagtag                                        19

<210> SEQ ID NO 245
<211> LENGTH: 17
<212> TYPE: DNA
<213> ORGANISM: homo sapiens

<400> SEQUENCE: 245
ttgtagttgt gtatgac                                          17

<210> SEQ ID NO 246
<211> LENGTH: 17
<212> TYPE: DNA
<213> ORGANISM: homo sapiens

<400> SEQUENCE: 246
ataatatgga aaaacga                                          17

<210> SEQ ID NO 247
<211> LENGTH: 20
<212> TYPE: DNA
<213> ORGANISM: mus musclulus

<400> SEQUENCE: 247
tattaaatta aaagtagtat                                       20

<210> SEQ ID NO 248
<211> LENGTH: 20
<212> TYPE: DNA
<213> ORGANISM: mus musclulus

<400> SEQUENCE: 248
atttaagtga gtgaaatgag                                       20

<210> SEQ ID NO 249
<211> LENGTH: 16
<212> TYPE: DNA
<213> ORGANISM: mus musclulus

<400> SEQUENCE: 249
aggatttggt ttcata                                           16

<210> SEQ ID NO 250
<211> LENGTH: 17
<212> TYPE: DNA
```

```
<213> ORGANISM: mus musclulus

<400> SEQUENCE: 250
taaagaagat ggctatg                                          17

<210> SEQ ID NO 251
<211> LENGTH: 15
<212> TYPE: DNA
<213> ORGANISM: mus musclulus

<400> SEQUENCE: 251 tagggtacg tgttg                                             15

<210> SEQ ID NO 252
<211> LENGTH: 16
<212> TYPE: DNA
<213> ORGANISM: mus musclulus

<400> SEQUENCE: 252
agtaatagaa gtgact                                           16

<210> SEQ ID NO 253
<211> LENGTH: 19
<212> TYPE: DNA
<213> ORGANISM: mus musclulus

<400> SEQUENCE: 253
tatagtgtat gaagaaaag                                        19

<210> SEQ ID NO 254
<211> LENGTH: 16
<212> TYPE: DNA
<213> ORGANISM: mus musclulus

<400> SEQUENCE: 254
ttgggttaag tggggt                                           16

<210> SEQ ID NO 255
<211> LENGTH: 18
<212> TYPE: DNA
<213> ORGANISM: mus musclulus

<400> SEQUENCE: 255
tgggaatagg atttctgt                                         18

<210> SEQ ID NO 256
<211> LENGTH: 17
<212> TYPE: DNA
<213> ORGANISM: mus musclulus

<400> SEQUENCE: 256
gggattgtgg caagtag                                          17

<210> SEQ ID NO 257
<211> LENGTH: 16
<212> TYPE: DNA
<213> ORGANISM: mus musclulus

<400> SEQUENCE: 257
ttgtaagggt ctgaat                                           16

<210> SEQ ID NO 258
<211> LENGTH: 16
```

```
<212> TYPE: DNA
<213> ORGANISM: mus musclulus

<400> SEQUENCE: 258
aaaggtgtga gtaatg                                                      16

<210> SEQ ID NO 259
<211> LENGTH: 17
<212> TYPE: DNA
<213> ORGANISM: mus musclulus

<400> SEQUENCE: 259
agatgggtac ttatggg                                                     17

<210> SEQ ID NO 260
<211> LENGTH: 16
<212> TYPE: DNA
<213> ORGANISM: mus musclulus

<400> SEQUENCE: 260
atgggagcaa atagat                                                      16

<210> SEQ ID NO 261
<211> LENGTH: 16
<212> TYPE: DNA
<213> ORGANISM: mus musclulus

<400> SEQUENCE: 261
aatagatggt acagag                                                      16

<210> SEQ ID NO 262
<211> LENGTH: 18
<212> TYPE: DNA
<213> ORGANISM: mus musclulus

<400> SEQUENCE: 262
agagattttg ttatttgc                                                    18

<210> SEQ ID NO 263
<211> LENGTH: 17
<212> TYPE: DNA
<213> ORGANISM: mus musclulus

<400> SEQUENCE: 263
agaatgaaga taaaagg                                                     17

<210> SEQ ID NO 264
<211> LENGTH: 18
<212> TYPE: DNA
<213> ORGANISM: mus musclulus

<400> SEQUENCE: 264
tgagttttga aattgtca                                                    18

<210> SEQ ID NO 265
<211> LENGTH: 15
<212> TYPE: DNA
<213> ORGANISM: mus musclulus

<400> SEQUENCE: 265
agggtgtaaa ctagg                                                       15

<210> SEQ ID NO 266
```

```
<211> LENGTH: 16
<212> TYPE: DNA
<213> ORGANISM: mus musclulus

<400> SEQUENCE: 266
aatgtgaact aggaaa                                                 16

<210> SEQ ID NO 267
<211> LENGTH: 16
<212> TYPE: DNA
<213> ORGANISM: mus musclulus

<400> SEQUENCE: 267
atgagtgatt gcagtt                                                 16

<210> SEQ ID NO 268
<211> LENGTH: 16
<212> TYPE: DNA
<213> ORGANISM: mus musclulus

<400> SEQUENCE: 268
gtggaaaact gtagat                                                 16

<210> SEQ ID NO 269
<211> LENGTH: 16
<212> TYPE: DNA
<213> ORGANISM: mus musclulus

<400> SEQUENCE: 269
tgtagatgag agaagc                                                 16

<210> SEQ ID NO 270
<211> LENGTH: 17
<212> TYPE: DNA
<213> ORGANISM: mus musclulus

<400> SEQUENCE: 270
aaggagagaa gtattct                                                17

<210> SEQ ID NO 271
<211> LENGTH: 15
<212> TYPE: DNA
<213> ORGANISM: mus musclulus

<400> SEQUENCE: 271
gaagaacgta tgtga                                                  15

<210> SEQ ID NO 272
<211> LENGTH: 17
<212> TYPE: DNA
<213> ORGANISM: mus musclulus

<400> SEQUENCE: 272
gatatgtgga catttta                                                17

<210> SEQ ID NO 273
<211> LENGTH: 19
<212> TYPE: DNA
<213> ORGANISM: mus musclulus

<400> SEQUENCE: 273
attgaagggt ttagaaatc                                              19
```

```
<210> SEQ ID NO 274
<211> LENGTH: 18
<212> TYPE: DNA
<213> ORGANISM: mus musclulus

<400> SEQUENCE: 274
tataaaattg gaaatgta                                              18

<210> SEQ ID NO 275
<211> LENGTH: 17
<212> TYPE: DNA
<213> ORGANISM: mus musclulus

<400> SEQUENCE: 275
gaaaataaag aaagcta                                               17

<210> SEQ ID NO 276
<211> LENGTH: 16
<212> TYPE: DNA
<213> ORGANISM: mus musclulus

<400> SEQUENCE: 276
ttaggagagt agacta                                                16

<210> SEQ ID NO 277
<211> LENGTH: 16
<212> TYPE: DNA
<213> ORGANISM: mus musclulus

<400> SEQUENCE: 277
gtatattgta ggcata                                                16

<210> SEQ ID NO 278
<211> LENGTH: 19
<212> TYPE: DNA
<213> ORGANISM: mus musclulus

<400> SEQUENCE: 278
aatgggagtt gttgttcat                                             19

<210> SEQ ID NO 279
<211> LENGTH: 18
<212> TYPE: DNA
<213> ORGANISM: mus musclulus

<400> SEQUENCE: 279 atgtttataag gtagatgg                                             18

<210> SEQ ID NO 280
<211> LENGTH: 17
<212> TYPE: DNA
<213> ORGANISM: mus musclulus

<400> SEQUENCE: 280
tggatagtaa atgcagg                                               17

<210> SEQ ID NO 281
<211> LENGTH: 16
<212> TYPE: DNA
<213> ORGANISM: mus musclulus

<400> SEQUENCE: 281 tgtaagggt tctaat                                                 16
```

```
<210> SEQ ID NO 282
<211> LENGTH: 16
<212> TYPE: DNA
<213> ORGANISM: mus musclulus

<400> SEQUENCE: 282
tatgtaagga ttctat                                                   16

<210> SEQ ID NO 283
<211> LENGTH: 16
<212> TYPE: DNA
<213> ORGANISM: mus musclulus

<400> SEQUENCE: 283
attggagtaa aatcag                                                   16

<210> SEQ ID NO 284
<211> LENGTH: 16
<212> TYPE: DNA
<213> ORGANISM: mus musclulus

<400> SEQUENCE: 284
attgggaatc atttag                                                   16

<210> SEQ ID NO 285
<211> LENGTH: 17
<212> TYPE: DNA
<213> ORGANISM: mus musclulus

<400> SEQUENCE: 285
tgtaggaaga tcaagta                                                  17

<210> SEQ ID NO 286
<211> LENGTH: 18
<212> TYPE: DNA
<213> ORGANISM: mus musclulus

<400> SEQUENCE: 286
atggagttta tatgatga                                                 18

<210> SEQ ID NO 287
<211> LENGTH: 16
<212> TYPE: DNA
<213> ORGANISM: mus musclulus

<400> SEQUENCE: 287
tgtaaagaac atggtg                                                   16

<210> SEQ ID NO 288
<211> LENGTH: 18
<212> TYPE: DNA
<213> ORGANISM: mus musclulus

<400> SEQUENCE: 288
tgttgagatg aagagtag                                                 18

<210> SEQ ID NO 289
<211> LENGTH: 16
<212> TYPE: DNA
<213> ORGANISM: mus musclulus

<400> SEQUENCE: 289
atgaaatgag ttgttg                                                   16
```

<210> SEQ ID NO 290
<211> LENGTH: 17
<212> TYPE: DNA
<213> ORGANISM: mus musclulus

<400> SEQUENCE: 290
tggtttgttc aaagagg                                                   17

<210> SEQ ID NO 291
<211> LENGTH: 16
<212> TYPE: DNA
<213> ORGANISM: mus musclulus

<400> SEQUENCE: 291
aaggtagagt aaaagg                                                    16

<210> SEQ ID NO 292
<211> LENGTH: 17
<212> TYPE: DNA
<213> ORGANISM: mus musclulus

<400> SEQUENCE: 292
taatgtaaat aagctga                                                   17

<210> SEQ ID NO 293
<211> LENGTH: 17
<212> TYPE: DNA
<213> ORGANISM: mus musclulus

<400> SEQUENCE: 293
gttgtgaatg taaagca                                                   17

<210> SEQ ID NO 294
<211> LENGTH: 16
<212> TYPE: DNA
<213> ORGANISM: mus musclulus

<400> SEQUENCE: 294
atgtaaggta aaagcc                                                    16

<210> SEQ ID NO 295
<211> LENGTH: 18
<212> TYPE: DNA
<213> ORGANISM: mus musclulus

<400> SEQUENCE: 295
gattgtatga aatcgtgt                                                  18

<210> SEQ ID NO 296
<211> LENGTH: 17
<212> TYPE: DNA
<213> ORGANISM: mus musclulus

<400> SEQUENCE: 296
gttgaagttg aaaacat                                                   17

<210> SEQ ID NO 297
<211> LENGTH: 17
<212> TYPE: DNA
<213> ORGANISM: mus musclulus

```
<400> SEQUENCE: 297
gggtgaaatg ggtattc                                                  17

<210> SEQ ID NO 298
<211> LENGTH: 17
<212> TYPE: DNA
<213> ORGANISM: mus musclulus

<400> SEQUENCE: 298
gaaaatttag acatagg                                                  17

<210> SEQ ID NO 299
<211> LENGTH: 18
<212> TYPE: DNA
<213> ORGANISM: mus musclulus

<400> SEQUENCE: 299
ataagataga tagataaa                                                 18

<210> SEQ ID NO 300
<211> LENGTH: 16
<212> TYPE: DNA
<213> ORGANISM: mus musclulus

<400> SEQUENCE: 300
taatgtaatg acagtg                                                   16

<210> SEQ ID NO 301
<211> LENGTH: 17
<212> TYPE: DNA
<213> ORGANISM: mus musclulus

<400> SEQUENCE: 301
gattgtagga gttcagg                                                  17

<210> SEQ ID NO 302
<211> LENGTH: 16
<212> TYPE: DNA
<213> ORGANISM: mus musclulus

<400> SEQUENCE: 302
taagtaattt taggga                                                   16

<210> SEQ ID NO 303
<211> LENGTH: 19
<212> TYPE: DNA
<213> ORGANISM: mus musclulus

<400> SEQUENCE: 303
gtaattttag ggaattaat                                                19

<210> SEQ ID NO 304
<211> LENGTH: 15
<212> TYPE: DNA
<213> ORGANISM: mus musclulus

<400> SEQUENCE: 304
tgtggttaga gccga                                                    15

<210> SEQ ID NO 305
<211> LENGTH: 17
<212> TYPE: DNA
```

```
<213> ORGANISM: mus musclulus

<400> SEQUENCE: 305
agtatgtgtt tcatgta                                                17

<210> SEQ ID NO 306
<211> LENGTH: 17
<212> TYPE: DNA
<213> ORGANISM: mus musclulus

<400> SEQUENCE: 306
ttgataaagg tcaaatg                                                17

<210> SEQ ID NO 307
<211> LENGTH: 17
<212> TYPE: DNA
<213> ORGANISM: mus musclulus

<400> SEQUENCE: 307
tatgaatgtt ttaggga                                                17

<210> SEQ ID NO 308
<211> LENGTH: 17
<212> TYPE: DNA
<213> ORGANISM: mus musclulus

<400> SEQUENCE: 308
tgtgaggtgt gcaaaat                                                17

<210> SEQ ID NO 309
<211> LENGTH: 16
<212> TYPE: DNA
<213> ORGANISM: mus musclulus

<400> SEQUENCE: 309
gaagagtagg tattaa                                                 16

<210> SEQ ID NO 310
<211> LENGTH: 17
<212> TYPE: DNA
<213> ORGANISM: mus musclulus

<400> SEQUENCE: 310
agattttggt agctttg                                                17

<210> SEQ ID NO 311
<211> LENGTH: 18
<212> TYPE: DNA
<213> ORGANISM: mus musclulus

<400> SEQUENCE: 311
tttgagattt gaaataca                                               18

<210> SEQ ID NO 312
<211> LENGTH: 17
<212> TYPE: DNA
<213> ORGANISM: mus musclulus

<400> SEQUENCE: 312
tgagatttga aatacag                                                17

<210> SEQ ID NO 313
<211> LENGTH: 17
```

```
<212> TYPE: DNA
<213> ORGANISM: mus musclulus

<400> SEQUENCE: 313
gtgtaaaagg atgtggg                                                17

<210> SEQ ID NO 314
<211> LENGTH: 16
<212> TYPE: DNA
<213> ORGANISM: mus musclulus

<400> SEQUENCE: 314
tgtaaaagga tgtggg                                                 16

<210> SEQ ID NO 315
<211> LENGTH: 17
<212> TYPE: DNA
<213> ORGANISM: mus musclulus

<400> SEQUENCE: 315
aaagaaaatt agtacat                                                17

<210> SEQ ID NO 316
<211> LENGTH: 16
<212> TYPE: DNA
<213> ORGANISM: mus musclulus

<400> SEQUENCE: 316
tgaagataca gtgtgg                                                 16

<210> SEQ ID NO 317
<211> LENGTH: 16
<212> TYPE: DNA
<213> ORGANISM: mus musclulus

<400> SEQUENCE: 317
ggatattttg tatgct                                                 16

<210> SEQ ID NO 318
<211> LENGTH: 18
<212> TYPE: DNA
<213> ORGANISM: mus musclulus

<400> SEQUENCE: 318
agagttggaa aatgattt                                               18

<210> SEQ ID NO 319
<211> LENGTH: 17
<212> TYPE: DNA
<213> ORGANISM: mus musclulus

<400> SEQUENCE: 319
tgtagggaaa catggtt                                                17

<210> SEQ ID NO 320
<211> LENGTH: 16
<212> TYPE: DNA
<213> ORGANISM: mus musclulus

<400> SEQUENCE: 320
atggttatga taggaa                                                 16

<210> SEQ ID NO 321
```

```
<211> LENGTH: 16
<212> TYPE: DNA
<213> ORGANISM: mus musclulus

<400> SEQUENCE: 321
tgataggaac aagaat                                                   16

<210> SEQ ID NO 322
<211> LENGTH: 19
<212> TYPE: DNA
<213> ORGANISM: rattus norvegicus

<400> SEQUENCE: 322
gatcagagat taaggccaa                                                19

<210> SEQ ID NO 323
<211> LENGTH: 19
<212> TYPE: DNA
<213> ORGANISM: rattus norvegicus

<400> SEQUENCE: 323
gcagattgat tatacggta                                                19

<210> SEQ ID NO 324
<211> LENGTH: 19
<212> TYPE: DNA
<213> ORGANISM: homo sapiens

<400> SEQUENCE: 324
gtggaaggaa cacgactta                                                19

<210> SEQ ID NO 325
<211> LENGTH: 22
<212> TYPE: DNA
<213> ORGANISM: homo sapiens

<400> SEQUENCE: 325
gaataatatg gaaaaacgaa aa                                            22
```